(12) United States Patent
Max et al.

(10) Patent No.: US 10,968,443 B2
(45) Date of Patent: Apr. 6, 2021

(54) METHOD OF RNA ISOLATION FROM CLINICAL SAMPLES

(71) Applicant: The Rockefeller University, New York, NY (US)

(72) Inventors: Klaas Max, New York, NY (US); Karl Bertram, Bullay (DE); Kemal Akat, New York, NY (US); Thomas H. Tuschl, Brooklyn, NY (US); Jenny Li, New York, NY (US); Kimberly Bogardus, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 15/540,528

(22) PCT Filed: Dec. 31, 2015

(86) PCT No.: PCT/US2015/068287
§ 371 (c)(1),
(2) Date: Jun. 28, 2017

(87) PCT Pub. No.: WO2016/109799
PCT Pub. Date: Jul. 7, 2016

(65) Prior Publication Data
US 2018/0119131 A1 May 3, 2018

Related U.S. Application Data

(60) Provisional application No. 62/099,112, filed on Dec. 31, 2014.

(51) Int. Cl.
*C12Q 1/68* (2018.01)
*C12N 15/10* (2006.01)
*C07H 21/02* (2006.01)
*C07H 1/08* (2006.01)
*C12Q 1/6806* (2018.01)

(52) U.S. Cl.
CPC ........... *C12N 15/1006* (2013.01); *C07H 1/08* (2013.01); *C07H 21/02* (2013.01); *C12Q 1/68* (2013.01); *C12Q 1/6806* (2013.01); *C12Q 2527/125* (2013.01)

(58) Field of Classification Search
None
See application file for complete search history.

(56) References Cited

U.S. PATENT DOCUMENTS

| 6,218,531 | B1 * | 4/2001 | Ekenberg | C12N 15/1003 210/656 |
| 2002/0009794 | A1 * | 1/2002 | Danenberg | C12N 15/1003 435/270 |
| 2011/0172405 | A1 * | 7/2011 | Dhulipala | C12N 15/1006 536/23.1 |
| 2013/0245245 | A1 * | 9/2013 | Conrad | C12N 15/1003 536/25.42 |
| 2014/0272993 | A1 * | 9/2014 | Van Keuren-Jensen | C12Q 1/6806 435/6.12 |

* cited by examiner

*Primary Examiner* — Kenneth R Horlick
(74) *Attorney, Agent, or Firm* — Hoffman & Baron, LLP

(57) ABSTRACT

The disclosure provides methods for isolating nucleic acids from a biological fluid. In one aspect, the disclosure provides a method for isolating RNA. In another aspect, the disclosure provides a method for isolating DNA. In one aspect, the methods described herein utilize a protocol that combines a detergent-based initial denaturation, protease digestion, and organic extraction followed by column purification that maximizes RNA/DNA yield and preserves RNA/DNA integrity. In yet another aspect, the disclosure provides a kit for isolating RNA and/or DNA.

20 Claims, 27 Drawing Sheets
(16 of 27 Drawing Sheet(s) Filed in Color)
Specification includes a Sequence Listing.

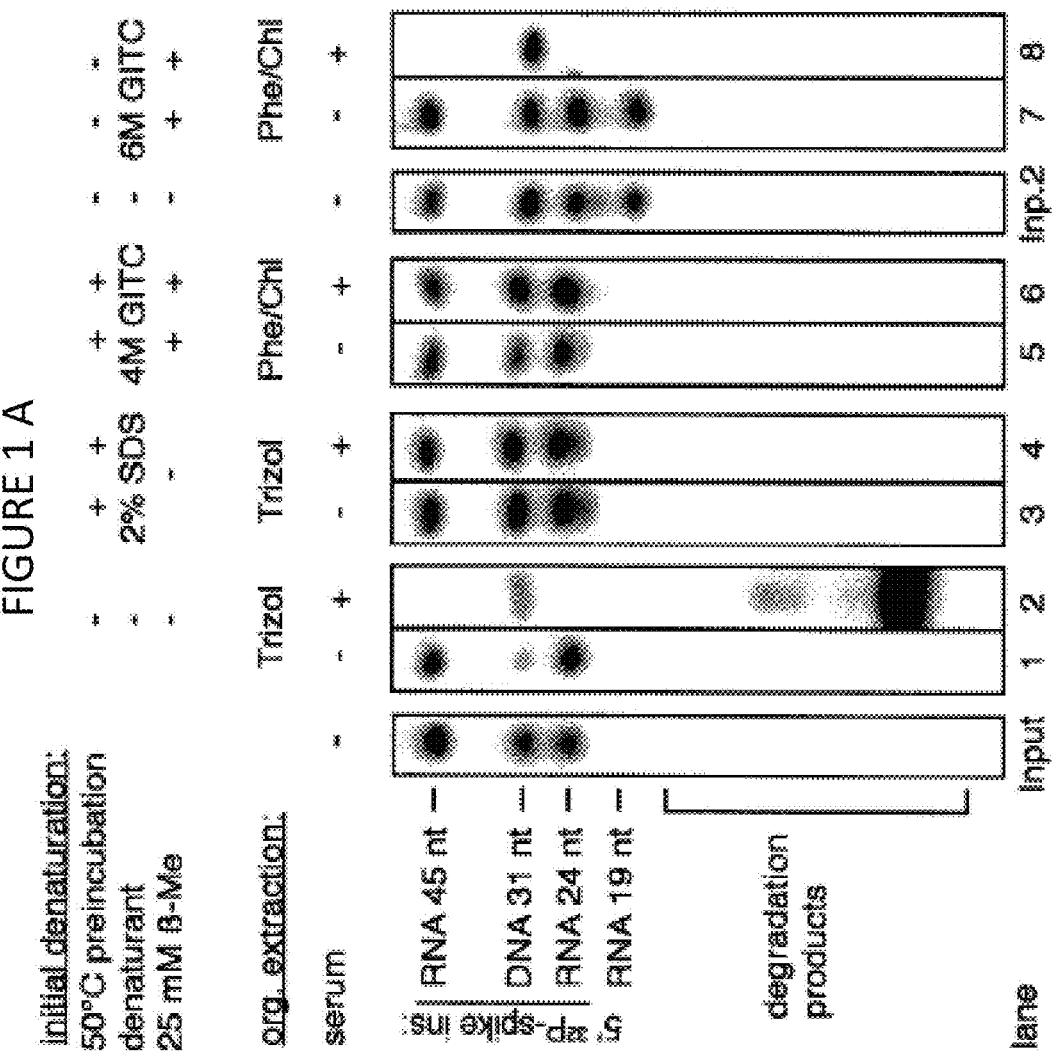

Fully automated

Aqueous phases

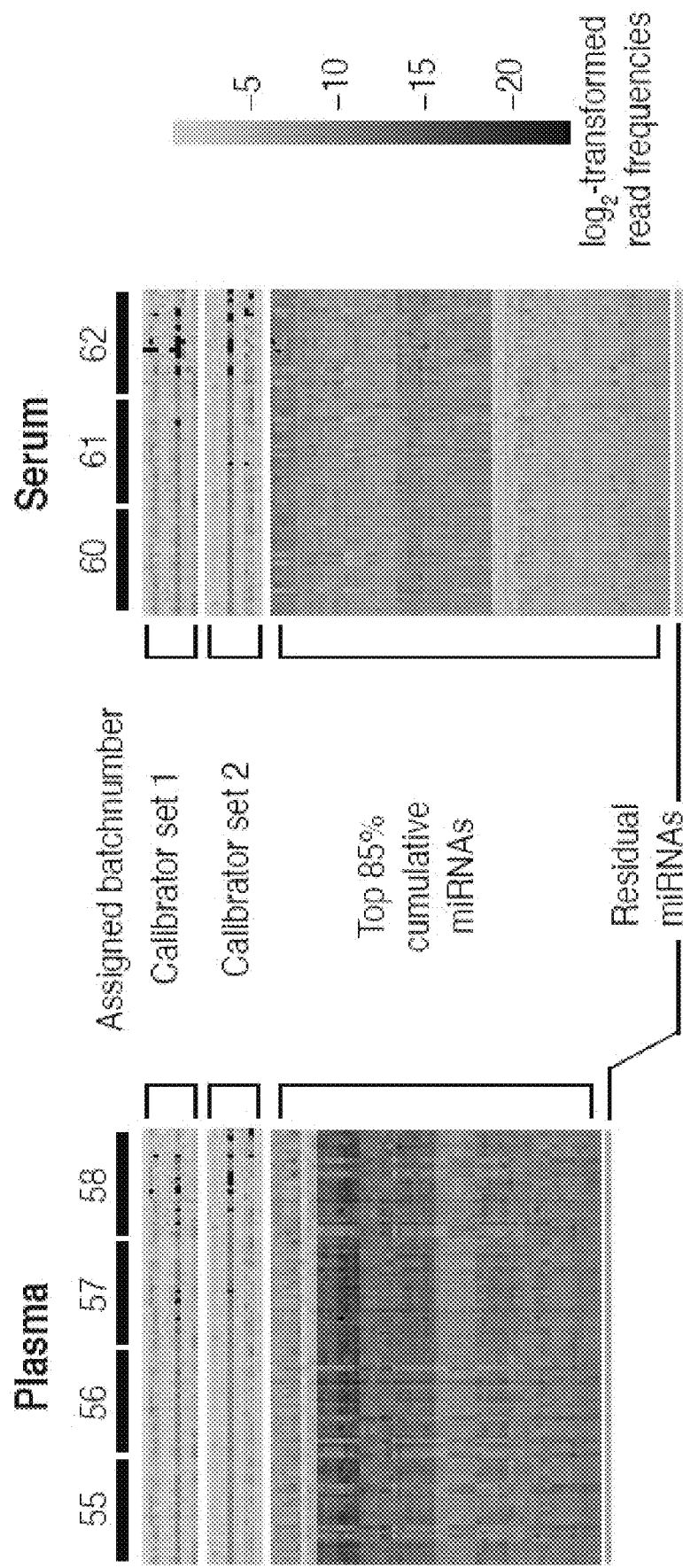

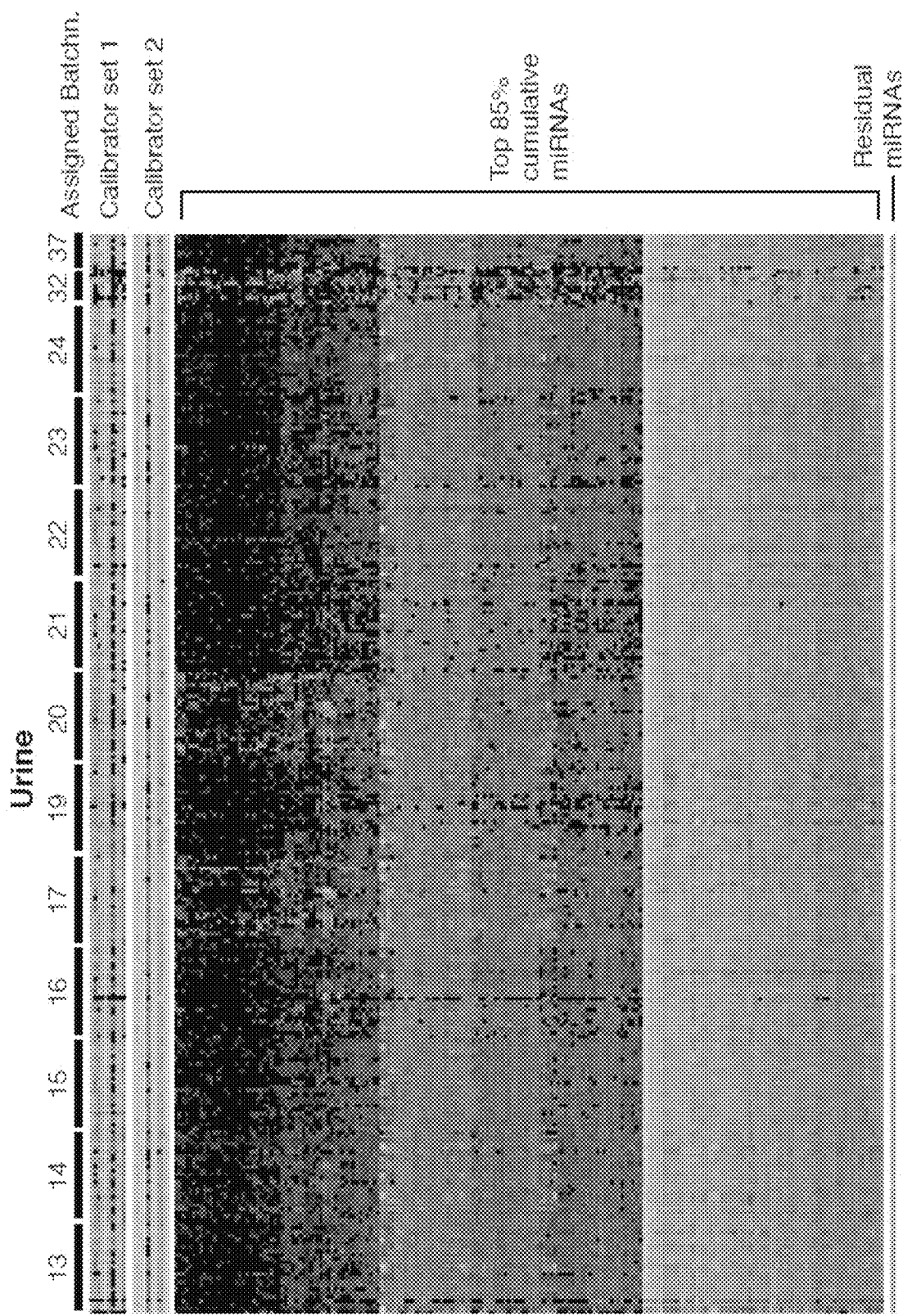
FIGURE 5C Urine

SEQUENCE LISTING

<160> NUMBER OF SEQ ID NOS: 11

<210> SEQ ID NO 1
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 1
uccacgacgu cucauguauu uc                                              22

<210> SEQ ID NO 2
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 2
ggguaccaua ccgguugucu ua                                              22

<210> SEQ ID NO 3
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 3
ucaugagucc guaccuugau ug                                              22

<210> SEQ ID NO 4
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 4
aucauuuacg auucggagcu gu                                              22

<210> SEQ ID NO 5
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 5
gauaguucgg gaucgcugua ac                                              22

<210> SEQ ID NO 6
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 6
ugcuacuccg aucuuuagcc uc                                              22

<210> SEQ ID NO 7
<211> LENGTH: 22
<212> TYPE: RNA
<213> ORGANISM: Artificial Sequence

```
<220> FEATURE:
<223> OTHER INFORMATION: Synthetic Sequence

<400> SEQUENCE: 7
agggcccuuu aggcacuaau ag                                                 22

<210> SEQ ID NO 8
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 8
guagcuguca guacguucgu gc                                                 22

<210> SEQ ID NO 9
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 9
ucuaguugcg ugauggagag aa                                                 22

<210> SEQ ID NO 10
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 10
agccgcauuu cguagugaua uu                                                 22

<210> SEQ ID NO 11
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 11
tcgaagtatt c                                                             11
```

METHOD OF RNA ISOLATION FROM CLINICAL SAMPLES

CROSS-REFERENCE TO RELATED APPLICATIONS

This application is a national stage filing under 35 USC § 371 of international application number PCT/US2015/068287, filed on Dec. 31, 2015, which claims benefit of US Provisional Application No. 62/099,112, filed Dec. 31, 2014, all of which are hereby incorporated by reference in their entirety.

STATEMENT OF GOVERNMENT RIGHTS

The present application was made with government support under project numbers UH2TR000933 and U19CA179564 awarded by the National Institutes of Health (NIH). The United States government has certain rights in the invention(s).

BACKGROUND

RNA impacts nearly every aspect of gene expression and many human diseases are caused by or result in mistakes in RNA metabolism, e.g. mutations in pre-mRNAs lead to splicing defects or degradation of mRNAs by trigger nonsense-mediated mRNA decay. It has been shown that in addition to RNA's fundamental roles in information transfer from DNA to protein, RNA molecules play crucial roles in gene regulation as their stability or rate of protein synthesis is regulated by mRNA binding proteins or ribonucleoprotein complexes (RNPs), e.g. microRNA-containing RNPs. Accordingly, RNAs present a possible new class of biomarkers.

In a medical context, biomarkers are indicators for the presence or severity of disease and are usually detected in tissue samples or body fluids by various assays. Proteins, nucleic acids, lipids and other metabolites are commonly utilized in order to evaluate or diagnose a patient's status. In order for all biomarker substances to be analyzed ex vivo, they need to be extracted from the host body fluid, tissue material or cell sample, processed and analyzed accordingly. Ideally, all experimental steps, consequently leading to clinically valuable results, are performed with great caution to minimize any bias introduced by extraction or specific evaluation procedures.

Ribonucleic acids show potential to serve as biomarkers in today's clinical routine for the diagnosis of various types of cancer but also cardiovascular, kidney or autoimmune diseases. Ribonucleotide biomarkers presently studied are often based on small RNA types like microRNAs, isolated from body fluids or tissue samples, or longer ribonucleic acids, based on the study of long noncoding RNAs (lncRNA) generally isolated from tissue or cell samples. In order to analyze ribonucleic acids by using various techniques they need to be isolated, purified and protected from ubiquitously expressed ribonucleases. Common methods identifying specific, possibly disease-related ribonucleic acids in biological samples include but are not limited to: Northern blotting, RT-PCR, microarray and sequencing analysis. After clinically relevant and significant differences in RNA composition between samples of diseased patients and healthy controls were found, the change in abundance of one or more specific RNAs can then be used as a biomarker in order to detect this disease pattern in future applications.

The process of isolating RNA raw material is one of the most crucial steps concerning the detection of (micro)RNA-based biomarkers. Where stable RNA isolation procedures are vital to obtain meaningful results, multiple reports pointed out that differences in RNA isolation and library preparation procedures introduced substantial biases during sample analysis. Numerous studies compared these differences and pointed out inconsistencies during RNA isolation utilizing frequently used commercial kits or components like TRIzol or column based approaches. Considering these substantial biases introduced during the isolation procedure, deviations in yield after RNA extraction were shown to cause significant variability in qPCR and microarray-based results when several already available RNA isolation techniques were used and compared. In summary, significant discrepancies in RNA isolation, preparation procedures, and downstream analysis were highlighted in recent literature, possibly caused by the utilization of potentially unstable and uncontrolled RNA purification approaches.

Isolating ribonucleic acids (RNA) from biological samples is a frequently utilized method in biochemical, medical and biological research. Since circulating microRNAs (miRNA) in various body fluids were initially proposed to potentially serve as biomarkers in clinical routine, the immanent need for successful small RNA purification procedures concerning these samples arose.

The isolation of small RNAs from biological sample material, however, is not trivial as prevalence is generally low and intrinsic ribonucleases (RNases) naturally present in body fluids rapidly degrade and destroy unprotected RNA. Furthermore, the isolation and purification procedures currently described in the literature or offered through commercial kits provide varying results terms of ribonuclease protection, automation capabilities, and homogeneity of RNA extracted from multiple samples.

Therefore, there remains a need for improved methods to isolate RNA from nuclease-rich and RNA-poor human clinical samples, which maximizes yield and preserves RNA integrity.

SUMMARY OF THE INVENTION

In one aspect, the disclosure provides a method for isolating RNA from a biological fluid. The method includes contacting the biological fluid with a denaturing solution comprising at least one of reducing agent and detergent to form a biological fluid mixture; contacting the biological fluid mixture with a protease to form a protease treated biological fluid mixture;

contacting the protease treated biological fluid mixture with an organic extraction solution, forming a solution having an aqueous phase containing the RNA and an organic phase; binding the RNA to a silica based solid phase by contacting the aqueous phase with said silica based solid phase; contacting the silica based solid phase with a first wash solution comprising alcohol, chaotropic agent, and reducing agent; and eluting the RNA from the silica based solid phase comprising contacting the silica based solid phase with an aqueous solution to provide isolated RNA.

In another aspect, the disclosure provides a kit for isolating RNA from a biological fluid. The kit includes a denaturing solution; an organic extraction solution; a nucleic acid binding solution; and a first wash solution comprising alcohol, chaotropic agent, and reducing agent.

In another aspect, the disclosure provides a method for isolating DNA from a biological fluid. The method includes contacting the biological fluid with a denaturing solution comprising at least one of reducing agent and detergent to form a biological fluid mixture; contacting the biological fluid mixture with a protease to form a protease treated biological fluid mixture; contacting the protease treated biological fluid mixture with an organic extraction solution, forming a solution having an first aqueous phase containing RNA and an organic phase containing DNA; contacting the organic phase with a DNA extraction solution containing a buffer and a chaotropic agent to form a second solution having a second aqueous phase containing DNA; binding the DNA to a silica based solid phase by contacting the second aqueous phase with said silica based solid phase; contacting the silica based solid phase with a first wash solution comprising alcohol, chaotropic agent, and reducing agent; and eluting the DNA from the silica based solid phase comprising contacting the silica based solid phase with an aqueous solution to isolate DNA.

BRIEF DESCRIPTION OF THE SEVERAL VIEWS OF THE DRAWING

The patent or patent application contains at least one drawing executed in color. Copies of this patent or patent application publication with color drawing(s) will be provided by the U.S. Patent and Trademark Office upon request and payment of the necessary fee.

FIGS. 1A-1C depict the use of spike-in calibrators to find optimized conditions for RNA isolation from biofluids. A mix of synthetic 5' $^{32}$P-labeled spike-in ssRNA (19, 24 nt, 21 nt 2'O-methyl RNA and 45 nt) and ssDNA (31 nt) oligonucleotides was used to monitor damages resulting from ribonuclease activity during and after purification. Different oligonucleotide combinations (see each individual input lane for each experiment) of less than 0.1 pmol per oligo were added to the initial denaturation condition (a, b: lane 3-6, c: lane 1-6) or to extraction agents (A, B: lane 1,2). The concentration labels in this figure refer to the resulting concentrations of the aqueous conditions after mixing the sample with the denaturing solutions.

FIG. 1A depicts a hot initial denaturation significantly improves RNA intactness in biofluid sample extracts using protocols that combine organic extraction with nucleic acid precipitation.

Figure 1B:
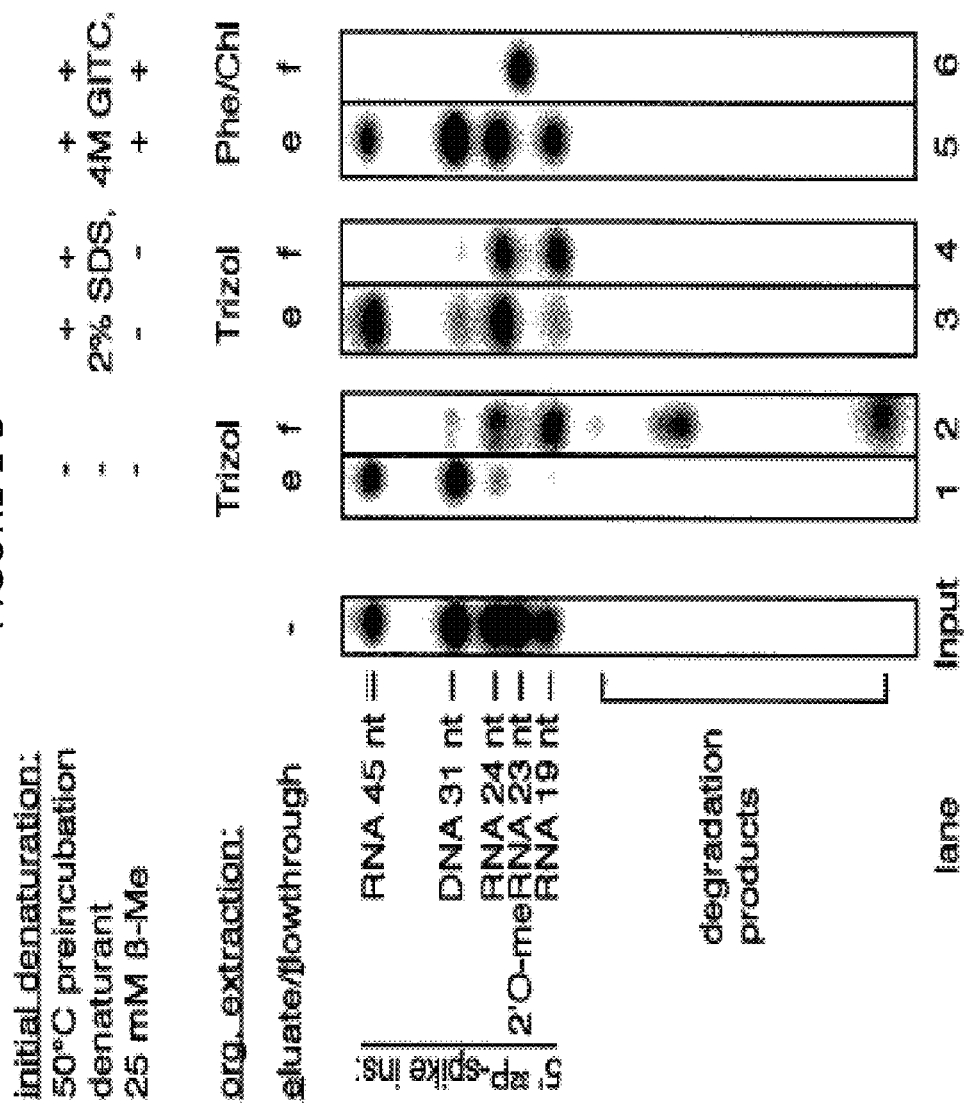

Reaction conditions: RNA isolation using organic extraction combined with ethanol precipitation. Samples used in this setup could either be serum samples or water controls. 150 µl samples were either directly extracted with 3 volumes of Trizol LS reagent (Thermofisher Scientific) (lane 1,2), or mixed 1:1 with 50° C.-pre-heated denaturation solutions containing either 4% SDS, 4 mM EDTA, 20 mM TRIS, pH 7.5 (lanes 3, 4) or 8M GITC, 80 mM Na citrate, 0.13 g sarcosyl, 50 mM 2-mercaptoethanol (lanes 5, 6), incubated at 50° C. for five minutes, cooled to room temperature for two minutes, followed by organic extraction with 3 volumes of Trizol LS (lanes 3, 4) or acidic phenol (lanes 5, 6). One additional sample (v=125 µl was mixed with an 375 µl of 8M GITC, 80 mM Na citrate, 0.13 g sarcosyl, 33 mM 2-mercaptoethanol without thermal denaturation (lanes 7, 8), followed by extraction with 3 volumes of acidic phenol. Phase separation in all samples was induced by addition of 0.2 vol. of chloroform. After adding 1/10 volume of 3 M Na acetate pH 4.6, the aqueous phases were reextracted with 1 vol. of phenol/chloroform/isoamylalcohol (25:24:1) and precipitated with 3 vol. of ethanol. Samples were incubated on ice for 30 min., spun at 12000×g for 30 min. Then supernatants were carefully removed and pellets were air-dried until glossy and resuspended in 20 µl water. 5 µl aliquots were loaded.

FIG. 1B depicts hot initial denaturation significantly improve RNA intactness in biofluid sample extracts using protocols that combine organic extraction with column purification.

Reaction conditions: A 150 µl serum sample was extracted with 3 vol. Trizol (lane 1), or mixed 1:1 with 50° C.-pre-heated denaturation solutions containing either 4% SDS, 4 mM EDTA, 20 mM TRIS, pH 7.5 (lane 3) or 8M GITC, 80 mM Na citrate, 0.13 g sarcosyl, 50 mM 2-mercaptoethanol (lane 5), incubated at 50° C. for five minutes, cooled to room temperature for two minutes, followed by organic extraction with 3 volumes of Trizol LS (lanes 3) or acidic phenol (lanes 5). Phase separation in all samples was induced by addition of 0.2 vol. of chloroform. After addition 1/10 vol. of 3 M Na acetate pH 4.6 and 1.5 vol. of ethanol, the aqueous supernatants were subjected to column purification using the RNeasy minElute kit for serum/plasma using buffer RWP and RPE. Samples were eluted from the columns in 20 µl water. Column flow through fractions of aqueous phases were subjected to nucleic acid precipitation by adding additional 1.5 vol. of ethanol, followed by cooling on ice for 30 min., centrifugation at 12000×g for 30 min., aspiration of the supernatant, air-drying of the pellets until they look glossy, followed by dissolving the pellets in 20 µl water. 5-µl aliquots of eluate and flow through fractions were loaded.

Figure 1C:
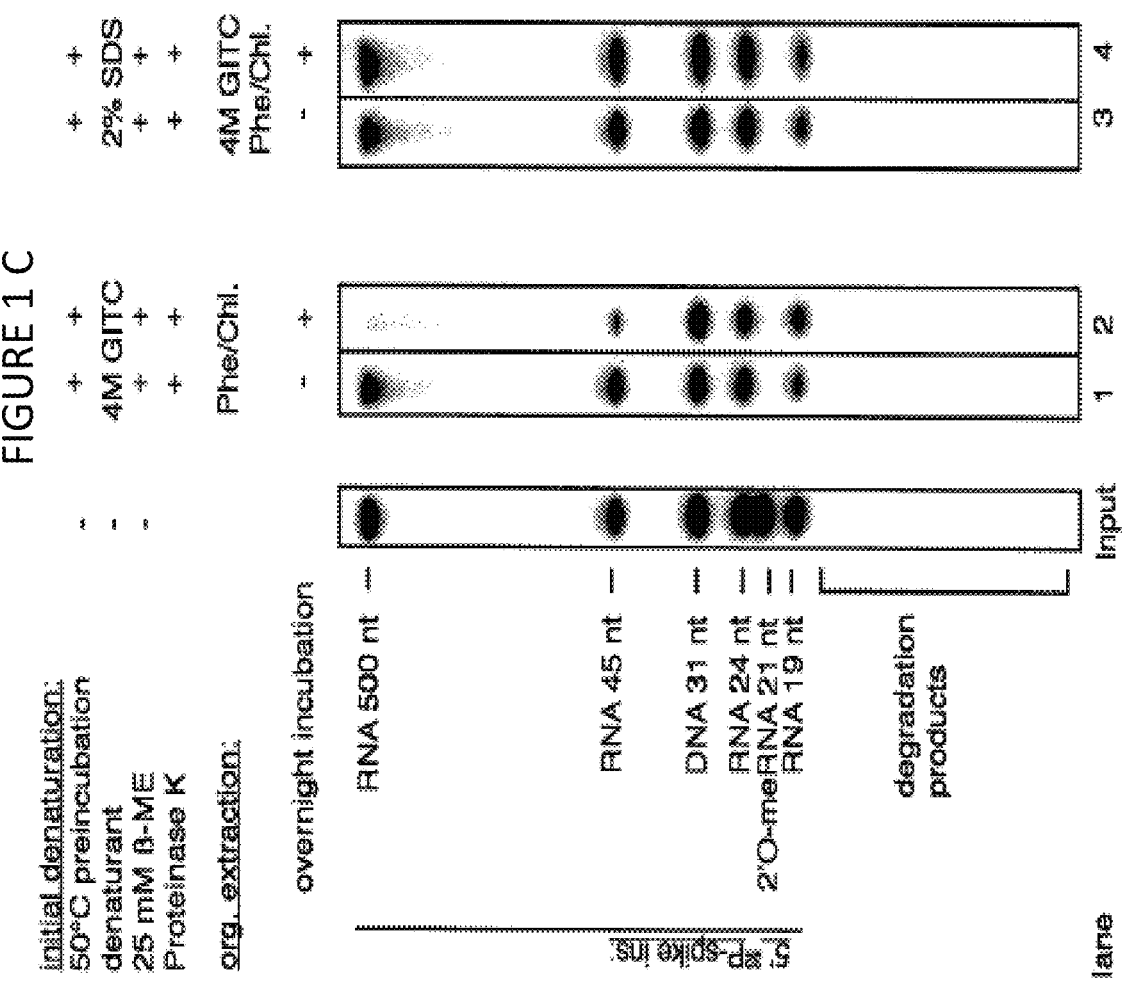

FIG. 1C depicts optimized RNA extraction conditions combining detergent-based initial denaturation, proteinase K digestion and organic extraction followed by column purification provide superior protection of RNAs.

Reaction conditions: A 250 µl serum sample mixed 1:1 with 50° C.-pre-heated denaturation solutions containing either 4% SDS, 4 mM EDTA, 20 mM TRIS, pH 7.5 (lane 3) or 8M GITC, 80 mM Na citrate, 0.13 g sarcosyl, 50 mM 2-mercaptoethanol (lane 5), incubated at 50° C. for two minutes, followed by addition of 50 µg proteinase K and proteolytic digestion for 15 minutes at 50° C. After digestion, solutions were cooled to room temperature for two minutes, followed by organic extraction with 1.5 volumes of 4M GITC extraction solution or acidic phenol (lanes 5). Phase separation in all samples was induced by addition of 0.2 vol. of chloroform. After addition 1/10 vol of 3 M Na acetate pH 4.6 and 1.5 ethanol, the aqueous supernatants were subjected to column purification using the RNeasy minElute kit for serum/plasma using buffer RWP and RPE. Samples were eluted from the columns in 20 µl water. 50 fractions from frozen eluates and of 4° C. overnight incubations of eluates were loaded.

Figure 2A:
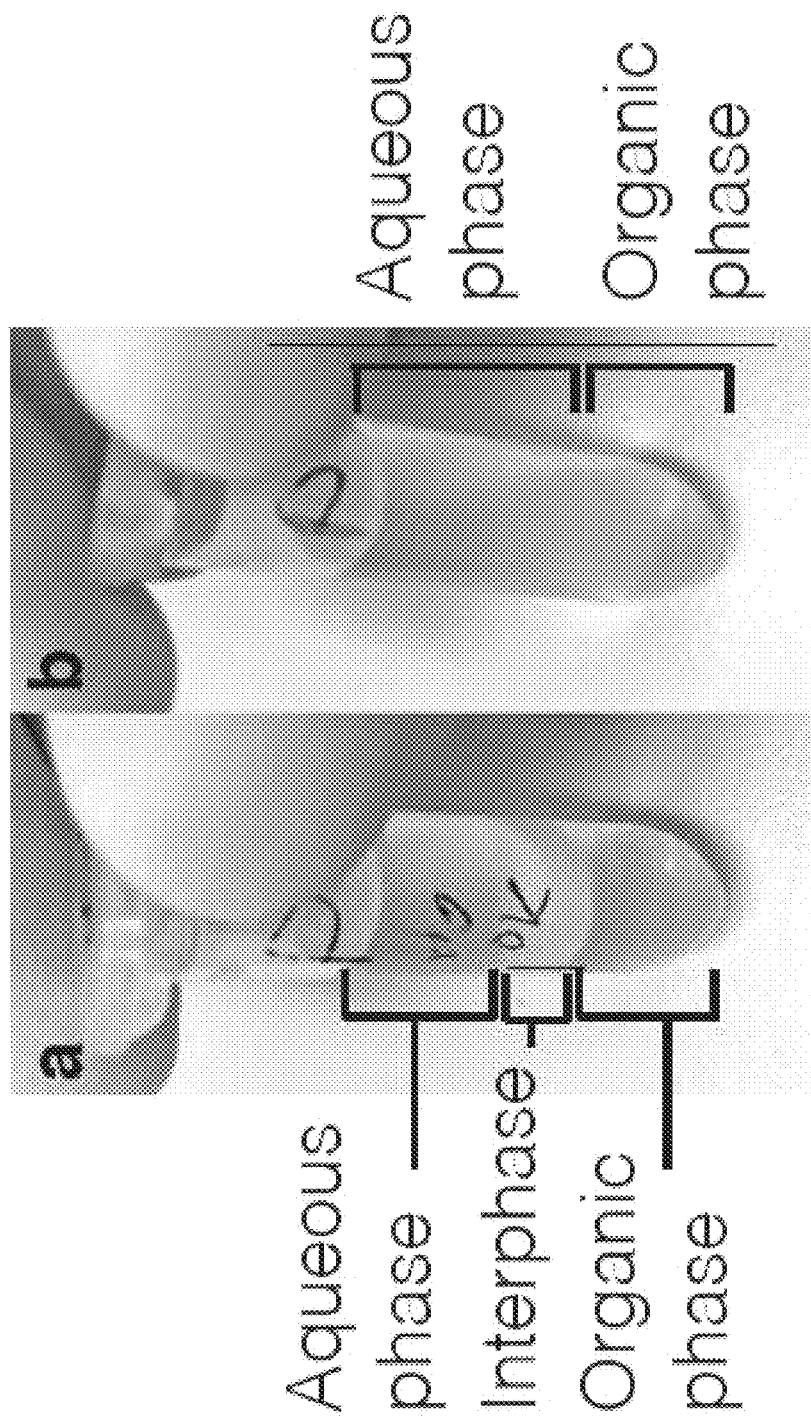
Figure 2:
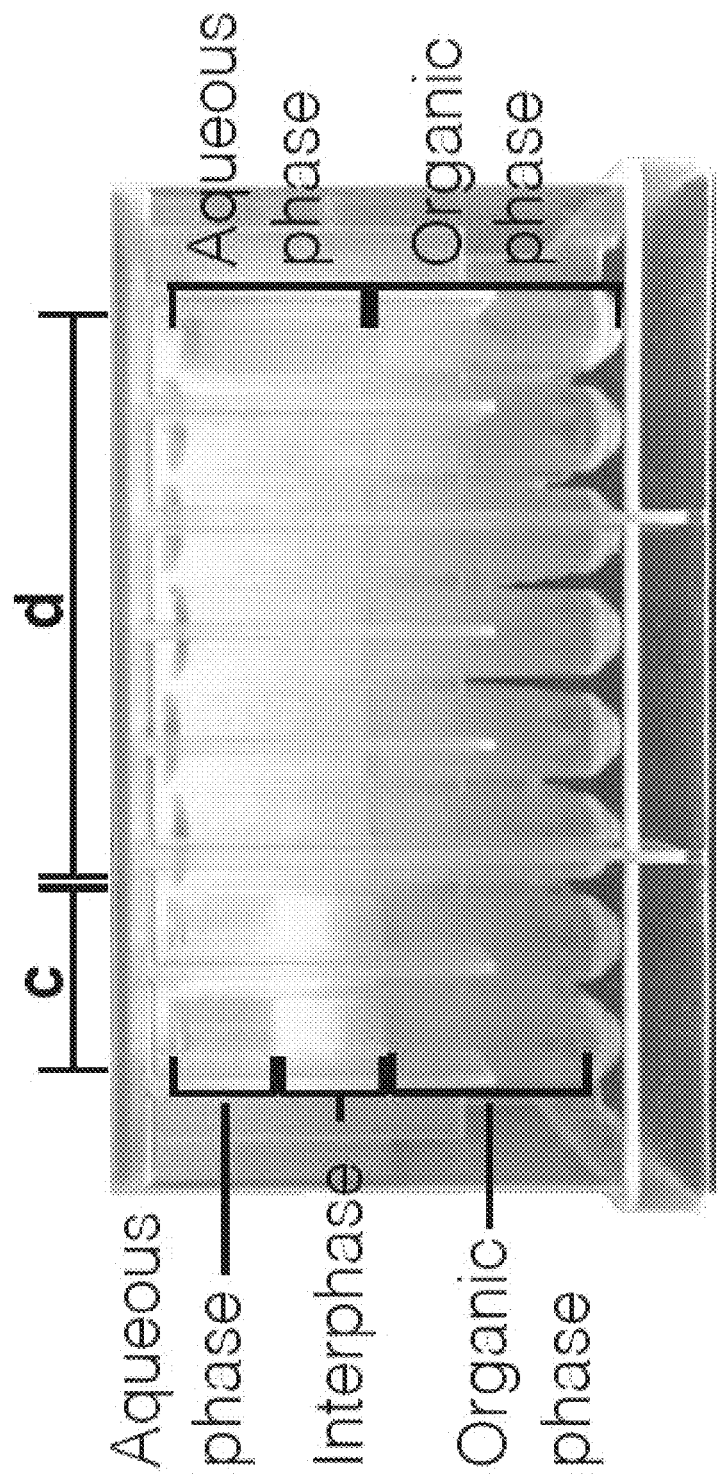

FIGS. 2A-2B depict the interphase during extraction. Avoiding interphase formation after organic extraction of biofluid samples by proteolytic digestion with proteinase K. By performing protein digestion with proteinase K in a denaturation buffer, interphase formation typically observed in serum and plasma samples after subsequent organic extractions (a, c) can be prevented or significantly reduced (b, d). This has important implications:

1. It allows phase separation to be achieved at lower centrifugal speeds; 3700×g or less is sufficient for complete separation of phases with prior proteinase K treatment. In contrast, complete separation of phases was not achieved at 12000×g, the speed recommended for comparable phase separations, without proteinase K treatment.

2. It allows the time of phase separation by centrifugation to be significantly reduced to 5 min or less. In contrast, protocols for organic extraction without prior proteinase K treatment frequently recommend centrifugation times of 15 min and more.

3. Implications 1 and 2 in samples treated with proteinase K allow for the maximization and timely optimization of aqueous phase recovery, thereby maximizing RNA recovery using standard microtitre deep-well plates (e.g. eppendorf 96 standard DeepWell Plate), in inexpensive general purpose centrifuges (e.g. Sorvall legend RT) equipped with a swing-out rotor (Sorvall Heraeus 6434/75006434 Swingout Rotor) and microplate adapters.

Although it is also possible to recover the aqueous phase from biofluid samples processed without proteinase K treatment (C), due to the reduced compactness of interphases at centrifugal speeds of 3700×g or less, the volume of the aqueous phase is reduced to approximately 50% of the total aqueous phase volume under these conditions. This cannot be overcome by longer centrifugation times. High-speed centrifugation e.g. 12000 xg would compact interphases (A) further, but requires different centrifugation equipment and consumables.

4. Implications 1. and 2. in proteinase K-treated samples simplify automatic aspiration of aqueous phases containing RNA using automated liquid handling equipment (e.g. epMotion 5075) since no special sensory mechanism is required to prevent aspiration of interphases.

Aspiration of interphases could potentially clog the apparatus, lead to carryover of impurities such as ribonucleases, or clog columns used in subsequent column-based RNA purification steps.

5. Implications 1. and 2. in PNK-treated samples enable DNA recovery from organic phases obtained by initial organic extraction by simplifying automated re-extraction of existing organic phases with suitable reextraction solution, followed by subsequent second phase separation in the absence of interphases and allowing automated aspiration of resulting aqueous phases which then contain the DNA.

FIGS. 3A-3B: Depict (A.) GITC concentration controls partitioning of $^{32}$P-labled ssDNA during organic extraction. Using extraction solutions containing 1.5 M GITC (5.91 g GITC (Mr=118.2 g/mol), 290 μl M citric acid, 150 μl 4 M NaOH, 0.13 g sacrosyl (Mr=293.4 g/mol), 3.06 ml water, 25 ml phenol (citrate-buffered pH 4.3) in a total vol. of 34 ml) this product remained in the aqueous phase, with a resulting GITC concentration of approximately 1.7 M after phase separation (Lane 1 and 3). Using an extraction solution with 3.0 M GITC (see previous formulation, but use of 11.81 g GITC and do not add water) the ssDNA was observed to partition into the organic phase, apparent by its absence in the aqueous phase and a detectable amount of radioactivity in the resulting organic phase using a β-counter. Reaction conditions: The aqueous phase consisted of 450 μl heparin plasma, 125 μl buffer P, 3 μl proteinase K stock solution and 25 μl M NaCl (see protocol, formulations in section 2) and was processed according to the current version of the protocol, with the modified volumes given here. Approximately 603 μl of aqueous phase were mixed with 750 μl organic extraction agent, followed by 1 min incubation at 65° C. and 1 min incubation at 4° C. During the incubation at 65° C. formation of a single phase was observed which is expected to contain approximately 0.8 M GITC and 1.6 M GITC for samples extracted with 1.5 M and 3.0 M GITC-containing extraction solution, respectively. Phase separation was induced by adding 150 μl chloroform (0.2 vol. of the original organic phase, followed by mixing for 1 min at 4° C. in a eppendorf thermomixer at 1200 rpm and 5-minute centrifugation at 12000×g in tabletop centrifuge at 4° C. (B.) Separation of RNA and DNA in biofluid samples using two sequential organic extractions. The RNA isolation method described here utilizes the above finding of GITC dependence on DNA partitioning (see A): In a first organic extraction an extraction solution containing 1.6 M GITC (solution ED2, section 2.6.3.1) is used to allow DNA molecules to partition into the organic phase. RNA remains in the aqueous phase under these conditions, which is aspirated and subjected to column purification and subsequent RNA elution (lane 1,2; 5,6; 9,10, 13,14). In a second extraction step, the organic phase is extracted with an aqueous solution containing 4M GITC (solution EA3, section, 2.6.5.1) which causes the DNA to redistributes from the organic phase into the resulting aqueous phase, followed by subsequent column purification and DNA elution (lane 3,4; 7,8; 11,12; 15,16). The current extraction protocols use slightly modified volumes of aqueous and organic solutions than those originally used (see figure A and section 3.3 for comparison). However, the resulting concentrations (summarized in section 4) are virtually identical. Trace amounts of $^{32}$P-labeled RNA spikes in the DNA-containing fractions in the fully automated procedure (lanes 7,8; 11,12; 15,16), are a consequence of incomplete aspiration of aqueous phases phase after the first organic extraction due to shortcomings of our automated liquid handling system and are not expected to interfere with DNA analysis. If a higher level of purity is desired, an additional wash step with an aqueous solution containing 1.5 M GITC may help to avoid RNA carryover.

All lanes in this figure show aliquots of aqueous phases from organic extractions that were subjected to a column purification as described in the protocol, section 3.3.4), prior to gel loading.

Figure 4:
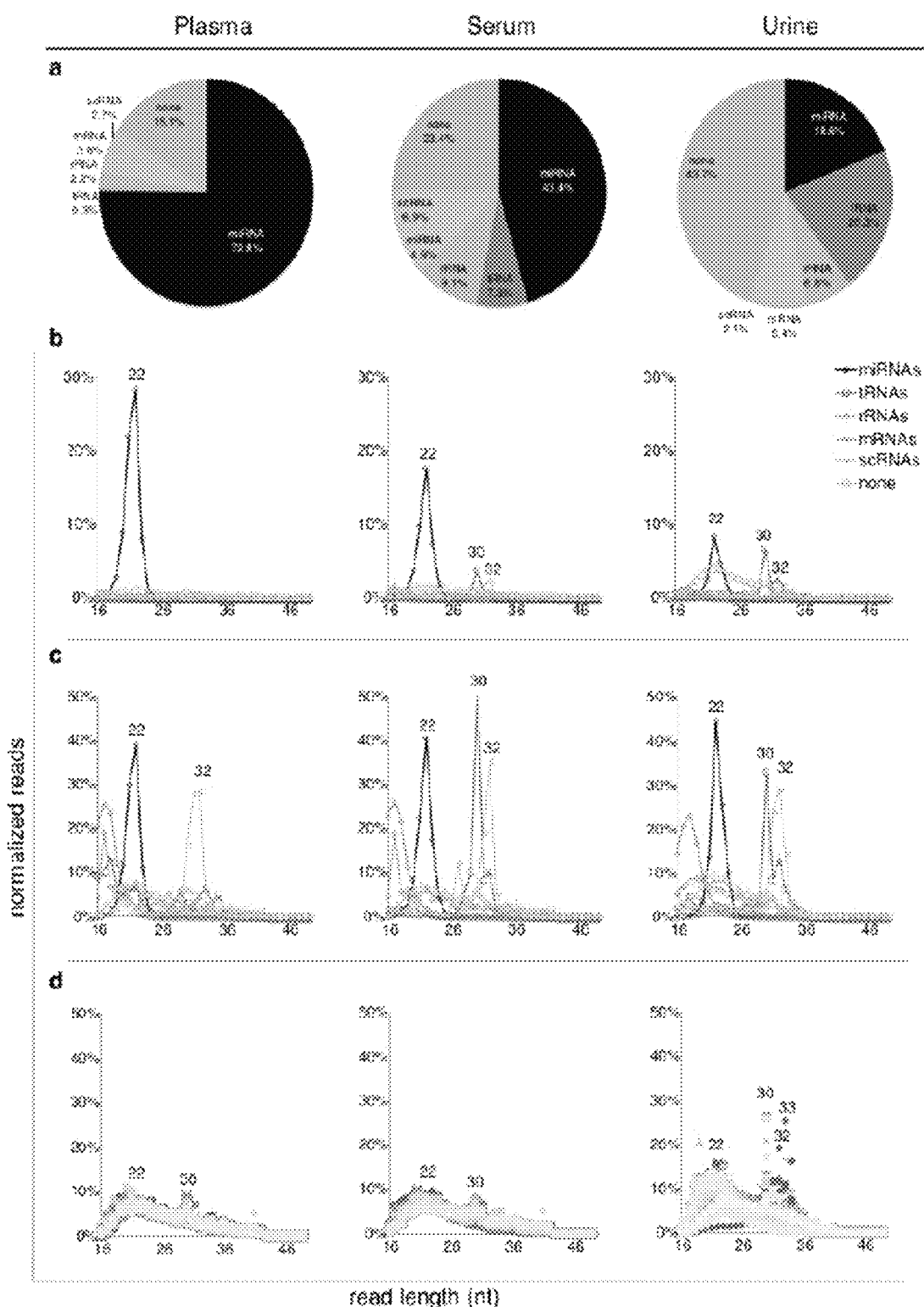

FIG. 4 depicts sequence length distributions of miRNAs, tRNAs, scRNAs, mRNAs and unmapped sequences in serum, plasma and urine. a) Average sample compositions considering only selected sRNA categories. For plasma miRNA represents 72.8%, scRNA represents 2.7%, mRNA represents 3.6%, rRNA represents 2.2%, and tRNA represents 0.3%. For serum miRNA represents 43.4%, scRNA represents 6.9%, mRNA represents 4.9%, rRNA represents 9.1%, and tRNA represents 0.3%. For urine miRNA represents 18.6%, scRNA represents 2.1%, mRNA represents 6.4%, rRNA represents 6.8%, and tRNA represents 20.3%. b) Total sequence length distributions in selected sRNA categories based on biofluid sample averages. c) relative sequence length distributions based on biofluid sample averages. d) Relative sequence length distributions for unmapped sequences using individual samples. For b), c), and d), miRNA correspond to 22, tRNA corresponds to 30, mRNA correspond to 33, and scRNA corresponds to 32.

FIGS. 5A-5C depict miRNA composition in biofluid samples (plasma, serum, and urine). 282 individual samples of kidney transplant patients, (FIG. 5A) 96 plasma and (FIG. 5B) 72 serum samples of eight individuals participating in a referencing study were processed using input volumes of 450 μl. Isolation of (FIG. 5C) urine samples sRNA was semi-automated, serum and plasma samples were processed using the automated protocol. Biofluid samples of each cohort were organized in batches of 24 samples (numbered bars). The final 17 samples of the urine cohort did not fill a batch and were hence added to batches of two other urine sample cohorts.

Log$_2$-transformed calibrator heatmaps of ten synthetic 5'P-, 3'OH spike-in RNAs absent in the human genome were added at to the denaturation buffer at the beginning of RNA isolation (calibrator set 1) and at the beginning of sRNA-based cDNA library generation (calibrator set 2) allow to detect low RNA recovery yields and/or damage by RNases by absence of the typical abundance pattern observed in other samples (e.g. batch 12).

Log$_2$-transformed heatmaps showing the combined most abundant 85% miRNAs across all samples. miRNA abundance data of each cohort was arranged by unsupervised clustering with pHeatmap of the bioconductor package using the Manhattan clustering method and complete clustering of miRNA annotations only, the sequence of samples across the Y-axis corresponds to the position of the sample during RNA isolation.

Figure 6:
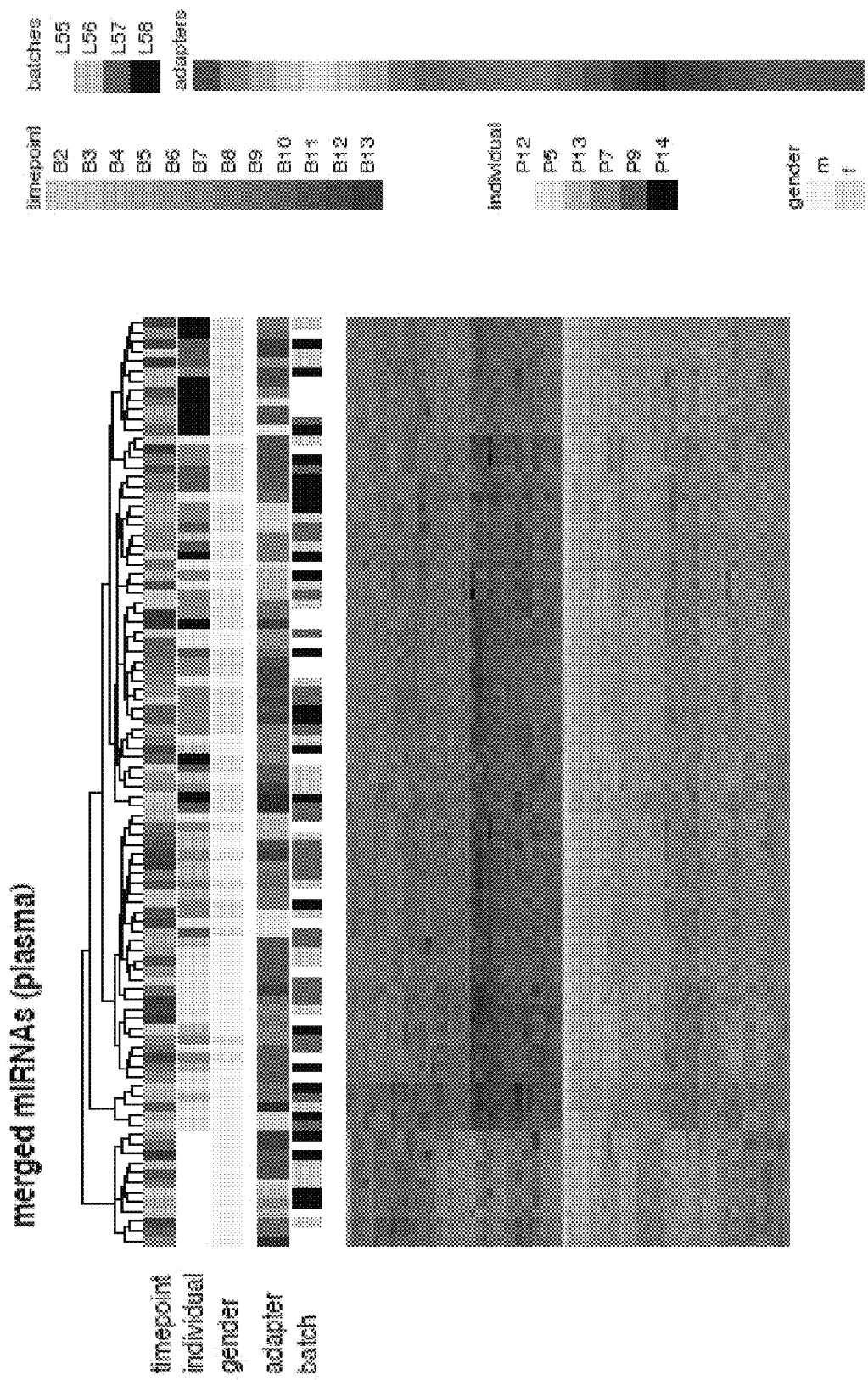
Figure 6:
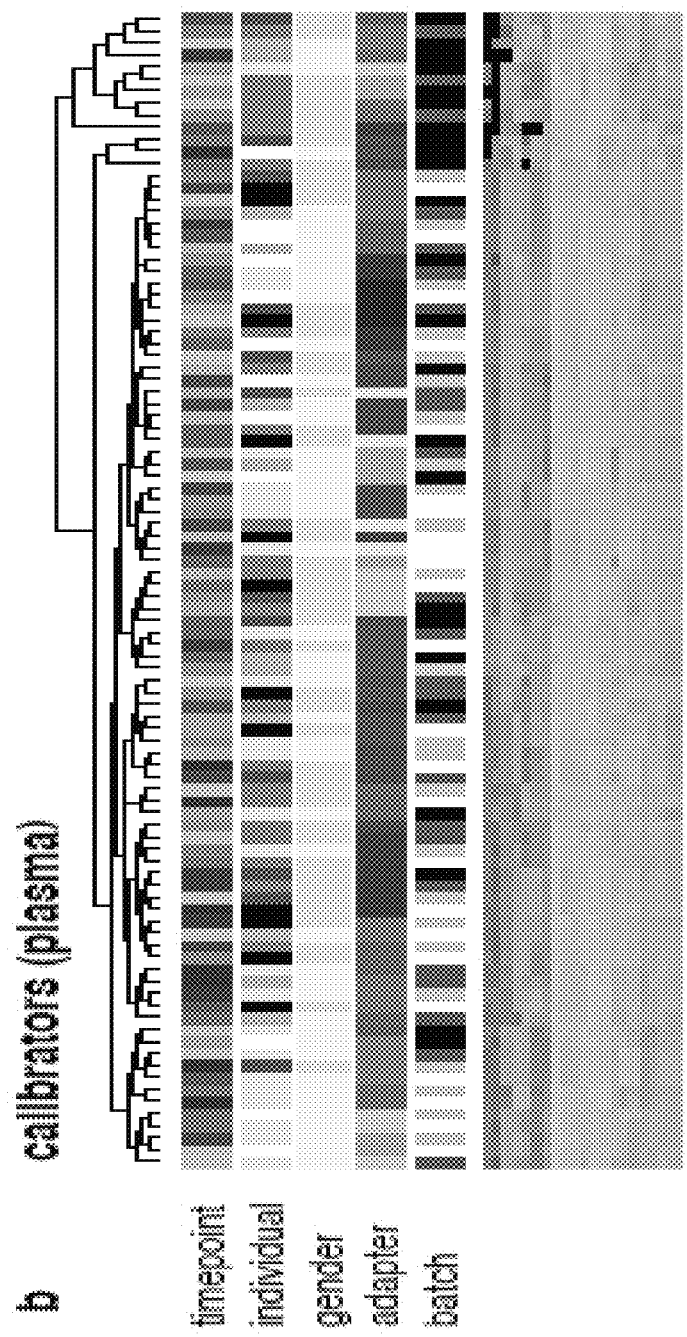

FIGS. 6A-6B depict unsupervised clustering of calibrators and miRNAs from 96 human plasma sample isolations helps to identify biological replicates of certain individuals. Sequencing data plasma samples from 8 individuals taken at 12 different timepoints over the course of two months (described in FIG. 5) was subjected to unsupervised clustering with pHeatmap of the bioconductor package using the Manhattan clustering method and complete clustering for both miRNA annotations and sample order. Sample annotation categories such as timepoints, individuals, gender, adapters used for barcoding and batches were included. (FIG. 6A) clustering of the combined sets 1 and 2 of calibrators. (FIG. 6B) most abundant 90% of miRNAs combined across all samples.

Figure 7:
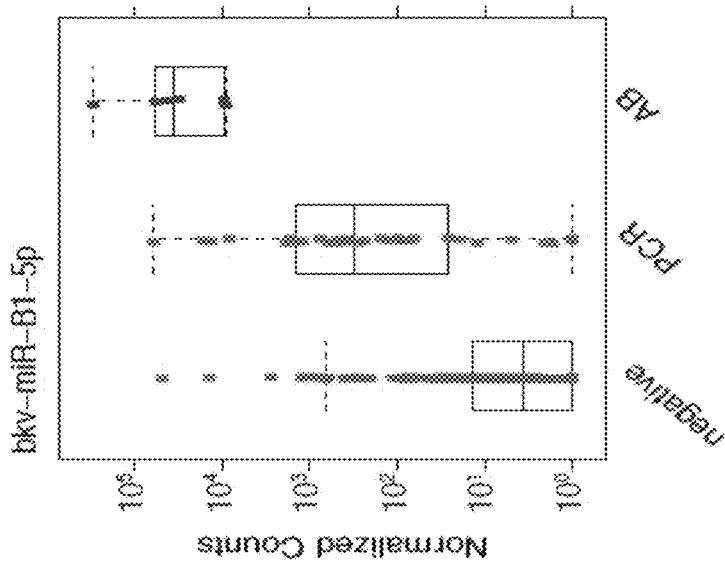
Figure 7:
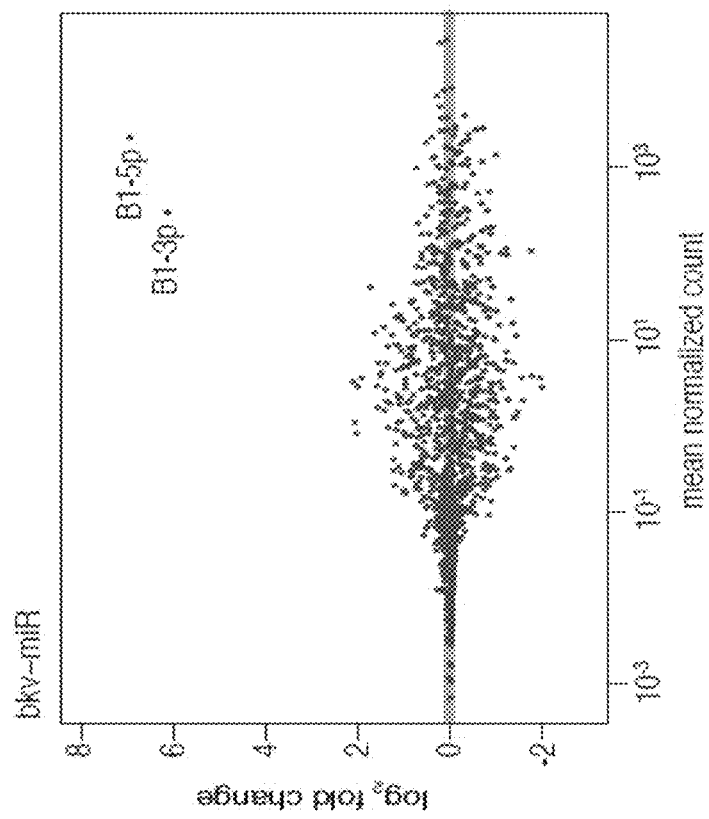
Figure 7:
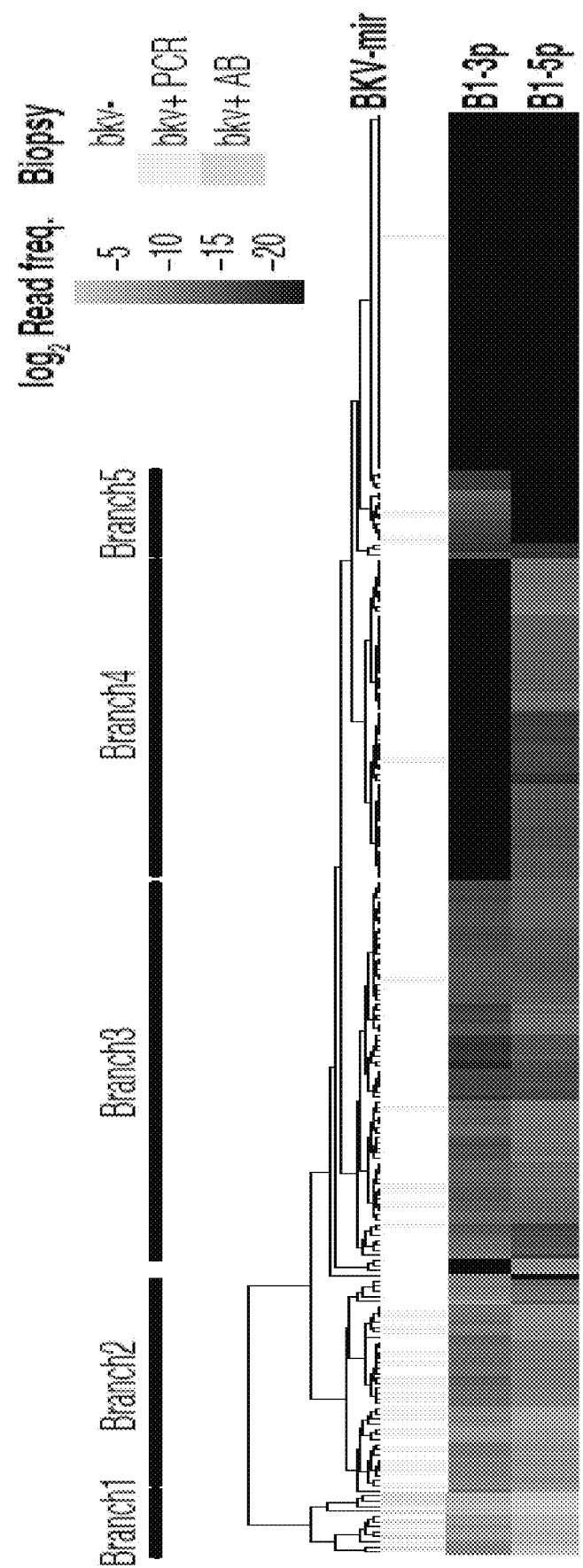

FIGS. 7A-7C depict identification of samples with high BK-virus activity. a) Differential expression analysis, comparing average abundance values of miRNAs and their fold-change comparing two populations of 282 samples, of which one population tested virus-positive by blood-based antibody test or rt-per-based assay of cells from urine, while the other population tested virus negative. Statistically significant fold changes are shown as red dots ($p_{adj}$<0.01). b) boxplots of bkv miRNA abundance in populations which tested bkv-positive by antibody test, bkv-positive by rt-per based assay, or bkv-negative. c) unsupervised clustering bkv miRNA in 282 urine samples using before-mentioned populations.

Figure 8:
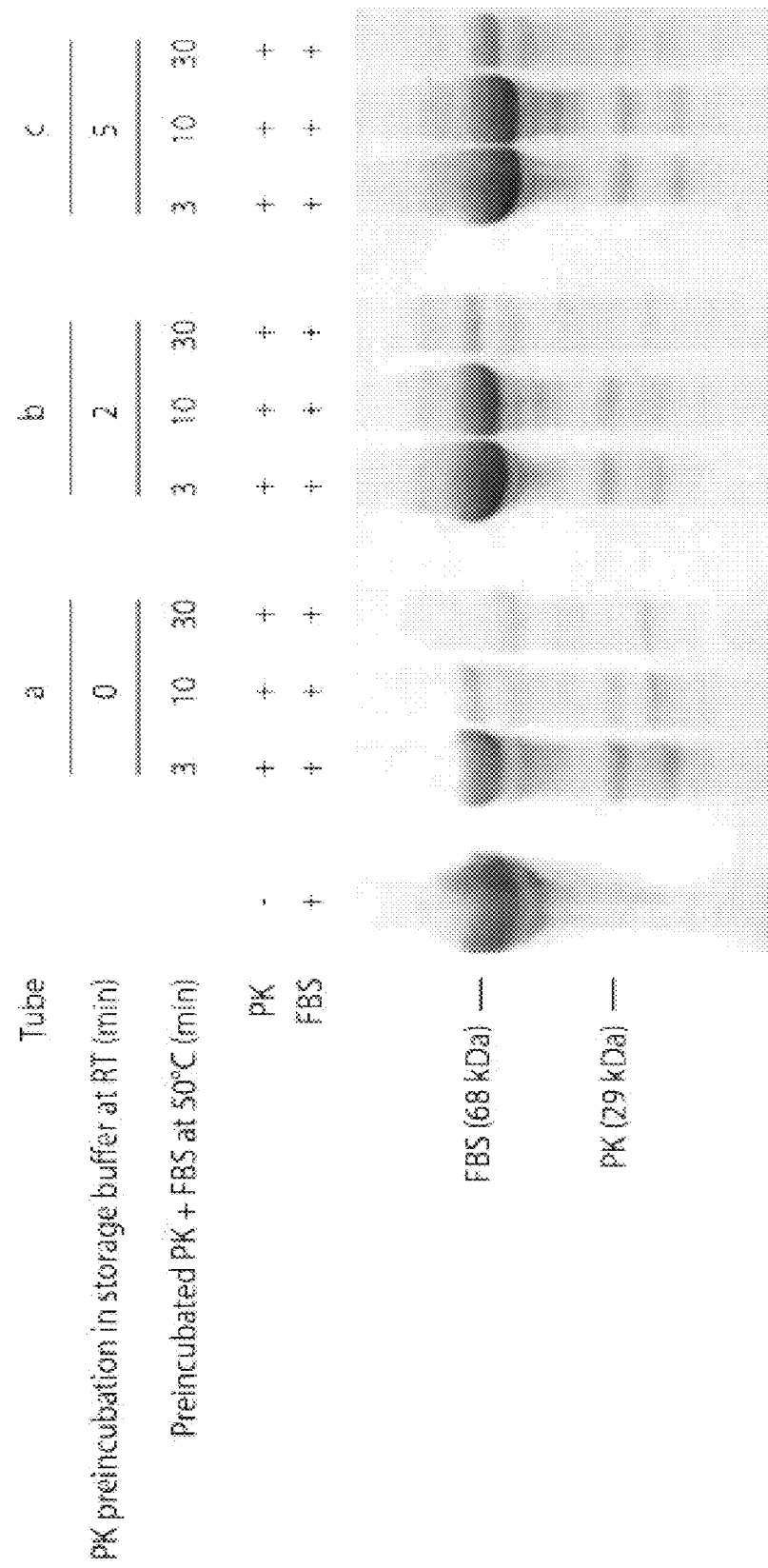

FIG. 8 depicts loss of PK activity following 0-5 min pre-incubation of PK stock solution at room temperature. For this assay, FBS was incubated for 3, 10 or 30 min with a PK stock solution (tube a, b, c). To evaluate appropriate storage conditions for PK stock solution, the proteolytic activity of PK was evaluated after pre-incubating PK stock solution at RT for 0 (tube a), 2 (tube b) and 5 (tube c) min.

Figure 9:
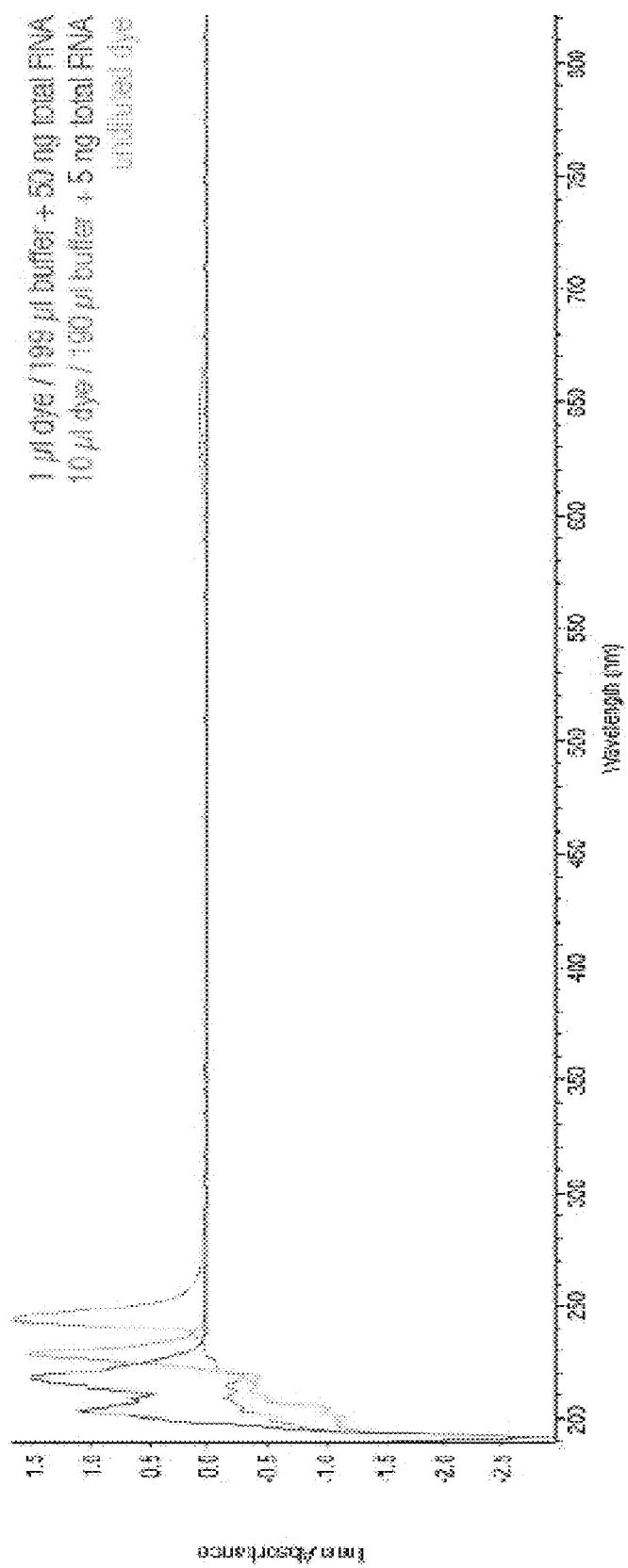

FIG. 9 depicts UV absorbance spectra for Qubit HS RNA dye diluted 1:20 and 1:200, (−) RNA.

Figure 10:
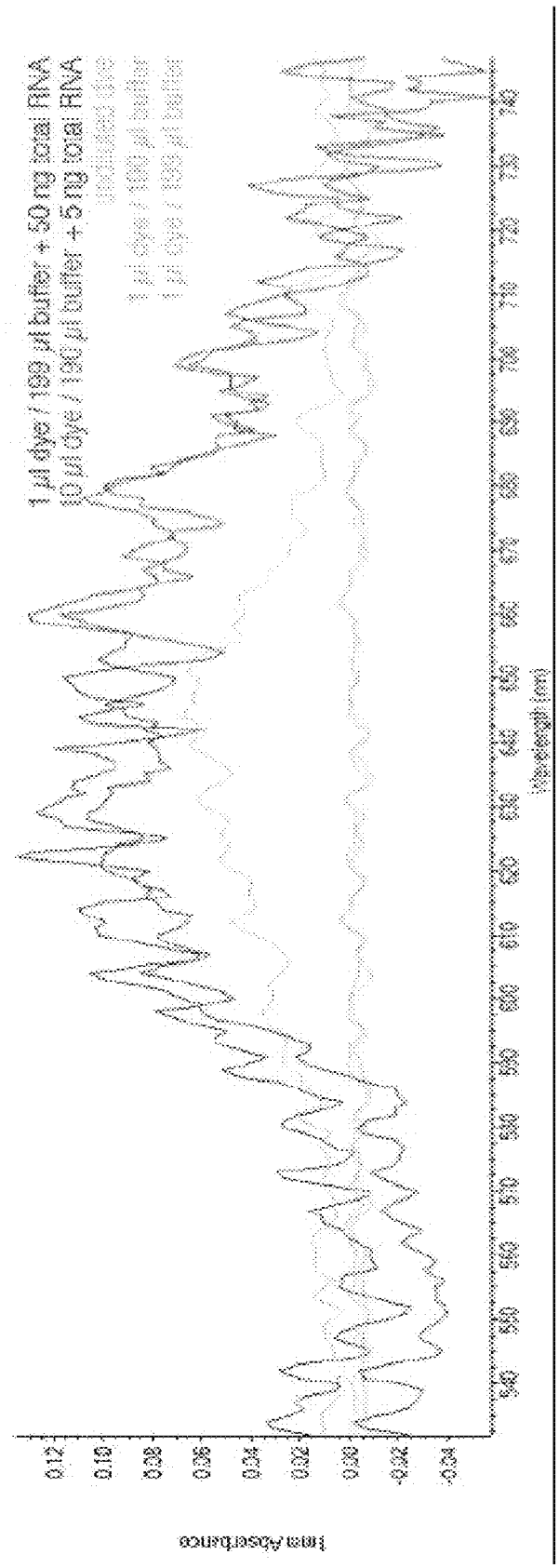

FIG. 10 depicts UV absorbance spectra for Qubit HS RNA dye (+/−) HEK293 total RNA dye diluted 1:20 and 1:200.

Figure 11:
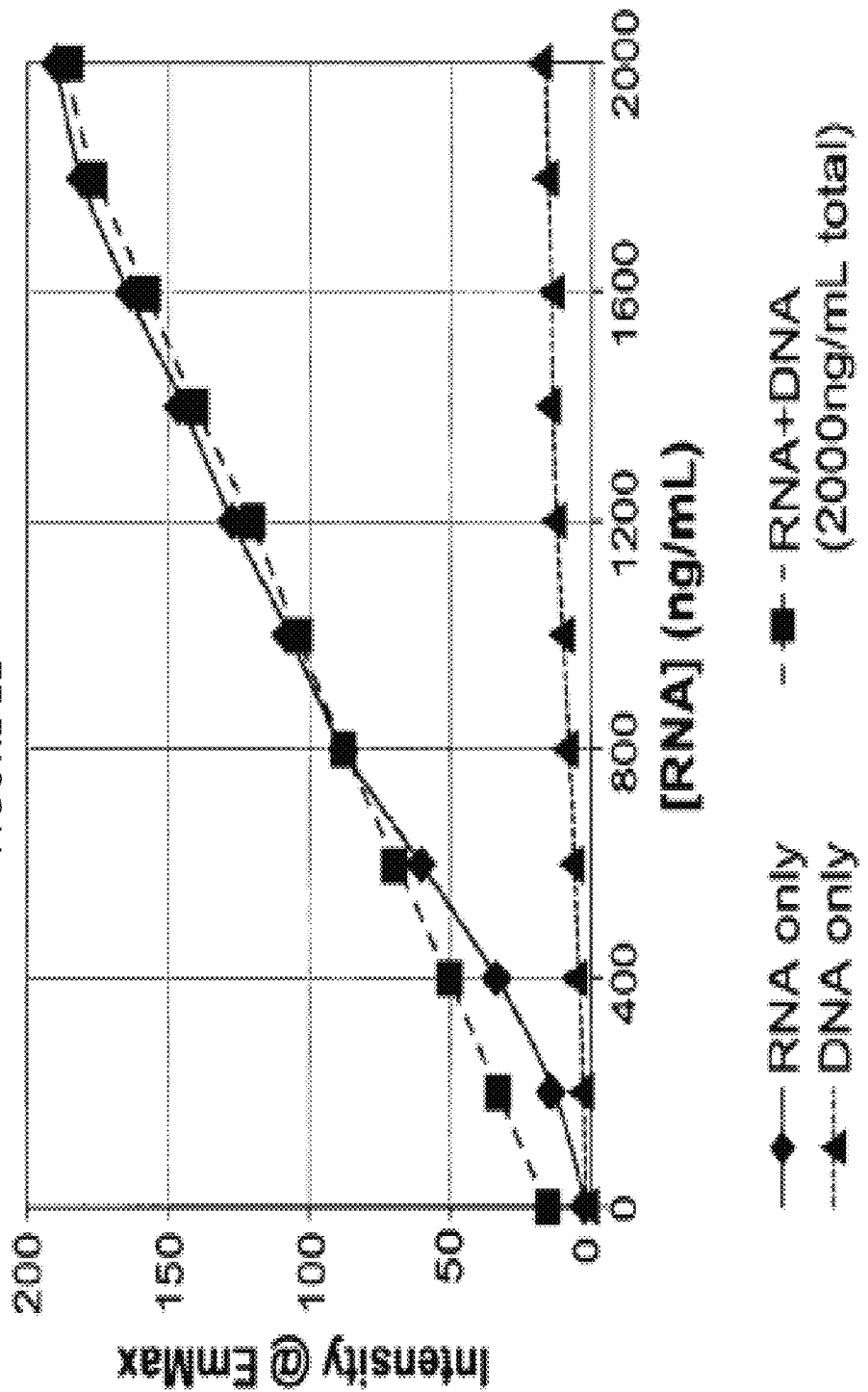

FIG. 11 depicts intensity of the fluorescent signal from Qubit HS RNA dye in the presence of rRNA, DNA and a mixture of RNA and DNA in solution.

Figure 12:
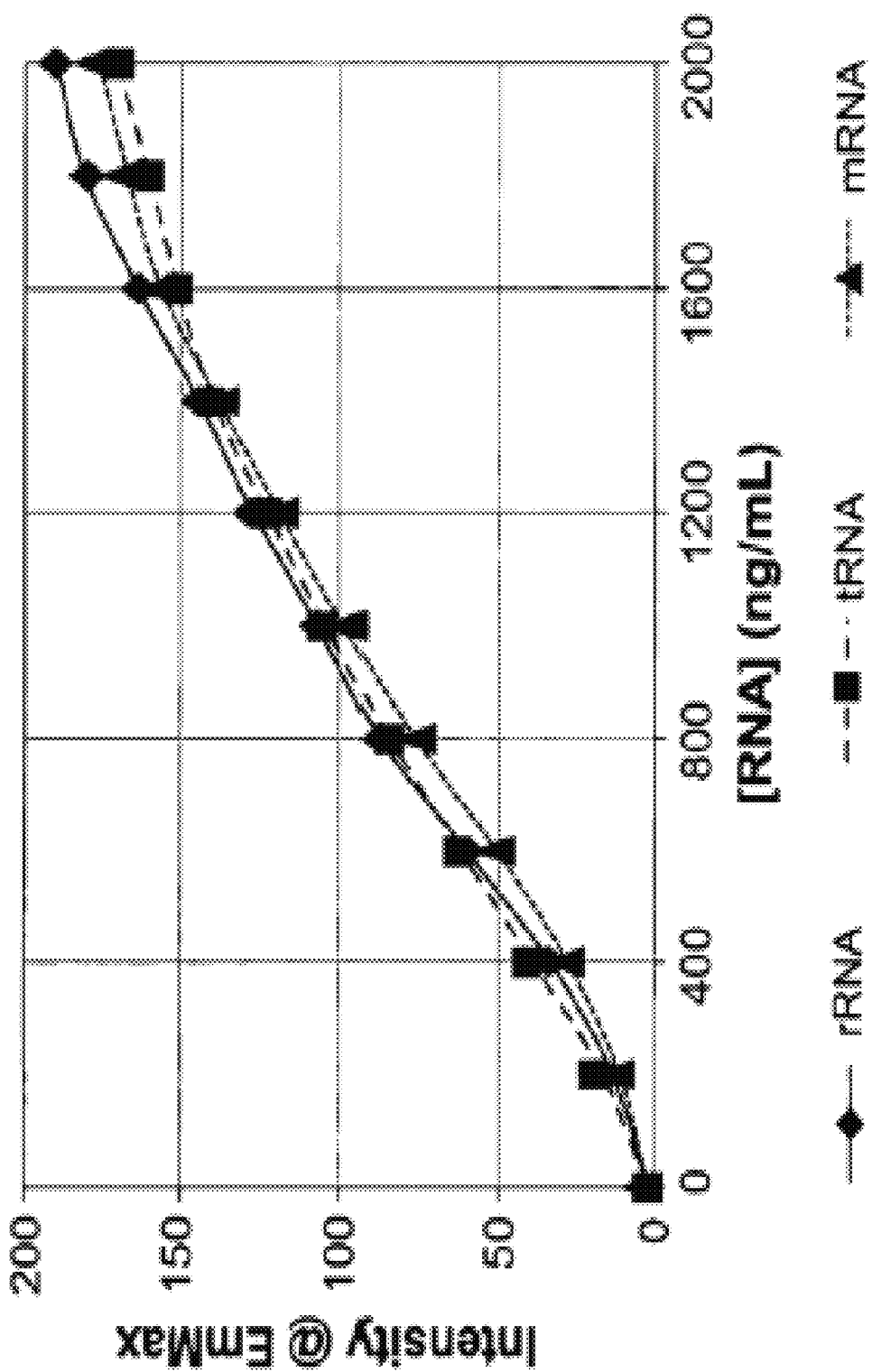

FIG. 12 depicts a plot showing the fluorescence intensity of Qubit HS RNA dye when associated with rRNA, tRNA and mRNA, respectively, in increasing concentrations of the RNA.

Figure 13:
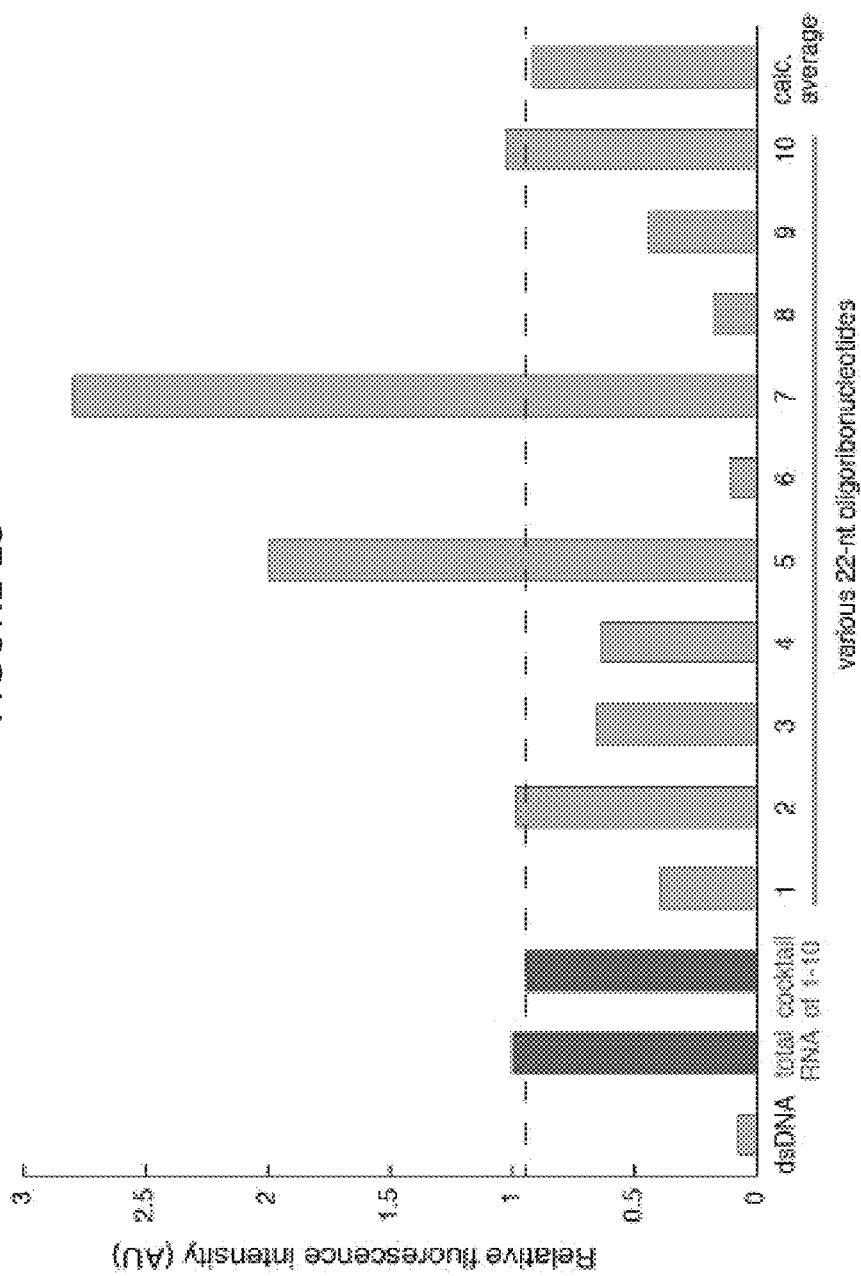

FIG. 13 depicts Qubit fluorophore is sensitive to RNA sequence and structure.

Figure 14:
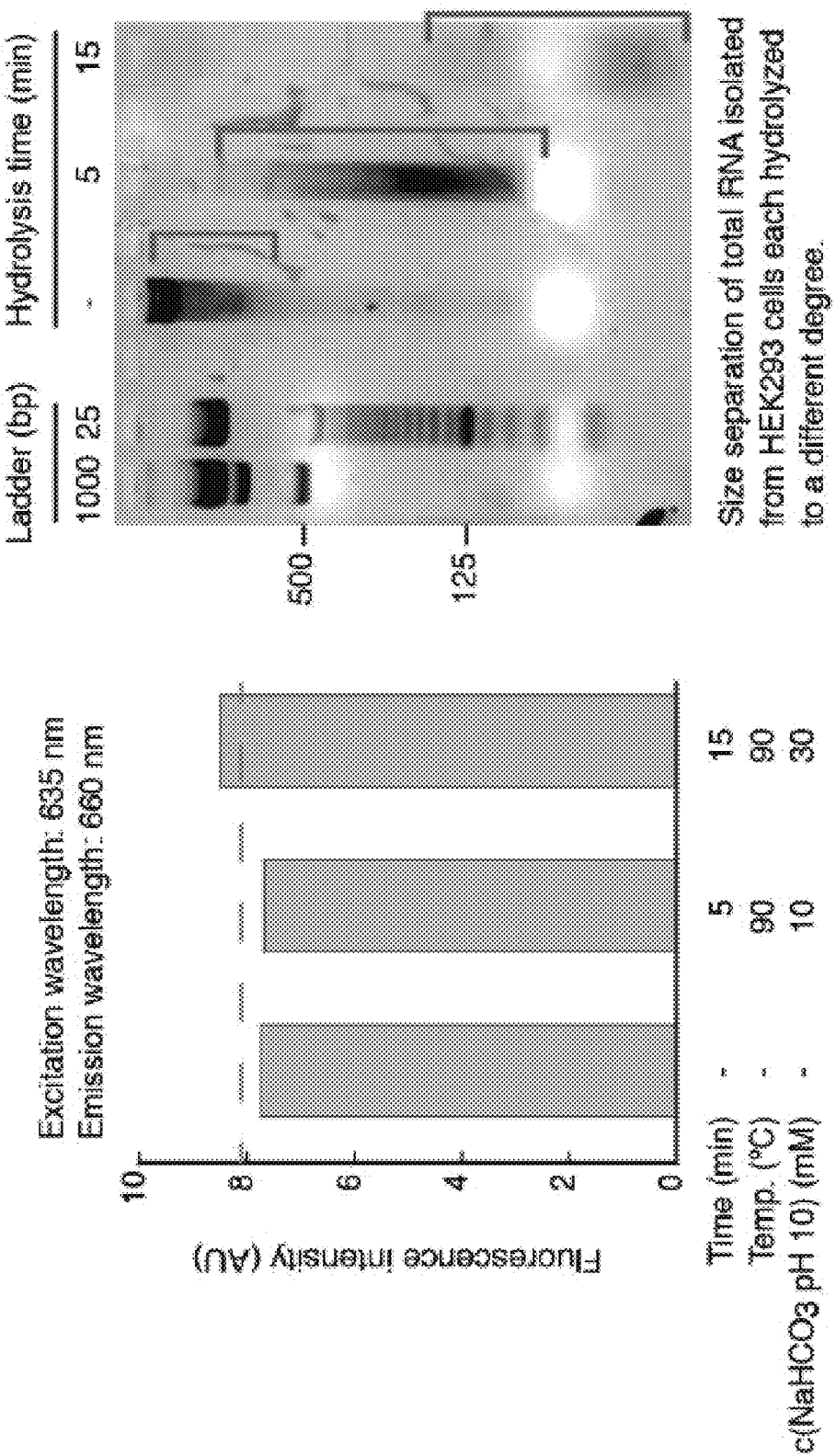

FIG. 14 depicts effect of total RNA length on Qubit HS RNA fluorescence assay.

Figure 15:
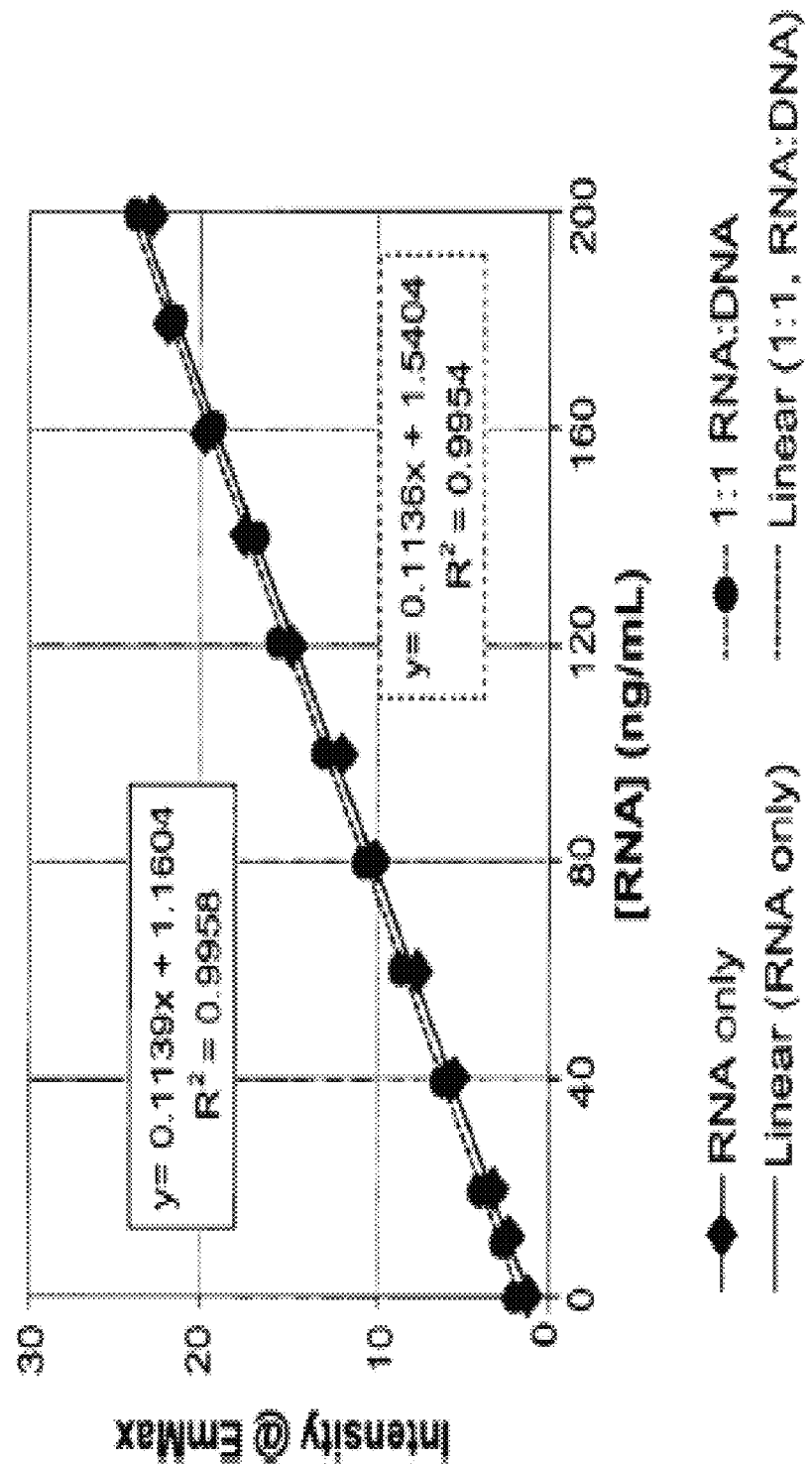

FIG. 15 depicts reported linear range for Qubit RNA HS assay measurements.

Figure 16:
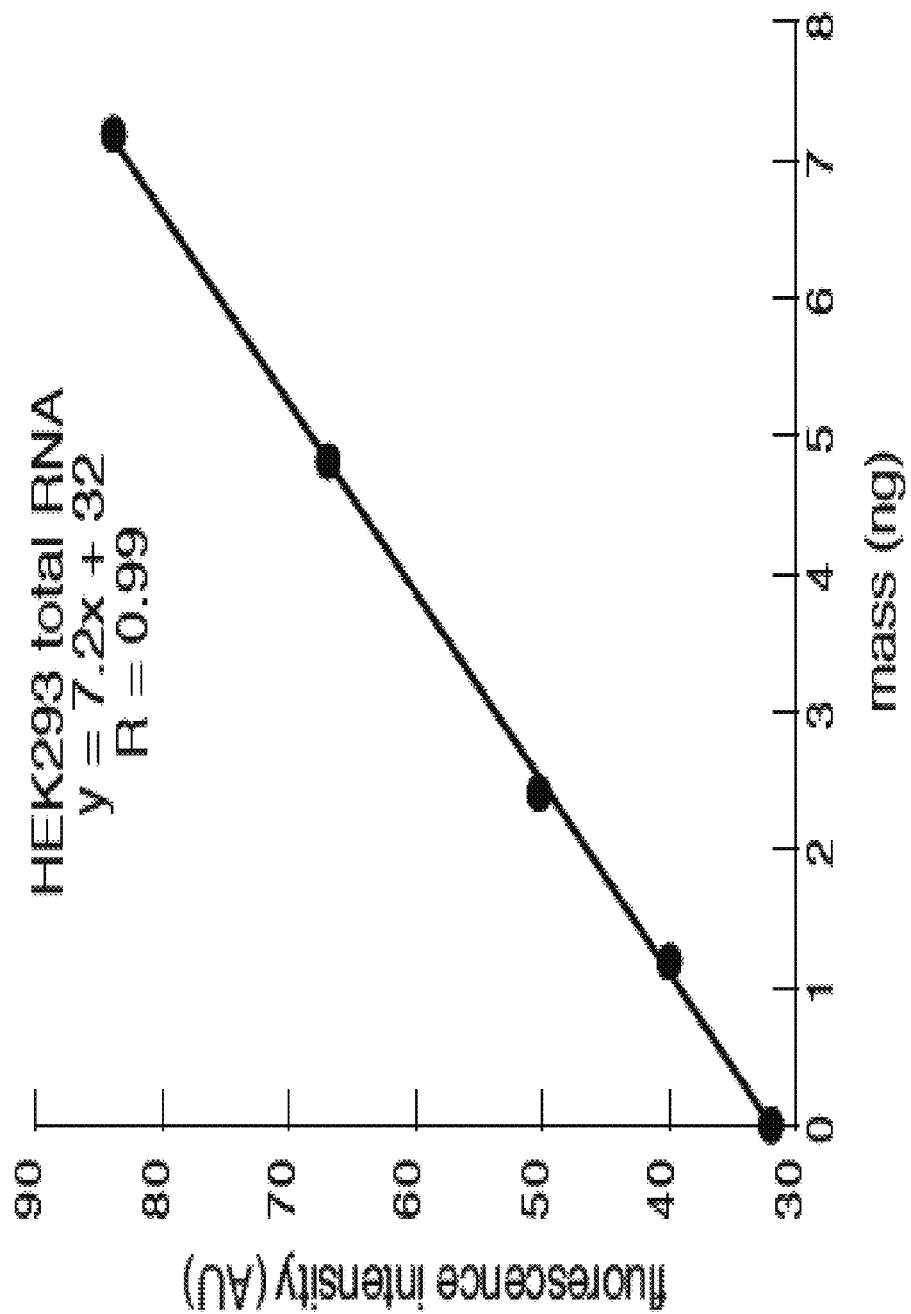

FIG. 16 depicts linear range of Qubit RNA HS Assay dye with HEK293 total RNA. The values on the x-axis correspond to mass of input RNA.

Figure 17:
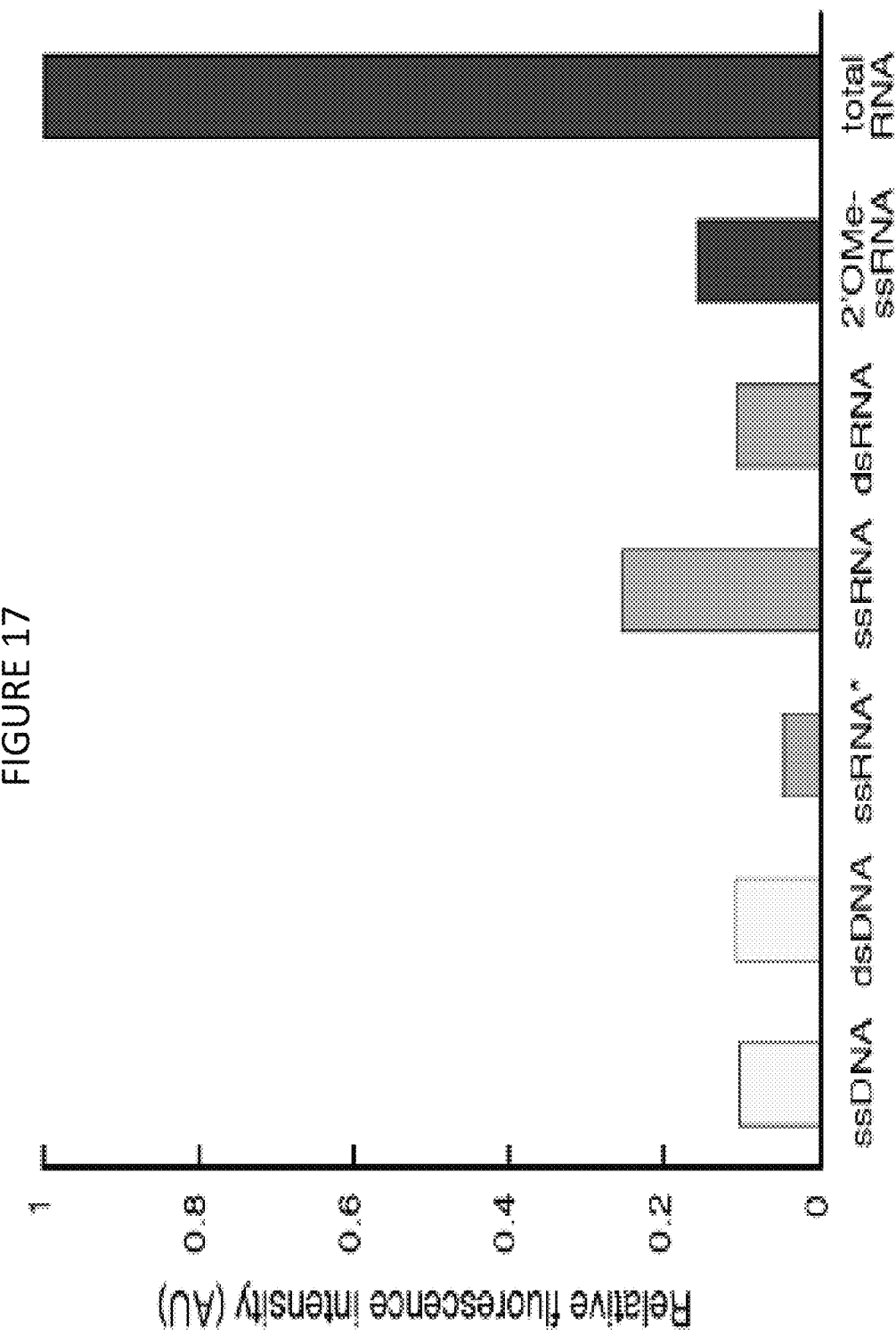

FIG. 17 depicts 2'-OMe-let-7a shows a similar fluorescence enhancement compared to all-ribo let-7a, and 10× lower fluorescence enhancement than total RNA.

Figure 18:
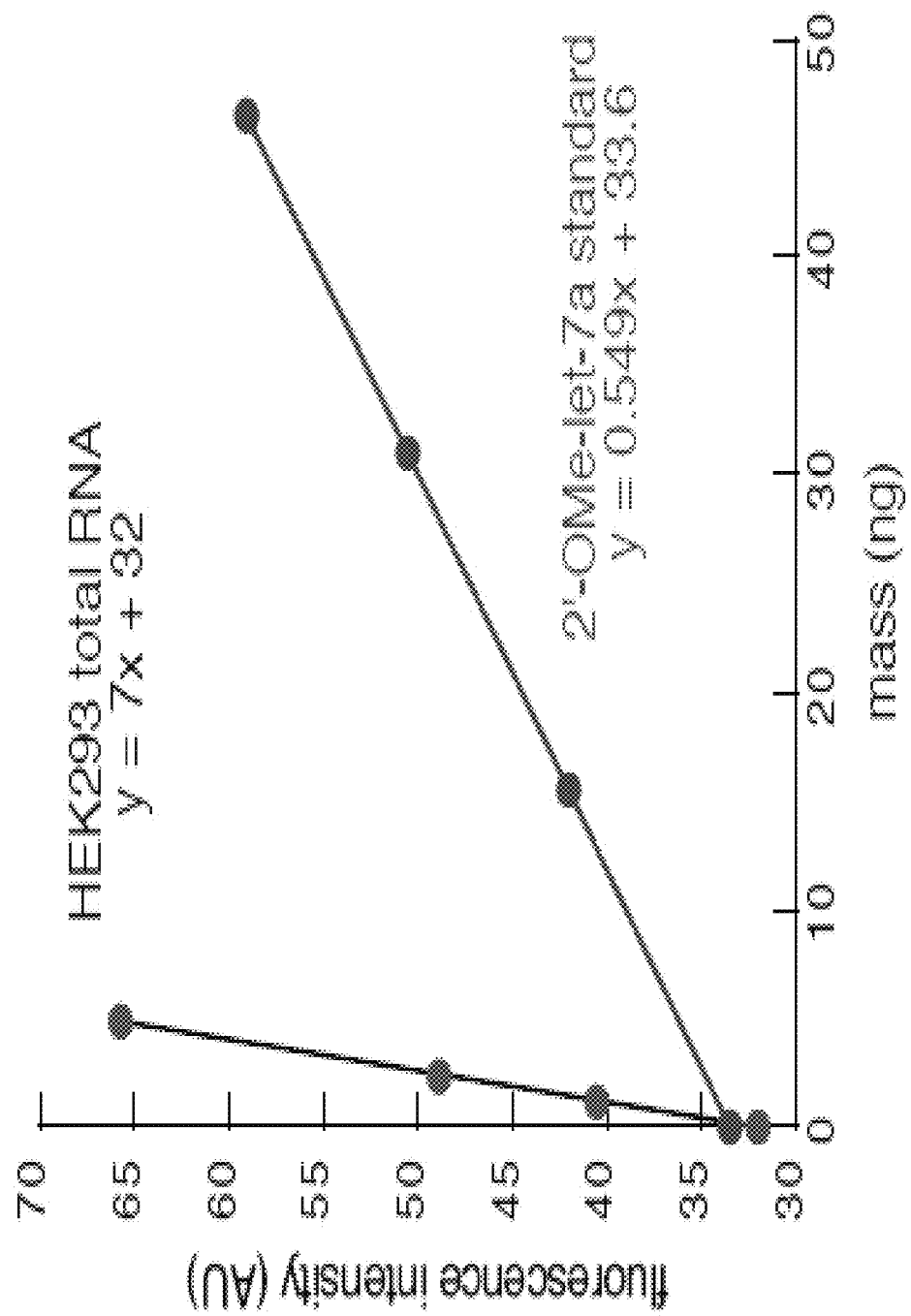

FIG. 18 depicts a dilution series of total RNA and 2'-OMe-let-7a standard show expected linearity. The ratio of the slopes can be used to calculate total RNA concentrations.

Figure 19:
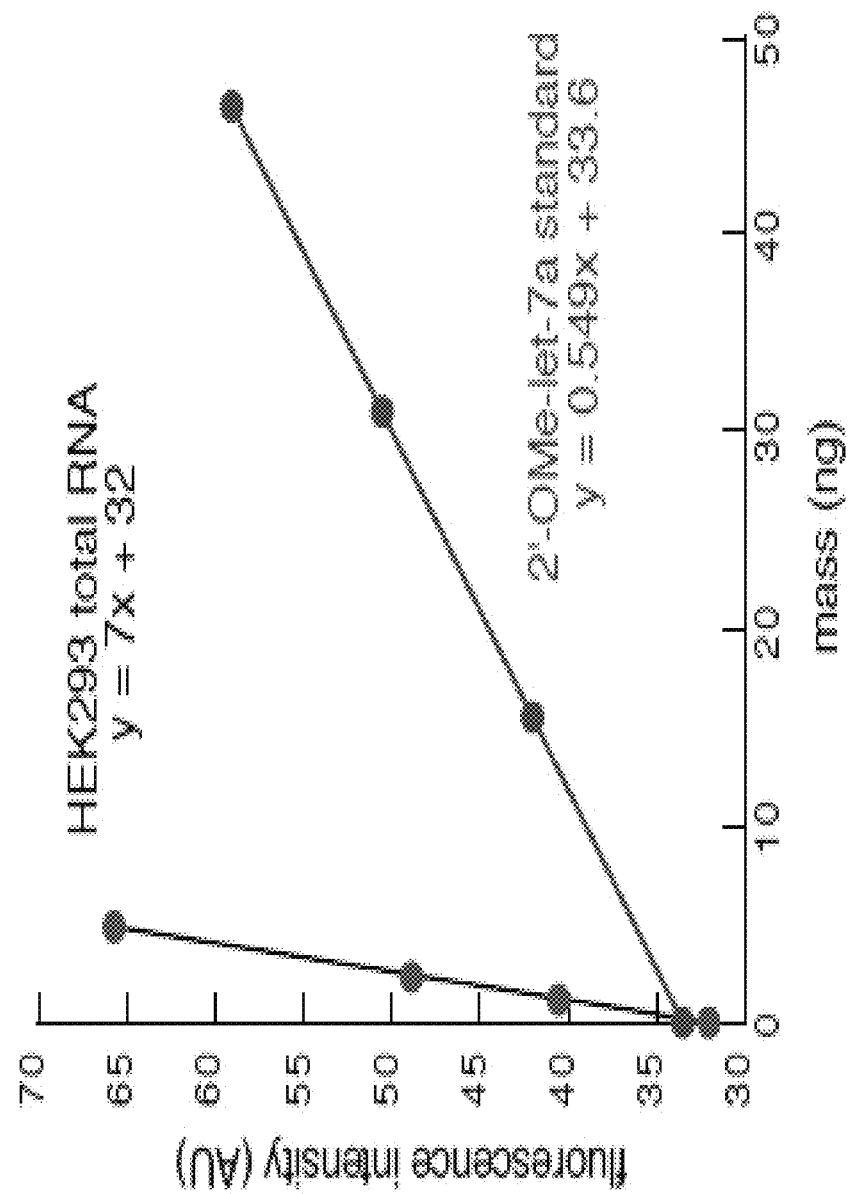

FIG. 19 depicts a dilution series of total RNA and the 2'-OMe-let-7a standard show expected linearity. The total RNA series yields standard curves with an average slope of 7, and the 2'-OMe-let-7a series yields an average slope of 0.55. The slopes differ by an average factor of 13. This ratio is used to determine total RNA concentrations. RNA sample concentrations can be calculated from the Qubit RFU units using the following equation:

$$c_{sample}(\text{ng}/\mu\text{l}) = \frac{RFU(\text{sample}) - RFU(\text{reagent blank})}{V(\mu\text{l}) \cdot 7/\text{ng}}$$

Figure 20:
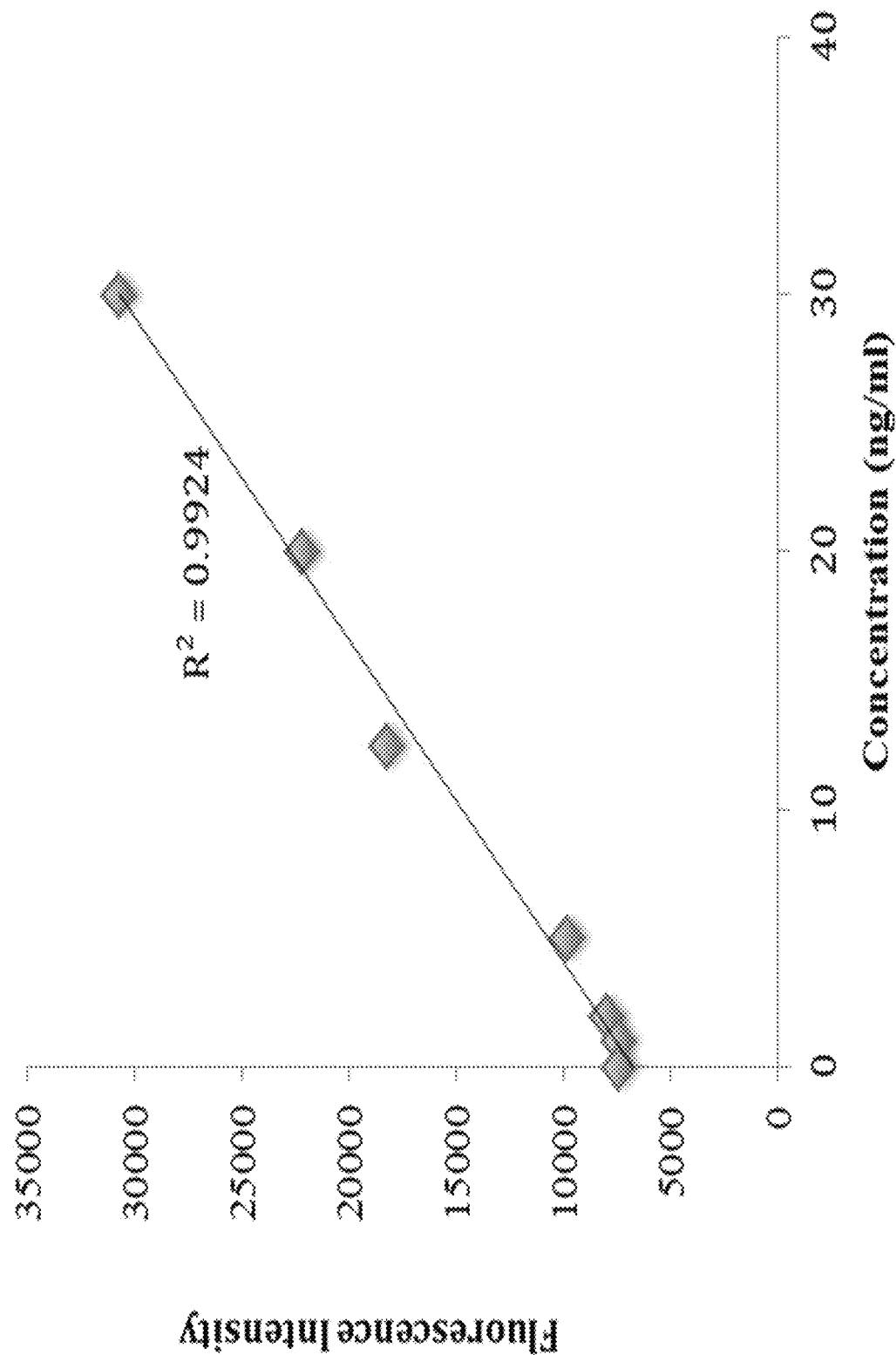

FIG. 20 depicts a representative standard curve used to calculate RNA concentration using the Quant-iT™ RiboGreen® RNA Reagent.

DETAILED DESCRIPTION

In one aspect, the disclosure provides a method for isolating RNA from a biological sample.

As used herein, "RNA" is defined as at least two ribonucleotides covalently linked together. The RNA may be any type of RNA.

Exemplary short RNAs include mRNA, tRNA, rRNA, shRNA, circRNA, scaRNA, scRNA, snRNA, siRNA or Piwi-interacting RNA, or a pri-miRNA, pre-miRNA, miRNA, snoRNA, long ncRNAs, anti-miRNA, precursors and any variants thereof. Further examples of RNA include RNA of a virus, or RNA sequences derived from a virus genome. Even further examples include RNA of a bacteria. In one embodiment, the RNA is a short RNA molecule derived from a degraded source, such as, for example, degraded mRNA, degraded rRNA, and degraded tRNA.

RNA may be single stranded or double stranded, or may contain portions of both double stranded and single stranded sequence. RNA may be synthesized as a single stranded molecule or expressed in a cell (in vitro or in vivo) using a synthetic gene. RNA may be obtained by chemical synthesis methods or by recombinant methods.

RNA also encompasses the complementary strand of a depicted single strand. Many variants of RNA may be used for the same purpose as a given RNA. Thus, RNA also encompasses substantially identical RNA and complements thereof. A single strand provides a probe that may hybridize to a target sequence under stringent hybridization conditions. Thus, RNA also encompasses a probe that hybridizes under stringent hybridization conditions.

In one embodiment, RNA is a short RNA. A "short" RNA refers to RNA that has a maximum number of bases in length of about 500, 400, 300, 200, 100, 90, 80, 70, 60, 50, 40, 35, 34, 33, 32, 31, 30, 29, 28, 27, 26, 25, 24, 23, 22, or 21 bases. The short RNA has a minimum number of bases in length of about 5, 6, 7, 8, 9, 10, 11, 12, 13, 14, 15, 16, 17, 18, 19, or 20 bases. Any minimum amount can be combined with any maximum amount to define a range for a short RNA.

In another embodiment, the RNA is between 5-500 nucleotides, 5-250 nucleotides, 5-100 nucleotides, or 5-50 nucleotides.

Exemplary short RNAs include mRNA, tRNA, rRNA, shRNA, circRNA, scaRNA, scRNA, snRNA, siRNA or Piwi-interacting RNA, or a pri-miRNA, pre-miRNA, miRNA, snoRNA, long ncRNAs, anti-miRNA, precursors and any variants thereof. Further examples of RNA include RNA of a virus, or RNA sequences derived from a virus genome. Even further examples include RNA of a bacteria or In one embodiment, the RNA is a short RNA molecule derived from a degraded source, such as, for example, degraded mRNA, degraded rRNA, and degraded tRNA.

In a preferred embodiment, the RNA acid is microRNA (miRNA). MicroRNA molecules are known in the art (see, for example, Bartel, *Cell*, 2004, 116, 281-297 for a review on microRNA molecules). The definitions and characterizations of microRNA molecules in the article by Bartel are hereby incorporated by reference. Such molecules are derived from genomic loci and are produced from specific microRNA genes.

miRNAs are typically small RNA molecules of generally about 13-33, 18-24, or 21-23 nucleotides in length. The miRNA may also have a total of at about 5-40 nucleotides in length. These microRNAs are non-coding RNAs which are cleaved from hairpin precursors. miRNAs are naturally 5' phosphorylated and carry 2', 3' dihydroxyl termini. The sequence of the miRNA may comprise the sequence of a miRNA disclosed in U.S. patent application Ser. Nos. 11/384,049, 11/418,870 or 11/429,720, the contents of which are incorporated herein, or variants thereof.

A source of the short target RNA is a biological sample. A "biological sample" as used herein refers to a sample of "biological tissue or solid" or "biological fluid" that includes nucleic acids. Such samples include, but are not limited to, tissue or fluid isolated from animals or plants, including plant or animal derived cell suspensions, and cell free extracts of animal or plant origin. Biological samples also include viruses or unicellular organisms.

It has been contemplated that the biological sample may contain bacteria, virus, amoeba, or fungus.

Furthermore, the biological sample may include bacterial, fungal, or human cell cultures.

Examples of biological tissue include sections of tissues such as biopsy and autopsy samples, frozen sections taken for histologic purposes, asbcess material, hair, and skin. Examples of tissue include tissue from the brain, muscle, heart, fat, pancreas, lung, spleen, and bone.

In a preferred embodiment, the biological sample is a biological fluid. Examples of biological fluids include blood, a blood fraction, plasma, serum, urine, pleural effusion, pericardial effusion, synovial fluid, mucus, ascitic fluid, amniotic fluid, stool, tears, saliva, cerebrospinal fluid, cervical secretions, vaginal secretions, abscess discharge, puss, endometrial secretions, gastrointestinal secretions, bronchial secretions, sputum, secretions from ovarian cyst, sperm, seminal fluid, secretions from the breast, cell line. In a preferred embodiment, the biological samples include urine, serum, and plasma.

In another embodiment, the plasma sample includes citrate-, EDTA-, and heparin-plasma samples.

"Biological fluids" as defined herein also include a biological tissue or solid that has been physically or chemically disrupted, e.g. by maceration or homogenation, as is known in the art, to form a liquid sample.

When the biological sample is a tissue or in solid form, or viscous, the biological sample can also be homogenized or disrupted to maximize contact between the extraction solvent and the biological sample. Methods to homogenize tissue are commonly known in the art. Such methods include chemical or mechanical means. Mechanical means include grinding, shearing, freeze-thaw, beating, shocking, sonicating, or a combination thereof. For example, grinding techniques can be accomplished through manual means such as a mortar and pestle. Automated methods for disrupting tissue can be used as well to lyse cells, and are commonly known in the art. Examples of automated homogenizers include HT Homogenizer from OPS Diagnostics, the Homogenizer from Invitrogen, or Stomacher paddle mixer from Seward Laboratory Systems.

Any remaining insoluble materials can be cleared by any known means. For example, the homogenized material can be centrifuged and the supernatant is used.

A biological sample may be provided by removing a sample of cells from an animal, or plant, but can also be accomplished by using previously isolated cells (e.g., isolated by another person, at another time, and/or for another purpose), or by performing the methods described herein in vivo. "Animal" as used herein refers to any animal, including fish, amphibians, reptiles, birds, and mammals, such as mice, rats, rabbits, goats, cats, dogs, cows, apes, and humans.

The method includes contacting the biological sample with a denaturing solution to form a biological fluid mixture.

The denaturing solution includes at least one of a detergent and reducing agent.

A "detergent" as defined herein is any substance that reduces the surface tension of water, and is used synonymously with the term "surfactant". Examples of detergents suitable for the claimed invention include anionic, nonionic, and zwitterionic detergents. In our specific application, detergents are used which disrupt the tertiary structure of most proteins including ribonucleases and thereby inactivate their function.

Preferred anionic detergents include sulfates of $C_6$-$C_{20}$ alkylalcohols and N—$C_6$-$C_{20}$-acylaminoacids. Examples of anionic detergents include sodium dodecyl sulfate (SDS), sodium lauryl sarcosin(sarcosyl), and sodium deoxycholate. The preferred detergent from this group includes SDS and sarcosyl.

Preferred non-ionic detergents include polymers of poly-($C_2$-$C_6$)-alkoxy-($C_2$-$C_6$)-alkylenes, esters and ethers of poly-($C_2$-$C_6$)-alkyleneglycols and glycosides of $C_6$-$C_{20}$ alkylalcohols. Specifically preferred non-ionic detergents include Synperonic (block copolymer made from poloxyethylene and polyethoxypropylene, Pharmacia), Tween 20 (polyethylene glycol (20) sorbitan monolaurate), Thesit™ (dodecylpolyethylene glycol ether), NP-40 (ethylenephenol-polyethyleneglycolether), TritonX-100 (polyethylene glycol (9-10) p-t-oktylphenol) and glycosidic detergents, e.g. octyl: β-D-glucopyranoside.

Preferred zwitterionic detergents are N—$C_1$-$C_{16}$-alkyl-ammonio-$C_2$-$C_6$-alkyl-sulfonates. Examples of zwitterionic detergents include Zwittergent 3-08 (N-octyl-N,N-dimethyl-3-amino-1-propane sulfonate) Zwittergent 3-12 (N-docecanyl-N,N-dimethyl-3-ammonio-1-propane sulfonate), CHAPS (3-[(3-cholamidopropyl)-dimethyl-ammonio]-1-propane sulfonate) and CHAPSO (3-cholamidopropyl)-di-methylamino]-2-hydroxy-1-propane sulfonate).

In one embodiment, the denaturing solution includes detergent at a concentration of about 10-70% (w/v), more preferably from 20-50% (w/v). The concentration of detergent in the biological fluid mixture is 1-10% (w/v), more preferably 5-8% (w/v). The detergent may have a concentration of at least about 1%, at least about 4%, at least about 10%, or at least about 15% (w/v). In another preferred embodiment, the detergent in the denaturing solution is SDS and is present at a concentration of at least about 5% (w/v). In a preferred embodiment, the detergent in the mixture is SDS and is present at a concentration of at least about 4% (w/v). In another preferred embodiment, the detergent in the denaturing solution is SDS and is present at a concentration of at least about 3% (w/v). In another preferred embodiment, the detergent in the denaturing solution is SDS and is present at a concentration of at least about 2% (w/v).

A "reducing agent" as defined herein is an element or compound that loses (or "donates") an electron to another chemical species in a redox chemical reaction. Examples of reducing agents suitable for the claimed invention include dithiothreitol (DTT), 2-Mercaptoethanol (BME), and tris(2-carboxyethyl)phosphine (TCEP). In some embodiments, the preferred reducing agent is TCEP.

The denaturing solution may also include a buffer. As used herein, buffers suitable for the claimed invention include biological buffers. Examples of biological buffers include TRIS, MPOS, MES, HEPES, citrate, and phosphate buffer.

The denaturing solution may contain other additives, to include ethylenediaminetetraacetic acid (EDTA), ethylene glycol tetraacetic acid (EGTA), and metal salts. As defined herein, "metal salts" include NaCl, KCl, $CaCl_2$, and $MgCl_2$.

In one embodiment, the denaturing solution contains SDS, TRIS, and EDTA. In a preferred embodiment, the denaturing solution contains from about 20-40% SDS, 10-100 mM TRIS buffer, 10-50 mM EDTA, and 100-500 mM BME.

In a preferred embodiment, the concentration of BME in the mixture of biological fluid mixture is about 1-100 mM. In a preferred embodiment, the concentration of BME in the mixture is 25-75 mM.

The denaturing solution may contain a visualization agent to monitor the mixing/agitation and phase extraction steps. The visualization agent allows visual inspection of the homogeneity of the aqueous phase. The visualization agent allows visual inspection of phase separation because the visualization agent partitions into the organic phase leaving an uncolored aqueous phase. Examples of a visualization agent include methylene blue.

Once the biological sample has been contacted with the denaturing solution, a protease is added to the resulting mixture. Contact with the protease creates a protease treated biological fluid mixture.

A "protease" as defined herein is an enzyme that hydrolyses peptide bonds. Conventional proteases may be used. It has been unexpectedly discovered that a protease will still be functional with such components being present in the mixture of the biological sample, protease, and denaturing solution in the conditions as set forth herein. Such conditions are not tolerated by, for example, RNases. Proteinase K is a preferred example.

It is preferred that the specific activity of the protease be high to degrade proteins in what can be a protein-rich biological sample and thereby protect the RNA from ribonucleases. The specific activity as determined by the Chromozym assay of the protease in the mixture of biological sample and denaturing solution is for example at least about 0.1 U/ml, at least about 1 U/ml, at least about 2.5 U/ml, at least about 5 U/ml, or at least about 10 U/ml. In another embodiment, the specific activity of the protease in the mixture is between 0.1 and 1000 U/ml.

In one embodiment, the denaturing solution is heated to at least about 45° C., at least about 50° C., at least about 55° C., or at least about 60° C. prior to contact with the biological sample. In some embodiments, the denaturing solution is heated to at least about 65° C. prior to contact with the biological sample. Upon addition of the biological sample to the denaturing solution, the mixture is further incubated at a temperature at least about 45° C., at least about 50° C., at least about 55° C., or at least about 60° C. In another embodiment, the mixture is incubated for at least about 2 minutes, at least about 5 minutes, at least about 10 minutes, or at least about 15 minutes.

The incubation step may be performed while agitating the mixture. Agitation is defined as any condition that causes turbulence or shearing within the mixture. Examples of agitation include pipetting, shaking, rocking, vibrating, or stirring.

The method further includes contacting the biological sample with an organic extraction solution to form an aqueous phase and an organic phase. The organic extraction solution includes at least one of phenol, chaotropic agent, phase separation inducing agent, and detergent.

A "chaotropic agent" as defined herein is a substance which disrupts the three dimensional structure in macromolecules such as proteins, DNA, or RNA and denatures them. Examples of suitable chaotropic agents for use in the claimed invention include: sodium perchlorate, sodium trichloroacetate, sodium triflouroacetate, sodium iodide, urea, and guanidine. In one embodiment the chaotropic agent is guanidine, in the form of guanidinium thiocyanate (GITC) or guanidinium hydrochloride (GuHCl).

As used herein, phase separation inducing agents are agents that promote or induce the formation of an organic phase. Such phase separation inducing agents are known in the art. Examples of such agents include chloroform, or dichloromethane. In a preferred embodiment, the phase separation inducing agent is chloroform.

In the alternative, if phase inversion is desired (top: organic phase, bottom aqueous phase), heptanol or other heavier alcohols (e.g. alcohols having 6 or more carbons). Examples of other suitable alcohols include hexanol, octanol, nonanol, and decanol.

In one embodiment, the organic extraction solution contains a chaotropic agent at a concentration of less than about 10 M, less than about 5M, or less than about 3M. In another embodiment, the chaotropic agent has a concentration between 1M and 10M, more preferably between 1M and 5M.

In one embodiment, the mixture obtained after contacting the biological sample with the organic extraction solution contains a chaotropic agent at a concentration of less than about 3M, less than about 2M, or less than about 1M. In a preferred embodiment, the chaotropic agent has a concentration between 0.5-3M.

It has been unexpectedly discovered that by lowering the overall chaotropic agent concentration to less than 2 M, in some embodiments less than 3 M, it was possible to deplete virtually all DNA from the aqueous phase while simultaneously retaining desired RNA. In particular, it is possible to deplete virtually all DNA in at least the size range of 30 bases to 2000 bases from the aqueous phase while simultaneously retaining the desired RNA It has been further unexpectedly discovered that, due to the efficient denaturing step as described above, the ratio of aqueous to organic phase in the organic extraction solution can be reduced. For example, the chaotropic agent concentration as described above, in combination with a mixing ratio of organic phase: aqueous phase can be less than 2 to 1, less than 1 to 1, or less than 0.75 to 1 (the phase separation inducing agent is between 0.1 to 0.5 volumes, more preferably between 0.3 and 0.5 volumes with regard to the organic phase). In another embodiment, the mixing ratio is 0.45-2.5 to 1, more preferably from 1-2 to 1. Commercially available products utilize ratios of 3:1 and 4:1, or even higher.

As defined herein, DNA includes genomic DNA, cDNA, or a hybrid wherein the DNA may contain combinations of deoxyribo- and ribo-nucleotides, and combinations of bases including uracil, adenine, thymine, cytosine, guanine, inosine, xanthine hypoxanthine, isocytosine and isoguanine. Further examples of DNA include DNA of a virus, or DNA sequences derived from a virus genome. In one embodiment, the DNA is a short DNA molecule derived from a degraded source, such as, for example degraded DNA. DNA may be single stranded or double stranded, or may contain portions of both double stranded and single stranded sequence. DNA may be synthesized as a single stranded molecule or expressed in a cell (in vitro or in vivo) using a synthetic gene. DNA may be obtained by chemical synthesis or synthesis methods or by recombinant methods.

In one embodiment, the biological sample is further contacted with phase separation inducing agent after contact with the organic extraction solution.

In another embodiment, the organic extraction solution contains isoamyl alcohol.

Phase separation may also include methods of physical separation, such as centrifugation. Such methods are well known in the art. Traditional methods of RNA isolation result in interphase formation between the aqueous and organic phases. The interphase is a separate layer between the aqueous phase and organic phase and often appears white and often includes proteinaceous material. The interphase can interfere with isolation of the aqueous phase. The inventors have unexpectedly discovered that the addition of protease to a mixture of a biological sample and the denaturing solution as described above prior to the organic extraction step as described herein permits the reduction of the ratio of organic to aqueous phase during the organic extraction step as described herein as well as removes or significantly reduces interphase formation. Thus, less organic solvent may be used.

In addition, the denaturing and protease treatment steps allow less force to be required to separate the aqueous and organic phases, for example centrifugation under lower relative centrifugal forces (RCF). Without wishing to be bound by theory, the biological sample may be protein-rich and have hydrophobic and hydrophilic groups (amino acids). Upon denaturation, proteins unfold and interact with both hydrophobic (organic) and hydrophilic (aqueous) phases, thereby acting as emulsifiers. The interphase is considered to be an emulsion containing both hydrophobic as well as hydrophilic properties. One way of overcoming the formation of an emulsion is to degrade proteins into peptides. Depending on their hydrophobicity these peptides will either partition into the organic phase or aqueous phase and will no longer act as emulsifiers and interphase formation is reduced. As a consequence, the centrifugation force needed to achieve phase separation is reduced, and the amount of aqueous phase, which contains the desired RNA, is maximized.

The aqueous phase is contacted with a nucleic acid binding solution. The nucleic acid binding solution contains at least one of an alcohol and reducing agent. In some embodiments, the aqueous phase is contacted with a nucleic acid binding solution containing at least one of an alcohol, at least one salt, a chaotropic agent, and a reducing agent.

In some embodiments, the concentration of the reducing agent in the nucleic acid binding solution is at least 0.05 mM, at least 0.5 mM, or at least 1 mM. In another embodiment, the concentration of the reducing agent in the solution is less than 100 mM, less than 50 mM, less than 25 mM, or less than 10 mM. In some embodiments, the reducing agent has a concentration between 1-10 mM, or 3-8 mM.

The alcohol has a concentration of at least about 70%, at least about 80%, at least about 90%, at least about 95%, or at least about 99% (v/v). As used herein, alcohols include, for example, methanol, ethanol, propanol, butanol, and mixtures thereof.

The nucleic acid binding solution may contain other additives, to include ethylenediaminetetraacetic acid (EDTA), ethylene glycol tetraacetic acid (EGTA), and metal salts. Examples of suitable metal salts include NaCl, KCl, $CaCl_2$, and $MgCl_2$.

In one embodiment, the nucleic acid binding solution contains from 80-99% (v/v) alcohol, 5-20 mM of a first salt, 0.5-10 mM of a second salt, 0.1-10 M chaotropic agent, and 0.1-10 mM reducing agent. In another embodiment, the solution contains from 90-99% (v/v) alcohol, 5-10 mM of a first salt, 0.5-5 mM of a second salt, 0.1-5 M chaotropic agent, and 2-7 mM reducing agent. In one embodiment, the alcohol is isopropanol, the first salt is $MgCl_2$, the second salt is $CaCl_2$, the chaotropic agent is GITC, and the reducing agent is TCEP.

In one embodiment, the nucleic acid binding solution includes 50-80% isopropanol and 0.5-5 M GITC. In another embodiment, the nucleic acid binding solution includes 60-70% isopropanol and 0.5-2.5 M GITC.

The aqueous phase is contacted with a silica-based solid phase. The term "solid phase" is not intended to imply any limitation regarding its form or structure. The solid phase may be porous, non-porous, permeable, or impermeable. The silica-based solid phase can be in the form of a matrix, beads, particles, fibers, gels, filters, sheets, or a membrane. The silica-based solid phase may be in the form of a column. In one embodiment, the silica is in the form of a magnetic particle.

Examples of suitable columns include Zymo-Spin™ I columns and Qiagen RNeasy Mini Spin Columns.

A vacuum manifold such as a QIA vac 24 Vacuum Manifold is preferably used for convenient vacuum processing of spin columns in parallel. Samples and wash solutions can be drawn through the column membranes by vacuum instead of centrifugation, providing greater speed, and reduced hands-on time in the extraction and purification of RNA from cells and tissues.

The column bound silica-based solid phase may be in the form of a 96 well plate. An example of a suitable plate includes Zymo-Spin™ 1-96 Plate.

According to another embodiment, after the aqueous phase is contacted with the silica-based solid phase, the silica-based solid phase is washed at least one of a first wash solution and second wash solution.

The silica-based solid phase with bound RNA acid is contacted with a first wash solution. The first wash solution includes alcohol, chaotropic agent, and a reducing agent.

In one embodiment, the concentration of the reducing agent in the first wash solution is at least 0.05 mM, at least 0.5 mM, or at least 1 mM. In another embodiment, the concentration of the reducing agent in the solution is less than 100 mM, less than 50 mM, less than 25 mM, or less than 10 mM. In some embodiments, the reducing agent has a concentration between 1-20 mM, 2-10 mM, or 3-8 mM.

In one embodiment, the alcohol is present in a concentration between 50-90% or 60-80% (v/v). In a preferred embodiment, the reducing agent is present in a concentration between 1 and 20 mM. In another preferred embodiment, the reducing agent is present in a concentration between 2 mM and 10 mM.

In one embodiment, the first wash solution includes at least one salt, a detergent, chaotropic agent, alcohol, and a reducing agent. In a preferred embodiment, the first wash solution includes NaCl, $MgCl_2$, $CaCl_2$, Triton X-100, GITC, isopropanol, and TCEP. In one embodiment, the first wash solution contains from 0.1-10 mM triton X-100, from 10-20 mM NaCl, from about 0.5-10 mM $MgCl_2$, from 0.1-10 mM $CaCl_2$ from 0.1-5 mM chaotropic agent; and from 40-80% (v/v) alcohol.

In one embodiment, the first wash solution includes at least one salt, a detergent, chaotropic agent, alcohol, and a reducing agent. In one embodiment, the first wash solution contains from 0.5 mM Triton-X-100, 18 mM NaCl, from 1.3-5.4 mM $MgCl_2$, from 0.4-1.8 mM $CaCl_2$; from 0.36 M GITC agent; and from 40-80% (v/v) alcohol. In a preferred embodiment, the first wash solution includes NaCl, $MgCl_2$, $CaCl_2$, Triton X-100, GITC, isopropanol, and TCEP.

In one embodiment, the first wash solution includes Qiagen™ buffer RWT supplemented with TCEP. For example, buffer RWT may be supplemented with between 2 mM and 10 mM TCEP.

The silica-based solid phase with bound RNA is optionally contacted with a second wash solution. The second wash solution includes alcohol, and a reducing agent. In a preferred embodiment, the second wash solution further contains a chaotropic agent in an amount equal to or less than that in the first wash solution.

In one embodiment, the alcohol is present in a concentration between 50-95% (v/v), 60-90% (v/v).

In one embodiment, the concentration of the reducing agent in the second wash solution is at least 0.05 mM, at least 0.5 mM, or at least 1 mM. In another embodiment, the concentration of the reducing agent in the solution is less than 100 mM, less than 50 mM, less than 25 mM, or less than 10 mM. In some embodiments, the reducing agent has a concentration between 1-20 mM, 2-10 mM, or 3-8 mM.

In one embodiment, the second wash solution includes Qiagen™ buffer RPE supplemented with TCEP. For example, buffer RPE may be supplemented with between 1 mM and 10 mM TCEP.

The first and second wash solution may contain other additives. For example, the first and second wash solution may include ethylenediaminetetraacetic acid (EDTA), ethylene glycol tetraacetic acid (EGTA), detergents, or metal salts. Examples of suitable metal salts include NaCl, KCl, $CaCl_2$, and $MgCl_2$.

In one embodiment, silica-based solid phase is contacted with at least one alcohol after contact with the first wash solution or the second wash solution. In one embodiment, the silica-based solid phase may be contacted with an alcohol having a concentration of at least about 70%, at least about 80%, at least about 90%, at least about 95%, at least about 99%, or 100% (v/v).

In a preferred embodiment, after contact with the first wash solution or the second wash solution, the silica-based solid phase is contacted with a solution of 100% alcohol. In another preferred embodiment, after contact with the first or second wash solution, the silica-based solid phase is contacted with a solution of 100% alcohol and a solution having at least about 70% alcohol.

In a preferred embodiment, after contact with the first wash solution or the second wash solution, the silica-based solid phase is contacted with a solution of 100% alcohol. In another preferred embodiment, after contact with the second wash solution, the silica-based solid phase is contacted with a solution of 100% alcohol and a solution having at least about 80% alcohol.

In some embodiments, the silica based wash solution is contacted with any combination and any number of a first wash solution and second wash solution.

The RNA bound to the silica-based solid phase may be eluted from the solid phase by contacting the solid phase with an aqueous elution solution, such solutions are known in the art. The aqueous elution solution may contain at least one of water, a buffer, and a RNA preservative. RNA preservatives are commonly known in the art. An example of a suitable RNA preservative includes RNase inhibitor.

Elution may include methods of physical elution, such as subjecting the silica-based solid phase to vacuum or centrifugation. Such methods are known in the art.

In another aspect, the DNA partitioned into the organic phase described above may be further processed to isolate DNA contained therein.

In one embodiment, the organic phase described above is contacted with a DNA extraction solution containing a chaotropic agent and a buffer to form a mixture to form a second aqueous phase and a second organic phase. In one embodiment, the buffer is sodium citriate and the chaotropic agent is GITC. In one embodiment, solution contains at least 3M GITC, preferably at least 4 M GITC.

The mixture is agitated. The second aqueous phase is separated from the second organic phase. Separation of the second aqueous phase and second organic phase may be accomplished by physical means, including a centrifuge.

The separated second aqueous phase containing the DNA is contacted with a solution containing alcohol, at least one salt, a chaotropic agent, and a reducing agent to form a mixture. In one embodiment, the solution contains from 80-99% (v/v) alcohol, 5-20 mM of a first salt, 0.5-10 mM of a second salt, 0.1-10 M chaotropic agent, and 0.1-10 mM reducing agent. In another embodiment, the solution contains from 90-99% (v/v) alcohol, 5-10 mM of a first salt, 0.5-5 mM of a second salt, 0.1-5 M chaotropic agent, and 2-7 mM reducing agent. In one embodiment, the alcohol is isopropanol, the first salt is $MgCl_2$, the second salt is $CaCl_2$, the chaotropic agent is GITC, and the reducing agent is TCEP.

This mixture is agitated.

The mixture containing the DNA is then contacted with a silica-based solid phase.

The silica-based solid phase with bound RNA acid is contacted with a first wash solution. The first wash solution includes alcohol, chaotropic agent, and a reducing agent.

In one embodiment, the concentration of the reducing agent in the first wash solution is at least 0.05 mM, at least 0.5 mM, or at least 1 mM. In another embodiment, the concentration of the reducing agent in the solution is less than 100 mM, less than 50 mM, less than 25 mM, or less than 10 mM. In some embodiments, the reducing agent has a concentration between 1-20 mM, 2-10 mM, or 3-8 mM.

In one embodiment, the alcohol is present in a concentration between 50-90% or 60-80% (v/v). In a preferred embodiment, the reducing agent is present in a concentration between 1 and 20 mM. In another preferred embodiment, the reducing agent is present in a concentration between 2 mM and 10 mM.

In one embodiment, the first wash solution includes at least one salt, a detergent, chaotropic agent, alcohol, and a reducing agent. In a preferred embodiment, the first wash solution includes NaCl, $MgCl_2$, $CaCl_2$, Triton X-100, GITC, isopropanol, and TCEP. In one embodiment, the first wash solution contains from 0.1-10 mM triton X-100, from 10-20 mM NaCl, from about 0.5-10 mM $MgCl_2$, from 0.1-10 mM $CaCl_2$ from 0.1-5 mM chaotropic agent; and from 40-80% (v/v) alcohol.

In one embodiment, the first wash solution includes at least one salt, a detergent, chaotropic agent, alcohol, and a reducing agent. In one embodiment, the first wash solution contains from 0.5 mM Triton-X-100, 18 mM NaCl, from 1.3-5.4 mM $MgCl_2$, from 0.4-1.8 mM $CaCl_2$; from 0.36 M GITC agent; and from 40-80% (v/v) alcohol. In a preferred embodiment, the first wash solution includes NaCl, $MgCl_2$, $CaCl_2$, Triton X-100, GITC, isopropanol, and TCEP.

In one embodiment, the first wash solution includes Qiagen™ buffer RWT supplemented with TCEP. For example, buffer RWT may be supplemented with between 2 mM and 10 mM TCEP.

In one embodiment, the first wash solution includes at least one salt, a detergent, chaotropic agent, alcohol, and a reducing agent. In a preferred embodiment, the first wash solution includes NaCl, $MgCl_2$, $CaCl_2$, Triton X-100, GITC, isopropanol, and TCEP.

In one embodiment, silica-based solid phase is contacted with at least one alcohol after contact with the first wash solution. In one embodiment, the silica-based solid phase may be contacted with an alcohol having a concentration of at least about 70%, at least about 80%, at least about 90%, at least about 95%, at least about 99%, or 100% (v/v).

In a preferred embodiment, after contact with the first wash solution, the silica-based solid phase is contacted with a solution of 100% alcohol. In another preferred embodiment, after contact with the second wash solution, the silica-based solid phase is contacted with a solution of 100% alcohol and a solution having at least about 70% alcohol.

In some embodiments, the silica-based solid phase may be washed with a second wash solution as described above.

In a preferred embodiment, after contact with the first wash solution or the second wash solution, the silica-based solid phase is contacted with a solution of 100% alcohol. In another preferred embodiment, after contact with the second wash solution, the silica-based solid phase is contacted with a solution of 100% alcohol and a solution having at least about 80% alcohol.

The DNA bound to the silica-based solid phase may be eluted from the solid phase by contacting the solid phase with an aqueous elution solution, such solutions are known in the art. The aqueous elution solution may contain at least one of water, a buffer, and a DNA preservative. DNA preservatives are commonly known in the art.

Elution may include methods of physical elution, such as subjecting the silica-based solid phase to vacuum or centrifugation. Such methods are known in the art.

In the specification, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Throughout this specification, quantities are defined by ranges, and by lower and upper boundaries of ranges. Each lower boundary can be combined with each upper boundary to define a range. The lower and upper boundaries should each be taken as a separate element.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such non-limiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

EXAMPLES

The present embodiments of the disclosure are illustrated in further details by the following non-limiting examples
2 Materials and buffers
2.1 Procedural Considerations Regarding Number of Samples and Manual, Semi-Automated or Automated Processes The volumes and amounts of all solutions and consumables were chosen for parallel processing of 24 biofluid samples unless stated otherwise. Twenty four (24) samples are typically processed in a single multiplexed library preparation and sequencing reaction using 24 different barcoded 3' DNA adapters. The RNA purification procedure consists of (1) an initial denaturation step with detergent at an elevated temperature, followed by (2) an enzymatic digestion of protein, (3) an organic extraction step to remove hydrophobic peptides and other hydrophobic substances, and (4) a column purification step.

There are three protocols using different degrees of automation:
A. Manual purification using either a vacuum manifold or centrifugation in order to pass solutions through columns.
B. Semi-automated purification where the lysis step and the organic extraction step are carried out manually while the column purification is performed using an automated liquid handling system.
C. Fully automated purification where all steps are performed using the fully equipped liquid epMotion 5075 liquid handling system (see section 1.4 for equipment).

Formulations of buffers and solutions are provided for 8, 24, and 96 extractions. For manual RNA isolations any number of samples up to a total of 24 samples are done at once. For semi-automated sample processing denaturation, digestion, and organic extraction in batches of up to 24 samples, one batch at a time. After organic extraction, samples can be stored in binding buffer for an intermitted period of up to three hours until all batches (of up to 4) are denatured and extracted. Multiple batches are then subjected to automated column purification. For semi-automated or fully automated setups, samples are processed in multiples of 8 samples at a time, since microtiter plates and filter plates of manifolds are typically organized in a 12×8 well format. Using a total of 96 samples (4×24 samples) takes full advantage of this form factor.

2.2 Chemicals
   2-Propanol (also named: isopropanol, Fisher Sci, Cat #314, $M_r$ 60.1 g/mol)
   Acetic acid, glacial (Fisher Sci, Cat # A38-212, $M_r$ 60.05 g/mol)
   2-Mercapthoethanol (also named: β-mercaptoethanol, Sigma, Cat # M3148, $M_r$ 78.13 g/mol)
   Brilliant Blue R, powder (Sigma, Cat # B0149, $M_r$ 825.99 g/mol)
   Bromphenol blue, technical grade (Sigma, Cat # B6131, $M_r$ 691.94 g/mol)
   Calcium dichloride dihydrate ($CaCl_2.2H_2O$, Applichem, Cat # A1873, $M_r$ 147.02 g/mol)
   Citric acid monohydrate, crystalline (Fisher Sci, Cat # A1112-12, $M_r$ 210.14 g/mol)
   Disodium ethylenediaminetetraacetic acid dihydrate ($Na_2EDTA.2H_2O$, Sigma, Cat # E6635, $M_r$ 372.24 g/mol)
   Glycerol (Fisher Sci, Cat # G31-1, $M_r$ 92.09 g/mol)
   Guanidium thiocyanate (GITC, Sigma, Cat #50981, $M_r$ 118.16 g/mol)
   Magnesium dichloride hexahydrate ($MgCl_2.6H_2O$, Applichem, Cat # A1036, $M_r$ 203.3 g/mol)
   Mini-PROTEAN TGX 4-20% SDS PAGE gel, 15-well, 15 µl (Bio-Rad, Cat #456-1096)
   Phenol solution, saturated with 0.1 M citrate buffer, pH 4.3±0.2 (Sigma, Cat # P4682, $M_r$ 94.11 g/mol) or phenol, water saturated, stabilized, pH 4.0 (Applichem, Cat # A1624, $M_r$ 94.11 g/mol)
   Phenylmethylsulfonyl fluoride (PMSF, Sigma, Cat # P7626, $M_r$ 174.19 g/mol)
   Sarcosyl (Fisher Sci, Cat # BP234, $M_r$ 293.38 g/mol)
   Sodium chloride (NaCl, Fisher Sci, Cat #5271500, $M_r$ 58.44 g/mol)
   Sodium dodecyl sulfate (SDS, Fisher Sci, Cat # BP166-500, $M_r$ 288.38 g/mol)
   Sodium hydroxide, pellets (NaOH, Fisher Sci, Cat # S318-1, $M_r$ 40.00 g/mol)
   Tri(2-carboxyethyl)phosphine hydro-chloride, 10 g (TCEP.HCl, Hampton Research, Cat # HR2-801, $M_r$ 286.65 g/mol)
   Tris base (Fisher Sci, Cat # BP152, Stock #336,000, $M_r$ 121.14 g/mol)
   Tris-HCl (Sigma, Cat # T3253, $M_r$ 157.60 g/mol)
   Tris/glycine buffer (10×) (Bio-rad, Cat #161-0734)

2.3 Enzymes
   Proteinase K (recombinant, Storeroom, 100 mg, from Roche Ref #03 115 879 001, Cat #301104)

2.4 Oligonucleotides
Calibrator pool 1 consists of 10 equimolar concentrated 5' phosphorylated 3' hydroxyl 22-nt RNA oligonucleotides, which were ordered from Dharmacon at a 0.05 µmol scale. They have no match to the human or mouse genome.

| Calibrator (synthesis no.) | Sequence | Extinction coefficient ($L \cdot mol^{-1} \cdot cm^{-1}$) |
|---|---|---|
| 01 (cali 01 rc) | pUCCACGACGUCUCAUGUAUUUC | 191700 |
| 02 (cali 04 rc) | pGGGUACCAUACCGGUUGUCUUA | 201900 |
| 03 (cali 17 rc) | pUCAUGAGUCCGUACCUUGAUUG | 201900 |
| 04 (cali 18 rc) | pAUCAUUUACGAUUCGGAGCUGU | 203100 |
| 05 (cali 20 rc) | pGAUAGUUCGGGAUCGCUGUAAC | 208400 |
| 06 (cali 24 rc) | pUGCUACUCCGAUCUUUAGCCUC | 182900 |
| 07 (cali 25 rc) | pAGGGCCCUUUAGGCACUAAUAG | 209500 |
| 08 (cali 27 rc) | pGUAGCUGUCAGUACGUUCGUGC | 198000 |
| 09 (cali 43 rc) | pUCUAGUUGCGUGAUGGAGAGAA | 218000 |
| 10 (cali 44 rc) | pAGCCGCAUUUCGUAGUGAUAUU | 204300 | p: 5' phosphate

Measure the concentrations of each calibrator using a spectrophotometer.

The preparation of diluted solutions of the calibrator pools requires the use of a carrier oligonucleotide to prevent surface adsorption during preparation of the dilution series in the nanomolar concentration range. For example, an 11-nt oligodeoxynucleotide, 5'-TCGAAGTATTC, at a final concentration of 500 nM may be used.

Prepare 50 µl of a concentrated stock containing 1 µM of each calibrator RNA, which does not require addition of carrier DNA.

Dilute the 1 µM calibrator each stock 1:10 into 500 nM TCGAAGTATTC resulting in a concentration of 0.1 µM each calibrator (10 µl calibrator stock plus 90 µl500 nM 11-nt carrier DNA).

Further dilute the 0.1 µM calibrator pool 1:10 in 500 nM TCGAAGTATTC resulting in a calibrator concentration of 10 nM each calibrator (50 µl calibrator dilution plus 450 µl 500 nM 11-nt carrier DNA).

Further dilute the 10 nM calibrator pool 1:10 in 500 nM TCGAAGTATTC resulting in a calibrator concentration of 1 nM each (50 µl calibrator dilution plus 450 µl500 nM 11-nt carrier DNA).

Further dilute the 1 nM calibrator pool 1:10 in 500 nM TCGAAGTATTC resulting in a calibrator concentration of 100 pM each (50 µl calibrator dilution plus 450 µl500 nM 11-nt carrier DNA).

Further dilute the 100 pM calibrator pool 1:10 in 500 nM TCGAAGTATTC resulting in a calibrator concentration of 10 pM each (50 μl calibrator dilution plus 450 μl500 nM 11-nt carrier DNA). This dilution will be used for plasma and serum samples.

Dilute the 10 pM calibrator pool one last time 1:10 to reach a calibrator concentration of 1 pM each (50 μl calibrator solution plus 450 μl500 nM 11-nt carrier DNA). This dilution will be used for urine samples.

Example for using calibrator pool 1:

The suggested final amount of calibrator per sample is 0.2" each oligoribonucleotide for urine and 2 attomol each oligoribonucleotide for serum or plasma per 450 μl of input biofluid.

For urine add 2.8 μl 1 pM each oligoribonucleotide of "Calibrator pool 1" to 1.467 ml of buffer P with 2-mercaptoethanol and methylene blue added to obtain 14 aliquots of 105 μl of denaturing buffer with 0.2 attomol of each RNA per aliquot:

2.8 μl×1 pM of each "calibrator pool 1" RNA/14 aliquots
=2.8×$10^{-6}$1×$10^{-12}$ M of each "calibrator pool 1" RNA/14 aliquots
=2.8×$10^{-18}$ mol of each "calibrator pool 1" RNA/14 aliquots
=2.8 attomol of each "calibrator pool 1" RNA/14 aliquots
=0.2 attomol of each "calibrator pool 1" RNA/aliquot.

2.4 Equipment

Qubit 2.0 Fluorometer (Invitrogen)
A set of pipettes (20 μl, 200 μl, 1000 μl), (e.g. Gilson)
Repeater pipette (e.g. eppendorf M4)
Spectrofluorometer or fluorescence microplate reader A. For Manual Processing/Semi-Automated Processing
Vacuum manifold 24×, (e.g. QIAGEN, QIAval 24 Plus Vacuum Manifold, Cat #19413)
Table top centrifuge (e.g. SORVALL Legend Micro 21R centrifuge), set to 4° C.
Table top centrifuge (e.g. SORVALL Biofuge pico) or eppendorf centrifuge, at room temperature
eppendorf thermomixer set to 10° C.
eppendorf thermomixer set to 60° C.

B. For Semi-Automated and Automated Processing
epMotion 5075 or similar liquid handling system with vacuum manifold option, for fully automated processing also equipped with one thermoplate heater/cooler and the thermomixer option
Single-channel dispensing tool TS 50 (Cat #960001010)
Single-channel dispensing tool TS 300 (Cat #960001028)
Single-channel dispensing tool TS 1000 (Cat #960001036)
Eight-channel-dispensing tool TM 50-8 (Cat #960001044)
Eight-channel-dispensing tool TM 300-8 (Cat #960001052)
Eight-channel-dispensing tool TM 1000-8 (Cat #960001061)
Gripper (Cat #960002270)
Gripper holder (Cat #960002211)
Thermoblock for PCR 96 wells (Cat #960002083)
Thermorack for 24 Safe Lock tubes (Cat #960002067)
Deep well plate 96/2000 μl (Cat #951033561)
Eppendorf heat sealer (5390 000.024, from Sigma Aldrich)
Eppendorf heat sealing foil (Cat #0030127.845, from Sigma Aldrich)
Centrifuge with holder for 96-well plates (e.g. SORVALL Legend RT), set to 4° C.

2.5 Consumables 2.5.1 RNA Extractions from Biofluids

Items listed for processing of 24 samples. For manual, semi-automated or automated processing of 48, 72 or 96 samples, multiply by two, three or four, respectively. When performing semi-automated or automated purification only one Zymo-Spin™ I 96 filter plate is needed for up to 96 samples.

A. For Manual Processing
Filter pipet tips (10 μl, 200 μl, 1000 μl)
48×2 ml eppendorf Lo-Bind tubes (VWR, DNA LoBind Tube 2.0 ml, PCR clean, CS/250 (5× PK/50); 22431048, Cat #470202-584)
24×1.5 ml siliconized tubes (VWR, G-Tube® Snap Cap Siliconized Microcentrifuge Tubes, Cat #22179-004)
24× Zymo-Research Zymo-Spin™ I columns (Zymo-Research, Zymo-Spin™ I columns, 50, Cat # C1003-50), B. For Semi-Automated and Automated Processing
1× Zymo-Research Zymo-Spin™ 1-96 filter plate, Cat # C2004
26×2 ml microcentrifuge tube
380 μl RNase free water
1 ml deep well plate 96 well, green border (Eppendorf, Cat #0030 502.230, Cat #951032760
2 ml deep well plate 96 well, green border (Eppendorf, Cat #0030 502.337, Cat #951033561)
250 μl twin.tec 96 well, semi-skirted, colorless per plate (Eppendorf, Cat #0030 128.575, Cat #951020303)
epMotion® PCR clean reservoir 100 ml (Eppendorf, Cat #960051017)

C. Optional. For Automated Initial Sample Addition Using Width Adjustable Multichannel Pipette
Rainin EA8 1200XLS multichannel and adjustable spacer electronic pipette (Cat #17012331)
Rainin LTS 1 ml Filter RT-L1000FLR Low Retention Tips (Cat #17007954)

2.5.2 Qubit Assay
Qubit RNA HS assay kit (Invitrogen, Cat # Q32852), including Qubit RNA HS assay dilution buffer and Qubit RNA HS assay dye
2'-OMe-let-7a oligoribonucleotide standard (A260=0.5)
1.5 ml siliconized tubes
0.5 ml Qubit assay tubes (500 tubes, Invitrogen, Cat # Q32856) or Axygen PCR-05-C tubes (VWR, part number 10011-830).

2.5.3 Quant-iT™ RiboGreen® RNA assay
Quant-iT™ RiboGreen® RNA Assay Kit (Life Technologies, Cat # R11490)
Quant-iT™ RiboGreen® RNA Reagent
20× TE Buffer, RNase-free
Ribosomal RNA standard, 16S and 23S rRNA from *E. coli* (100 μg/ml)
Costar™ 96-well clear-bottom plates (Fisher Scientific, Cat #07-200-565)

2.6 Buffers, Reagents and Enzyme Solutions

All buffers should be prepared in advance and stored under the recommended conditions to minimize degradation and microbial growth. All buffers are made using MilliQ deionized and sterile filtered water, from now on referred to as 'water'.

2.6.1 Stock Solutions

The following stock solutions will be required to prepare working solutions used during the isolation procedure.

2.6.1.1 1 M Tris-HCl, 1000 ml

In a 1000 ml glass bottle equipped with a magnetic stir bar, weigh out 157.6 g of Tris-HCl ($M_r$ 157.60 g/mol). Add approx. 800 ml water and dissolve powder.

Transfer solution to 1000 ml graduated cylinder, fill up to 1000 ml with water and return solution to 1000 ml bottle.

Store at room temperature.

2.6.1.2 1 M Tris base, 1000 ml

In a 1000 ml glass bottle equipped with a magnetic stir bar, weigh out 121.1 g of Tris base ($M_r$ 121.14 g/mol). Add approx. 800 ml water and dissolve powder.

Transfer solution to 1000 ml graduated cylinder, fill up to 1000 ml with water and return solution to 1000 ml bottle.

Store at room temperature.

2.6.1.3 1 M Buffer Tris-HCl (pH 6.8), 50 ml

Combine 47.4 ml of 1 M Tris-HCl and 2.6 ml of 1 M Tris base in a 50 ml FALCON tube.

Volume (Tris base)=$(10^{(pH-pKa)}/(1+10^{(pH-pKa)}))\times$ 1000 ml; pKa=8.06 at 25° C.

Dispense into aliquots.

Store at room temperature.

2.6.1.4 1 M Buffer Tris-HCl (pH 7.5), 50 ml

Combine 39.2 ml of 1 M Tris-HCl and 10.8 ml of 1 M Tris base in a 1000 ml glass bottle.

Volume (Tris base)=$(10^{(pH-pKa)}/(1+10^{(pH-pKa)}))\times$ 1000 ml; pKa=8.06 at 25° C. Dispense into aliquots.

Store at room temperature.

2.6.1.5 1 M Buffer Tris-HCl (pH 8.0), 50 ml

Combine 26.7 ml of 1 M Tris-HCl and 23.3 ml of 1 M Tris base in a 1000 ml glass bottle.

Volume (Tris base)=$(10^{(pH-pKa)}/(1+10^{(pH-pKa)}))\times$ 1000 ml; pKa=8.06 at 25° C.

Dispense into aliquots.

Store at room temperature.

2.6.1.6 0.5 M EDTA (pH 8.0), 1000 ml

In a 1 l graduated cylinder, add 186.1 g of $Na_2EDTA.2H_2O$ ($M_r$ 372.24 g/mol) to 800 ml water. Stir vigorously on a magnetic stirrer. Adjust pH to 8.0 with NaOH pellets (~20 g). Add pellets slowly and wait for pH to stabilize. Expect EDTA to dissolve fully before pH can reach 8.0. Adjust volume to 1 liter.

Store at room temperature.

Note: The disodium salt of EDTA will not go into solution until the pH of the solution is adjusted to pH 8.0 by adding NaOH.

2.6.1.7 4 M NaOH, 50 ml

Place an appropriately sized tube holder on a scale and tare with a 50 ml FALCON tube. Add 8.00 g NaOH pellets ($M_r$ 40.00 g/mol) to this tube. Add water to reach a final weight of 56.3 g.

Close lid and vortex until a clear solution has formed.

Store at room temperature.

2.6.1.8 4 M Citric acid, 50 ml

Place an appropriately sized tube holder on a scale and tare with a 50 ml FALCON tube. Add 42.03 g citric acid monohydrate ($M_r$ 210.14 g/mol) to this tube. Add water to reach a final weight of 64.1 g. Close lid and vortex until a clear solution has formed.

Store at room temperature.

2.6.1.9 1 M $MgCl_2$ 50 ml

Place an appropriately sized tube holder on a scale and tare with a 50 ml FALCON tube. Add 10.17 g of $MgCl_2.6H_2O$ ($M_r$ 203.30 g/mol) to this tube. Add water to reach a final weight of 53.1 g. Close lid and vortex until a clear solution has formed.

Store at room temperature.

2.6.1.10 1 M $CaCl_2$ 50 ml

Place an appropriately sized tube holder on a scale and tare with a 50 ml FALCON tube. Add 10.95 g of $CaCl_2.6H_2O$ ($M_r$ 219.08 g/mol) to this tube. Make sure to return the $CaCl_2.6H_2O$ powder to its recommended storage temperature of 4° C. immediately after use. Add water to reach a final weight of 53.7 g. Close lid and vortex until a clear solution has formed.

Store at room temperature.

2.6.1.11 5 M NaCl, 50 ml

Dissolve 14.61 g NaCl ($M_r$ 58.44 g/mol) in 45 ml water in a 50 ml FALCON tube. Adjust the volume to 50 ml with water and vortex.

Store at room temperature.

2.6.1.12 0.5 M TCEP 5 ml

Dissolve 0.72 g TCEP-HCl in 4 ml water in a 15 ml FALCON tube. Adjust the volume to 5 ml with water and vortex. Wrap the labeled tube with aluminum foil in order to protect the solution from light. TCEP is light sensitive.

Store at 4° C. for up to one week.

2.6.1.13 0.63 M SDS Solution (20%), 10 ml

Dissolve 2.00 g SDS ($M_r$ 288.37 g/mol) in 8 ml water in a 15 ml FALCON tube. To dissolve the SDS, remove the cap of the 15 ml FALCON and place upright (using a FALCON tube stand) inside the microwave. Heat with 4×5 s pulses at 1250 W. The temperature of the solution must not rise above lukewarm; close tube, check and invert after every pulses. Since the volume will decrease as the powdered SDS dissolves, readjust volume to exactly 10 ml with water. Heat the solution again with 1-3×5 s pulses at 1250 W inside the microwave using the above procedure and precautions. Do not vortex as the solution will easily foam.

Store at room temperature.

2.6.1.14 Coomassie Brilliant Blue Protein Gel Staining Solution, 1000 ml

In a 1 l flask, weigh 500 mg of brilliant blue powder. Then, add 400 ml ethanol, 100 ml acetic acid and fill up to 1 l with water. Close lid and mix by inverting the bottle.

Store at room temperature.

2.6.1.15 Coomassie Gel De-Staining Solution, 1000 ml

In a 1 l flask, add 200 ml methanol to 100 ml acetic acid and fill up to 1 l with water. Close lid and mix by inverting the bottle.

Store at room temperature.

2.6.2 Buffers for Sample Protein Degradation 2.6.2.1 Buffer P (Proteolysis), 50 ml Never vortex this buffer as it will foam! Only gently invert tubes. For 380 samples. Buffer can be stored at room temperature.

In a 50 ml FALCON tube combine:

| Reagent or solution | Amount | Buffer concentration |
|---|---|---|
| Sodium dodecyl sulfate (SDS) | 15 g | 30% (w/v) |
| 1M Buffer Tris-HCl (pH 7.5) | 3.3 ml | 66 mM |
| 0.5M EDTA (pH 8.0) | 1.98 ml | 19.8 mM |

Add Buffer Tris-HCl, EDTA solution and 15 ml water in a 50 ml FALCON tube. Weigh out SDS powder and add to the previously added solutions. Adjust volume to roughly 50 ml with water. Mix by gently inverting the tube multiple times. Adjust volume again to 50 ml with water. Close the tube tightly and invert for 6 hours at room temperature until a clear solution has formed.

Adjust volume again to exactly 50 ml with water and invert multiple times to prepare a homogenous solution.

Be prepared to add 2-mercapthoethanol to a Buffer P aliquot just before use.

Store at room temperature. Do not autoclave.

Refrigeration will cause SDS to precipitate. DO NOT refrigerate. If precipitate forms at room temperature, use 1-3×10 s pulses at 1250 W in the microwave and invert repeatedly until all precipitates are dissolved.

2.6.3 Buffers for Protein and Detergent Removal by Organic Extraction 2.6.3.1 Buffer ED2, 24.5 ml This buffer is less acidic and approaches pH 4.5. For 8, 24 and 48 extractions prepare given amount in a 50-ml FALCON tube. For 96 samples prepare 2× the amount for 48 extractions in two separate 50-ml FALCON tubes. Use filter pipet tips to avoid contamination. Be prepared to add 2-mercapthoethanol to Buffer ED2 just before usage (see section 3.1.2, step 9).

In a 50 ml FALCON tube combine:

| Reagent or solution | 8 extr. | 24 extr. | 2 × 48 extr. = 96 extr. | Buffer conc. |
|---|---|---|---|---|
| 4M Citric acid | 74 µl | 222 µl | 2 × 444 µl | 37.4 mM |
| 4M Sodium hydroxide solution (NaOH) | 92 µl | 275 µl | 2 × 550 µl | |
| Sarcosyl | 33 mg | 100 mg | 2 × 200 mg | 0.4% (w/v) |
| Guanidium thiocyanate (GITC) | 1.5 g | 4.51 g | 2 × 9.02 g | 1.6M |
| Phenol solution, saturated with 0.1M citrate buffer (pH 4.3) | 6.4 ml | 19.1 ml | 2 × 38.2 ml | 80% (v/v) |

Add citric acid and NaOH solutions to a 50 ml FALCON tube, then add GITC and sarcosyl powder. Dissolve all components by adding 19.1 ml buffer equilibrated phenol, close tube and mix by inverting until a clear, colorless liquid is formed. Do not adjust pH or volume, the expected final volume is about 47.5 ml. Short-term storage at 4° C., long-term storage at −20° C.

Buffer ED may contain 0.15 M NaCl. In the alternative, NaCl is added either before the lysis step or during the addition of the protease since protease activity is higher in the presence of 0.2-0.35 M NaCl.

2.6.4 Buffers for RNA Purification Using Zymo-Research Columns and the Vacuum Manifold or the Zymo-Spin™ 1-96 Plate This buffer minimizes precipitation of peptides and clogging of columns, which was observed when aqueous supernatants from organic extractions were applied using other buffers. VB2G appears to work well for all sample types thereby eliminating the need to specifically adjust divalent cation concentrations.

2.6.4.1 Buffer VB2G (Vacuum-Manifold Binding)—For Serum, Plasma (EDTA and Citrate) and Urine For 8 and 24, and 32 extractions prepare given amount in a 50-ml FALCON tube. For 96 samples prepare 3× the amount for 32 extractions in three separate 50-ml FALCON tubes (8 extr.=15 ml, otherwise 50 ml).

| Reagent or solution | 8 extr. | 24 extr. | 3 × 32 extr. = 96 extr. | Buffer conc. |
|---|---|---|---|---|
| Isopropanol (100%) | 12.2 ml | 36.8 ml | 3 × 49.1 ml | 98.2% (v/v) |
| 1M MgCl₂ | 84.5 µl | 271.5 µl | 3 × 362 µl | 7.2 mM |
| 1M CaCl₂ | 28.2 µl | 84.5 µl | 3 × 121 µl | 2.4 mM |
| GITC | 1.5 g | 4.4 g | 5.9 g | 1M |
| Add before use: 0.5M TCEP | 123 µl | 367 µl | 500 µl | 5.0 mM |

Do not adjust volume. Combine isopropanol, MgCl₂ and CaCl₂ solutions and GITC. Mix well and store solution at room temperature. Before use, add 1% 0.5 M TCEP. Upon storage, precipitate may form. Shake well before use. It has not been tested how long TCEP will remain stable; according to the literature it should be stable for at least a week.

2.6.4.2 Buffer EWL Wash Buffer for Silica Columns During RNA or DNA Purification EWL aqueous concentrate, 50 ml:

| Reagent or solution | |
|---|---|
| 5M NaCl | 600 µl |
| 1M MgCl₂ | 450 µl |
| 1M CaCl₂ | 150 µl |
| Triton X-100 | 750 µl |
| GITC | 7.08 g |

Dissolve GITC in 20 ml of Water, add NaCl, MgCl₂, CaCl₂ solution, add TRITON X-100. Fill up to a final volume 50 ml with water.

EWL Stock solution:

| Reagent or solution | 8 extr. | 24 extr. | 96 extr. = 2 × 50 ex | Buffer conc. |
|---|---|---|---|---|
| EWL aqueous concentrate | 5 ml | 15 ml | 4 × 15 ml | 1x |
| Isopropanol | 11.7 ml | 35 ml | 4 × 35 ml | |
| Add before use: 0.5M TCEP | 150 µl | 0.5 ml | 4 × 0.5 ml | 5 mM |

Do not adjust volume. Combine EWL aqueous concentrate and Isopropanol. Mix well and store solution at room temperature. Before use, add TCEP. Shake well before use. It has not been tested how long TCEP will remain stable; according to the literature it should be stable for at least a week.

2.6.5 Buffers for DNA Re-Extraction from Organic Phase 2.6.5.1 Buffers EA3 24.5 ml For 8, 24 and 48 extractions prepare given amount in a 50-ml FALCON tube. For 96 samples prepare 2× the amount for 48 extractions in two separate 50-ml FALCON tubes. Use filter pipet tips to avoid contamination.

In a 50 ml FALCON tube, combine:

| Reagent or solution | 8 extr. | 24 extr. | 96 extr. | Buffer concentration |
|---|---|---|---|---|
| 4M Citric acid | 74 µl | 222 µl | 2 × 444 µl | 35.5 mM |
| 4M Sodium hydroxide (NaOH) | 110 µl | 330 µl | 2 × 660 µl | sodium citrate |
| Guanidium thiocyanate (GITC) | 3.55 g | 10.64 g | 2 × 21.27 g | 4.00M |
| H₂O | 7.5 ml | 22.5 ml | 45 ml | |

Add citric acid and NaOH solutions first, then add GITC. Dissolve all components by adding H$_2$O, close tube and mix by inverting until a clear, colorless liquid is formed. Do not adjust pH or volume. The final volume is approximately 50 ml. For short-term storage keep a convenient volume of a working stock at 4° C.

2.6.6 Proteinase K Solutions and Quality Control Assay 2.6.6.1 PK (Proteinase K) Stock Solution (20 mg/ml), 1 ml Use filter pipet tips to avoid contamination.

First, prepare proteinase K storage buffer, which is then used to dissolve the crystalline enzyme.

In a 50 ml FALCON tube, combine:

| Reagent or solution | Amount (ml) | Buffer concentration |
| --- | --- | --- |
| Glycerol (100%) | 25 | 50% (v/v) |
| 1M CaCl$_2$ | 1.5 | 30 mM |
| 1M Buffer Tris-HCl (pH 8.0) | 2.5 | 50 mM |

Start by adding 25 ml 100% glycerol (reading from the graded 50 ml tube), then add water to 40 ml followed by all other stock solutions. Mix gently and thoroughly by inverting the tube many times. Adjust volume to 50 ml. Mix again and readjust volume if necessary. Prepare 1 ml aliquots in 1.5 ml eppendorf tubes, and store at −20° C.

To prepare PK stock solution, pre-chill the above proteinase K storage buffer on ice. Weigh 20 mg of proteinase K (Roche Diagnostics, recombinant) in one 1.5 ml eppendorf tube, then add 1 ml pre-chilled proteinase K storage buffer and immediately transfer to a thermal pack pre-cooled to −20° C. Prepare 80 µl aliquots in pre-chilled 1.5 ml tubes (enough for 24 extractions) and store at −20° C.

PK stock solution loses activity within minutes should it ever reach room temperature. Always prepare and keep PK stock solution in a thermal pack or other suitable container pre-chilled to −20° C.

2.6.6.2 Buffer PKQC (Proteinase K Quality Control), 10 ml

In a 15 mFALCON tube, combine:

| Reagent or solution | Amount (ml) | Buffer concentration |
| --- | --- | --- |
| 1M Buffer Tris-HCl (pH 7.5) | 1 | 100 mM |
| 0.5M EDTA (pH 8.0) | 0.25 | 12.5 mM |
| 5M NaCl | 0.3 | 150 mM |
| SDS solution (20%) | 0.5 | 1% (v/v) |

Add all solutions and adjust volume to 10 ml with water. Mix by inverting the tube.

Store at room temperature.

2.6.6.3 1 M Phenylmethylsulfonyl Fluoride (PMSF) Solution, 1 ml

Dissolve 0.17 g of PMSF powder in 1 ml of 100% DMSO by vortexing.

Store at −20° C.

2.6.6.4 Stop Mix Solution, 10×10 µl

SDS gel loading buffer with PMSF.

In a 1.5 ml eppendorf tube, add 8 µl of 1 M PMSF solution to 100 µl of 4×SDS loading buffer. Mix well by vortexing. Store at room temperature.

2.6.7 Gel Loading Buffer 2.6.7.1 SDS Gel Loading Buffer (4×), 20 ml

In a 50 ml FALCON tube, combine:

| Reagent or solution | Amount | Buffer concentration |
| --- | --- | --- |
| 1M Buffer Tris-HCl (pH 6.8) | 4 ml | 200 mM |
| SDS powder | 1.6 g | 8% |
| Glycerol (100%) | 8 ml | 40% |
| Bromophenol blue | 8 mg | 0.4 mg/ml |
| 2-mercaptoethanol | 4 ml | 2.6M |

Start by adding 8 ml 100% glycerol, then add water to 11 ml followed by all other stock solutions. Mix gently and thoroughly by inverting the tube many times. Adjust volume to 20 ml. Mix again and readjust volume if necessary. Store at room temperature.

3 Procedures 3.1 Introduction

The following RNA extraction protocol was developed to isolate RNA from human urine, serum or citrate-, heparin- and EDTA-plasma samples. The presence of endogenous ribonucleases in these body fluids requires protective steps to recover intact RNA from otherwise protein-bound and thereby protected extracellular RNA. Be aware that biofluids are rich in RNases and DNases and that any spills or contamination of pipetmans, centrifuges or tube holder carry the risk of contaminating and degrading recovered RNA or DNA otherwise free of nucleases.

Using a vacuum manifold, the column-based RNA isolation procedure is at least 2-times faster compared to the usual centrifuge spin protocols.

For sample processing, the specimen is initially mixed with Buffer P (Proteolysis) and heated in order to denature ribonucleoprotein complexes, vesicle-enclosed RNA and RNases. Subsequent proteinase K digestion at 60° C. efficiently degrades protein including RNases, eliminating any possibility for RNA degradation due to renaturation of RNases.

A subsequent organic extraction, using custom-made buffers containing guanidinium isothiocyanate (GITC) and phenol/chloroform, allows the transfer of the majority of DNA and hydrophobic peptide fragments into the organic phase while retaining RNA within the aqueous phase.

The solubility of the RNA is subsequently lowered by the addition of isopropanol and divalent cations to the aqueous phase. This solution is applied to a Zymo-Spin™ I column and handled on the vacuum manifold. Several wash steps ensure the removal of residual DNA, peptides and salts while RNA of 19-nt or longer is retained on the column matrix.

The bound RNA is eluted from the columns in volumes as small as 15 µl, thereby yielding a maximum final RNA concentration for subsequent procedures.

3.2 Organization of Samples and Workflow

The following recommendations (especially points 1-3) are intended for the organization of large sample collections into batches of 24 samples, which are subsequently used for small RNA-based multiplexed cDNA library preparation and high-throughput sequencing. They may however also be relevant for other types of RNA characterization.

1. Avoid combining different biofluid type samples (serum/plasma with urine) into one batch of 24 samples.
2. Include "standardized" samples, which are present at least once in each batch in order to assess the level of reproducibility between batches.

3. If necessary, randomize your samples to avoid introducing biases in ligation, amplification or sequencing caused by adapters or sample categories (healthy or diseased), e.g. avoid assigning samples from one category to the same slot of 24 across different batches, therefore barcoding them with the same 3' adapter.
4. Avoid having sample categories coincide with individual batches, e.g. avoid having one sample category (healthy) that is only present in one batch and another (diseased) that is present only in the other batch.
5. Make sure that all samples contain enough input material (preferably, sample is least a minimum of 475 µl, even more preferably the sample size is 500 µl).
6. Organize the samples you want to use for extraction, make sample lists and print stickers to label the sample tubes.
7. Assess the amount of reagents needed for your purification scale. Make sure you have all the solutions and additives that are required. An overview is given in Table 1S.

TABLE 1S

Overview of reagent solutions needed for RNA isolation of 8, 24 or 96 samples.
3.3 Manual RNA extraction of up to 24 samples

| | Number of Samples (Multiples of 8) | | | | | |
|---|---|---|---|---|---|---|
| | RNA isolation only | | | RNA and DNA isolation combined | | |
| Reagent (ml) | 8 | 24 | 96 | 8 | 24 | 96 |
| Buffer P working solution | 1.0 | 3.0 | 11.3 | 1.0 | 3.0 | 11.3 |
| Proteinase K working solution | 0.3 | 0.9 | 3.1 | 0.3 | 0.9 | 3.1 |
| Buffer ED2 working solution | 5.2 | 15.6 | 52.2 | 5.2 | 15.6 | 52.2 |
| EA3 | — | — | — | 5.5 | 16.5 | 10.5 |
| VB2G + TCEP | 12.1 | 36.0 | 133.2 | 24.2 | 72.0 | 266.4 |
| EW + TCEP | 19.8 | 59.4 | 198.0 | 39.6 | 118.8 | 396.0 |
| 100% ethanol | 9.8 | 24.4 | 98.0 | 19.6 | 48.8 | 196.0 |
| 80% ethanol | 5.0 | 15.0 | 50.0 | 10.0 | 30.0 | 100.0 |

DO NOT cool, heat or centrifuge samples unless instructed by the protocol. If not specified, carry out steps at room temperature. Use thermomixers for both heating and mixing. The term 'tube holder' refers to a piece of equipment of the eppendorf thermomixer and thermomixer R series that allows the transfer of 24 tubes at a time between two mixers. Use filter pipet tips at all times to minimize contamination of pipette shafts with ribonucleases from the sample. Clean your workplace and all technical equipment with 70% ethanol prior to starting to reduce possible contamination by particles carrying RNases. Change gloves frequently or wash gloved hands and dry them using a paper towel, especially after handling nuclease active sample material. Keep centrifuges and pipets clean. Mix working solutions by vortexing unless otherwise instructed when adding additives such as methylene blue, 2-mercaptoethanol, and TCEP.

Before choosing the sample denaturation option in this protocol (see 0 step 5), please also consider looking into the alternative sample denaturation protocol (section 3.3.2), which combines sample aspiration, which combines sample aspiration, addition of Proteinase K working solution, and mixing with buffer P into a single work step using a programmable Rainin multichannel pipette. This approach may be used in automated sample processing.

When using the repeater pipette be careful not to aspirate air bubbles. Also test the dispense function at least once before applying aspirated solutions to samples since every first dispense tends to not contain the entire adjusted volume.

Once started, the procedure should be carried out continuously. Try to avoid pauses during the preparation procedure. Do not process more than 24 samples at a time.

Duration: Initial preparation: 30 min. Extraction: 30 min per batch of 24 samples. Column purification: 60 min per batch of 24. Optional DNA purification and column purification: 90 min per batch of 24.

3.3.1 Preparation of Reagents and Consumables (Manual Processing)

1. Organize your samples (see section 3.2) but keep them frozen at this time.
2. Preheat one heatblock to 60° C. and a second heatblock to 10° C. Make sure these temperatures are reached.
3. Label a first set of 8× or 24×2 ml eppendorf Lo-Bind tubes, e.g. 1.1-1.24 (set 1).
4. Label a second set of 8× or 24×2 ml eppendorf Lo-Bind tubes, e.g. 2.1-2.24 (set 2). Optional: If DNA isolation is intended label a third set of 8× or 24×2 ml eppendorf Lo-Bind tubes, e.g. 3.1-3.24 (set 3).
5. Prepare Buffer P working solution:
   For 8 samples, aliquot 1 ml of Buffer P with 5 µl methylene blue stock into one 2 ml tube and add 19 µl β-mercaptoethanol and 1.9 µl "calibrator pool 1", either c=1 pM each oligonucleotide (urine) or c=10 pM each oligonucleotide (serum or plasma).
   For 24 samples, aliquot two aliquots of 1.47 ml of Buffer P with 7.4 methylene blue stock into two separate 2 ml tubes and to each aliquot add 28.0 µl β-mercaptoethanol and 2.8 µl "calibrator pool 1", c=1 pM each oligonucleotide (urine) or c=10 pM each oligonucleotide (serum or plasma).
   Make sure that buffer P working solution is properly mixed by tumbling or vortexing and is free of bubbles. Buffer P solution may get discolored if kept too long and the level of reducing agent may have dropped due to oxidation. Centrifuge buffer P at room temperature.
6. Aliquot 8× or 24×105 µl of Buffer P working solution (prepared in step 5) into set 1 tubes.
7. Aliquot 8×, or 24×, or 96×1200 µl (twice 600 µl) of Buffer VB2G with TCEP added (0) into each tube set. Optional: if DNA re-extraction from the organic phase is intended, prepare & fill third set of tubes (set 3) accordingly.
8. Label 8× or 24×1.5 ml siliconized tubes with sample identification number (e.g. 1.1 to 1.24, 2.1 to 2.24, etc.). Keep lids closed. The eluted RNA will be collected in these tubes at the end of the purification process. Optional: For DNA re-extraction from organic phase: prepare another set of tubes.
9. Prepare Buffer ED working solution:
   For 8 samples, aliquot 6.75 ml Buffer ED2 (9× master mix) in a 15 ml FALCON tube. Before continuing with RNA extraction, add 23.6 µl 2-mercaptoethanol to Buffer ED.
   For 24 samples, aliquot 18.75 ml Buffer ED2 (25× master mix) in a 50 ml FALCON tube. Before continuing with RNA extraction, add 65.5 µl 2-mercaptoethanol to Buffer ED.

10. Prepare EWL working solution
    For 8 samples, aliquot 17 ml EWL stock solution and add 170 µl of 0.5M TCEP (section 2.6.4.2) into 50 ml FALCON tube.
    For 24 samples, aliquot 50 ml EWL stock solution and add 500 µl of 0.5M TCEP added (section 2.6.4.2) into 50 ml FALCON tube.
    Optional: if DNA re-extraction from the organic phase is intended, prepare twice the amounts listed before.
11. Prepare 100% and 80% ethanol
    For 8 samples, prepare 10 ml 80% ethanol and 10 ml 100% ethanol in 15 ml FALCON tubes. For 24 samples, prepare 30 ml 80% ethanol and 30 ml 100% ethanol in 50 ml FALCON tubes.
    Optional: if DNA re-extraction from the organic phase is intended, prepare twice the amounts listed before.
12. Prepare Proteinase K working solution:
    For 8 samples, aliquot 250 µl 5 M NaCl and 30 µl proteinase K stock (20 mg/ml) into a 1.5 ml reaction tube, mix gently by pipetting.
    For 24 samples, aliquot 750 µl 5 M NaCl and 90 µl proteinase K stock (20 mg/ml) into a 1.5 ml reaction tube, mix gently by pipetting. If a multichannel pipette is to be used for sample aspiration/mixing/proteinase K addition, aliquot PK/NaCl solution as 105 µl fractions into 8 tubes.
    Dispose Proteinase K working solution, and prepare a fresh working solution for the next isolation. The 20 mg/ml proteinase K stock should always be kept at −20° C. using suitable equipment (cooling containers, etc.). At this concentration the enzyme quickly loses activity at all other temperatures. Aliquots of proteinase K solution that reached room temperature should be disposed.
13. Optional: For DNA re-extraction from organic phase:
    For 8 samples, prepare 6.75 ml buffer EA3 in a 15 ml FALCON tube.
    For 24 samples, prepare 18.75 ml buffer EA3 in a 50 ml FALCON tube.
    Also: prepare a third set of tubes (step 4), double the amount of VB2G (step 7), EWL working solution (step 10), 80% ethanol & 100% ethanol (step 11).

3.3.2 Denaturation and Proteolytic Digestion of Samples to Inactivate Ribonucleases 1. Organize your workspace: Have all three tube sets ready in individual tube holders. Tube set 1 containing buffer P working solution, tube set 2 and (optional for DNA isolation) tube set 3 filled with TCEP-added VB2G. Have all required pipettes and tips in place. If you want to use a repeater pipette for applying Proteinase K working solution (step 6), wrap a 1-ml repeater pipette tip in aluminum foil inside a zip lock bag and pre-chill in −20° C. freezer for each batch of samples that you want to process.
2. Preheat one eppendorf thermomixer to 60° C. and a second eppendorf thermomixer to 10° C. Make sure these temperatures are reached.
3. Thaw biofluid samples. For samples in 1.5 ml microcentrifuge tubes thawed with warm air, e.g. by placing sample tubes in tube holders that allow airflow to pass through inside an incubator/shaker pre-heated to 37° C. shaking at 130 rpm for 5-10 min. Watch samples during thawing procedure, remove from incubator when thawed and store at room temperature.
    Homogenize samples by inverting tube racks with sample tubes several times to allow precipitates to dissolve and liquid fractions to mix. Thawed samples are typically maintained at room temperature. DO NOT put thawed urine samples on ice, since this will cause precipitation of salts and other compounds in some samples.
    If the provided sample volume is very low, spin tubes at 50×g for 10 s to minimize losses due to adhesion of sample to the lids.
    Organize sample tubes in a separate tube rack and check sample order.
4. Preheat all 8 or 24 2-ml tubes (tube set 1) containing 105 µl of Buffer P working solution (prepared in section 3.3.1, step 4 & 5) to 60° C. in eppendorf thermomixer for 2 min. Keep tubes at 60° C. in eppendorf thermomixer at until instructed to remove them. At the end of the incubation period open all lids of tube set 1 and of your sample tubes.
5. Addition of biofluid samples:
    Alternative 1: Switch eppendorf thermomixer to interval mixing mode at 60° C. featuring a 3 s mixing phase at 1200 rpm followed by a 3 s pause. During the mixing phase add 450 µl of sample (plasma, serum or urine) to a "set 1" tube containing Buffer P working solution. Aspirate the next sample and position pipette tip with next sample into the next "set 1" tube during mixing pause. You may need to adjust the pause time according to your work speed.
    Alternative 2: Switch eppendorf thermomixer to continuous mixing mode at 60° C. but do not turn on mixing. Add 450 µl biofluid sample to "set 1" tube and immediately after addition of each sample, press quick mixing button for 3 s. Repeat by adding the next biofluid sample into the next "set 1" tube. Upon each sample addition, press the quick mixing button to allow rapid mixing.
    Partially mixed solutions may expose RNA released from proteins to more stable, partially denatured ribonucleases followed by its degradation.
    Alternative 3: Do not switch on mixing function of eppendorf thermomixer. Add 450 µl biofluid sample to "set 1" tube and mix by pipetting up and down at least five times. This can be done reproducibly using automated single channel or multi channel pipettes. If using mixing by eppendorf thermomixer shaking DO NOT EXCEED the recommended mixing speed or time to prevent spillage of the sample. It may be necessary to determine the optimal speed for mixing when using different equipment. Make sure the sample is properly mixed and does not spill out during mixing with open lids!PCT/US
6. Proteolytic digestion:
Alternative 1: Adjust eppendorf thermomixer to 1200 rpm but do not turn on. Add 28 µl Proteinase K working solution (prepared 0, step 12) to each sample. Without closing the tube, mix by activating the thermomixer for a 2 s pulse at 1200 rpm after each addition.
Alternative 2: For faster addition of proteinase K allowing for higher throughput use a repeater pipette and a prechilled 1.0-ml repeater tip (from step 1) to dispense Proteinase K working solution (prepared 0, step 12). Avoid formation of air-bubbles when loading solution. Set dispense volume to 30 µl. Switch eppendorf thermomixer to interval mixing mode at 60° C. featuring a 2 s mixing phase at 1200 rpm followed by a 2 s pause and position repeater pipette above the tube during pause time while ejecting before or during mixing phase. Strictly aim for the liquid to be ejected to the center of the tube, not the tube wall. The viscous PK stock solution sticking to the tube wall at high temperatures will be rendered inactive otherwise.

DO NOT EXCEED suggested mixing speed or time to prevent spillage of the sample. It may be necessary to determine the optimal speed for mixing when using different equipment. Make sure the sample is properly mixed and does not spill out during mixing with open lids!

7. Close all lids, perform protease digestion for 10 min at 60° C., during this period shake gently at 550 rpm. Then stop eppendorf thermomixer mixing but do not turn off heating.
8. Organic extraction
    Alternative 1: Open tubes and add 513 µl of Buffer ED2 working solution containing 2-mercaptoethanol (from 0 step 9). Close tubes after addition, mix vigorously at 1400 rpm for 30 s.
    Alternative 2: Use repeater pipette to dispense Buffer ED2 working solution containing 2-mercaptoethanol (from 0 step 9). Set dispensing volume to 550 µl and aim for the liquid to be ejected against the lower half of the tube wall, not the liquid interface. Aiming directly at the center of the tube will result in spilling of tube contents. Close tubes after addition, mix vigorously at 1400 rpm for 30 s.
9. Transfer entire tube holder (with 24 samples) to second eppendorf thermomixer previously set to 10° C. Cool down sample by mixing vigorously at 1400 rpm for 1 minute.
10. Centrifuge samples in tube holder for 30 s at 50×g to prevent contamination when opening tubes for next step.
11. Add 103 µl chloroform to each tube. Close tubes, mix vigorously at 1400 rpm for 30 s at 10° C. [or: Close tubes, vortex tubes by hand for 30 s at full speed before proceeding. If previously 550 µl of Buffer ED2 working solution had been added using a repeater pipette use 110 µl chloroform instead, the chloroform: ED2 ratio should be 1:5.
12. Centrifuge all tubes at full speed in a microcentrifuge at 4° C. for 5 min.
13. Remove all tubes from the centrifuge, keep at room temperature from now on.
14. Transfer 650 µl from the upper aqueous phase to numbered tubes containing Buffer VB2G (containing TCEP as prepared in section 3.3.1 step 7). Try to avoid carrying over any white interphase material if present. Optional: Keep the organic phase if DNA re-extraction is intended.
15. Vortex. A precipitate may form. DO NOT centrifuge at high speed as an RNA pellet may form that remains behind in the tube.

3.3.3 Optional: Manual DNA Re-Extraction from Organic Phases
1. Add 500 µl of Buffer EA3 to each organic phase (from section 3.3.2, step 14). Close tubes after addition, mix vigorously at 1400 rpm for 30 s.
    When using the repeater pipette to dispense Buffer EA3, aim for the liquid to be ejected against the lower half of the tube wall, not the liquid interface. Aiming directly at the center of the tube will result in spilling of tube contents.
2. Centrifuge all tubes at full speed in a microcentrifuge at 4° C. for 5 min.
3. Remove all tubes from the centrifuge, keep at room temperature from now on.
4. Transfer 600 µl from the upper aqueous phase to numbered tubes containing buffer VB2G, prepared in section 3.3.1, step 7. DO NOT forget to add TCEP in advance. Try to avoid carrying over any white interphase material if present.
5. Vortex. A precipitate may form. DO NOT centrifuge at high speed as an RNA pellet may form that remains behind in the tube.

3.3.4 Column Purification of Nucleic Acids (For Both DNA and RNA Isolation)
1. Load the vacuum manifold with 8 or 24 Zymo-Spin™ I columns for parallel processing of all samples.
2. Connect the vacuum manifold to a vacuum source (in-house lab vacuum valve is sufficient). Turn on vacuum, leave on at all times until prompted to turn off.
3. Carefully pour the isopropanol-containing solution/suspension of each tube (from section 3.3.2, step 15) onto the respective column mounted on the manifold.
4. Wash spin columns with 900 µl EWL working solution (from section 3.3.1 step 10), dispense quickly to remove remaining liquid drops on column walls.
5. Wash spin columns for a second time with 900 µl EWL working solution with (from section 3.3.1 step 10), using previous conditions.
6. Wash spin columns with 900 µl 100% ethanol (from section 3.3.2, step 11) using previous conditions.
    Omitting this step will decrease sample yield at molecular ranges smaller than 45 nt.
7. Wash spin columns with 500 µl 80% ethanol using previous conditions (from section 3.3.2, step 11).
8. Wash spin columns with 500 µl 80% ethanol using previous conditions (from section 3.3.2, step 11).
9. Turn off vacuum. Carefully remove the first column to release the vacuum.
10. Transfer all Zymo-Spin™ I columns into fresh 2-ml collection tubes (use any 2-ml microcentrifuge tube) and place into a microcentrifuge at room temperature.
11. Spin at full speed (≥13,000 rpm) for 5 min to dry silica matrix.
12. Carefully transfer columns into earlier pre-numbered, siliconized 1.5 ml collection tubes (prepared in section 3.3.2, step 8). Discard the 2 ml collection tubes with any liquid inside.
13. To elute, apply 20 µl 10 mM TRIS-HCl, pH 7.4 directly onto the filter matrix.
14. Place all Zymo-Spin™ I column-collection tube assemblies into a microcentrifuge.
15. Incubate for 1 min.
16. To collect eluates, spin at full speed (≥13,000 rpm) for 1 min.
17. Approximately 18 µl of liquid are collected in each siliconized tube (step 12), which is stored at −20° C. Discard Zymo-Spin™ I columns after elution.
18. Store eluates at −20° C.

3.4 Semi-Automated RNA Extraction of Up to 96 Samples
DO NOT cool, heat or centrifuge samples unless instructed by the protocol. If not specified, carry out steps at room temperature. Use thermomixers for both heating and mixing. Tube holder refers to a piece of equipment of the eppendorf thermomixer and thermomixer R series that allows the transfer of 24 tubes at a time between two mixers. Use filter pipet tips at all times.

Clean your workplace and all technical equipment with 70% ethanol prior to starting to reduce possible contamination by particles carrying RNases. Change gloves frequently or wash gloved hands and dry them using a paper towel, especially after handling nuclease active sample material.

Keep centrifuges and pipets clean. Mix working solutions by vortexing unless otherwise instructed when adding additives such as methylene blue, 2-mercaptoethanol, and TCEP.

Before choosing the sample denaturation option in this protocol (see 3.3.2 step 5), please also consider looking into the alternative sample denaturation protocol (section 3.6), which combines sample aspiration, addition of Proteinase K working solution, and mixing with buffer P into a single work step using a programmable Rainin multichannel pipette. This approach may be used in automated sample processing.

When choosing to use the repeater pipette be careful not to aspirate air bubbles when aspirating solutions. Also test the dispense function at least once before applying aspirated solutions to samples since every first dispense tends to not contain the entire adjusted volume.

Once started, the procedure should be carried out continuously. Try to avoid pauses during the preparation procedure. Organize your samples in batches of 24 samples (if applicable). For sample denaturation, RNA extraction and optional DNA extraction do not process more than 24 samples at a time (manual part). For column purification do not process more than 96 samples at a time (automated part).

Duration: Initial preparation: 30 min for 96 samples. Extraction: 30 min per batch of 24 samples. Automated column purification: 90 min. Optional DNA purification and automated column purification: 120 min.

3.4.1 Preparation of Reagents And Consumables (Semi-Automated Processing)

1. Preheat one heatblock to 60° C. and a second heatblock to 10° C. Make sure these temperatures are reached.
2. Label one set of 8× or 24× or 96×2 ml eppendorf Lo-Bind tubes, e.g. 1-24, set 1.
3. When running in low or intermediate throughput (8 to 24 samples), label another set of 8× or 24×2 ml eppendorf Lo-Bind tubes, e.g. 1-24, set 2, and place into epMotion 5075 tube holder. For higher throughput use a 2 ml 96× deep well plate, labeled as set 2.
   Optional: If DNA isolation is intended, label a third set or prepare another 2 ml 96× deep well plate accordingly (set 3). When processing up to 48 samples, you may use the second half of the 2 ml 96× deep well plate.
4. Prepare Buffer P working solution:
   For 8 samples, aliquot 1 ml of Buffer P with 5 µl methylene blue into one 2 ml tube and add 19 µl 2-mercapthoethanol and 1.9 µl "calibrator pool 1", either c=1 pM each oligonucleotide (urine) or c=10 pM each oligonucleotide (serum or plasma). For 24 samples, prepare two aliquots of 1.47 ml of Buffer P with 7.4 methylene blue stock in two separate 2 ml tubes and to each aliquot add 28.0 µl β-mercaptoethanol and 2.8 µl "calibrator pool 1", c=1 pM each oligonucleotide (urine) or c=10 pM each oligonucleotide (serum or plasma).
   For 96 samples, aliquot 11 ml buffer P with 55 µl methylene blue into a 15 ml tube and add 209 µl 2-mercaptoethanol and 20.9 µl "calibrator pool 1", c=1 pM each oligonucleotide (urine) or c=10 pM each oligonucleotide (serum or plasma).
   It is important buffer P is properly mixed by tumbling or vortexing and is free of bubbles. Buffer P solution may get discolored if kept too long and the level of reducing agent may have dropped due to oxidation. Buffer P is centrifuged at room temperature.
5. Use epMotion 5075 script "Xx_BufferP_aliq" to dispense 8× or 24× or 96×105 µl of Buffer P with additives from step 4 into tube set 1 where X=8, 24, or 96.
6. Use epMotion 5075 to aliquot 1200 µl (twice 600 µl) of TCEP-added buffer VB2G (0) into a 2-ml 96× deep well plate (set 2) using the script "S1VBadd only 96s1" for 96 samples. For 48 or 24 samples use the S1 file ending in 48samp or 24samp, respectively).
   Optional: if DNA re-extraction from the organic phase is intended, prepare and fill a third set of tubes (set 3) accordingly.
   After dilution in the experimental setup by addition of 650 µl aqueous RNA sample, as obtained after organic extraction, Buffer concentrations correspond to: VB2G: 15 mM $MgCl_2$ and 5 mM $CaCl_2$, approx. 1 M GITC.
7. Label 96 well PCR plate "elution plate" with sample identification information. Seal plate with adhesive plastic film. The eluted RNA will be collected in this plate at the end of the purification process. Optional: For DNA re-extraction from organic phase: prepare another PCR plate OR use the second half of the PCR plate (for up to 48 samples).
8. Prepare Buffer ED2 working solution:
   For 8 samples aliquot 6.75 ml Buffer ED2 (9× master mix), add 23.6 µl 2-mercaptoethanol and fill into 100 ml tub reservoir.
   For 24 samples aliquot 18.75 ml Buffer ED2 (25× master mix), add 65.5 µl 2-mercaptoethanol and fill into 100 ml tub reservoir.
   For 96 samples aliquot 75 ml Buffer ED2 (100× master mix), add 262 µl 2-mercaptoethanol and fill into 100 ml tub reservoir.
9. Prepare EWL working solution
   For 8 samples, aliquot 17 ml EWL stock solution, add 170 µl TCEP and fill into a 100 ml tub reservoir.
   For 24 samples, aliquot 50 ml EWL stock solution, add 500 µl TCEP and fill into a 100 ml tub reservoir.
   For 96 samples, aliquot 2×100 ml EWL stock solution, add 2×1000 µl TCEP, and fill each aliquot into 100 ml tub reservoir.
   Optional: if DNA re-extraction from the organic phase is intended, prepare twice the amounts listed before.
10. For 8 samples, prepare 10 ml 80% ethanol and 100% ethanol, fill solutions into 100 ml tub reservoirs.
    For 24 samples, prepare 30 ml 80% ethanol and 100% ethanol, fill solutions into 100 ml tub reservoirs.
    For 96 samples, prepare 100 ml 80% ethanol and 100% ethanol, fill solutions into 100 ml tub reservoirs.
    Optional: if DNA re-extraction from the organic phase is intended, prepare twice the amounts listed before.
11. Prepare Proteinase K working solution:
    For 8 samples, aliquot 250 µl 5 M NaCl and 30 µl proteinase K stock (20 mg/ml) into a 1.5 ml reaction tube, mix gently by pipetting.
    For 24 samples, aliquot 750 µl 5 M NaCl and 90 µl proteinase K stock (20 mg/ml) into a 1.5 ml reaction tube, mix gently by pipetting. If a multichannel pipette is to be used for proteinase K addition, aliquot PK/NaCl solution as 105 µl fractions into 8 separate 1.5 ml tubes.
    For 96 samples, aliquot 2750 µl 5 M NaCl and 330 µl proteinase K stock (20 mg/ml) into a 5 ml reaction tube, mix gently by pipetting. If a multichannel pipette is to be used for sample proteinase K addition, aliquot PK/NaCl solution as 385 µl fractions into 8 separate 1.5 ml tubes.

Dispose Proteinase K working solution, and prepare a fresh working solution for the next isolation. The 20 mg/ml proteinase K stock should always be kept at −20° C. using suitable equipment (cooling containers, etc.). At this concentration the enzyme quickly loses activity at all other temperatures. Aliquots that reach room temperature should be disposed of right away.

12. Optional: For DNA re-extraction from organic phase:
    For 8 samples, prepare 6.75 ml buffer EA3 in a 100 ml tub reservoir.
    For 24 samples, prepare 18.75 ml buffer EA3 in a 100 ml tub reservoir.
    For 96 samples, prepare 75 ml EA3 in a 100 ml tub reservoir.
    Also: prepare, double the amount of VB2G (step 6), EWL (step 9), 80% & 100% ethanol (step 10) and prepare a third set of tubes or another 96-well plate filled with VB2G (step 6)

3.4.2 Initial Denaturation and Proteolytic Digestion of Sample to Inactivate Ribonucleases—Manual Part 1. Organize your workspace: Have all three tube sets ready in individual tube holders. Tube set 1 containing buffer P working solution, tube set 2 and (optional for DNA isolation) tube set 3 filled with buffer VB2G with TCEP added. Have all required pipettes and tips in place.
   If you want to use a repeater pipette for applying Proteinase K working solution (see 0 step 6), wrap a 1-ml repeater pipette tip in aluminum foil inside a zip lock bag and pre-chill in −20° C. freezer for each batch of samples that you want to process.

2. Preheat one heatblock to 60° C. and a second heatblock to 10° C. Make sure these temperatures are reached.

3. Thaw biofluid samples. For samples in 1.5 ml microcentrifuge tubes are thawed with warm air, e.g. by placing sample tubes in tube holders that allow airflow to pass through inside an incubator/shaker pre-heated to 37° C. shaking at 130 rpm for 5-10 min. Watch samples during thawing procedure, remove from incubator when thawed and store at room temperature.
   Homogenize samples by inverting tube racks with sample tubes several times to allow precipitates to dissolve and liquid fractions to mix. Thawed samples are maintained at room temperature. Urine samples are never thawed on ice, since this will cause precipitation of salts and other compounds in some samples.
   If the provided sample volume is very low, spin tubes at 50×g for 10 s to minimize losses due to adhesion of sample to the lids.
   Organize sample tubes in a separate tube rack and check sample order.

4. Preheat all 8 or 24 2-ml tubes (tube set 1) from one batch containing 105 µl of Buffer P working solution (prepared in section 3.4.1, step 4 & 5) to 60° C. in eppendorf thermomixer for 2 min. Keep tubes at 60° C. in eppendorf thermomixer at all times until instructed to remove them. At the end of the incubation period open all lids of "set 1" tubes and the biofluid samples.

5. Addition of biofluid samples:
   Alternative 1: Switch eppendorf thermomixer to interval mixing mode at 60° C. featuring a 3 s mixing phase at 1200 rpm followed by a 3 s pause. During the mixing phase add 450 µl of sample (plasma, serum or urine) to a "set 1" tube containing Buffer P working solution. Aspirate the next sample and position the pipette tip with next sample into the next "set 1" tube during mixing pause. You may need to adjust the pause time according to your work speed.
   Alternative 2: Switch eppendorf thermomixer to continuous mixing mode at 60° C. but do not turn on mixing. Add 450 µl biofluid sample to "set 1" tube and immediately after addition of each sample, press quick mixing button for 3 s. Repeat by adding the next biofluid sample into the next "set 1" tube. Upon each sample addition, press the quick mixing button to allow rapid mixing.
   Partially mixed solutions may expose RNA released from proteins to more stable, partially denatured ribonucleases followed by its degradation.
   Alternative 3: Do not switch on mixing function of eppendorf thermomixer. Add 450 µl biofluid sample to "set 1" tube and mix by pipetting up and down at least five times. This can be done reproducibly using automated single channel or multi channel pipettes.
   If mixing by eppendorf thermomixer DO NOT EXCEED the recommended mixing speed or time to prevent spillage of the sample. It may be necessary to determine the optimal speed for mixing when using different equipment. Make sure the sample is properly mixed and does not spill out during mixing with open lids!

6. Proteolytic Digestion:
   Alternative 1: Adjust eppendorf thermomixer to 1200 rpm but do not turn on. Add 28 µl Proteinase K working (prepared 0, step 12) to each sample. Without closing the tube, mix by activating the thermomixer for a 2 s pulse at 1200 rpm after each addition.
   Alternative 2: For faster addition of proteinase K allowing for higher throughput use a repeater pipette and a pre-chilled 1-ml repeater tip (from step 1) to dispense Proteinase K working solution (prepared 0, step 12). Avoid formation of air-bubbles when loading solution. Set dispense volume to 30 µl. Switch eppendorf thermomixer to interval mixing mode at 60° C. featuring a 2 s mixing phase at 1200 rpm followed by a 2 s pause and position repeater pipette above the tube during pause time while ejecting before or during mixing phase. Strictly aim for the liquid to be ejected to the center of the tube, not the tube wall. The viscous PK stock solution sticking to the tube wall at high temperatures will be rendered inactive otherwise.
   DO NOT EXCEED suggested mixing speed or time to prevent spillage of the sample. It may be necessary to determine the optimal speed for mixing when using different equipment. Make sure the sample is properly mixed and does not spill out during mixing with open lids!

7. Close all lids, perform protease digestion for 10 min at 60° C., during this period shake gently at 550 rpm. Then stop eppendorf thermomixer mixing but do not turn off heating.

8. Organic extraction
   Alternative 1: Open tubes and add 513 µl of Buffer ED2 working solution containing 2-mercaptoethanol (from 0 step 9). Close tubes after addition, mix vigorously at 1400 rpm for 30 s.
   Alternative 2: Use repeater pipette to dispense Buffer ED2 containing 2-mercaptoethanol (from 0 step 9). Set dispensing volume to 550 µl and aim for the liquid to be ejected against the lower half of the tube wall, not the liquid interface. Aiming directly at the center of the tube will result in spilling of tube contents. Close tubes after addition, mix vigorously at 1400 rpm for 30 s.
9. Transfer entire tube holder (with 24 samples) to second eppendorf thermomixer previously set to 10° C. Cool down sample by mixing vigorously at 1400 rpm for 1 min.
10. Centrifuge samples in tube holder for 30 s at 50×g to prevent contamination when opening tubes for next step.
11. Add 103 µl chloroform to each tube. Close tubes, mix vigorously at 1400 rpm for 30 s at 10° C. [or: Close tubes, vortex tubes by hand for 30 s at full speed before proceeding. If previously 550 µl of Buffer ED2 working solution had been added using a repeater pipette use 110 µl chloroform instead, the chloroform: ED2 ratio should be 1:5.
12. Centrifuge all tubes at full speed in a microcentrifuge at 4° C. for 5 min.
13. Remove all tubes from the centrifuge, keep at room temperature from now on.
14. Transfer 650 µl from the upper aqueous phase to numbered tubes or 2-ml deep well plate containing buffer VB2G with TCEP added 0, step 6. Try to avoid carrying over any white interphase material if present. Optional: Keep the organic phase if DNA re-extraction is intend
15. Vortex the tubes, or heat-seal the plate and mix by inverting 10 times. A precipitate may form. DO NOT centrifuge at high speed as an RNA pellet may form that remains behind in the tube.

3.4.3 Optional: Manual DNA Re-Extraction from Organic Phase, Manual Part
1. Add 500 µl of Buffer EA3 to each tube (from section 3.4.2, step 14). Close tubes after addition, mix vigorously at 1400 rpm for 30 s.
   When using the repeater pipette to dispense Buffer EA3, aim for the liquid to be ejected against the lower half of the tube wall, not the liquid interface. Aiming directly at the center of the tube will result in spilling of tube contents.
2. Centrifuge all tubes at full speed in a microcentrifuge at 4° C. for 5 min.
3. Remove all tubes from the centrifuge, keep at room temperature from now on.
4. Transfer 600 µl from the upper aqueous phase to deep well plate containing buffer VB2G with TCEP added (see 0 step 6). Try to avoid carrying over any white interphase material if present.
5. Vortex. A precipitate may form. DO NOT centrifuge at high speed as an RNA pellet may form that remains behind in the tube.

3.4.4 Column Purification of Nucleic Acids, Automated Part (Both RNA and DNA Isolation)
1. Load the vacuum manifold with an unused Zymo-I filter plate for parallel processing of all samples. Make sure that "set 2" or "set 3" plate is placed into epMotion 5075. "Set 2" and "set 3" plate refer to VB2G-plate mixed with aqueous phase from organic extraction (section 3.4.2, step 15) or organic re-extraction (section 3.4.3, step 5), respectively.
2. Start epMotion 5075 automated exRNA isolation script "S6-1dfill1+2 96s1" in the folder labeled "RNA only 96s1". From here on out, the script names given will be for 96 samples in this folder. For 24 or 48 samples, find the corresponding script in the folders "DNA+RNA 24 samples" or "RNA 48 samples", respectively.
3. epMotion 5075 loads first portion (1 ml) of isopropanolic aqueous phase (from section 3.4.2, step 15) onto Zymo-I filter plate followed by application of 600 mPa vacuum for 6 min. Confirm that all liquid was applied to the filter plate or apply vacuum for a longer time.
4. epMotion 5075 loads first portion (1 ml) of isopropanolic aqueous phase (from section 3.4.2, step 15) onto Zymo-I filter plate followed by application of 600 mPa vacuum for 7 min and 900 mPa vacuum for 1 min. Confirm that all liquid was applied to the filter plate or apply vacuum for a longer time.
5. Start epMotion 5075 automated exRNA isolation script "S10-Wash pt1 96s1" to apply 970 µl Buffer EWL working solution (from section 3.4.1, step 9) to sample-loaded columns (step 3), followed by application of 800 mPa vacuum for 7 min and high-vacuum for 1 min.
6. epMotion 5075 loads columns with 970 µl Buffer EWL working solution (from 3.4.1, step 9), and applies 600 mPa vacuum for 7 min, followed 900 mPa vacuum for 1 min. Confirm that all liquid was applied to the filter plate or apply vacuum for a longer time.
7. Start epMotion 5075 automated exRNA isolation script "S11-Wash pt2 elute 96s1" to load columns in filter plate with 970 µl 100% ethanol (section 3.4.1, step 10), followed by vacuum for 7 min and high-vacuum for 1 min.
   Omitting this step will result in sample loss, especially at molecular ranges smaller than 45 nucleotides.
8. epMotion 5075 loads columns with 500 µl 80% ethanol (section 3.4.1, step 10), followed by vacuum for 5 min and high-vacuum for 1 min.
9. epMotion 5075 loads columns with 500 µl 80% ethanol (section 3.4.1, step 10), followed by vacuum for 5 min and high-vacuum for 1 min.
10. Remove Zymo-I filter plate from vacuum manifold, seal it with adhesive foil (no heat seal) and place it above 96 well PCR plate. Place this assembly into centrifuge basket for 96 well plates and place into a centrifuge. Insert an appropriate counterweight to balance weight inside centrifuge rotor.
11. Spin at full speed (e.g. 3700×g) for 5 min to dry silica matrix.
12. Remove seal and place Zymo-I filter plate back into epMotion 5075 vacuum manifold. Discard the liquid in 96 well PCR plate used for collection. If sealed and stored clean, this 96 PCR plate can be reused for step 8 & 9 in another purification.
13. To elute RNA, have epMotion 5075 apply 21 µl 10 mM TRIS, pH 7.4 directly onto the filter matrix.
14. Remove Zymo-I filter plate from vacuum manifold, seal it with an adhesive seal (no heat seal) and place it above 96 PCR plate. Place this assembly into centrifuge basket for 96 well plates and place into a centrifuge. Insert an appropriate counterweight to balance weight inside centrifuge rotor.
15. Incubate for 1 min.
16. To collect eluates, spin Zymo-I at full speed (3700×g) for 5 min.
17. Approximately 18 µl of liquid are collected in each siliconized tube, which is stored at −20° C. Discard Zymo-I filter plate or label the used sections of the plate for later purifications.
18. Seal PCR plate and store eluates at −20° C.

3.5 Fully Atomated RNA Etraction of U to 96 Smples
DO NOT cool, heat or centrifuge samples unless instructed by the protocol. If not specified, carry out steps at room temperature. Clean your workplace, the epMotion 5075 and all technical equipment with 70% ethanol prior to starting to reduce possible contamination by particles carrying RNases. Change gloves frequently or wash gloved hands and dry them using a paper towel, especially after handling nuclease active sample material. Keep centrifuges and pipets clean.

Before choosing the sample denaturation option in this protocol (see 3.5.2 step 5), please also consider looking into the alternative sample denaturation protocol (section 3.6), which combines sample aspiration/addition of Proteinase K working solution and mixing with buffer P into a single work step using a programmable Rainin multichannel pipette. This approach may be used in automated sample processing.

When choosing to use the repeater pipette be careful not to aspirate air bubbles when aspirating solutions. Also test the dispense function at least once before applying aspirated solutions to samples since every first dispense tends to not contain the entire adjusted volume.

Once started, the procedure should be carried out continuously. Try to avoid pauses during the preparation procedure. Organize your samples in batches of 24 samples (if applicable). Do not process more than 96 at a time.

Duration: Initial preparation: 30 min. for 96 samples. Extraction: 60 min for 96 samples. Automated column purification: 90 min. Optional DNA purification: 120 min for 96 samples.

3.5.1 Preparation of Reents and Consumables (Fully Automated Processing)

1. Organize your samples (see section 3.2) but keep them frozen at this time.
2. Preheat one heatblock to 60° C. and a second heatblock to 10° C. Make sure these temperatures are reached.
3. Preparation of Buffer P working solution:
   For 8 samples, aliquot 1 ml of Buffer P with 5 µl methylene blue stock into one 2 ml tube and add 19 µl β-mercaptoethanol and 1.9 µl "calibrator pool 1", either c=1 pM each oligonucleotide (urine) or c=10 pM each oligonucleotide (serum or plasma).
   For 24 samples, prepare two aliquots of 1.47 ml of Buffer P with 7.4 methylene blue stock in two separate 2 ml tubes and to each aliquot add 28.0 µl β-mercaptoethanol and 2.8 µl "calibrator pool 1", c=1 pM each oligonucleotide (urine) or c=10 pM each oligonucleotide (serum or plasma).
   For 96 samples, aliquot 11 ml buffer P with 55 µl methylene blue stock into a 15 ml tube and add 209 µl 2-mercaptoethanol and 20.9 µl "calibrator pool 1", c=1 pM each oligonucleotide (urine) or c=10 pM each oligonucleotide (serum or plasma).
   Make sure that buffer P working solution is properly mixed by tumbling or vortexing and is free of bubbles. Buffer P working solution may get discolored if kept too long and the level of reducing agent may have dropped due to oxidation.
   Label a 1-ml deep well plate "set 1". Use epMotion 5075 script "S1-P+VBadd96s1" to aliquot 105 µl buffer P with additives from step 1 into a 1-ml deep well plate.
4. Label 2-ml 96× deep well plate "set 2". Use epMotion 5075 script "S1-P+VBadd96s1" to aliquot 1200 µl (twice 600 µl) of TCEP-added buffer VB2G into a 2-ml 96× deep well plate (set 2). Optional: if DNA re-extraction from the organic phase is intended, prepare and fill a third plate ("set 3") accordingly using epMotion script "S1-VB add only 96s1" in the folder "DNA 2ndext 96s1".
5. Label 96 well PCR plate "elution plate" with sample identification information. Seal plate with adhesive plastic film. The eluted RNA will be collected in this plate at the end of the purification process. Optional: For DNA re-extraction from organic phase: prepare another PCR plate OR use the second half of the PCR plate (for up to 48 samples).
6. Prepare Buffer ED working solution:
   For 8 samples aliquot 6.75 ml Buffer ED2 (9× master mix), add 23.6 µl 2-mercaptoethanol and fill into 100 ml tub reservoir.
   For 24 samples aliquot 18.75 ml Buffer ED2 (25× master mix), add 65.5 µl 2-mercaptoethanol and fill into 100 ml tub reservoir.
   For 96 samples aliquot 75 ml Buffer ED2 (100× master mix), add 262 µl 2-mercaptoethanol and fill into 100 ml tub reservoir.
7. Prepare EWL working solution
   For 8 samples, aliquot 17 ml EWL stock solution, add 170 µl TCEP and fill into a 100 ml tub reservoir.
   For 24 samples, aliquot 50 ml EWL stock solution, add 500 µl TCEP and fill into a 100 ml tub reservoir.
   For 96 samples, aliquot 2×100 ml EWL stock solution, add 1000 µl TCEP, and fill each aliquot into 100 ml tub reservoir.
   Optional: if DNA re-extraction from the organic phase is intended, prepare twice the amounts listed before.
8. For 8 samples, prepare 10 ml 80% ethanol and 100% ethanol, fill solutions into 100 ml tub reservoirs.
   For 24 samples, prepare 30 ml 80% ethanol and 100% ethanol, fill solutions into 100 ml tub reservoirs.
   For 96 samples, prepare 100 ml 80% ethanol and 100% ethanol, fill solutions into 100 ml tub reservoirs.
   Optional: if DNA re-extraction from the organic phase is intended, prepare twice the amounts listed before.
9. Prepare Proteinase K working solution:
   For 8 samples, aliquot 250 µl 5 M NaCl and 30 µl proteinase K stock (20 mg/ml) into a 1.5 ml reaction tube, mix gently by pipetting.
   For 24 samples, aliquot 750 µl 5 M NaCl and 90 µl proteinase K stock (20 mg/ml) into a 1.5 ml reaction tube, mix gently by pipetting. If a multichannel pipette is to be used for sample proteinase K addition, aliquot PK/NaCl solution as 105 µl fractions into 8 tubes.
   For 96 samples, aliquot 2750 µl 5 M NaCl and 330 µl proteinase K stock (20 mg/ml) into a 5 ml reaction tube, mix gently by pipetting. If a multichannel pipette is to be used for sample proteinase K addition, aliquot PK/NaCl solution as 385 µl fractions into 8 tubes.
   Dispose Proteinase K working solution, and prepare a fresh working solution for the next isolation. The 20 mg/ml proteinase K stock should always be kept at −20° C. using suitable equipment (cooling containers, etc). At this concentration the enzyme quickly loses activity at all other temperatures. Aliquots of proteinase K that reach room temperature should be disposed.
10. Optional: For DNA extraction from organic phase:
    For 8 samples, prepare 6.75 ml buffer EA3 in a 100 ml tub reservoir.
    For 24 samples, prepare 18.75 ml buffer EA3 in a 100 ml tub reservoir.
    For 96 samples, prepare 75 ml EA3 in a 100 ml tub reservoir.

Also: double the amount of EWL working solution (step 9), 80% & 100% ethanol (step 10), VB2G and prepare another 96-well plate filled with VB2G (step 4).

3.5.2 Denaturation and Proteolytic Digestion of Samples to Inactivate Ribonucleases 1. Organize your workspace: Have all deep well plate sets ready. Plate "set 1" is filled with Buffer P working solution, "set 2" and (optional for DNA isolation) "set 3" is filled with buffer TCEP-added VB2G. Have all required filled reservoir tubs: 2-mercaptoethanol-added ED2 working solution, chloroform, TCEP-added EWL working solution, 80% ethanol, 100% ethanol (and EA3 if doing DNA extractions) and place them into epMotion 5075. Make sure pipette tools and tips are in in place. Check that epMotion's liquid and consumable waste containers are empty.
2. Start epMotion 5075 automated exRNA isolation script "S2-ED2+chloEx 96s1" in the folder labeled "RNA only 96s1". From here on out, the script names given will be for 96 samples in this folder. For 24 or 48 samples, find the corresponding script in the folders "DNA+RNA 24 samples" or "RNA 48 samples", respectively. It will take about 10 min for the heat blocks to reach their assigned temperatures 65° C. and 10° C. During this time you can proceed with the next step.
3. Thaw your samples. For biofluid samples in 1.5 ml microcentrifuge tubes thawed with warm air, e.g. by placing sample tubes in tube holders that allow airflow to pass through inside an incubator/shaker pre-heated to 37° C. shaking at 130 rpm for 5 to 10 min. Watch thawing process, remove samples from incubator once thawed.
   Homogenize samples by inverting tube racks with sample tubes several times to allow precipitates to dissolve and liquid fractions to mix. Thawed samples are maintained at room temperature. DO NOT put thawed urine samples on ice, since this will cause precipitation of salts and other compounds in some samples. Manually fill samples into a 0.5 ml deep well plate (input plate) with at least 475 µl of sample per well. If the provided sample volume is very low, spin tubes at 50×g for 10 s to minimize losses due to adhesion of sample to the lids.
4. Before proceeding, make sure that the epMotion heatblocks have reached their temperatures 65° C. and 10° C. Use epMotion 5075 to preheat 1-ml lysis plate containing 105 µl of Buffer P working solution (prepared in section 3.5.1, step 3, 4) to 65° C. in eppendorf thermomixer for 2 min.
5. Place 0.5 ml input plate filled with biofluid samples into epMotion 5075. Press "Continue" to continue script "S1.5-Sampleadd_BufferP" 450 µl of biofluid sample will be transferred into set 1 deep well plate (sample denaturation), followed by quick mixing at 1200 rpm for 10 s.
   Note: DO NOT EXCEED this speed to prevent spillage of the sample. It may be necessary to determine the optimal speed for mixing when using different equipment. Make sure the sample is properly mixed!
6. epMotion 5075 adds 28 µl Proteinase K working solution to each lysis reaction, followed by mixing at 1200 rpm for 1 min.
7. epmotion 5075 mixes samples for 8 min at 65° C. at 450 rpm.
8. epMotion 5075 adds 517 µl of Buffer ED2 working solution with 2-mercaptoethanol added (from section 3.5.1, step 5) to each sample position, followed by mixing at 800 rpm for two min.
9. epMotion 5075 transfers set 1 plate (denaturation plate) to thermoblock at 10° C. and cools plate and sample for 8 min.
10. epMotion 5075 adds 103 µl chloroform to each "set 1" sample position, followed by 5 mixing tasks by up and down pipetting.
11. Remove denaturation plate ("set 1") from epMotion 5075 and check lysis plate for spillage/splashing. Remove any splashed liquid by carefully patting the top of the plate with a Kim wipe. Seal plate with adhesive seal made of aluminum foil.
12. Centrifuge "set 1" plate at 3700×g for 5 min at 4° C. Check that two phases well separated phases formed: The lower (organic) phase should be blue, there should be no interphase, and the top (aqueous) phase should be colorless.
13. Carefully remove sealing foil and place the plate back into epMotion 5075. Start epMotion 5075 automated exRNA isolation script "S3-aquaasp1 96s1".
14. epMotion 5075 transfers 645 µl from aqueous phase (top) of the lysis plate (including some air) to "set 2" deep well plate (RNA binding plate) containing buffer VB2G, (prepared in section 3.5.1, step 4). Step 3.5.4 for RNA purification is done prior to re-extraction DNA (3.5.3).

3.5.3 Optional: Automated DNA Re-Extraction from Organic Phase

The following steps should be carried out continuously, try to avoid pauses during the preparation procedure.

1. Run epMotion 5075 automated exRNA isolation script "S4-2ndorgex 96s1".
2. epMotion 5075 adds 500 µl of Buffer EA3 to each tube (from section 3.5.2, step 14).
3. Heat seal the multiwell plate by pressing down on the foil with the sealer for at least 2 s. Mix by inverting 10 times.
4. Centrifuge multiwall plate at full speed in a microcentrifuge at 4° C. for 5 min.
5. Remove multiwell plate from the centrifuge, keep at room temperature from now on.
6. Use epMotion 5075 script "S5-aquaasp2 96s1" to transfer 600 µl from the upper (aqueous) phase to "set 3" deep well plate containing Buffer VB2G with TCEP added, prepared in section 3.5.1 step 4, followed by five-fold mixing by pipetting up and down.

3.5.4 Column Purification of Nucleic Acids—Automated Part

1. Load the vacuum manifold with an unused Zymo-I filter plate for parallel processing of all samples. Make sure that "set 2" or "set 3" plate is placed into epMotion 5075. "Set 2" and "set 3" plate refer to VB2G-plate mixed with aqueous phase from organic extraction (section 3.5.2 step 14) or organic re-extraction (section 3.5.3, step 6), respectively.
2. Start epMotion 5075 automated exRNA isolation script "S6-1dfill1+2 96s1".
3. epMotion 5075 loads first portion (1 ml) of isopropanolic aqueous phase (from section 3.5.2, step 14, or 3.5.3, step 6) onto Zymo-I filter plate, followed by application of 600 mPa vacuum for 6 min. Confirm that all liquid was applied to the filter plate or apply vacuum for a longer time.

4. epMotion 5075 loads second portion (1 ml) of isopropanolic aqueous phase, followed by application of 600 mPa vacuum for 7 min and 900 mPa vacuum for 1 min. Confirm that all liquid was applied to the filter plate or apply vacuum for a longer time.
5. Start epMotion 5075 automated exRNA isolation script "S10-Wash pt1 96s1" to load columns with 970 µl Buffer EWL with TCEP added (from section 3.5.1, step 7), and applies vacuum for 7 min, followed by high-vacuum for 1 min. Confirm that all liquid was applied to the filter plate or apply vacuum for a longer time.
6. epMotion 5075 loads columns with 970 µl Buffer EWL with TCEP added (from section 3.5.1, step 7), and applies 600 mPa vacuum for 7 min, followed 900 mPa vacuum for 1 min. Confirm that all liquid was applied to the filter plate or apply vacuum for a longer time.
7. Start epMotion 5075 automated exRNA isolation script "S11-Wash pt2 elute 96s1" to load columns with 970 µl 100% ethanol (section 3.5.1, step 8), followed by vacuum for 7 min and high-vacuum for 1 min.
   Omitting this step will result in sample loss, especially at molecular ranges smaller than 45 nucleotides.
8. epMotion 5075 loads columns with 500 µl 80% ethanol (section3.5.1, step 8), followed by vacuum for 7 min and high-vacuum for 1 min.
9. epMotion 5075 loads columns with 500 µl 80% ethanol (section3.5.1, step 8), followed by vacuum for 7 min and high-vacuum for 1 min.
10. Remove Zymo-I filter plate from vacuum manifold, seal it with adhesive foil (no heat seal) and place it above 96 well PCR plate. Place this assembly into centrifuge basket for 96 well plates and place into a centrifuge. Insert an appropriate counterweight to balance weight inside centrifuge rotor.
11. Spin at full speed (e.g. 3700×g) for 5 min to dry silica matrix.
12. Remove seal and place Zymo-I filter plate back into epMotion 5075 vacuum manifold. Discard the liquid in 96 well PCR plate used for collection. If sealed and stored clean, this 96 PCR plate can be reused for step 8 & 9 in another purification.
13. To elute RNA, have epMotion 5075 apply 21 µl 10 mM TRIS, pH 7.4 directly onto the filter matrix.
14. Remove Zymo-I filter plate from vacuum manifold, seal it with an adhesive seal (no heat seal) and place it above 96 PCR plate. Place this assembly into centrifuge basket for 96 well plates and place into a centrifuge. Insert an appropriate counterweight to balance weight inside centrifuge rotor.
15. Incubate for 1 min.
16. To collect eluates, spin at full speed e.g. 3700×g for 5 min.
17. Approximately 18 µl of liquid are collected in each siliconized tube, which is stored at −20° C. Discard Zymo-I filter plate. Or label which part has been used and save unused columns for additional purifications.
18. Seal PCR plate and store eluates at −20° C.

3.6 Alternative Denaturation Procedure

A 96-deep well lysis plate filled with 105 µl aliquots of buffer P (section3.5.1, step 3) is preincubated at 65° C. for 2 min.

Using a Rainin multichannel electronic pipette with adjustable spacing, aspirate 28 µl of Proteinase K working solution (section3.5.1, step 9) from 8 1.5 ml microcentrifuge tubes, followed by a brief rinse of the pipette tips with water. Next, 100 µl of air are aspirated followed by 450 µl of biofluid sample from 8 1.5 or 2 ml microcentrifuge tubes. During this step the PK/NaCl and biofluid are aspirated into the same tip, but the two liquids do not mix.

The spacing of the pipette is then adjusted such that the tips fit into the 2-ml deep well plate filled with buffer P working solution. The contents of the tips are added to the first column and mixed with the buffer P working solution by pipetting up and down 5 times. This is repeated twelve times until all 96 samples have been added.

The deep well plate containing the denaturation samples/ proteolytic digestions is then inserted into epMotion 5075, and the RNA isolation is continued at step 7 (section3.5.2).

4 Effective Concentrations During Purification and Parameters Influencing Purification Efficiency Denaturation Step:

To each sample of 450 µl biofluid, 105 µl Buffer P to 25 µl 5 M NaCl, 3 µl proteinase K were added to obtain a final volume of 583 µl and a final working concentration of approx. 12 mM Buffer Tris-HCl (pH 7.5), 215 mM NaCl, 2 mM EDTA, 50 mM 2-mercapthoethanol and 5.4% SDS during extraction. Lower Proteinase K activity was observed at a lower NaCl concentration of 50 mM.

NaCl is not added to Buffer P before the biofluid sample is added because the resulting high NaCl and SDS concentrations would lead to precipitation of Na SDS.

Proteolysis Step:

Proteinase K stock loses activity within minutes if not at cold temperatures. Proteinase K stock is maintained at −20° C. at all times. However, proteinase K diluted to approximately 2.1 mg/ml in 5 M NaCl can tolerate higher temperatures, and this stock is maintained on ice at the time of preparation or at room temperature when it is added to the samples.

To accelerate proteolysis and obtain a more complete denaturation of ribonucleases, the digest is performed at 60° C. An incubation temperature of 65° C. was chosen for the automated setup to compensate for the fact that the heat transfer is less optimal when using the epMotion thermomixer 5075.

Organic Extraction Step:

After denaturation and proteolysis, addition of 513 µl buffer ED2 working solution containing 37.4 mM Na Citrate, 0.4% sarcosyl, 1.6 M GITC and 80.4% Phenol, brought the effective concentrations to approximately 3.0% SDS, 6.6 mM TRIS, 1.0 mM EDTA, 120 mM NaCl, 18.5 mM Na Citrate, 0.2% sarcosyl, 0.8 M GITC, 30 mM 2-ME and 40% phenol at total volume of approximately 1040 µl. Phase separation is induced by adding 103 µl of chloroform, followed centrifugation.

After phase separation, the effective concentrations in the aqueous phase are approximately 12.5 mM TRIS, 1.9 mM EDTA, 225 mM NaCl, 35 mM Na Citrate and 1.5 M GITC.

Make sure that chloroform is added at a ratio of 1:5 with regards to ED2 working solution to partition DNA into the organic phase while keeping RNA in the aqueous phase.

Noticeable interphase after organic extraction likely indicates failure incomplete proteolytic digestion. Prepare a fresh Proteinase K stock and working solution.

If a more stringent organic extraction is required, e.g. to address remaining RNase activity observed during purification, 750 µl of ED2 working solution can be added and phase separation can be induced by addition of 150 µl chloroform. If this variant is used, make sure to maintain the same ratio of aqueous phase to VB2G working solutions, e.g. mix approx. 650 µl of aqueous phase obtained after aqueous phase with 1600 µl of VB2G.

Binding to Silicate Columns

After mixing approximately 525 µl of aqueous phases from organic extractions with buffer VB1G working solution resulting effective concentrations are approximately 10.5 mM sodium citrate, 0.3 mM EDTA, 68.5 mM NaCl, 5.0 mM MgCl$_2$, 2.1 mM CaCl$_2$, 0.9 M GITC, 68.3% isopropanol.

Please make sure the isopropanol concentration is at least 66% to avoid losses of RNAs shorter than 25 nt due to incomplete column binding.

Make sure that the GITC concentration is at least 0.9 M to avoid precipitation of peptides in the aqueous phase upon addition of isopropanol.

Organic Re-Extraction

The concentrations of the aqueous phase after re-extraction of the organic phase with solution EA3 are expected to resemble those of solution EA3 which contains 4 M GITC.

Please make sure that you use an aqueous solution containing at least 3 M GITC to partition DNA from the organic phase into the aqueous phase.

5 Proteinase K Quality Control Assay 5.1.1 Introduction

This assay evaluates the proteolytic activity of a batch of proteinase K (PK) stock solution (prepared in section 2.6.6.1) using fetal bovine serum (FBS) as protein substrate for degradation.

It compares proteolytic activity of fresh PK stock solution (prepared in section 2.6.6.1) stored at −20° C. and PK stock solutions incubated at room temperature for 2 and 5 min, respectively. To compare proteolytic potency, all three PK stock solutions will be incubated with substrate (FBS) for 3, 10 and 30 min, respectively.

To stop the reaction at a precise time point, a stop mix solution containing PMSF protease inhibitor and SDS is used.

PK activity is assessed for every new commercial PK powder batch to verify that it has the desired activity for follow-up applications. PK solutions may lose activity even when incubated shortly at room temperature or above. PK stock solutions are prepared and stored at −20° C. at all times and using pre-chilled thermal packs while PK stock solutions are handled.

5.1.2 Setup

Always keep PK stock solution at −20° C. in a thermal pack if not deliberately instructed to do otherwise.

1. Preheat eppendorf thermomixer to 50° C.
2. In a 1.5 ml eppendorf tube, prepare a 4× master mix as proposed in the table below and mix by vortexing. Aliquot 148.5 µl of this master mix into three 1.5 ml eppendorf tubes labeled with 'a', 'b' and 'c'. Keep tubes at room temperature.

| Reagent or solution | Per sample, 1x (µl) | Master mix, 4x (µl) |
|---|---|---|
| FBS | 120 | 420 |
| Buffer PKQC | 28.5 | 114 |

3. To prepare a negative control sample, transfer 30 µl of the master mix prepared in step 2 into one 10 µl aliquot of stop mix solution (prepared in section 2.6.6.4).
4. Label two 1.5 ml eppendorf tubes with 2 and 5 min, respectively. Place them into an appropriate tube rack at room temperature.

5.1.3 Quality Control Assay

5. Prepare a Timer.
6. Start the timer and swiftly transfer 5 µl PK stock solution in one 1.5 ml eppendorf tube labeled in step 4 and kept at room temperature. Incubate 5 min at room temperature.
7. 3 min after completing step 6, swiftly transfer 5 µl PK stock solution in one 1.5 ml eppendorf tube labeled in step 4 and kept at room temperature. Incubate 2 min at room temperature.
8. Start the assay reaction by adding 1.5 µl PK stock solution (chilled at −20° C.) to tube 'a' (prepared in step 2), 1.5 µl 2 min pre-incubated PK stock solution (from step 7) to tube 'b' (prepared in step 2), and 1.5 µl 5 min pre-incubated PK stock solution (from step 6) to tube 'c' (prepared in step 2). Briefly mix by vortexing and immediately transfer all three tubes to the 50° C. eppendorf thermomixer.
9. After 3 min, 10 min and 30 min, transfer 30-µl aliquots of each tube (a, b, c) into the according 10 µl stop mix tube (prepared and labeled in section 0).

| | PK stock solution, time at RT (min) | | incubation at 50° C. (min) | | stop mix tube label |
|---|---|---|---|---|---|
| tube a (prepared in step 2) | 0 | → | 3 | → | a3 |
| | | | 10 | | a10 |
| | | | 30 | | a30 |
| tube b (prepared in step 2) | 2 | → | 3 | → | b3 |
| | | | 10 | | b10 |
| | | | 30 | | b30 |
| tube c (prepared in step 2) | 5 | → | 3 | → | c3 |
| | | | 10 | | c10 |
| | | | 30 | | c30 |

10. Denature all sample tubes (from step 9) at 90° C. for 3 min.
11. Prepare a mini-PROTEAN TGX 4-20% gradient gel for SDS PAGE in the appropriate running chamber using a 1× dilution of the 10× Tris/glycine buffer (Bio-rad).
12. Load 2 µl of each denatured sample on this gel.
13. Run the gel at 150 V for 50 min until the blue dye ran to the bottom edge of the gel.
14. To stain the gel, disassemble the plastic scaffold and place gel in a plastic tray. Add 50 ml Coomassie brilliant blue protein gel staining solution and keep on shaker at room temperature and shake gently for one hour. Make sure the entire gel is covered in staining solution. To de-stain, remove the staining solution and add 50 ml of Coomassie gel de-staining solution. Keep on shaker at room temperature, shake gently and make sure that the gel is covered completely in solution at all times. De-stain for 1-3 h, change de-staining solution once in-between.

5.1.4 Exemplary Results

On a 4-20% PAGE gel, running FBS only shows two major bands at 68 and 60 kDa, respectively FIG. 8. Using a correctly stored PK stock solution, a 30 min incubation time is sufficient to completely degrade the most prominent 68 kDa FBS band (FIG. 8; tube a, 30 min). Decreasing this incubation time generally results in less FBS degradation, hence the increase protein band strengths (FIG. 8; tube a, b & c, 3-10 min). Pre-incubation of PK stock solutions at room temperature for 2 or 5 min impairs the expected degradation process of the 68 kDa band (FIG. 8; tube b & c).

6 RNA Concentration Determination

6.1.1 Nanodrop (ThermoScientific)

The Nanodrop photometer allows for the determination of RNA concentrations in sample volumes of 0.5-2 µl. Typically 1 µl is used to avoid variability in the reading. The reported upper and lower concentration limits for accurate detection are 4 ng/µl and 14 µg/µl, respectively, according to the manufacturer's specifications. Samples in an expected concentration range greater than 10 ng/µl should be photometrically evaluated whereas samples with suspected lower concentrations (0.1-4 ng/µl), or samples containing possible UV-absorbent contaminants (e.g. protein, phenol) should be processed using the Qubit RNA HS assay.

6.1.2 Qubit RNA HS QAssay Dye (Invitrogen)

The Qubit 2.0 fluorometer is a small instrument used for low concentration DNA, RNA, and protein quantification (U.S. Pat. No. 7,776,529). The Qubit RNA HS assay utilizes a methionine-substituted cyanine dye. The Qubit HS RNA assay has some advantages over UV-absorbance-based quantification methods (e.g. Nanodrop; ThermoScientific). Since it is a fluorescence-based method, it is very sensitive and UV-absorbing compounds unresponsive to the fluorophore do not interfere.

In absence of nucleic acid, the dye alone shows little fluorescence emission in the 600-700 nm range (FIG. 9). Addition of RNA to diluted Qubit HS RNA dye increased fluorescence intensity within this range (FIG. 10).

The fluorescent adduct formed with RNA is approximately 10 times than for DNA. The substituted group on the methine bridge is believed to confer specificity to RNA over DNA (FIG. 11). The fluorescence intensity increases with increasing concentration of RNA or DNA.

The dye demonstrates an equal affinity for the three different species of rRNA, tRNA, and mRNA as long as these are composed of pools of variable sequence (FIG. 12).

Fluorescence emission of the dye is dependent on the RNA sequence and presumably also secondary structure of the RNA. Short oligoribonucleotides (22 nt) display rather variable fluorescence, but when combined, the average mirrors the signal observed for HEK293 total RNA at the same nucleic acid concentration (FIG. 13).

Hydrolyzed total RNA shows comparable fluorescent enhancement compared to non-hydrolyzed total RNA, i.e. the length of the RNA is not critical (FIG. 14).

Invitrogen recommends the assay for the undiluted input RNA concentrations between 5-100 ng per ml. Sample volumes of 5-10 10 µl are used and the detection range for 1-80 ng input total RNA in that volume (FIG. 15) is verified.

This means that in order to accurately report the concentration of a RNA solution of 0.1 ng/µl, 10 µl of the solution needs to be combined with 190 µl of Qubit working solution to yield sufficient fluorescence increase over background to be measured accurately.

6.1.2.1 Calibration Standards for the Qubit RNA HS Assay

Fully 2'-OMe-modified oligoribonucleotide resistant to nuclease degradation as calibration standard for the Qubit RNA HS Assay (Invitrogen) is used herein. 2'-OMe-let-7a-1 RNA is purchased from IDT DNA ($170 for 100 nmol). Enter below sequence into custom DNA oligonucleotide synthesis form (IDT considers 2'-OMe a DNA and not an RNA modification). 'm' before base designates 2'-OMe modification. This particular RNA sequence shows about 13× lower fluorescence than total RNA at the same concentration, otherwise the fluorescence signal is linear with increasing concentrations (FIG. 16).

6.1.2.2 Preparation of RNA Standards for Concentration Measurements Using the Qubit Fluorometer 1. Determine the concentration of the 2'-OMe let-7a calibration standard by measuring the absorbance on the Nanodrop. Alternatively, a 1:100 dilution of the standard can also be measured using the traditional UV spectrophotometer at 260 nm.

2. Dilute the calibration standard in water to produce 1000 µl of standard of $OD_{260}=4$ (Table. 1). Measure the mass of volumes to accurately determine the final expected A260 absorbance.

3. Dilute 125 µl of this $OD_{260}=4$ standard with 875 µl water to arrive at 1000 µl of an $OD_{260}=0.5$ standard (Table. 1). This concentration produces fluorescence values 1.5× above background with the Qubit HS assay and corresponds to approximately 2.5 ng/µl total RNA.

4. Make 50 µl aliquots of both 2'-OMe-let-7a $OD_{260}=4$ and $OD_{260}=0.5$ calibration standards. Store aliquots both short and long-term at −20° C.

TABLE 2S

Example preparation of 2'-OMe-let-7a-1 standard for Qubit

| $C_1 V_1 = C_2 V_2$ | $C_1$ | $C_2$ | $V_2$ | $V_1$ | $V_2 - V_1$ | | |
|---|---|---|---|---|---|---|---|
| | concentrated standard $OD_{260}$ (AU) | diluted standard $OD_{260}$ (AU) | final volume (µl) | concentrated standard (µl) | water (µl) | mass $dH_2O$ (g) | final mass (g) |
| $V_2 = \frac{C_1}{C_2} \times V_1$ | | | | | | | |
| $V_2 = \frac{4}{70} \times 1000 \, \mu l$ | 70 | 4 | 1000 | 57.2 | 942.8 | 0.94 | 1.00 |
| $V_2 = \frac{0.50}{4} \times 1000 \, \mu l$ | 4 | 0.50 | 1000 | 125 | 875 | 0.88 | 1.00 |

A260 to ng/µl conversion

| $A = \varepsilon \times l \times c$ | A | ε | l | c | | | |
|---|---|---|---|---|---|---|---|
| $c = \frac{A}{\varepsilon \times l}$ | $OD_{260}$ (AU) | extinction coefficient $\left(\frac{L}{mol \times cm}\right)$ | path length (cm) | concentration (M) | concentration (µM) | molecular mass (g/mol) | concentration (ng/µl) |

TABLE 2S-continued

Example preparation of 2'-OMe-let-7a-1 standard for Qubit

| | | | | | | | |
|---|---|---|---|---|---|---|---|
| $c = \dfrac{0.5}{228000 \times 1}$ | 0.5 | 228000 | 1 | $2.19 \times 10^{-6}$ | 2.19 | 7089.6 | 15.5 |

6.1.2.3 Measuring Samples with the Qubit 2.0 Fluorometric Assay

General Information

The assay requires a 2 min incubation of the RNA with the diluted assay dye before measurement on the Qubit device. The fluorescence signal of the Qubit RNA HS assay dye is stable for 3 h at RT after the addition of RNA. To work within this timeframe, plan an appropriate number of samples to measure together in parallel. (Sets of 24 samples or less are recommended)

All tubes must be inserted into the Qubit device in the same orientation.

This assay is very sensitive to temperature fluctuations. Do not warm the tubes in your hand.

When measuring a sample multiple times remove tube from device for 5 s before re-measuring.

Disregard all concentration readouts and low concentration errors given on the Qubit screen. Concentrations will be calculated from the data that is found in the exported measurement report.

Setup

1. Set up and label the necessary number of siliconized tubes needed for samples. Additionally, a single 0.5 ml PCR tube will be used repeatedly for all measurements taken with the Qubit.
2. Prepare 199 µl Qubit working solution for each sample, 1 standard, and an additional 10% extra to accommodate for variation in aliquoting the solution. Prepare the Qubit working solution by diluting the Qubit RNA HS assay dye 1:200 in Qubit RNA dilution buffer using a clean plastic tube. For example, ~200 µl for 8 samples and 1 standard, with an additional 10% extra yields 2 ml of working solution (10 µl of Qubit reagent plus 1,990 µl of Qubit buffer).
3. Transfer 199 µl Qubit working solution to each individual labeled siliconized tube.
4. Load 199 µl Qubit working solution into the 0.5 ml Qubit assay tube. This blank sample will be used to determine the background and measure the calibration standard. The minimum volume in a tube that can be measured accurately is approximately 130 µL)
5. On the Home Screen of the Qubit, press RNA, and then press RNA as the assay type. On the Standards Screen, the Qubit will prompt you to choose between reading new standards and using the previous calibration. Press No to use the last calibration. 2'-OMe-let-7a is used as our calibration standard, so one initial calibration with the Invitrogen-supplied standards is only needed to bypass the Standards Screen.

Calibration Method (Chose One)

Short Calibration—10 min

A single 2'-OMe-let-7a calibration standard measurement is generally sufficient to ensure that the Qubit assay and device are working properly for measurements of low RNA concentrations (less than 10 ng/µl). Proceed to step 11.

Full Calibration Curve—20 min

To measure samples of higher concentrations (greater than 10 ng/µl), that you do not want to measure on the Nanodrop, measure a full calibration standard curve. Additionally, it may be necessary to reevaluate expected RFU values with new batches of dye. Proceed to step 16.

Short Calibration: Measure Background and 2'-OMe-let-7a Qubit Calibration Standard 1. Read the blank sample, 199 µl of the Qubit working solution without RNA, 3 times to determine the background. Remove tube from device for at least 5 s between measurements.
2. Add 1 µl of the 2'-OMe-let-7a standard to the Qubit assay tube used to determine the background, containing 199 µl of Qubit working solution, and vortex tube 2-3 s. Follow with a short spin. Allow the Qubit assay tube to incubate at room temperature for 2 min.
3. Read the 2'-OMe-let-7a calibration standard on the Qubit.
4. Transfer readings to computer using a flash drive.
5. Average the background readings from the blank sample. The RFU values for each reading should be stable (+/−3 RFU units). The average background reading should be 30-35 RFU and the 2'-OMe-let-7a calibration standard value should be approximately 15-20 RFU above the background. This value corresponds to approximately 2.5 ng/µl total RNA.

If the 2'-OMe-let-7a calibration standard measurement does not appear above the background measurement, or if the value deviates significantly from a 15-20 RFU increase above background, it may be necessary to measure a full calibration standard curve. To do so, continue to step 15. Otherwise, continue to step 22.

Full Calibration: Measure a 3-Point 2'-OMe-let-7a Qubit CValibration Standard Curve 1. Prepare a second standard value by adding 1 µl more of the 2'-OMe-let-7a standard to the same Qubit assay tube amounting to 2 µl standard/199 µl Qubit working solution. Mix by vortexing 2-3 s, follow with a short spin, and allow tube to incubate for 2 more min.
2. Read this second 2'-OMe-let-7a calibration standard three times on the Qubit.
3. Prepare a third standard value by repeating steps 15 and 16. (3 µl standard/199 µl Qubit working solution).
4. Prepare a fourth standard value by adding 1 µl of the higher concentration calibration standard (OD=4) to the same Qubit assay tube amounting to 4 µl standard/199 µl Qubit working solution, final OD=5.5. This value corresponds to approximately 35 ng/µl total RNA.
5. Discard the diluted calibration standard.
6. Transfer readings to computer using flash drive.
7. Plot a standard curve with the averaged values. The curve should be linear and have a high correlation coefficient. Calibration standard values should increase in consistent steps.

After calibration standards measurements are complete, measure samples

1. Add 1 µl of samples to siliconized tubes containing 199 µl of Qubit working solution and mix by vortexing 2-3 s. Follow with a short spin.
2. Allow tube to incubate for 2 min at room temperature.
3. Transfer the first diluted sample from the siliconized tube to the Qubit assay tube.
4. Read your diluted sample.
5. Transfer diluted sample back to a labeled siliconized tube.
6. Repeat steps 3-5 for additional samples.
7. When finished, transfer readings to computer using flash drive.

8. Copy the three RFU values for each sample to the provided template table. Write the volume of sample added to the "RNA added (µl)" column. The average RFU will be calculated for each sample. If this value is not above background, add an additional 1 µl and return to step 20 (2 µl sample+199 µl Qubit working solution). NOTE: If there is not a change in RFU after the second addition, assume the RNA concentration to be less than 1 ng/µl.

9. Calculate sample RNA concentrations using the equation provided below.

If 1 µl of sample was measured V=1, if an additional 1 µl of sample was added V=2.

RNA Sample Concentration Calculation:

$$c_{sample}(\text{ng}/\mu l) = \frac{RFU(\text{sample}) - RFU(\text{reagent blank})}{V(\mu l) \cdot 7/\text{ng}}$$

6.1.2.4 Example Qubit Measurements with 1-point 2'-OMe-let-7a Calibration

6.1.3 Ribogreen Assay (Invitrogen)

The Quant-iT Ribogreen assay from Invitrogen offers a similar sensitivity of 1 ng/ml at the lower limit as the Qubit HS RNA assay from Invitrogen. The Ribogreen has a higher range (upper limit according to the manufacturer 1 µg/ml) and, more importantly for our purposes, can be scaled up more easily for a large number of samples.

Materials

Quant-iT™ RiboGreen® RNA Assay Kit (Life Technologies, Cat # R11490)

Quant-iT™ RiboGreen® RNA Reagent

20× TE Buffer, RNase-free

Ribosomal RNA standard, 16S and 23S rRNA from *E. coli* (100 µg/ml)

Costar™ 96-Well Clear-Bottom Plates (Fisher Scientific, Cat #07-200-565)

Procedure

Preparing the RNA Standards

1. Prepare 125 µl of 2 µg/ml ribosomal RNA standard by adding 2.5 µl of the included RNA Standard (100 µg/ml) to 122.5 µl 1× TE Buffer.
2. Prepare the dilution series shown in Table 1S1, starting with the 2 µg/ml RNA standard, in an 8-well PCR strip.

| RNA | Total vol. (µl) | RNA added (µl) | RNA total added (µl) | RNA total added (ng) | RFU 1 | RFU 2 | RFU 3 | Average RFU (AU) | STD | Expected 2'-OMe-let-7a standard values (AU) | $c_{sample}$ (ng/µl) |
|---|---|---|---|---|---|---|---|---|---|---|---|
| Reagent blank | 199 | 0 | 0 | 0 | 30.93 | 31.07 | 31.02 | 31.01 | 0.07 | | |
| 2'-OMe-let-7a | 200 | 1 | 1 | 15.5 | 47.72 | 48.18 | 48.22 | 48.04 | 0.28 | blank + (P)* | 2.4 |
| HEK293 total RNA | 200 | 1 | 1 | | 40.11 | | | | | | 1.3 |
| HEK293 total RNA | 201 | 2 | 2 | | 50.67 | | | | | | 2.7/2 = 1.35 |

*P is in the range of 10 to 20 and may need to reevaluate this value with new batches of Qubit dye 6.1.2.5 Example Qubit Measurements with 4-point 2'-OMe-let-7a Calibration Curve

| RNA | Total vol. (µl) | RNA added (µl) | RNA total added (µl) | RNA total added (ng) | RFU 1 | RFU 2 | RFU 3 | Average RFU (AU) | STD | Expected 2'-OMe-let-7a standard values (AU) | $c_{sample}$ (ng/µl) |
|---|---|---|---|---|---|---|---|---|---|---|---|
| Reagent blank | 199 | 0 | 0 | 0 | 30.93 | 31.07 | 31.02 | 31.01 | 0.07 | | |
| 2'-OMe-let-7a | 200 | 1 | 1 | 15.5 | 47.72 | 48.18 | 48.22 | 48.04 | 0.28 | blank + (P)* | 2.4 |
| 2'-OMe-let-7a | 201 | 1 | 2 | 31 | 60.33 | 60.88 | 61.24 | 60.82 | 0.46 | | 4.3 |
| 2'-OMe-let-7a | 202 | 1 | 3 | 46.5 | 75.34 | 75.52 | 77.37 | 76.08 | 1.12 | | 6.4 |
| 2'-OMe-let-7a | 203 | 1 | 4 | 170.5 | | | | | | | ~35 |
| HEK293 total RNA | 200 | 1 | 1 | | 40.11 | | | | | | 1.3 |
| HEK293 total RNA | 201 | 1 | 2 | | 50.67 | | | | | | 2.7/2 = 1.35 |

*P is in the range of 10 to 20 and may need to reevaluate this value with new batches of Qubit dye.

TABLE 1S1

Dilution series for quantifying RNA isolated from biofluids.

| Dilution Number | Volume of 1X TE (μl) | Volume transferred from previous dilution (μl) | Dilution concentration (μg/ml) | Final concentration in plate (ng/ml) |
|---|---|---|---|---|
| 1 | — | 122 (2 μg/ml stock) | 2.00 | 50.00 |
| 2 | 48 | 72 (from dilution #1) | 1.20 | 30.00 |
| 3 | 35 | 70 (from dilution #2) | 0.80 | 20.00 |
| 4 | 33 | 55 (from dilution #3) | 0.50 | 12.50 |
| 5 | 48 | 32 (from dilution #4) | 0.20 | 5.00 |
| 6 | 45 | 30 (from dilution #5) | 0.08 | 2.00 |
| 7 | 25 | 25 (from dilution #6) | 0.04 | 1.00 |
| 8 (blank) | 50 | 0 | 0.00 | 0.00 |

Sample RNA Quantification

The assay plate setup is performed using the epMotion 5075 liquid handling system.

3. Prepare a 1:2000 dilution of the Quant-iT™ RiboGreen® RNA Reagent in 1× TE Buffer. Make sure that the RiboGreen has fully thawed before making the dilution. The dye is light-sensitive, so wrap the tube in foil and use within a few hours of preparation.
4. The first column of the 96-well assay plate will contain the 8 RNA dilutions prepared in step 2. The standards are diluted 20-fold from their starting concentrations to their final concentrations in the plate, as shown in Table 1S1. The final volume in each well will be 200 μl, so use the EpMotion 5075 to transfer 10 μl of each standard to the first column. Add 90 μl of 1× TE Buffer for a total volume of 100 μl.
5. The isolated RNA of unknown concentration will be added to the subsequent columns. First use the EpMotion 5075 to transfer 97 μl of 1× TE Buffer to the appropriate number of wells in the assay plate. Next, transfer 3 μl of the isolate to each well for a total volume of 100 μl.
6. Add 100 μl of the 1:2000 RiboGreen® RNA Reagent prepared in step 3 to all wells, for a final volume of 200 μl.
7. Mix thoroughly by shaking the plate for 1 minute at 1200 rpm.
8. Cover the plate from light by wrapping it in foil and incubate for 2 min at room temperature.
9. Measure the fluorescence of the samples using a fluorescence microplate reader (excitation: 480 nm, emission: 530 nm). Generate a standard curve using the concentrations of the standards in the plate (Table 1S1) and their measured absorbances. The curve should be linear in this concentration range (FIG. 1).
10. Calculate the RNA concentration of each sample from the standard curve. The amount of RNA from each sample used for cDNA library generation should be equal as to not limit sequencing depth of individual samples. If there is significant variance in the RNA content of each sample to be used in library preparation, adjust the concentration accordingly.

7. Steps of Method Development

I. Isolating DNA and RNA from biofluids can be challenging due to their low of exRNA and high levels of RNase activity in these samples. Fluctuations in high-quality RNA recovery from biofluids (plasma and serum) prompted to examine the RNA isolation process. Using a set of radiolabeled ($^{32}$P-labeled) oligonucleotides (ssRNA, ssDNA), spikeins, transcripts (RNA), PCR products (dsDNA) and restriction fragments (dsDNA), as well as a set of 22-nt spike-in calibrators, steps that limited RNA recovery and intactness were detected and optimized. The spike in were applied to the denaturant or extraction solution prior to addition of a biofluid samples. Typical organic extraction protocols used to denature and remove ribonucleases were insufficient in preventing RNA spike-in degradation in certain biofluid samples, as exemplary shown for a serum sample processed using a standard Trizol LS based protocol (FIG. 1a, lane 2).

II. In contrast, a 5-minute initial denaturation at 50° C. with a buffered detergent, 2% (w/v) sodium dodecylsulfate (SDS) solution, followed by TRIZOL extraction and ethanol precipitation could significantly reduce RNA spike-in damage (lane 4). Likewise, a 5-minute hot initial denaturation with a buffered chaotroph and a reducing agent, 4M guanidinium iso thiocyanate (GITC) solution with 25 mM 2-mercaptoethanol, followed by organic extraction and ethanol precipitation could prevent degradation of RNA spike-ins to a similar extent (lane 6), while treatment with the same reducing agent and a harsher, 6M, GITC concentration at room temperature failed to achieve this (lane 8). In contrast, RNA spike-ins in water controls processed in parallel using the same conditions did not show any degradation (FIG. 1A, lanes 1, 3, 5, 7), suggesting that residual intrinsic RNase activities in the serum are likely responsible for the degradation of the RNA spike ins and that thermal denaturation at 50° C. alone or in combination with chaotrophs, detergents and/or reducing agents used effectively reduce these activities to a level where no obvious damage is observed.

III. In order to simplify the purification effort, 50° C. preincubations were combined with column-based RNA purification. While damage of $^{32}$P-RNA spike-ins appeared to be lower in column-purified RNA samples even in the Trizol sample (FIG. 1b, lane 1,2), the initial therma denaturation step with denaturants and reducing agents, followed by either Trizol or phenol/chloroform extraction appeared to protect the spike-ins further against ribonuclease activity, as suggested by the absence of degradation product in the eluates and flow through fraction (lanes 3-6). However, the column-based RNA purification method showed substantial losses of 19 to 24 nt RNA spike ins, when Trizol was used as an extraction agent. (FIG. 1b, lane 2, 4) or wash fractions.

As a next step the thermal denaturation with 2% buffered SDS buffer or GITC and reducing agent with proteolysis followed by column purification were combined. Proteinase K digestion removes or markedly reduces interphase formation after organic extraction and phase separation (FIG. 2b). Interphases at this step tended to be very prominent in blood-based biofluids (FIG. 2a), probably due to high protein concentrations in plasma and serum.

VIa Greater interphase reduction and higher protection against lower levels of RNA spike in degradation in SDS-treated & proteinase K digested samples (FIG. 1C, lane 4 vs. lane 2) suggested higher lead to the preference of SDS-based solutions in initial denaturation over GITC-based formulations over the and lead to the development of SDS-based denaturing buffer P which has been used as initial denaturing agent from here on (see Total RNA isolation from urine, serum, citrate-, EDTA- and heparin-plasma samples, section 2.6.2.1).

Figure 3:
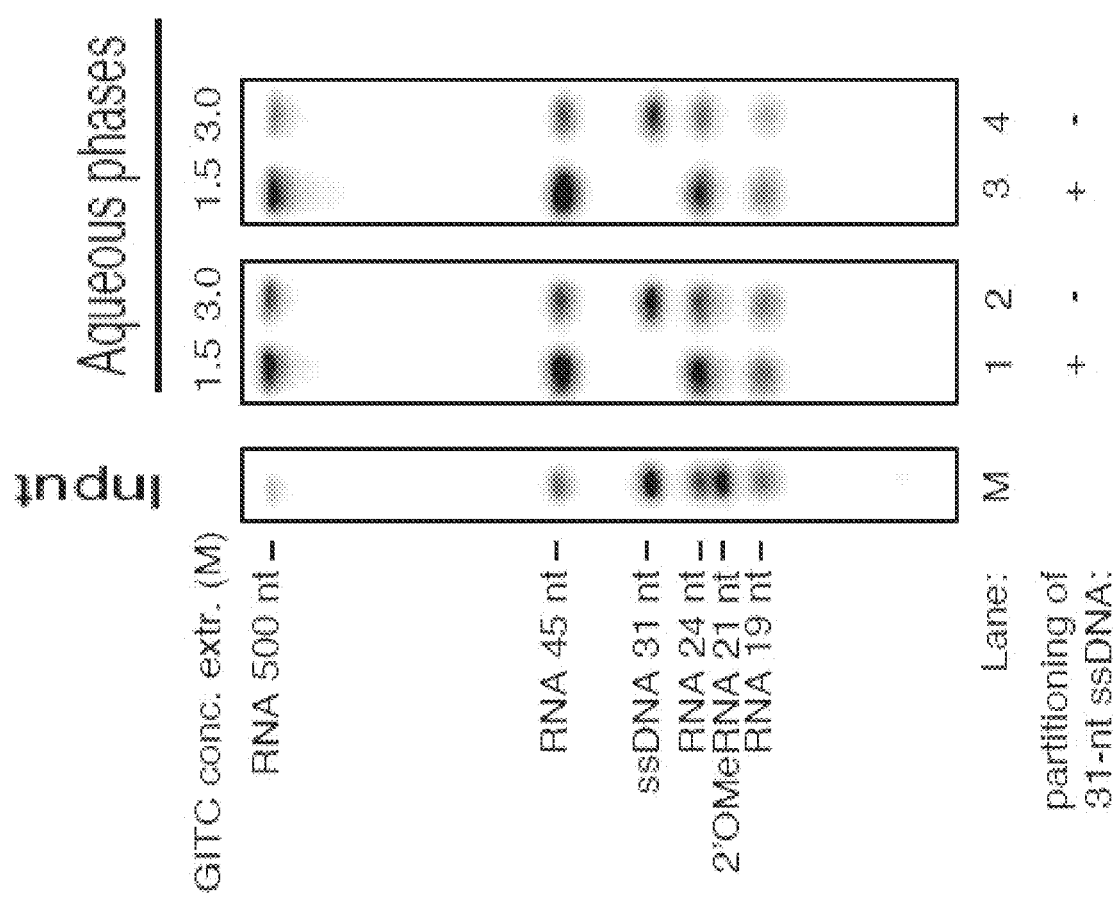
Figure 3:
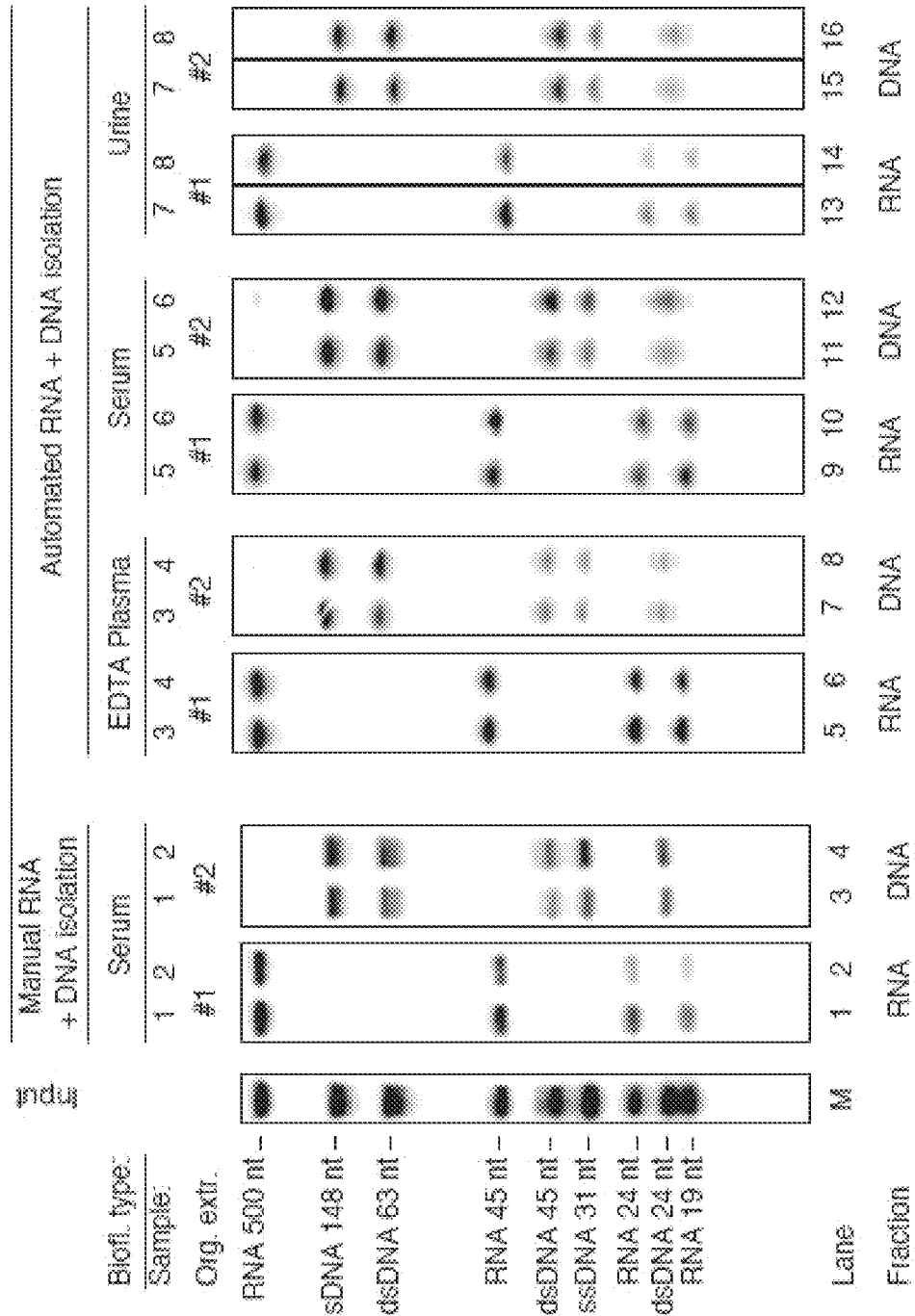

VIb. Column binding of small 19-nt and 24-nt $^{32}$P-labelled spikes ins could be improved by increasing the GITC concentration during organic extraction (FIG. 1c, lanes 1,3). High GITC concentrations in the extraction buffer, however, appeared to abolish DNA partitioning into the organic phase and hence prevented separation of DNA and RNA, while at low concentrations, separation of RNA and DNA could be achieved (FIG. 3a). High GITC concentration in commercial extraction solutions such as Trizol LS may be the reason, why these agents under all conditions tested also failed to separate these two nucleic acids (FIG. 1a, 1-4, FIG. 1b, 1,3).

V. The GITC dependence on DNA partitioning lead to the development of organic extraction solution ED2 and aqueous re-extraction solution AE3, (see Total RNA isolation from urine, serum, citrate-, EDTA- and heparin-plasma samples, section 2.6.3.1 and 2.6.5.1) which can be used to sequentially purify DNA and RNA: First an organic extraction is performed using a low concentration of GITC, which allows $^{32}$-P-labelled DNA spike-ins to partition into the organic phase, while $^{32}$-P-labelled spike-ins remain in the aqueous phase, which and are subjected to column purification. Then, the organic phase is re-extracted with an aqueous buffer containing 4M GITC, which causes the $^{32}$-P-labelled DNA spike-ins to relocate into the aqueous phase, which is consequently aspirated and subjected to a similar column purification (FIG. 3b).

VI. The resulting lower GITC in the aqueous phase containing RNA required adjustments in the column binding conditions of nucleic acids, which could be overcome be replacing ethanol by isopropanol, increasing the isopropanol concentration to approximately 66% and adding divalent cations.

VII. The concomitant increase in precipitation of presumably aqueous peptides due to lower GITC/higher alcohol concentration increased the tendency of silica columns used in nucleic acid purification to clog. This could be overcome by adding GITC to isopropanol and led to the development of binding buffer VB2G.

VIII. Finally, unusually high and/or persistent RNase activities in biofluids present in certain biofluid samples such as certain urine samples which reproducibly degrade $^{32}$P-RNA RNA spike ins during RNA isolation could be overcome by increasing the SDS concentration and temperature in the initial denaturation step and adding by adding 5 mM TCEP reducing agent to the binding and wash buffers. Our routine method now uses an initial SDS concentration of 5.5 mM SDS at 60° C. for 10 min. incubation time. Under these conditions proteinase K is still sufficiently active to prevent interphase formation after organic extraction/phase separation (see Total RNA isolation from urine, serum, citrate-, EDTA- and heparin-plasma samples, section 3).

8. Library Preparation and sRNA Sequencing of Biofluids Isolated with the Current RNA Isolation Protocol.

RNA isolation protocol presented here were used to isolate RNA from three biofluid types, including 96 human EDTA plasma samples, 72 human serum samples, and 182 human urine samples. Prior to RNA isolation, samples were organized in batches of 24 with up to four batches processed in parallel (see chapter 3.2). RNA quality and recovery efficiencies were monitored using two different synthetic RNA calibrator sets, which were spiked to the 1) denaturant solution prior to contacting the biofluid (calibrator set 1) and 2) to the barcoded 3' adapter ligation reaction during cDNA library preparation (set 2). The sample batches were ligated using a set of 24 individual 3' DNA adapters which introduce a specific 3' barcode to each RNA molecule in a sample. Barcoding is done prior to cDNA library generation and allowed to combine up to 24 samples into one sequencing reaction, the resulting reads read contains all sequences from the batch of 24 samples. During cDNA library preparation step, selection was applied to a size range of 19-30 nt for urine-based RNAs and 19-45 nt for serum- and plasma-based RNAs. It was chosen to specifically enrich for small RNAs such as miRNAs, with a typical length of 22 nt without enriching too much information from molecules that are too short for to be unambiguously identified in the reference transcriptome based on the human reference genome assembly GRCh37,hg 19. Barcoding, multiplexing and small RNA cDNA library preparation was followed by single end 1llumina HiSeq sequencing yielding up to 150 million reads per batch and typically 1-2 million reads per sample, although the range can greatly vary from a about 14.000 to almost 59 million reads per individual sample in the case of urine (summarized in table 1a, detailed lists available in tables 1c, d and e, for plasma, serum and urine, respectively). Sequence reads were demultiplexed and mapped against our curated human reference transcriptome to obtain abundance data of miRNAs, tRNAs, scRNAs, rRNAs, mRNAs and other RNA classes.

9. RNA Composition of Biofluids Isolated with the Current RNA Isolation Protocol.

The protocol sRNA cloning protocol described herein was used was designed for enriching and cloning of 22-nt miRNAs by selecting 5'phosphorylated 3'OH RNA molecules in a size range of typically less than 50 nucleotides. Although most other intact ncRNAs are larger and RNase-degraded fragments do not usually have a matching phosphorylation signature at their 5' and 3' ends, sequences of other RNA classes in each biofluid samples were observed as well. Due to the selection criteria however, the proportions observed and reported here do not reflect the actual RNA composition in the biofluid samples; due to favoring of miRNAs the abundance of other RNA types is in fact expected to be much higher. After correcting for technical reads, such as adapter-ligation products without sample insert, calibrators, and markers which can differ in proportion depending on the amount of RNA isolated from a biofluid sample, the RNA composition shows a high degrees of variability (summarized in Table 2a, detailed lists available in Tables 1b, c and d, for plasma, serum and urine, respectively). The biofluid with the most defined RNA composition appears to be human plasma, with a miRNA content of approximately 75%, typically less than 3% rRNA, scRNA, and mRNA, less than 0.5% tRNA and typically 15% of hg19-unmapped sequences. Serum has a lower proportion of miRNAs (med. approximately 45%) and higher proportions than plasma but typically less than 10% rRNA, scRNA, tRNA, and mRNA. Urine is the least defined biofluid with an even lesser proportion of miRNAs (med. approx. 16%) and typically less than 10% of rRNA, tRNA and mRNA and a median proportion of hg19-unmappted sequences of approximately 45%. However, relative abundance of miRNAs, tRNAs and unmapped sequences can reach almost every proportion from less than 2% to more than 85%. In two of 282 urine samples, 16-4, and 16-19, the unmapped sequences contributed to more than 95% of the total sequences, with more than 50 million reads in total. Using averaged RNA composition data for the categories miRNA, tRNA, rRNA, scRNA, mRNA and unmatched samples and their distribution of insert lengths throughout all samples for each biofluid type (summarized 4a-d) found distinctive fragments of each RNA class were observed. In agreement with the biological definition for miRNAs, miRNA-derived sequences show a peak of 22nt length in all biofluids, while tRNA based fragments in serum and urine show a peak at 30 nt (FIG. 4b,c). scRNAs show a peak at 32 nucleotides. The lengths distribution of mRNA-based fragments begins with a wide peak a 17 nt and ends at 25 nt. Most fragments are smaller than 22 nt. rRNA fragments show peak at 17, followed by a declining tail which covers the range up to about 40 nt. The average size distributions of the unmapped RNA fragments is are flat curves which shows an increase towards 22nt, a local maximum, followed by long tails to approximately 40 nt.

While average size distributions of ncRNA types represent their distributions in all originating samples well, unmapped sequences show a much higher degree of variability with respect to their average length distributions (FIG. 4d) which appears to be highest in urine: Here, several samples show deviating size distributions with additional maxima at 30 to 33 nucleotides, similar to distributions in tRNA, and scRNA. The large contribution of unmapped sequences prompted us to analyze their source of origin on a per-sample basis for selected samples with more than 2 million total reads and more than 80% unmapped sequences (14-16, 16-4, 16-16, and 16-19). Two randomly selected samples with less than 25% unmapped sequences (13-6, and 14-17) were also included. Unmapped reads longer than 25 nt were used in a contig-building process followed by a BLASTN search using the assembled contigs as queries against the NCBI non-redundant database. Several target hits include rRNAs and tRNAs genes of non-human origin. For unambiguously identified targets, taxonomic information was assigned to queries; assignments of similar or identical orders, genera and species were then combined and endowed with total read counts of sequences substantiating their queries. An overview of the most prevalent sources of unmapped RNA is given in Table 3. Interestingly, the composition of organisms found in the selected samples vary considerably: 16-4, a sample of 56 million unmapped reads, the highest number observed here, has major contributions from a few taxonomic orders, mainly enterobacteria (48.9% of all unmapped reads), providing evidence for a handful of genera. One of its main contributors appears be from the *Klebsialla* genus (support by 165 individual contig assignments), with *Klebsialla pneumoniae* as the most likely candidate (53 individual supporting assignments). Although this organism usually causes systemic infections originating in the lungs, this bacterium has been reported to cause urinary tract infections in immunocompromised hosts such as diabetic patients and can cause emphysematous pyelonephritis and urosepsis.

In sample 16-19 with almost 50 million unmapped reads, evidence for members of more than ten taxonomic orders of bacteria was found, including proteobacteria, hi-gc gram positive bacteria, fusibacteria and firmicutes, with more than 20 contributing genera and species and without evidence for a predominant contributor.

In sample 14-16 the main contributions of unmapped sequences (38.8% of all unmapped reads) appear to originate from the taxonomic order of *Firmicutes*, with *Lactobacillus* (35.9% of all unmapped reads) as the most likely genus. *Lactobacillus acidophilus* is a major part of the vaginal flora.

In sample 13-6 evidence, a sample with 23.3% unmapped reads, evidence was found for the presence of amoeba (5% of all unmapped reads), with vermamoeba vermiformis (4.9% of all unmapped reads), as the most likely candidate. This amoeba belongs to the group of free living amoeba which can commonly be found in water supplies, industrial waters and cooling towers and isn't known as a human pathogen.

It was unexpected discovered that evidence from RNA from Eudicots an order of flowering plants, which contains many fruit and vegetable families including soy, broccoli, mango and cashew were observed. In at least two samples, 16-16 and 16-19, evidence for trace amounts of RNA derived from the 5.8S ribosomal RNA of *Anacardium occidentale* (cashew) were observed, with E values of $10^{-79}$ and $10^{-81}$ respectively, suggesting that assignable fragments of food-derived RNA at least under certain conditions prevail the human metabolism and can be found in the urine of human subjects. Using our method of contig-assisted RNA identification, between 6.5% and 53.6% of unmapped reads could be identified. This high level of assigned data supports the assumption that that the non-hg19 mapable RNA present in urine mainly originate from organisms in the urine and are not an artifactual entities of side reactions (template switch) or by products of spike-in RNAs.

10. miRNA Composition of Biofluids miRNA and spike-in calibrator abundance based on fractional read counts was used to generate frequency profiles which were visualized as heat maps (FIG. 5). Calibrator heatmaps and ratios of set2: set1 calibrator reads helped to detect samples with less than expected RNA content, indicative of low-input RNA content in the biofluid, inefficient RNA isolation, or damage of RNA spike-ins by RNases.

Unsupervised clustering of calibrator RNAs tended to cluster samples according to the 3' adapters used for barcoding in sRNA-based cDNA library generation (FIG. 6a). This is not unexpected since the same calibrator sets were added to all samples and it was observed earlier, that the group of 24 adapters cause a bias in ligation towards, favoring associations of certain miRNAs and calibrator molecules over others, which can result in differences greater than one order of magnitude. Clustering of calibrator RNAs was not driven by batches, suggesting that sample processing and library generation did not strongly influence RNA composition. Some samples of batch 58 cluster together but the clustering is driven by the absence of two less abundant calibrator sequences due to overall lower read coverage in these samples.

Unsupervised clustering of merged miRNAs from plasma based on twelve individual samples of eight different individuals taken at different timepoints over the course of two months revealed distinctive groups of individuals (FIG. 6b): an isolated branch of the dendrogram contains a cluster of all twelve samples of individual P12; similarly 8 out of 12 samples from individual P14 are localized on another branch, which is not as clearly separated since four samples of two other individuals are located here. On a third branch, eight samples from another individual, P5, are co-localized but their distance to other samples is less, indicated by additional members on this branch. For the rest of the samples, clustering does not strictly discriminate individuals, but many samples of the same source are co-localized. For those the isolated groups of P12 and P14, no obvious batch or adapter effects on clustering are observed, although within these groups samples generated using the same 3' adapter tend to be located next to each other in the dendrograms. For with very similar miRNA composition, those processed using the same 3' barcoding adapter frequently cluster together, suggesting that adapter bias takes over when no distinctive miRNA pattern exists which separates groups of samples. In addition to clustering of individuals, each gender appears to be enriched on separate sides of the dendrograms, without being completely separated. Strong influence of timepoint was not observed when the sample was taken onto clustering.

Using miRNA annotations for human viruses, two bk virus (bkv) miRNAs B1-5p and B1-3p in urine of kidney transplant patients were detected. Initial infection of bkv is asymptomatic and leads to persistence at a low level in the urinary tract and kidneys in 82% of normal healthy controls.

In individuals treated with immunosuppressants, however, virus activity can increase and lead to the renal failure. Differential expression analysis shows that bkv-derived miRNAs B1-5p and B1-3p show respective 61-fold and 91-fold differences in abundance when comparing the population that tested virus positive using either an antibody or an rt-per-based assay with those that did not (FIG. 7c). All antibody-positive samples show normalized read counts of at least 10000 for B1-5p (FIG. 7b), and they are located on branch 1 of a dendrogram (FIG. 7c), which shows very high levels of both bkv miRNA B1-5p and B1-3p in a heatmap generated by unsupervised clustering. The first to third quantile of the per-positive samples, range from 25 to 1250 normalized read counts for B1-5p, FIG. 7b, others are in the range of the previously observed antibody positive samples, and most of the PCR-positive samples (25 of 34) are located on the first two branches of the dendrogram (FIG. 7a). In contrast, the first to third quantile of samples tested virus negative show counts from 0 to 15 normalized reads counts (FIG. 7b). Hence, bkv B1-5p read abundance data for quantiles 1 to 3 clearly separates the three populations: virus negatives, per positives and antibody positives. Based on this data, a lower threshold of 25 normalized reads could be used to discriminate virus-negative from virus-positive samples. However, in population of the samples tested virus negative by per or antibody, several additional samples are above this threshold ($3^{rd}$ quantile, FIG. 7b), suggesting that this miRNA-based detection method bkv allows to potentially find more samples with detectable bkv abundance than the other two tests. It is definitely more sensitive than the antibody-based test, which could only detect very high bkv levels.

Summary

Sequencing data was used for differential analysis of miRNAs abundance, in order to identify and study markers for disease subcategories and disease-associated conditions. Using miRNA sequence data from biofluids, it was possible to identify key components discriminating biofluid types, discriminate biological replicates of individuals from each other, and identify non-human RNAs.

TABLE 1a

| Biofluid type | | Total reads | Adapter reads | Calibrators used | | Additional technical categories | | | Remaining reads |
|---|---|---|---|---|---|---|---|---|---|
| | | | | set 1 | set 2 | set 3 calibrators | long calibrators | Markers | |
| Plasma, | n = 96 | | | | | | | | |
| | median | 2,836,382 | 573,748 | 5,937 | 12,792 | 7 | 1 | 67 | 2,009,283 |
| | min | 146,768 | 43,942 | 305 | 991 | 0 | 0 | 3 | 89,015 |
| | max | 19,671,378 | 15,579,690 | 23,503 | 81,127 | 51 | 45 | 1,100 | 16,605,906 |
| Serum | n = 72 | | | | | | | | |
| | median | 2,729,874 | 621,591 | 5,207 | 12,821 | 5 | 1 | 91 | 1,749,152 |
| | min | 91,780 | 15,564 | 214 | 723 | 0 | 0 | 0 | 59,160 |
| | max | 31,993,329 | 11,876,862 | 124,488 | 193,438 | 186 | 33 | 2,274 | 26,489,291 |
| Urine | n = 282 | | | | | | | | |
| | median | 1,394,313 | 13,069 | 1,215 | 15,566 | 5 | 2 | 50 | 1,355,370 |
| | min | 16,402 | 43 | 5 | 355 | 0 | 0 | 0 | 14,058 |
| | max | 58,464,218 | 400,371 | 8,000 | 117,434 | 513 | 2,964 | 22,389 | 58,443,672 |

TABLE 1b

| Sample ID | Biofl. type | Total reads | Adapter reads | Calibrators used | | Additional technical categories | | | Remaining reads |
|---|---|---|---|---|---|---|---|---|---|
| | | | | set 1 | set 2 | set 3 calibrators | long calibrators | markers | |
| 55-1 | plasma | 3,480,235 | 276,752 | 13,476 | 19,153 | 14 | 3 | 22 | 3,170,815 |
| 55-2 | plasma | 6,788,399 | 286,368 | 9,048 | 14,456 | 19 | 11 | 97 | 6,478,400 |
| 55-3 | plasma | 4,701,381 | 745,142 | 16,377 | 21,330 | 31 | 0 | 10 | 3,918,491 |
| 55-4 | plasma | 2,615,875 | 622,209 | 7,641 | 19,053 | 10 | 3 | 12 | 1,966,946 |
| 55-5 | plasma | 5,177,172 | 433,290 | 14,116 | 15,225 | 18 | 1 | 9 | 4,714,513 |
| 55-6 | plasma | 15,297,676 | 13,214,331 | 4,558 | 12,871 | 6 | 4 | 102 | 2,065,804 |
| 55-7 | plasma | 5,554,418 | 2,347,770 | 5,459 | 14,577 | 11 | 0 | 30 | 3,186,571 |
| 55-8 | plasma | 8,701,539 | 4,111,760 | 11,739 | 19,670 | 20 | 8 | 40 | 4,558,302 |
| 55-9 | plasma | 8,967,447 | 760,179 | 12,806 | 26,109 | 27 | 1 | 247 | 8,168,078 |
| 55-10 | plasma | 2,634,070 | 513,744 | 6,965 | 11,827 | 9 | 0 | 1,100 | 2,100,425 |
| 55-11 | plasma | 910,423 | 189,606 | 1,563 | 6,752 | 4 | 0 | 271 | 712,227 |
| 55-12 | plasma | 2,825,090 | 305,509 | 4,756 | 10,495 | 1 | 1 | 76 | 2,506,252 |
| 55-13 | plasma | 1,547,443 | 270,663 | 3,904 | 7,495 | 2 | 0 | 10 | 1,265,369 |
| 55-14 | plasma | 2,052,360 | 278,194 | 4,227 | 9,487 | 3 | 1 | 238 | 1,760,210 |
| 55-15 | plasma | 3,307,533 | 1,236,764 | 5,498 | 13,252 | 4 | 1 | 395 | 2,051,619 |
| 55-16 | plasma | 4,186,024 | 302,221 | 6,837 | 10,780 | 7 | 0 | 24 | 3,866,155 |
| 55-17 | plasma | 7,928,175 | 820,077 | 6,148 | 15,575 | 22 | 4 | 127 | 7,086,222 |
| 55-18 | plasma | 7,043,690 | 1,561,968 | 7,180 | 16,834 | 6 | 1 | 248 | 5,457,453 |
| 55-19 | plasma | 721,727 | 165,466 | 2,266 | 7,533 | 1 | 0 | 19 | 546,442 |
| 55-20 | plasma | 2,153,807 | 688,293 | 5,681 | 11,556 | 7 | 3 | 487 | 1,447,780 |
| 55-21 | plasma | 4,706,986 | 1,694,196 | 7,222 | 15,670 | 12 | 2 | 68 | 2,989,816 |
| 55-22 | plasma | 3,614,675 | 779,077 | 9,592 | 10,266 | 18 | 4 | 311 | 2,815,407 |
| 55-23 | plasma | 1,634,450 | 470,186 | 4,592 | 9,116 | 2 | 0 | 32 | 1,150,522 |
| 55-24 | plasma | 3,361,674 | 758,370 | 7,703 | 12,089 | 0 | 1 | 106 | 2,583,405 |

TABLE 1b-continued

| Sample ID | Biofl. type | Total reads | Adapter reads | Calibrators set 1 | Calibrators set 2 | Additional technical categories set 3 calibrators | Additional technical categories long calibrators | markers | Remaining reads |
|---|---|---|---|---|---|---|---|---|---|
| 56-1 | plasma | 3,658,072 | 182,933 | 7,317 | 19,597 | 10 | 1 | 10 | 3,448,204 |
| 56-2 | plasma | 1,928,208 | 178,159 | 8,581 | 15,902 | 10 | 0 | 82 | 1,725,474 |
| 56-3 | plasma | 3,719,718 | 490,606 | 9,370 | 21,304 | 20 | 2 | 10 | 3,198,406 |
| 56-4 | plasma | 5,998,569 | 526,641 | 12,053 | 21,520 | 18 | 0 | 16 | 5,438,321 |
| 56-5 | plasma | 3,653,221 | 361,362 | 9,035 | 18,200 | 5 | 0 | 13 | 3,264,606 |
| 56-6 | plasma | 17,685,847 | 15,579,690 | 5,878 | 17,749 | 8 | 5 | 124 | 2,082,393 |
| 56-7 | plasma | 4,055,848 | 2,201,864 | 6,020 | 19,462 | 12 | 1 | 7 | 1,828,482 |
| 56-8 | plasma | 7,206,722 | 3,220,090 | 12,547 | 22,279 | 12 | 17 | 30 | 3,951,747 |
| 56-9 | plasma | 10,342,616 | 540,881 | 12,706 | 25,228 | 29 | 0 | 251 | 9,763,521 |
| 56-10 | plasma | 1,788,654 | 459,721 | 4,991 | 13,819 | 2 | 1 | 1,097 | 1,309,023 |
| 56-11 | plasma | 644,156 | 241,207 | 1,533 | 9,821 | 3 | 0 | 477 | 391,115 |
| 56-12 | plasma | 2,256,680 | 410,209 | 5,523 | 15,693 | 7 | 0 | 113 | 1,825,135 |
| 56-13 | plasma | 1,718,768 | 254,993 | 3,645 | 9,740 | 3 | 2 | 14 | 1,450,371 |
| 56-14 | plasma | 2,424,987 | 314,025 | 5,855 | 12,594 | 13 | 2 | 307 | 2,092,191 |
| 56-15 | plasma | 4,044,496 | 1,000,422 | 10,511 | 13,658 | 16 | 1 | 444 | 3,019,444 |
| 56-16 | plasma | 1,332,640 | 311,397 | 6,965 | 13,180 | 7 | 2 | 22 | 1,001,067 |
| 56-17 | plasma | 4,539,925 | 605,412 | 7,406 | 17,423 | 27 | 0 | 137 | 3,909,520 |
| 56-18 | plasma | 4,189,108 | 1,536,072 | 9,604 | 16,071 | 5 | 0 | 288 | 2,627,068 |
| 56-19 | plasma | 1,102,759 | 107,312 | 4,035 | 9,363 | 2 | 0 | 24 | 982,023 |
| 56-20 | plasma | 3,202,638 | 679,413 | 5,056 | 12,921 | 5 | 2 | 537 | 2,504,704 |
| 56-21 | plasma | 2,474,244 | 1,148,067 | 4,567 | 15,800 | 8 | 1 | 64 | 1,305,737 |
| 56-22 | plasma | 2,328,442 | 686,343 | 6,284 | 12,685 | 15 | 8 | 369 | 1,622,736 |
| 56-23 | plasma | 2,227,740 | 429,271 | 8,914 | 12,275 | 16 | 0 | 47 | 1,777,217 |
| 56-24 | plasma | 2,118,075 | 777,346 | 6,827 | 14,477 | 6 | 3 | 87 | 1,319,327 |
| 57-1 | plasma | 3,754,381 | 550,480 | 9,009 | 24,854 | 15 | 4 | 47 | 3,169,972 |
| 57-2 | plasma | 3,825,111 | 751,521 | 12,605 | 24,410 | 40 | 2 | 215 | 3,036,318 |
| 57-3 | plasma | 5,249,098 | 1,780,587 | 15,966 | 35,375 | 35 | 0 | 32 | 3,417,103 |
| 57-4 | plasma | 2847,633 | 663,271 | 5,131 | 17,012 | 0 | 0 | 4 | 2,162,215 |
| 57-5 | plasma | 3,318,293 | 625,223 | 7,714 | 16,091 | 0 | 9 | 40 | 2,669,216 |
| 57-6 | plasma | 9,383,724 | 8,334,026 | 2,067 | 6,195 | 6 | 1 | 52 | 1,041,377 |
| 57-7 | plasma | 2,725,931 | 1,529,341 | 2,969 | 10,370 | 0 | 0 | 31 | 1,183,220 |
| 57-8 | plasma | 11,637,602 | 7,314,452 | 12,192 | 30,604 | 34 | 45 | 58 | 4,280,217 |
| 57-9 | plasma | 14,446,860 | 1,634,235 | 23,503 | 37,836 | 50 | 4 | 301 | 12,750,931 |
| 57-10 | plasma | 1,388,412 | 454,441 | 2,785 | 8,690 | 6 | 0 | 668 | 921,822 |
| 57-11 | plasma | 379,083 | 104,910 | 831 | 3,919 | 0 | 0 | 160 | 269,263 |
| 57-12 | plasma | 1,222,703 | 256,074 | 2,926 | 8,199 | 0 | 0 | 90 | 955,414 |
| 57-13 | plasma | 818,688 | 219,660 | 1,702 | 4,866 | 0 | 0 | 12 | 592,448 |
| 57-14 | plasma | 11,446,507 | 258,940 | 2,538 | 7,372 | 3 | 0 | 116 | 1,177,538 |
| 57-15 | plasma | 3,292,635 | 1,341,654 | 4,896 | 12,712 | 10 | 0 | 483 | 1,932,880 |
| 57-16 | plasma | 1,918,498 | 378,900 | 5,206 | 10,941 | 6 | 0 | 50 | 1,523,395 |
| 57-17 | plasma | 4,302,159 | 1,623,985 | 9,777 | 29,565 | 10 | 0 | 246 | 2,638,576 |
| 57-18 | plasma | 3,855,593 | 1,300,827 | 8,784 | 18,053 | 2 | 0 | 230 | 2,527,697 |
| 57-19 | plasma | 647,739 | 166,942 | 1,840 | 4,616 | 0 | 0 | 4 | 474,337 |
| 57-20 | plasma | 2,254,526 | 661,096 | 6,810 | 11,253 | 8 | 0 | 366 | 1,574,993 |
| 57-21 | plasma | 9,124,100 | 3,769,896 | 14,407 | 22,309 | 9 | 3 | 80 | 5,317,396 |
| 57-22 | plasma | 2,964,377 | 766,354 | 6,590 | 8,393 | 14 | 2 | 243 | 2,182,781 |
| 57-23 | plasma | 1,540,630 | 465,935 | 3,822 | 6,270 | 2 | 0 | 22 | 1,064,579 |
| 57-24 | plasma | 1,664,638 | 521,506 | 5,996 | 8,665 | 0 | 0 | 46 | 1,128,425 |
| 58-1 | plasma | 3,281,733 | 552,228 | 11,811 | 20,030 | 19 | 1 | 42 | 2,697,602 |
| 58-2 | plasma | 10,550,723 | 1,547,565 | 13,275 | 45,268 | 15 | 14 | 247 | 8,944,339 |
| 58-3 | plasma | 13,813,847 | 3,679,954 | 19,097 | 62,476 | 33 | 10 | 20 | 10,052,257 |
| 58-4 | plasma | 959,246 | 308,008 | 1,662 | 4,462 | 6 | 0 | 3 | 645,105 |
| 58-5 | plasma | 1,832,477 | 595,267 | 4,025 | 12,494 | 0 | 0 | 5 | 1,220,686 |
| 58-6 | plasma | 2283,870 | 2,109,494 | 449 | 1,145 | 2 | 0 | 25 | 172,755 |
| 58-7 | plasma | 1,014,480 | 634,065 | 577 | 2,623 | 0 | 0 | 3 | 377,212 |
| 58-8 | plasma | 19,374,108 | 11,672,840 | 16,134 | 28,562 | 15 | 13 | 29 | 7,656,513 |
| 58-9 | plasma | 13,377,454 | 3,589,808 | 18,239 | 81,127 | 35 | 14 | 680 | 9,687,351 |
| 58-10 | plasma | 527,663 | 183,836 | 802 | 2,160 | 1 | 1 | 139 | 340,724 |
| 58-11 | plasma | 146,768 | 56,302 | 305 | 1,095 | 0 | 0 | 51 | 89,015 |
| 58-12 | plasma | 294,610 | 97,239 | 442 | 1,917 | 3 | 3 | 66 | 194,940 |
| 58-13 | plasma | 226,722 | 87,358 | 466 | 1,076 | 0 | 6 | 7 | 137,809 |
| 58-14 | plasma | 388,000 | 122,718 | 1,292 | 2,277 | 0 | 0 | 31 | 261,682 |
| 58-15 | plasma | 2,030,586 | 922,255 | 1,444 | 3,993 | 7 | 4 | 121 | 1,102,762 |
| 58-16 | plasma | 867,511 | 305,907 | 3,009 | 5,702 | 5 | 0 | 13 | 552,875 |
| 58-17 | plasma | 19,671,378 | 2,998,901 | 22,496 | 43,632 | 51 | 5 | 387 | 16,605,906 |
| 58-18 | plasma | 4,117,902 | 1,361,699 | 5,105 | 12,116 | 0 | 2 | 187 | 2,738,793 |
| 58-19 | plasma | 190,747 | 43,942 | 506 | 991 | 1 | 0 | 5 | 145,302 |
| 58-20 | plasma | 1,075,290 | 515,733 | 1,831 | 4,047 | 10 | 0 | 230 | 553,439 |
| 58-21 | plasma | 10,651,760 | 5,037,385 | 11,006 | 17,486 | 13 | 10 | 122 | 5,585,738 |
| 58-22 | plasma | 908,174 | 378,695 | 1,587 | 2,383 | 6 | 0 | 79 | 525,424 |
| 58-23 | plasma | 542,598 | 183,785 | 1,243 | 1,760 | 0 | 1 | 6 | 355,803 |
| 58-24 | plasma | 611,175 | 254,088 | 1,400 | 2,372 | 0 | 0 | 8 | 353,307 |

TABLE 1c

| Sample ID | Biofl. type | Total reads | Adapter reads | Calibrators used set 1 | set 2 | Additional technical categories set 3 calibrators | long calibrators | markers | Remaining reads |
|---|---|---|---|---|---|---|---|---|---|
| 60-1 | serum | 5,423,727 | 552,503 | 23,865 | 35,480 | 42 | 9 | 43 | 4,811,785 |
| 60-2 | serum | 3,874,826 | 640,663 | 16,633 | 31,008 | 28 | 0 | 213 | 3,186,281 |
| 60-3 | serum | 8,011,747 | 1,399,992 | 32,232 | 40,578 | 32 | 1 | 54 | 6,538,858 |
| 60-4 | serum | 2,617,479 | 779,824 | 7,576 | 24,608 | 5 | 0 | 2 | 1,805,464 |
| 60-5 | serum | 3,137,594 | 668,919 | 12,058 | 25,037 | 22 | 2 | 28 | 2,431,528 |
| 60-6 | serum | 14,810,063 | 11,876,862 | 4,225 | 11,760 | 5 | 3 | 79 | 2,917,129 |
| 60-7 | serum | 4,448,773 | 2,043,563 | 8,066 | 15,670 | 21 | 9 | 13 | 2,381,431 |
| 60-8 | serum | 12,254,009 | 6,814,433 | 18,904 | 38,496 | 38 | 31 | 58 | 5,382,049 |
| 60-9 | serum | 7,117,242 | 1,311,196 | 27,276 | 50,291 | 64 | 3 | 569 | 5,727,843 |
| 60-10 | serum | 3,289,009 | 602,519 | 8,330 | 14,324 | 9 | 1 | 1,655 | 2,662,171 |
| 60-11 | serum | 395,500 | 137,970 | 993 | 5,506 | 1 | 0 | 416 | 250,614 |
| 60-12 | serum | 2,756,768 | 366,256 | 4,283 | 13,555 | 6 | 1 | 131 | 2,372,536 |
| 60-13 | serum | 1,280,885 | 269,506 | 3,668 | 7,306 | 8 | 3 | 12 | 1,000,182 |
| 60-14 | serum | 3,322,775 | 345,350 | 5,869 | 10,175 | 6 | 0 | 327 | 2,961,028 |
| 60-15 | serum | 5,557,662 | 1,502,029 | 13,718 | 16,992 | 14 | 3 | 663 | 4,024,243 |
| 60-16 | serum | 2,061,639 | 467,869 | 7,670 | 14,320 | 3 | 0 | 766 | 1,571,011 |
| 60-17 | serum | 7,476,782 | 1,682,134 | 16,988 | 33,363 | 21 | 6 | 303 | 5,743,967 |
| 60-18 | serum | 3,511,017 | 1,396,721 | 10,884 | 20,737 | 9 | 2 | 448 | 2,082,216 |
| 60-19 | serum | 876,094 | 229,714 | 2,863 | 7,599 | 5 | 0 | 12 | 635,901 |
| 60-20 | serum | 2,137,789 | 821,427 | 6,751 | 15,130 | 8 | 2 | 849 | 1,293,622 |
| 60-21 | serum | 8,535,154 | 3,356,964 | 13,041 | 25,447 | 11 | 10 | 125 | 5,139,556 |
| 60-22 | serum | 2,192,690 | 897,357 | 4,241 | 11,250 | 1 | 0 | 546 | 1,279,295 |
| 60-23 | serum | 1,417,074 | 324,087 | 3,622 | 5,491 | 1 | 0 | 49 | 1,083,824 |
| 60-24 | serum | 1,490,551 | 593,634 | 4,391 | 10,228 | 0 | 0 | 89 | 882,209 |
| 61-1 | serum | 11,892,582 | 648,952 | 20,565 | 30,959 | 23 | 0 | 28 | 11,192,055 |
| 61-2 | serum | 7,377,723 | 1,045,074 | 17,610 | 38,249 | 29 | 6 | 216 | 6,276,539 |
| 61-3 | serum | 6,907,068 | 2,321,210 | 29,255 | 50,756 | 49 | 7 | 31 | 4,505,760 |
| 61-4 | serum | 1,722,665 | 598,363 | 5,025 | 12,702 | 1 | 0 | 2 | 1,106,572 |
| 61-5 | serum | 2,165,371 | 665,887 | 7,981 | 18,468 | 13 | 2 | 28 | 1,472,992 |
| 61-6 | serum | 6,035,649 | 5,383,412 | 1,588 | 3,814 | 0 | 3 | 25 | 646,807 |
| 61-7 | serum | 1,846,704 | 1,297,342 | 2,190 | 7,377 | 7 | 0 | 11 | 539,777 |
| 61-6 | serum | 14,305,092 | 9,544,610 | 14,957 | 36,374 | 20 | 33 | 83 | 4,709,015 |
| 61-9 | serum | 14,602,645 | 1,846,575 | 45,687 | 49,422 | 80 | 3 | 647 | 12,660,231 |
| 61-10 | serum | 1,102,824 | 239,842 | 3,239 | 4,414 | 3 | 1 | 587 | 854,738 |
| 61-11 | serum | 984,090 | 106,401 | 1,354 | 3,560 | 0 | 0 | 245 | 872,530 |
| 61-12 | serum | 1,538,514 | 222,916 | 2,157 | 6,593 | 0 | 0 | 93 | 1,306,755 |
| 61-13 | serum | 667,800 | 229,388 | 1,869 | 4,629 | 12 | 2 | 7 | 431,893 |
| 61-14 | serum | 1,776,043 | 254,006 | 2,465 | 6,566 | 1 | 0 | 164 | 1,512,841 |
| 61-15 | serum | 3,019,794 | 1,833,351 | 2,893 | 14,431 | 5 | 0 | 458 | 1,168,656 |
| 61-16 | serum | 1,673,000 | 481,634 | 5,787 | 12,939 | 1 | 0 | 257 | 1,172,382 |
| 61-17 | serum | 8,766,826 | 2,686,663 | 18,401 | 46,831 | 39 | 8 | 564 | 6,013,320 |
| 61-18 | serum | 5,619,093 | 1,859,648 | 15,491 | 22,715 | 6 | 0 | 433 | 3,720,800 |
| 61-19 | serum | 486,160 | 141,958 | 1,588 | 3,575 | 0 | 0 | 7 | 339,032 |
| 61-20 | serum | 3,688,737 | 830,638 | 4,889 | 11,227 | 4 | 1 | 704 | 2,841,274 |
| 61-21 | serum | 9,522,524 | 5,914,103 | 14,800 | 32,095 | 22 | 13 | 253 | 3,561,238 |
| 61-22 | serum | 3,596,075 | 870,715 | 4,505 | 7,431 | 4 | 2 | 316 | 2,713,102 |
| 61-23 | serum | 4,307,325 | 475,344 | 4,892 | 5,431 | 11 | 0 | 34 | 3,821,613 |
| 61-24 | serum | 1,454,298 | 582,143 | 5,388 | 8,031 | 2 | 0 | 60 | 858,674 |
| 62-1 | serum | 2,965,724 | 439,920 | 12,450 | 22,981 | 19 | 3 | 52 | 2,490,299 |
| 62-2 | serum | 22,595,674 | 2,065,094 | 67,096 | 93,593 | 41 | 1 | 611 | 20,369,238 |
| 62-3 | serum | 26,246,626 | 5,043,593 | 81,598 | 144,746 | 93 | 4 | 3 | 20,976,589 |
| 62-4 | serum | 669,333 | 161,226 | 815 | 3,590 | 0 | 0 | 0 | 503,702 |
| 62-5 | serum | 2,702,979 | 653,874 | 13,359 | 21,494 | 5 | 0 | 44 | 2,014,203 |
| 62-6 | serum | 581,218 | 511,146 | 214 | 723 | 0 | 0 | 13 | 69,122 |
| 62-7 | serum | 549,264 | 265,784 | 579 | 2,490 | 1 | 0 | 12 | 280,398 |
| 62-8 | serum | 17,433,143 | 8,699,859 | 35,342 | 40,155 | 117 | 23 | 80 | 8,657,567 |
| 62-9 | serum | 31,993,329 | 5,183,635 | 124,488 | 193,438 | 186 | 17 | 2,274 | 26,469,291 |
| 62-10 | serum | 242,983 | 63,396 | 783 | 1,769 | 1 | 0 | 112 | 176,922 |
| 62-11 | serum | 91,780 | 31,473 | 314 | 793 | 0 | 0 | 40 | 59,160 |
| 62-12 | serum | 233,269 | 57,837 | 922 | 1,664 | 0 | 12 | 163 | 172,671 |
| 62-13 | serum | 141,192 | 43,077 | 255 | 899 | 0 | 0 | 41 | 96,920 |
| 62-14 | serum | 280,623 | 76,432 | 908 | 2,254 | 0 | 0 | 63 | 200,966 |
| 62-15 | serum | 672,666 | 373,931 | 1,328 | 3,089 | 0 | 0 | 162 | 294,156 |
| 62-16 | serum | 2,069,230 | 238,603 | 4,508 | 6,586 | 0 | 1 | 29 | 1,819,503 |
| 62-17 | serum | 18,849,878 | 3,095,532 | 46,976 | 86,005 | 88 | 26 | 737 | 15,620,514 |
| 62-18 | serum | 2,923,166 | 1,537,521 | 8,313 | 16,205 | 0 | 0 | 178 | 1,360,949 |
| 62-19 | serum | 103,062 | 15,564 | 316 | 911 | 0 | 0 | 14 | 86,257 |
| 62-20 | serum | 1,991,205 | 292,512 | 2,605 | 3,099 | 0 | 0 | 150 | 1,692,839 |
| 62-21 | serum | 5,388,478 | 2,105,268 | 18,079 | 14,838 | 0 | 0 | 96 | 3,250,197 |
| 62-22 | serum | 325,387 | 124,573 | 1,057 | 1,535 | 0 | 1 | 142 | 198,079 |
| 62-23 | serum | 255,045 | 62,339 | 1,118 | 1,375 | 11 | 0 | 27 | 190,175 |
| 62-24 | serum | 356,354 | 160,885 | 1,251 | 2,190 | 0 | 0 | 31 | 191,997 |

TABLE 1d

| Sample ID | Biofl. type | Total reads | Adapter reads | Calibrators used set 1 | set 2 | Additional technical categories set 3 calibrators | long calibrators | markers | Remaining reads |
|---|---|---|---|---|---|---|---|---|---|
| 13-1 | urine | 334,123 | 5,626 | 18 | 33,353 | 0 | 0 | 246 | 294,880 |
| 13-2 | urine | 27,777,856 | 4,111 | 4,436 | 20,042 | 0 | 2 | 181 | 27,749,084 |
| 13-3 | urine | 2,469,348 | 5,405 | 3,414 | 31,940 | 45 | 8 | 109 | 2,428,427 |
| 13-4 | urine | 345,574 | 4,447 | 26 | 774 | 0 | 0 | 43 | 340,284 |
| 13-5 | urine | 1,734,912 | 9,084 | 4,170 | 26,133 | 10 | 10 | 25 | 1,695,480 |
| 13-6 | urine | 12,712,093 | 94,915 | 2,012 | 22,192 | 9 | 7 | 108 | 12,592,770 |
| 13-7 | urine | 2,336,677 | 14,539 | 3,819 | 36,199 | 7 | 1 | 477 | 2,281,635 |
| 13-8 | urine | 2,311,228 | 13,052 | 3,721 | 26,909 | 28 | 0 | 90 | 2,267,428 |
| 13-9 | urine | 5,197,598 | 8,414 | 4,961 | 35,734 | 33 | 3 | 126 | 5,148,327 |
| 13-10 | urine | 3,891,968 | 4,641 | 2,354 | 20,378 | 0 | 1 | 90 | 3,864,504 |
| 13-11 | urine | 732,172 | 2,963 | 1,308 | 14,296 | 0 | 0 | 73 | 713,532 |
| 13-12 | urine | 4,462,281 | 3,681 | 3,083 | 25,205 | 46 | 2 | 259 | 4,430,005 |
| 13-13 | urine | 2,601,643 | 4,428 | 3,924 | 25,633 | 34 | 13 | 71 | 2,567,540 |
| 13-14 | urine | 1,528,149 | 4,710 | 3,057 | 30,661 | 4 | 1 | 302 | 1,489,414 |
| 13-15 | urine | 1,984,533 | 6,364 | 3,016 | 28,709 | 20 | 0 | 1,025 | 1,945,399 |
| 13-16 | urine | 1,928,102 | 4,249 | 3,497 | 32,129 | 1 | 0 | 149 | 1,888,077 |
| 13-17 | urine | 5,002,424 | 5,872 | 5,633 | 44,731 | 48 | 9 | 120 | 4,946,111 |
| 13-18 | urine | 16,107,771 | 7,739 | 8,000 | 29,098 | 21 | 2,964 | 83 | 16,059,866 |
| 13-19 | urine | 2,568,669 | 5,329 | 3,742 | 21,308 | 20 | 7 | 40 | 2,538,223 |
| 13-20 | urine | 1,411,543 | 6,056 | 3,389 | 23,238 | 32 | 9 | 53 | 1,378,766 |
| 13-21 | urine | 2,814,440 | 18,131 | 5,169 | 31,123 | 1 | 5 | 193 | 2,759,818 |
| 13-22 | urine | 31,478,462 | 7,144 | 3,868 | 30,795 | 12 | 277 | 300 | 31,436,066 |
| 13-23 | urine | 2,959,662 | 7,998 | 4,458 | 33,242 | 16 | 15 | 55 | 2,913,878 |
| 13-24 | urine | 6,516,725 | 8,015 | 3,567 | 24,072 | 0 | 16 | 142 | 6,480,913 |
| 14-1 | urine | 4,557,634 | 6,163 | 4,335 | 42,572 | 30 | 9 | 351 | 4,504,174 |
| 14-2 | urine | 1,374,041 | 4,873 | 5,839 | 30,553 | 17 | 0 | 215 | 1,332,544 |
| 14-3 | urine | 2,238,983 | 6,114 | 4,654 | 45,992 | 5 | 0 | 169 | 2,182,049 |
| 14-4 | urine | 1,360,455 | 3,346 | 2,494 | 47,392 | 11 | 4 | 10 | 1,307,198 |
| 14-5 | urine | 2,577,426 | 7,206 | 3,727 | 32,417 | 4 | 3 | 86 | 2,533,983 |
| 14-6 | urine | 26,255,476 | 11,247 | 2,347 | 26,235 | 2 | 20 | 223 | 26,215,402 |
| 14-7 | urine | 1,928,466 | 6,397 | 903 | 29,906 | 10 | 2 | 682 | 1,890,566 |
| 14-8 | urine | 2,039,139 | 15,655 | 5,102 | 40,350 | 34 | 23 | 95 | 1,977,880 |
| 14-9 | urine | 2,641,023 | 9,829 | 5,201 | 48,660 | 104 | 11 | 207 | 2,577,011 |
| 14-10 | urine | 1,763,016 | 4,689 | 2,991 | 25,981 | 5 | 3 | 155 | 1,729,192 |
| 14-11 | urine | 1,821,160 | 1,419 | 1,149 | 12,225 | 0 | 3 | 37 | 1,806,327 |
| 14-12 | urine | 5,001,164 | 3,894 | 4,347 | 29,426 | 14 | 1 | 250 | 4,963,232 |
| 14-13 | urine | 5,968,859 | 2,439 | 2,219 | 14,975 | 17 | 0 | 149 | 5,949,060 |
| 14-14 | urine | 1,393,871 | 3,625 | 2,098 | 18,974 | 31 | 22 | 247 | 1,368,874 |
| 14-15 | urine | 2,451,043 | 4,561 | 895 | 20,360 | 14 | 3 | 1,177 | 2,424,033 |
| 14-16 | urine | 7,415,337 | 4,241 | 2,278 | 25,964 | 18 | 245 | 210 | 7,382,381 |
| 14-17 | urine | 26,558,639 | 4,612 | 2,818 | 27,468 | 46 | 14 | 44 | 26,523,637 |
| 14-18 | urine | 2,850,346 | 3,627 | 4,184 | 19,337 | 46 | 1 | 71 | 2,823,080 |
| 14-19 | urine | 3,072,699 | 4,538 | 442 | 6,405 | 2 | 347 | 60 | 3,060,905 |
| 14-20 | urine | 2,622,696 | 3,895 | 3,032 | 19,053 | 2 | 5 | 100 | 2,596,609 |
| 14-21 | urine | 6,583,452 | 12,534 | 3,827 | 25,843 | 8 | 18 | 122 | 6,541,100 |
| 14-22 | urine | 18,126,633 | 4,433 | 1,230 | 20,473 | 11 | 0 | 121 | 18,100,365 |
| 14-23 | urine | 1,584,650 | 5,117 | 1,418 | 18,629 | 8 | 3 | 35 | 1,559,440 |
| 14-24 | urine | 1,599,114 | 3,236 | 1,250 | 12,996 | 0 | 6 | 110 | 1,581,514 |
| 15-1 | urine | 438,252 | 2,143 | 786 | 12,475 | 9 | 6 | 27 | 422,806 |
| 15-2 | urine | 685,328 | 1,626 | 1,308 | 6,591 | 0 | 1 | 23 | 675,779 |
| 15-3 | urine | 1,693,337 | 2,843 | 1,994 | 13,841 | 9 | 0 | 20 | 1,674,630 |
| 15-4 | urine | 2,044,790 | 1,786 | 1,388 | 14,663 | 1 | 20 | 1 | 2,026,929 |
| 15-5 | urine | 209,652 | 3,449 | 119 | 11,535 | 6 | 0 | 6 | 194,537 |
| 15-6 | urine | 556,921 | 16,946 | 1,351 | 10,142 | 5 | 3 | 28 | 528,446 |
| 15-7 | urine | 1,548,104 | 5,586 | 622 | 12,117 | 11 | 2 | 26 | 1,529,820 |
| 15-8 | urine | 58,237,017 | 10,271 | 1,847 | 10,791 | 11 | 4 | 21 | 58,214,072 |
| 15-9 | urine | 737,615 | 4,244 | 1,550 | 15,228 | 8 | 0 | 20 | 716,565 |
| 15-11 | urine | 5,311,871 | 2,907 | 773 | 8,180 | 6 | 0 | 14 | 5,299,991 |
| 15-11 | urine | 18,204,157 | 1,247 | 701 | 5,824 | 3 | 0 | 7 | 18,196,375 |
| 15-12 | urine | 552,120 | 1,892 | 1,003 | 7,983 | 8 | 0 | 38 | 541,196 |
| 15-13 | urine | 182,161 | 1,631 | 588 | 5,530 | 1 | 0 | 10 | 174,401 |
| 15-14 | urine | 454,446 | 1,961 | 916 | 7,562 | 5 | 0 | 33 | 443,969 |
| 15-15 | urine | 4,589,998 | 2,486 | 763 | 5,427 | 4 | 1 | 103 | 4,581,214 |
| 15-16 | urine | 1,949,547 | 1,897 | 821 | 6,232 | 4 | 1 | 19 | 1,940,573 |
| 15-17 | urine | 392,515 | 2,182 | 784 | 6,733 | 6 | 2 | 16 | 382,792 |
| 15-18 | urine | 480,561 | 2,313 | 1,002 | 5,750 | 6 | 2 | 19 | 471,469 |
| 15-19 | urine | 311,087 | 1,981 | 831 | 6,009 | 0 | 3 | 9 | 302,254 |
| 15-20 | urine | 731,074 | 2,047 | 775 | 4,834 | 0 | 0 | 13 | 723,405 |
| 15-21 | urine | 603,413 | 6,258 | 1,013 | 5,362 | 3 | 3 | 33 | 590,741 |
| 15-22 | urine | 719,800 | 2,944 | 913 | 6,222 | 2 | 0 | 44 | 709,675 |
| 15-23 | urine | 624,924 | 2,743 | 809 | 7,227 | 6 | 3 | 8 | 614,128 |
| 15-24 | urine | 2,294,059 | 1,987 | 545 | 5,446 | 2 | 1 | 16 | 2,286,062 |
| 16-1 | urine | 385,997 | 3,587 | 702 | 12,659 | 20 | 0 | 53 | 368,976 |

TABLE 1d-continued

| Sample ID | Biofl. type | Total reads | Adapter reads | Calibrators set 1 | used set 2 | Additional technical categories set 3 calibrators | long calibrators | markers | Remaining reads |
|---|---|---|---|---|---|---|---|---|---|
| 16-2 | urine | 951,614 | 2,714 | 687 | 9,522 | 1 | 0 | 57 | 938,633 |
| 16-3 | urine | 586,070 | 3,215 | 883 | 12,199 | 1 | 0 | 14 | 569,758 |
| 16-4 | urine | 58,464,218 | 2,899 | 1,644 | 15,994 | 3 | 0 | 6 | 58,443,672 |
| 16-5 | urine | 477,937 | 4,315 | 845 | 10,682 | 2 | 0 | 6 | 462,087 |
| 16-6 | urine | 654,740 | 17,482 | 927 | 10,805 | 3 | 2 | 34 | 625,487 |
| 16-7 | urine | 528,923 | 4,923 | 1,102 | 12,608 | 4 | 0 | 79 | 510,207 |
| 16-8 | urine | 628,615 | 6,859 | 889 | 11,654 | 8 | 0 | 18 | 609,187 |
| 16-9 | urine | 2,876,388 | 4,655 | 942 | 15,239 | 13 | 0 | 40 | 2,855,499 |
| 16-10 | urine | 1,196,321 | 3,503 | 760 | 8,213 | 6 | 0 | 40 | 1,183,799 |
| 16-11 | urine | 41,009 | 1,666 | 5 | 355 | 0 | 0 | 7 | 38,976 |
| 16-12 | urine | 580,434 | 3,522 | 555 | 7,087 | 4 | 0 | 61 | 569,205 |
| 16-13 | urine | 784,604 | 2,977 | 1,229 | 10,516 | 5 | 0 | 59 | 769,818 |
| 16-14 | urine | 661,160 | 3,924 | 1,201 | 16,798 | 9 | 0 | 89 | 639,139 |
| 16-15 | urine | 720,560 | 3,867 | 1,630 | 14,964 | 4 | 0 | 227 | 699,868 |
| 16-16 | urine | 4,756,128 | 3,472 | 812 | 12,134 | 15 | 3 | 57 | 4,739,635 |
| 16-17 | urine | 1,058,414 | 3,679 | 1,211 | 19,428 | 24 | 0 | 35 | 1,034,037 |
| 16-18 | urine | 4,018,366 | 4,406 | 2,078 | 15,611 | 17 | 0 | 28 | 3,996,226 |
| 16-19 | urine | 50,942,549 | 4,208 | 1,278 | 13,484 | 9 | 0 | 8 | 50,923,562 |
| 16-20 | urine | 854,496 | 3,420 | 1,463 | 11,035 | 6 | 0 | 37 | 838,535 |
| 16-21 | urine | 815,581 | 7,843 | 1,755 | 16,502 | 9 | 1 | 27 | 789,443 |
| 16-22 | urine | 1,150,745 | 4,096 | 1,692 | 18,411 | 10 | 4 | 146 | 1,126,386 |
| 16-23 | urine | 578,258 | 4,927 | 1,373 | 22,451 | 3 | 0 | 22 | 549,482 |
| 16-24 | urine | 1,533,721 | 4,458 | 1,495 | 19,090 | 4 | 1 | 25 | 1,508,648 |
| 17-1 | urine | 1,572,004 | 13,203 | 1,278 | 12,540 | 5 | 74 | 565 | 1,544,339 |
| 17-2 | urine | 1,023,690 | 13,221 | 1,033 | 8,297 | 4 | 5 | 474 | 1,000,656 |
| 17-3 | urine | 4,218,905 | 21,118 | 1,658 | 15,154 | 5 | 0 | 304 | 4,180,666 |
| 17-4 | urine | 1,498,569 | 17,021 | 2,027 | 17,581 | 5 | 2 | 2 | 1,461,931 |
| 17-5 | urine | 1,752,742 | 20,792 | 1,024 | 14,882 | 0 | 4 | 119 | 1,715,921 |
| 17-6 | urine | 412,777 | 43,148 | 859 | 15,832 | 1 | 3 | 309 | 352,625 |
| 17-7 | urine | 741,872 | 55,182 | 1,126 | 18,274 | 1 | 9 | 2,076 | 665,204 |
| 17-8 | urine | 2,623,150 | 108,708 | 1,606 | 15,201 | 11 | 8 | 143 | 2,497,473 |
| 17-9 | urine | 627,078 | 27,998 | 1,504 | 22,463 | 208 | 3 | 232 | 574,670 |
| 17-10 | urine | 561,010 | 21,108 | 764 | 9,177 | 0 | 0 | 240 | 529,721 |
| 17-11 | urine | 373,069 | 6,167 | 431 | 7,250 | 0 | 0 | 50 | 359,151 |
| 17-12 | urine | 822,180 | 9,285 | 969 | 10,309 | 13 | 2 | 356 | 801,246 |
| 17-13 | urine | 417,151 | 14,830 | 411 | 5,076 | 26 | 5 | 130 | 396,673 |
| 17-14 | urine | 1,728,063 | 10,183 | 935 | 9,051 | 59 | 2 | 328 | 1,707,505 |
| 17-15 | urine | 354,717 | 25,722 | 691 | 8,658 | 7 | 2 | 2,427 | 317,210 |
| 17-16 | urine | 1,084,291 | 14,229 | 1,208 | 10,446 | 3 | 2 | 236 | 1,058,167 |
| 17-17 | urine | 1,010,769 | 19,470 | 1,145 | 12,628 | 7 | 3 | 10 | 977,506 |
| 17-18 | urine | 696,150 | 13,156 | 1,070 | 6,365 | 2 | 4 | 35 | 675,518 |
| 17-19 | urine | 835,330 | 11,633 | 580 | 5,128 | 2 | 6 | 16 | 817,965 |
| 17-20 | urine | 759,980 | 11,500 | 898 | 5,263 | 2 | 1 | 23 | 742,293 |
| 17-21 | urine | 836,429 | 68,799 | 773 | 8,248 | 1 | 0 | 37 | 758,571 |
| 17-22 | urine | 937,639 | 28,581 | 863 | 7,888 | 4 | 6 | 92 | 900,205 |
| 17-23 | urine | 674,944 | 23,158 | 605 | 6,222 | 2 | 132 | 3 | 644,822 |
| 17-24 | urine | 506,243 | 10,012 | 613 | 6,287 | 1 | 0 | 18 | 489,312 |
| 19-1 | urine | 2,137,035 | 29,677 | 4,110 | 98,257 | 60 | 2 | 127 | 2,004,802 |
| 19-2 | urine | 4,923,933 | 21,395 | 7,481 | 96,740 | 29 | 14 | 120 | 4,798,154 |
| 19-3 | urine | 3,499,569 | 33,369 | 3,121 | 55,262 | 0 | 1 | 55 | 3,407,761 |
| 19-4 | urine | 3,780,535 | 36,174 | 2,141 | 52,188 | 12 | 1 | 7 | 3,690,012 |
| 19-5 | urine | 10,777,669 | 33,111 | 2,098 | 23,755 | 2 | 3 | 18 | 10,718,682 |
| 19-6 | urine | 2,750,288 | 338,678 | 1,151 | 20,699 | 4 | 28 | 40 | 2,389,688 |
| 19-7 | urine | 1,265,325 | 51,446 | 2,174 | 43,539 | 9 | 13 | 92 | 1,168,052 |
| 19-8 | urine | 1,968,567 | 85,091 | 2,235 | 116,335 | 14 | 25 | 64 | 1,764,803 |
| 19-9 | urine | 1,463,668 | 38,187 | 548 | 11,795 | 0 | 3 | 21 | 1,413,314 |
| 19-10 | urine | 1,709,054 | 15,025 | 1,474 | 21,845 | 3 | 0 | 76 | 1,670,631 |
| 19-11 | urine | 577,470 | 3,693 | 850 | 11,373 | 0 | 0 | 21 | 561,533 |
| 19-12 | urine | 818,023 | 17,768 | 1,050 | 23,314 | 6 | 2 | 90 | 775,793 |
| 19-13 | urine | 718,722 | 7,008 | 341 | 5,590 | 0 | 0 | 6 | 705,777 |
| 19-14 | urine | 448,563 | 13,684 | 330 | 9,399 | 0 | 0 | 50 | 425,100 |
| 19-15 | urine | 2,975,843 | 25,536 | 1,917 | 55,933 | 5 | 16 | 1,349 | 2,891,087 |
| 19-16 | urine | 920,436 | 19,628 | 2,267 | 48,211 | 7 | 6 | 24 | 850,293 |
| 19-17 | urine | 15,369,840 | 42,632 | 6,196 | 117,434 | 25 | 21 | 62 | 15,203,470 |
| 19-18 | urine | 11,384,262 | 130,274 | 3,130 | 51,636 | 53 | 15 | 65 | 11,199,089 |
| 19-19 | urine | 822,515 | 5,158 | 680 | 12,749 | 0 | 0 | 113 | 803,815 |
| 19-20 | urine | 2,201,254 | 25,804 | 3,030 | 27,462 | 14 | 0 | 130 | 2,144,806 |
| 19-21 | urine | 1,608,337 | 103,053 | 456 | 11,136 | 0 | 3 | 268 | 1,493,421 |
| 19-22 | urine | 1,355,294 | 40,053 | 622 | 9,377 | 0 | 22 | 245 | 1,304,975 |
| 19-23 | urine | 650,459 | 18,681 | 1,358 | 16,303 | 18 | 6 | 1 | 614,092 |
| 19-24 | urine | 1,326,836 | 34,333 | 1,430 | 24,843 | 0 | 9 | 8 | 1,266,213 |
| 20-1 | urine | 1,403,802 | 12,961 | 955 | 18,145 | 6 | 1 | 1,349 | 1,370,385 |
| 20-2 | urine | 1,296,775 | 7,736 | 846 | 12,917 | 0 | 3 | 1,214 | 1,274,059 |

TABLE 1d-continued

| Sample ID | Biofl. type | Total reads | Adapter reads | Calibrators used set 1 | set 2 | Additional technical categories set 3 calibrators | long calibrators | markers | Remaining reads |
|---|---|---|---|---|---|---|---|---|---|
| 20-3 | urine | 2,930,141 | 12,643 | 1,897 | 23,758 | 11 | 2 | 964 | 2,890,866 |
| 20-4 | urine | 593,064 | 17,352 | 921 | 25,003 | 13 | 2 | 8 | 549,765 |
| 20-5 | urine | 2,237,457 | 15,236 | 1,492 | 23,439 | 0 | 4 | 417 | 2,196,869 |
| 20-6 | urine | 2,410,747 | 400,371 | 712 | 18,772 | 7 | 47 | 736 | 1,990,102 |
| 20-7 | urine | 16,494,162 | 52,295 | 1,352 | 27,601 | 0 | 10 | 5,557 | 16,407,347 |
| 20-8 | urine | 1,848,861 | 29,935 | 1,675 | 26,288 | 0 | 0 | 354 | 1,790,609 |
| 20-9 | urine | 2,420,407 | 12,459 | 1,773 | 33,787 | 513 | 1 | 869 | 2,371,005 |
| 20-10 | urine | 1,678,558 | 12,473 | 904 | 13,899 | 4 | 0 | 602 | 1,650,676 |
| 20-11 | urine | 2,701,726 | 4,845 | 214 | 8,239 | 0 | 0 | 184 | 2,688,244 |
| 20-12 | urine | 864,079 | 14,928 | 334 | 6,488 | 0 | 0 | 1,130 | 841,199 |
| 20-13 | urine | 423,340 | 9,886 | 538 | 9,505 | 74 | 0 | 243 | 403,094 |
| 20-14 | urine | 577,143 | 16,102 | 558 | 19,440 | 132 | 0 | 737 | 540,174 |
| 20-15 | urine | 1,394,754 | 14,754 | 1,127 | 20,490 | 14 | 0 | 6,513 | 1,351,856 |
| 20-16 | urine | 1,503,611 | 14,028 | 786 | 19,398 | 0 | 0 | 874 | 1,468,525 |
| 20-17 | urine | 990,225 | 16,972 | 1,053 | 25,944 | 22 | 0 | 12 | 946,222 |
| 20-18 | urine | 1,463,350 | 67,432 | 1,462 | 16,461 | 4 | 3 | 7 | 1,377,981 |
| 20-19 | urine | 842,099 | 8,719 | 847 | 12,126 | 6 | 0 | 32 | 820,369 |
| 20-20 | urine | 547,726 | 22,344 | 975 | 14,097 | 0 | 4 | 51 | 510,255 |
| 20-21 | urine | 1,539,010 | 25,568 | 1,187 | 17,547 | 9 | 1 | 68 | 1,494,630 |
| 20-22 | urine | 644,003 | 21,804 | 748 | 17,422 | 0 | 1 | 133 | 603,895 |
| 20-23 | urine | 927,119 | 20,075 | 1262 | 17,451 | 11 | 7 | 19 | 888,294 |
| 20-24 | urine | 1,065,749 | 43,117 | 1,648 | 15,733 | 0 | 0 | 42 | 1,005,209 |
| 21-1 | urine | 572,455 | 13,277 | 888 | 26,174 | 0 | 0 | 78 | 532,038 |
| 21-2 | urine | 900,027 | 13,062 | 2,623 | 29,090 | 5 | 1 | 43 | 855,203 |
| 21-3 | urine | 5,064,989 | 16,063 | 3,445 | 26,801 | 7 | 1 | 51 | 5,018,621 |
| 21-4 | urine | 1,522,071 | 10,067 | 1,488 | 23,698 | 0 | 1 | 0 | 1,486,817 |
| 21-5 | urine | 552,249 | 15,026 | 647 | 15,694 | 0 | 0 | 13 | 520,869 |
| 21-6 | urine | 1,030,050 | 265,667 | 912 | 14,653 | 0 | 17 | 57 | 748,744 |
| 21-7 | urine | 612,044 | 23,889 | 1,323 | 16,718 | 16 | 0 | 80 | 570,018 |
| 21-8 | urine | 1,059,216 | 62,722 | 1,490 | 27,064 | 32 | 53 | 63 | 967,792 |
| 21-9 | urine | 2,138,006 | 17,348 | 3,582 | 41,151 | 1 | 3 | 90 | 2,075,831 |
| 21-10 | urine | 886,235 | 11,639 | 778 | 14,665 | 0 | 0 | 103 | 859,050 |
| 21-11 | urine | 514,692 | 3,744 | 444 | 5,653 | 0 | 1 | 30 | 504,820 |
| 21-12 | urine | 3,574,972 | 6,159 | 1,368 | 11,795 | 0 | 1 | 61 | 3,555,588 |
| 21-13 | urine | 2,063,272 | 6,248 | 800 | 8,510 | 0 | 0 | 63 | 2,047,651 |
| 21-14 | urine | 974,055 | 9,721 | 1,445 | 19,221 | 8 | 0 | 192 | 943,468 |
| 21-15 | urine | 1,790,976 | 20,111 | 2,175 | 19,227 | 0 | 2 | 331 | 1,749,130 |
| 21-16 | urine | 874,430 | 10,904 | 1,664 | 23,179 | 5 | 0 | 53 | 838,625 |
| 21-17 | urine | 20,844,475 | 18,513 | 2,439 | 45,486 | 20 | 47 | 70 | 20,777,900 |
| 21-18 | urine | 197,134 | 11,002 | 368 | 4,747 | 15 | 0 | 43 | 180,959 |
| 21-19 | urine | 465,680 | 7,140 | 652 | 11,607 | 0 | 5 | 72 | 446,204 |
| 21-20 | urine | 1,060,378 | 16,003 | 1,796 | 16,263 | 0 | 2 | 195 | 1,026,119 |
| 21-21 | urine | 2,214,533 | 50,175 | 2,699 | 31,629 | 23 | 16 | 395 | 2,129,596 |
| 21-22 | urine | 699,059 | 18,034 | 1,389 | 15,084 | 0 | 0 | 325 | 664,227 |
| 21-23 | urine | 1,341,901 | 14,236 | 1219 | 13,050 | 0 | 4 | 15 | 1,313,377 |
| 21-24 | urine | 3,231,522 | 21,862 | 1,333 | 16,395 | 6 | 76 | 15 | 3,191,835 |
| 22-1 | urine | 1,117,157 | 37,488 | 1,861 | 15,338 | 7 | 8 | 24 | 1,062,431 |
| 22-2 | urine | 973,372 | 35,568 | 554 | 13,155 | 6 | 0 | 23 | 924,066 |
| 22-3 | urine | 2,136,881 | 37,015 | 1,940 | 15,520 | 12 | 3 | 14 | 2,082,377 |
| 22-4 | urine | 367,714 | 26,311 | 75 | 1,692 | 2 | 9 | 0 | 339,625 |
| 22-5 | urine | 760,225 | 41,452 | 1,262 | 15,285 | 1 | 11 | 4 | 702,210 |
| 22-6 | urine | 3,092,179 | 153,426 | 1,101 | 15,238 | 7 | 23 | 37 | 2,922,347 |
| 22-7 | urine | 1,255,400 | 46,153 | 1,617 | 16,882 | 3 | 5 | 40 | 1,190,700 |
| 22-8 | urine | 1,294,795 | 72,791 | 1,496 | 16,491 | 15 | 8 | 42 | 1,203,952 |
| 22-9 | urine | 1,087,030 | 39,353 | 1,793 | 21,310 | 8 | 3 | 28 | 1,024,535 |
| 22-10 | urine | 674,938 | 35,003 | 795 | 12,721 | 0 | 4 | 30 | 626,385 |
| 22-11 | urine | 1,137,520 | 17,310 | 713 | 8,167 | 0 | 5 | 17 | 1,111,308 |
| 22-12 | urine | 3,922,484 | 22,765 | 1,480 | 13,727 | 3 | 6 | 45 | 3,884,458 |
| 22-13 | urine | 960,174 | 33,637 | 1,793 | 27,322 | 8 | 5 | 20 | 897,389 |
| 22-14 | urine | 905,691 | 34,230 | 772 | 6,240 | 2 | 8 | 48 | 864,391 |
| 22-15 | urine | 2,763,777 | 42,460 | 668 | 29,846 | 6 | 31 | 146 | 2,690,620 |
| 22-16 | urine | 4,396,900 | 35,325 | 3,074 | 35,542 | 11 | 143 | 43 | 4,322,762 |
| 22-17 | urine | 16,161,986 | 37,125 | 1,966 | 49,862 | 25 | 11 | 8 | 16,072,989 |
| 22-18 | urine | 484,449 | 41,429 | 301 | 7,027 | 0 | 2 | 5 | 435,685 |
| 22-19 | urine | 821,431 | 33,115 | 182 | 4,092 | 0 | 2 | 14 | 784,026 |
| 22-20 | urine | 2,837,329 | 34,688 | 517 | 11,110 | 7 | 32 | 41 | 2,790,934 |
| 22-21 | urine | 1,907,061 | 63,273 | 3,203 | 35,339 | 13 | 4 | 59 | 1,805,170 |
| 22-22 | urine | 1,380,840 | 36,014 | 3,250 | 34,090 | 8 | 7 | 213 | 1,307,258 |
| 22-23 | urine | 8,865,156 | 39,472 | 3,261 | 28,984 | 14 | 8 | 18 | 8,793,399 |
| 22-24 | urine | 2,934,655 | 53,469 | 3,445 | 34,311 | 15 | 7 | 45 | 2,843,363 |
| 23-1 | urine | 361,276 | 15,359 | 1,004 | 14,547 | 4 | 2 | 53 | 330,307 |
| 23-2 | urine | 1,007,364 | 16,119 | 1,032 | 11,840 | 7 | 2 | 43 | 978,321 |
| 23-3 | urine | 338,733 | 14,415 | 172 | 2,844 | 0 | 0 | 31 | 321,271 |

TABLE 1d-continued

| Sample ID | Biofl. type | Total reads | Adapter reads | Calibrators used set 1 | Calibrators used set 2 | Additional technical categories set 3 calibrators | Additional technical categories long calibrators | markers | Remaining reads |
|---|---|---|---|---|---|---|---|---|---|
| 23-4 | urine | 817,070 | 16,097 | 1,748 | 15,939 | 9 | 2 | 14 | 783,261 |
| 23-5 | urine | 1,137,184 | 20,261 | 1,601 | 13,281 | 8 | 11 | 13 | 1,102,009 |
| 23-6 | urine | 1,167,481 | 46,631 | 951 | 10,272 | 0 | 5 | 25 | 1,109,597 |
| 23-7 | urine | 1,284,768 | 32,449 | 1,219 | 13,823 | 0 | 12 | 59 | 1,237,206 |
| 23-8 | urine | 1,553,145 | 87,860 | 533 | 12,500 | 0 | 10 | 27 | 1,452,215 |
| 23-9 | urine | 1,545,171 | 25,905 | 1,384 | 16,301 | 5 | 2 | 27 | 1,501,547 |
| 23-10 | urine | 1,224,094 | 18,000 | 942 | 9,698 | 0 | 0 | 32 | 1,195,422 |
| 23-11 | urine | 762,552 | 9,011 | 277 | 8,048 | 0 | 1 | 5 | 745,210 |
| 23-12 | urine | 699,557 | 10,836 | 608 | 14,734 | 0 | 9 | 28 | 673,342 |
| 23-13 | urine | 1,402,904 | 20,706 | 2,332 | 20,937 | 12 | 1 | 32 | 1,358,884 |
| 23-14 | urine | 2,256,763 | 13,434 | 2,813 | 33,014 | 23 | 25 | 99 | 2,207,355 |
| 23-15 | urine | 402,530 | 30,933 | 404 | 5,855 | 0 | 0 | 228 | 365,110 |
| 23-16 | urine | 949,544 | 13,076 | 1,282 | 32,794 | 27 | 13 | 30 | 902,322 |
| 23-17 | urine | 607,061 | 25,153 | 493 | 15,124 | 3 | 0 | 8 | 566,280 |
| 23-18 | urine | 27,867,147 | 17,091 | 2,448 | 18,955 | 3 | 1,157 | 32 | 27,827,461 |
| 23-19 | urine | 1,726,524 | 18,117 | 2,263 | 28,052 | 2 | 9 | 104 | 1,679,977 |
| 23-20 | urine | 471,773 | 13,962 | 161 | 7,710 | 6 | 3 | 135 | 449,796 |
| 23-21 | urine | 1,934,071 | 72,102 | 3,682 | 33,463 | 32 | 10 | 276 | 1,824,506 |
| 23-22 | urine | 12,816,186 | 27,415 | 2,595 | 29,049 | 21 | 2 | 301 | 12,756,803 |
| 23-23 | urine | 459,640 | 30,118 | 156 | 3,276 | 0 | 10 | 13 | 426,065 |
| 23-24 | urine | 429,597 | 11,165 | 420 | 3,580 | 0 | 0 | 15 | 414,417 |
| 24-1 | urine | 8,137,350 | 36,183 | 1,893 | 20,461 | 6 | 4 | 28 | 8,078,775 |
| 24-2 | urine | 879,786 | 29,181 | 150 | 2,500 | 0 | 2 | 11 | 847,942 |
| 24-3 | urine | 1,957,954 | 41,249 | 2,663 | 20,502 | 5 | 11 | 6 | 1,893,518 |
| 24-4 | urine | 2,943,043 | 35,288 | 544 | 22,858 | 14 | 3 | 0 | 2,884,336 |
| 24-5 | urine | 4,727,977 | 39,618 | 3,640 | 17,604 | 3 | 2 | 6 | 4,667,104 |
| 24-6 | urine | 1,504,581 | 48,263 | 1,022 | 19,609 | 7 | 10 | 24 | 1,435,646 |
| 24-7 | urine | 5,590,070 | 53,465 | 2,208 | 20,309 | 11 | 1 | 20 | 5,514,056 |
| 24-8 | urine | 27,500,349 | 107,938 | 2,574 | 23,586 | 24 | 15 | 20 | 27,366,192 |
| 24-9 | urine | 7,230,779 | 46,622 | 2,408 | 29,486 | 25 | 2 | 6 | 7,152,230 |
| 24-10 | urine | 1,533,529 | 31,579 | 295 | 8,597 | 3 | 1 | 9 | 1,493,045 |
| 24-11 | urine | 4,098,516 | 10,537 | 635 | 5,192 | 1 | 4 | 12 | 4,082,135 |
| 24-12 | urine | 8,750,763 | 24,921 | 2,532 | 16,065 | 2 | 3 | 50 | 8,707,190 |
| 24-13 | urine | 7,887,031 | 12,369 | 813 | 5,353 | 0 | 0 | 9 | 7,868,487 |
| 24-14 | urine | 12,328,070 | 11,694 | 414 | 6,471 | 9 | 0 | 38 | 12,309,444 |
| 24-15 | urine | 1,550,305 | 18,654 | 606 | 7,340 | 10 | 1 | 132 | 1,523,562 |
| 24-16 | urine | 892,921 | 9,655 | 662 | 7,130 | 5 | 1 | 15 | 875,453 |
| 24-17 | urine | 1,640,256 | 5,462 | 515 | 4,552 | 5 | 8 | 3 | 1,629,711 |
| 24-18 | urine | 489,034 | 6,058 | 500 | 3,959 | 2 | 0 | 7 | 478,508 |
| 24-19 | urine | 5,116,504 | 6,758 | 296 | 2,771 | 0 | 2 | 52 | 5,106,625 |
| 24-20 | urine | 2,772,122 | 10,894 | 795 | 5,662 | 8 | 1 | 102 | 2,754,660 |
| 24-21 | urine | 10,895,346 | 22,091 | 985 | 6,324 | 5 | 31 | 261 | 10,865,649 |
| 24-22 | urine | 1,308,442 | 15,345 | 952 | 8,208 | 1 | 3 | 198 | 1,283,735 |
| 24-23 | urine | 1,184,667 | 13,676 | 658 | 5,776 | 2 | 0 | 2 | 1,164,553 |
| 24-24 | urine | 404,994 | 7,132 | 185 | 4,601 | 0 | 1 | 9 | 393,086 |
| 32-16 | urine | 1,863,823 | 10,830 | 2,242 | 30,025 | 0 | 0 | 8,662 | 1,812,064 |
| 32-17 | urine | 3,339,643 | 20,698 | 923 | 20,796 | 2 | 0 | 44 | 3,297,380 |
| 32-18 | urine | 12,477,265 | 42,482 | 2,283 | 17,745 | 2 | 0 | 111 | 12,414,642 |
| 32-19 | urine | 939,776 | 9,958 | 1,138 | 13,071 | 0 | 0 | 253 | 915,356 |
| 32-20 | urine | 4,368,840 | 10,759 | 2,350 | 15,984 | 0 | 0 | 352 | 4,339,395 |
| 32-21 | urine | 2,015,273 | 50,969 | 1,789 | 26,347 | 0 | 1 | 1,594 | 1,934,573 |
| 32-22 | urine | 3,320,913 | 24,153 | 1,918 | 53,739 | 16 | 20 | 22,389 | 3,218,678 |
| 32-23 | urine | 608,595 | 19,896 | 514 | 15,629 | 0 | 0 | 208 | 572,348 |
| 32-24 | urine | 1,134,140 | 21,079 | 859 | 16,751 | 0 | 1 | 354 | 1,095,096 |
| 37-13 | urine | 16,402 | 910 | 36 | 1,394 | 0 | 0 | 4 | 14,058 |
| 37-14 | urine | 81,435 | 415 | 203 | 2,720 | 3 | 0 | 20 | 78,074 |
| 37-15 | urine | 518,710 | 1,174 | 921 | 5,167 | 0 | 0 | 76 | 511,372 |
| 37-16 | urine | 131,687 | 596 | 730 | 4,816 | 0 | 0 | 11 | 125,534 |
| 37-17 | urine | 632,135 | 967 | 3,051 | 27,731 | 17 | 0 | 15 | 600,354 |
| 37-18 | urine | 640,658 | 8,529 | 1,555 | 6,076 | 3 | 0 | 17 | 624,478 |
| 37-19 | urine | 300,018 | 43 | 92 | 921 | 0 | 0 | 3 | 298,959 |
| 37-20 | urine | 224,479 | 1,116 | 378 | 3,253 | 0 | 0 | 26 | 219,704 |
| 37-21 | urine | 1,140,298 | 2,445 | 789 | 11,441 | 6 | 0 | 38 | 1,125,579 |

Table 1 Overview of RNA annotation categories of sRNA data from Biofluids a Summary table listing total read counts, quality control and other technical annotations as well as remaining reads. b, c, d, per-sample lists of a for plasma, serum, and urine.

TABLE 2a

| Biofluid | | Total reads* | Mapped to hg19 | miRNA | rRNA | tRNA | scRNA | Other ncRNA | mRNA | Unmapped to hg19 |
|---|---|---|---|---|---|---|---|---|---|---|
| Plasma | n = 96 | | | | | | | | | |
| | median | 2,009,283 | 84.5% | 75.2% | 2.3% | 0.3% | 2.5% | 0.7% | 2.7% | 15.5% |
| | min | 89,015 | 36.5% | 23.5% | 1.0% | 0.2% | 0.8% | 0.3% | 0.8% | 5.0% |
| | max | 16,605,906 | 95.0% | 90.8% | 4.9% | 0.6% | 7.1% | 1.7% | 22.2% | 63.5% |
| Serum | n = 72 | | | | | | | | | |
| | median | 1,749,152 | 75.0% | 44.8% | 8.3% | 4.7% | 6.2% | 1.4% | 4.0% | 25.0% |
| | min | 59,160 | 37.4% | 16.3% | 2.9% | 1.6% | 1.7% | 0.7% | 1.0% | 6.1% |
| | max | 26,489,291 | 93.9% | 78.7% | 16.4% | 15.3% | 17.1% | 2.2% | 19.5% | 62.6% |
| Urine | n = 282 | | | | | | | | | |
| | median | 1,355,370 | 54.3% | 15.7% | 5.8% | 9.4% | 1.1% | 1.4% | 6.1% | 45.7% |
| | min | 14,058 | 1.9% | 0.0% | 0.1% | 0.2% | 0.0% | 0.1% | 0.2% | 1.7% |
| | max | 58,443,672 | 98.3% | 85.4% | 32.6% | 94.0% | 37.3% | 7.9% | 27.9% | 98.1% |

TABLE 2b

| | | Sample statistics | | ncRNA annotation | | | | | | |
|---|---|---|---|---|---|---|---|---|---|---|
| Sample ID | Samp. Type | Total reads* | Mapped to hg19 | miRNA | rRNA | tRNA | scRNA | Other ncRNA | mRNA | Unmapped to hq19 |
| 55-1 | plasma | 3,170,815 | 85.3% | 77.0% | 2.8% | 0.4% | 2.7% | 0.6% | 1.6% | 14.7% |
| 55-2 | plasma | 6,478,400 | 36.5% | 23.5% | 1.5% | 0.5% | 2.0% | 1.2% | 7.9% | 63.5% |
| 55-3 | plasma | 3,918,491 | 85.0% | 77.0% | 1.8% | 0.4% | 3.5% | 0.6% | 1.7% | 15.0% |
| 55-4 | plasma | 1,966,946 | 80.6% | 71.7% | 2.5% | 0.4% | 2.5% | 0.6% | 2.9% | 19.4% |
| 55-5 | plasma | 4,714,513 | 91.3% | 85.0% | 1.3% | 0.3% | 3.4% | 0.4% | 1.0% | 8.7% |
| 55-6 | plasma | 2,065,804 | 73.8% | 51.8% | 2.4% | 0.3% | 2.0% | 0.7% | 16.5% | 26.2% |
| 55-7 | plasma | 3,186,571 | 86.8% | 80.0% | 1.6% | 0.2% | 2.1% | 0.6% | 2.3% | 13.2% |
| 55-8 | plasma | 4,558,302 | 83.0% | 71.7% | 2.9% | 0.5% | 4.7% | 0.7% | 2.5% | 17.0% |
| 55-9 | plasma | 8,168,078 | 88.9% | 81.1% | 1.9% | 0.3% | 3.1% | 0.9% | 1.7% | 11.1% |
| 55-10 | plasma | 2,100,425 | 84.3% | 75.3% | 2.5% | 0.6% | 3.1% | 0.7% | 2.1% | 15.7% |
| 55-11 | plasma | 712,227 | 86.9% | 76.5% | 1.9% | 0.3% | 6.1% | 0.6% | 1.6% | 13.1% |
| 55-12 | plasma | 2,506,252 | 60.0% | 49.3% | 1.7% | 0.4% | 2.3% | 0.9% | 5.4% | 40.0% |
| 55-13 | plasma | 1,265,369 | 87.8% | 77.0% | 2.8% | 0.4% | 5.5% | 0.6% | 1.5% | 12.2% |
| 55-14 | plasma | 1,760,210 | 64.9% | 55.4% | 2.7% | 0.4% | 1.2% | 0.9% | 4.4% | 35.1% |
| 55-15 | plasma | 2,051,619 | 82.5% | 70.3% | 3.6% | 0.4% | 5.1% | 0.8% | 2.3% | 17.5% |
| 55-16 | plasma | 3,866,155 | 92.2% | 84.3% | 1.8% | 0.3% | 4.0% | 0.5% | 1.3% | 7.8% |
| 55-17 | plasma | 7,086,222 | 93.6% | 89.3% | 1.1% | 0.2% | 1.5% | 0.4% | 1.0% | 6.4% |
| 55-18 | plasma | 5,457,453 | 91.3% | 84.1% | 2.7% | 0.3% | 2.3% | 0.5% | 1.4% | 8.7% |
| 55-19 | plasma | 546,442 | 66.3% | 56.6% | 1.8% | 0.3% | 2.5% | 0.8% | 4.2% | 33.7% |
| 55-20 | plasma | 1,447,780 | 76.7% | 66.5% | 2.8% | 0.4% | 3.2% | 0.9% | 2.9% | 23.3% |
| 55-21 | plasma | 2,989,816 | 84.8% | 78.0% | 1.6% | 0.3% | 2.6% | 0.5% | 1.8% | 15.2% |
| 55-22 | plasma | 2,815,407 | 89.4% | 81.6% | 1.9% | 0.3% | 3.4% | 0.6% | 1.5% | 10.6% |
| 55-23 | plasma | 1,150,522 | 81.6% | 70.4% | 2.7% | 0.4% | 5.1% | 0.7% | 2.4% | 18.4% |
| 55-24 | plasma | 2,583,405 | 81.6% | 75.9% | 2.0% | 0.3% | 0.9% | 0.5% | 2.0% | 18.4% |
| 56-1 | plasma | 3,448,204 | 87.6% | 81.7% | 1.9% | 0.3% | 1.7% | 0.6% | 1.5% | 12.4% |
| 56-2 | plasma | 1,725,474 | 82.6% | 72.3% | 2.4% | 0.3% | 4.9% | 0.6% | 2.1% | 17.4% |
| 56-3 | plasma | 3,198,408 | 88.1% | 81.8% | 1.6% | 0.3% | 2.6% | 0.4% | 1.4% | 11.9% |
| 56-4 | plasma | 5,438,321 | 93.5% | 88.0% | 1.8% | 0.3% | 1.6% | 0.5% | 1.3% | 6.5% |
| 56-5 | plasma | 3,264,606 | 87.1% | 81.3% | 1.4% | 0.4% | 2.0% | 0.4% | 1.5% | 12.9% |
| 56-6 | plasma | 2,082,393 | 65.4% | 38.7% | 2.0% | 0.3% | 1.5% | 0.7% | 22.2% | 34.6% |
| 56-7 | plasma | 1,828,482 | 77.7% | 67.5% | 2.3% | 0.3% | 3.3% | 0.7% | 3.6% | 22.3% |
| 56-8 | plasma | 3,951,747 | 87.0% | 79.6% | 1.6% | 0.2% | 3.0% | 0.5% | 2.0% | 13.0% |
| 56-9 | plasma | 9,763,521 | 95.0% | 90.8% | 1.1% | 0.2% | 1.7% | 0.5% | 0.8% | 5.0% |
| 56-10 | plasma | 1,309,023 | 79.5% | 70.6% | 1.9% | 0.3% | 3.4% | 0.6% | 2.7% | 20.5% |
| 56-11 | plasma | 391,115 | 72.2% | 58.2% | 2.7% | 0.4% | 6.4% | 0.9% | 3.7% | 27.8% |
| 56-12 | plasma | 1,825,135 | 80.1% | 70.5% | 2.7% | 0.4% | 3.0% | 0.7% | 2.8% | 19.9% |
| 56-13 | plasma | 1,450,371 | 85.7% | 77.7% | 2.7% | 0.2% | 2.6% | 0.5% | 2.0% | 14.3% |
| 56-14 | plasma | 2,092,191 | 88.6% | 83.8% | 1.4% | 0.2% | 1.3% | 0.4% | 1.4% | 11.4% |
| 56-15 | plasma | 3,019,444 | 88.4% | 78.1% | 2.3% | 0.3% | 5.4% | 0.6% | 1.8% | 11.6% |
| 56-16 | plasma | 1,001,067 | 77.9% | 67.2% | 2.6% | 0.4% | 4.0% | 0.7% | 2.8% | 22.1% |
| 56-17 | plasma | 3,909,520 | 92.8% | 88.5% | 1.0% | 0.2% | 1.5% | 0.3% | 1.2% | 7.2% |
| 56-18 | plasma | 2,627,068 | 71.5% | 61.6% | 2.4% | 0.3% | 2.1% | 0.7% | 4.3% | 28.5% |
| 56-19 | plasma | 982,023 | 81.4% | 72.3% | 2.1% | 0.3% | 3.5% | 0.7% | 2.5% | 18.6% |
| 56-20 | plasma | 2,504,704 | 82.1% | 74.6% | 2.0% | 0.3% | 1.7% | 0.8% | 2.7% | 17.9% |
| 56-21 | plasma | 1,305,737 | 72.8% | 62.1% | 3.5% | 0.3% | 2.7% | 0.7% | 3.4% | 27.2% |
| 56-22 | plasma | 1,622,738 | 72.4% | 63.8% | 1.6% | 0.3% | 2.0% | 0.7% | 3.9% | 27.6% |
| 56-23 | plasma | 1,777,217 | 83.2% | 72.3% | 2.5% | 0.4% | 4.8% | 0.7% | 2.5% | 16.8% |
| 56-24 | plasma | 1,319,327 | 79.8% | 72.6% | 2.5% | 0.3% | 1.1% | 0.7% | 2.7% | 20.2% |

TABLE 2b-continued

| | | Sample statistics | | ncRNA annotation | | | | | | |
|---|---|---|---|---|---|---|---|---|---|---|
| Sample ID | Samp. Type | Total reads* | Mapped to hg19 | miRNA | rRNA | tRNA | scRNA | Other ncRNA | mRNA | Unmapped to hq19 |
| 57-1 | plasma | 3,169,972 | 75.8% | 64.2% | 3.0% | 0.5% | 2.4% | 1.0% | 4.7% | 24.2% |
| 57-2 | plasma | 3,036,318 | 83.8% | 71.5% | 2.9% | 0.4% | 5.1% | 0.9% | 3.1% | 16.2% |
| 57-3 | plasma | 3,417,103 | 72.6% | 58.4% | 2.8% | 0.5% | 3.2% | 1.2% | 6.5% | 27.4% |
| 57-4 | plasma | 2,162,215 | 88.4% | 79.2% | 2.6% | 0.3% | 2.5% | 0.8% | 2.9% | 11.6% |
| 57-5 | plasma | 2,669,216 | 85.5% | 78.7% | 1.5% | 0.2% | 2.1% | 0.6% | 2.4% | 14.5% |
| 57-6 | plasma | 1,041,377 | 73.7% | 51.7% | 1.6% | 0.2% | 1.0% | 0.7% | 18.5% | 26.3% |
| 57-7 | plasma | 1,183,220 | 84.6% | 75.0% | 2.1% | 0.3% | 2.8% | 0.7% | 3.7% | 15.4% |
| 57-8 | plasma | 4,280,217 | 80.9% | 69.8% | 2.6% | 0.4% | 2.6% | 0.9% | 4.5% | 19.1% |
| 57-9 | plasma | 12,750,931 | 93.0% | 87.4% | 1.1% | 0.2% | 2.0% | 0.8% | 1.4% | 7.0% |
| 57-10 | plasma | 921,822 | 85.3% | 75.8% | 2.8% | 0.3% | 2.9% | 0.7% | 2.8% | 14.7% |
| 57-11 | plasma | 269,263 | 82.1% | 67.3% | 2.9% | 0.4% | 7.1% | 0.9% | 3.5% | 17.9% |
| 57-12 | plasma | 955,414 | 84.4% | 74.2% | 2.6% | 0.3% | 3.3% | 0.7% | 3.3% | 15.6% |
| 57-13 | plasma | 592,448 | 76.5% | 60.8% | 3.3% | 0.5% | 4.5% | 1.7% | 5.8% | 23.5% |
| 57-14 | plasma | 1,177,538 | 83.9% | 75.6% | 2.1% | 0.3% | 1.5% | 0.8% | 3.7% | 16.1% |
| 57-15 | plasma | 1,932,800 | 85.6% | 74.2% | 3.3% | 0.3% | 3.5% | 0.8% | 3.4% | 14.4% |
| 57-16 | plasma | 1,523,395 | 87.2% | 77.9% | 2.0% | 0.3% | 3.7% | 0.7% | 2.6% | 12.8% |
| 57-17 | plasma | 2,638,576 | 77.7% | 67.0% | 2.6% | 0.4% | 2.2% | 0.8% | 4.6% | 22.3% |
| 57-18 | plasma | 2,527,697 | 86.1% | 76.6% | 2.6% | 0.3% | 3.0% | 0.6% | 3.1% | 13.9% |
| 57-19 | plasma | 474,337 | 81.7% | 71.0% | 2.7% | 0.4% | 2.7% | 1.0% | 4.0% | 18.3% |
| 57-20 | plasma | 1,574,993 | 82.1% | 71.0% | 3.1% | 0.5% | 2.5% | 1.1% | 3.9% | 17.9% |
| 57-21 | plasma | 5,317,396 | 83.1% | 74.2% | 1.8% | 0.3% | 2.1% | 0.8% | 3.9% | 16.9% |
| 57-22 | plasma | 2,182,781 | 90.3% | 82.8% | 2.7% | 0.4% | 1.8% | 0.7% | 1.9% | 9.7% |
| 57-23 | plasma | 1,064,579 | 88.5% | 73.9% | 2.7% | 0.3% | 3.3% | 0.7% | 2.5% | 11.5% |
| 57-24 | plasma | 1,128,425 | 86.8% | 78.8% | 2.8% | 0.4% | 1.4% | 0.8% | 2.6% | 13.2% |
| 58-1 | plasma | 2,697,602 | 68.9% | 55.2% | 2.4% | 0.6% | 2.7% | 1.2% | 6.8% | 31.1% |
| 58-2 | plasma | 8,944,339 | 91.9% | 84.7% | 2.1% | 0.3% | 2.6% | 0.6% | 1.6% | 8.1% |
| 58-3 | plasma | 10,052,257 | 87.6% | 81.6% | 1.7% | 0.3% | 1.1% | 0.7% | 2.2% | 12.4% |
| 58-4 | plasma | 645,105 | 92.4% | 86.4% | 1.7% | 0.2% | 1.7% | 0.5% | 1.9% | 7.6% |
| 58-5 | plasma | 1,220,686 | 73.4% | 61.7% | 2.9% | 0.6% | 1.9% | 1.1% | 5.2% | 26.6% |
| 58-6 | plasma | 172,755 | 72.6% | 49.0% | 1.9% | 0.2% | 0.8% | 0.6% | 20.1% | 27.4% |
| 58-7 | plasma | 377,212 | 53.8% | 39.4% | 1.8% | 0.4% | 1.5% | 1.5% | 9.4% | 46.2% |
| 58-8 | plasma | 7,656,513 | 91.9% | 85.7% | 1.7% | 0.2% | 1.8% | 0.5% | 1.9% | 8.1% |
| 58-9 | plasma | 9,687,351 | 88.5% | 81.0% | 1.4% | 0.2% | 2.5% | 1.3% | 2.1% | 11.5% |
| 58-10 | plasma | 340,724 | 85.7% | 74.6% | 4.9% | 0.4% | 2.3% | 0.8% | 2.8% | 14.3% |
| 58-11 | plasma | 89,015 | 87.7% | 76.4% | 2.0% | 0.4% | 5.6% | 0.8% | 2.5% | 12.3% |
| 58-12 | plasma | 194,940 | 82.6% | 73.0% | 2.7% | 0.2% | 2.5% | 0.7% | 3.4% | 17.4% |
| 58-13 | plasma | 137,809 | 87.1% | 77.0% | 2.2% | 0.3% | 2.7% | 0.8% | 3.2% | 12.9% |
| 58-14 | plasma | 261,682 | 85.6% | 77.8% | 2.5% | 0.3% | 1.7% | 0.7% | 2.6% | 14.4% |
| 58-15 | plasma | 1,102,762 | 92.9% | 86.7% | 2.3% | 0.2% | 1.3% | 0.6% | 1.8% | 7.1% |
| 58-16 | plasma | 552,875 | 83.6% | 71.7% | 2.6% | 0.3% | 4.7% | 0.9% | 3.3% | 16.4% |
| 58-17 | plasma | 16,605,906 | 93.2% | 85.3% | 1.6% | 0.3% | 3.7% | 0.6% | 1.7% | 6.8% |
| 58-18 | plasma | 2,738,793 | 89.4% | 81.7% | 2.4% | 0.2% | 1.9% | 0.6% | 2.5% | 10.6% |
| 58-19 | plasma | 145,302 | 88.8% | 81.5% | 2.2% | 0.3% | 1.3% | 0.8% | 2.7% | 11.2% |
| 58-20 | plasma | 553,439 | 83.3% | 74.7% | 2.4% | 0.2% | 1.6% | 0.9% | 3.5% | 16.7% |
| 58-21 | plasma | 5,585,738 | 77.8% | 68.5% | 1.3% | 0.3% | 1.3% | 0.9% | 5.5% | 22.2% |
| 58-22 | plasma | 525,424 | 74.1% | 65.7% | 1.6% | 0.5% | 1.0% | 0.8% | 4.5% | 25.9% |
| 58-23 | plasma | 355,803 | 88.3% | 80.7% | 2.1% | 0.3% | 1.9% | 0.7% | 2.6% | 11.7% |
| 58-24 | plasma | 353,307 | 85.3% | 78.5% | 2.1% | 0.2% | 1.1% | 0.6% | 2.7% | 14.7% |

TABLE 2C

| | | Sample statistics | | ncRNA annotation | | | | | | |
|---|---|---|---|---|---|---|---|---|---|---|
| Sample ID | Samp. Type | Total reads* | Mapped to hg19 | miRNA | rRNA | tRNA | scRNA | Other ncRNA | mRNA | Unmapped to hq19 |
| 60-1 | serum | 4,811,785 | 77.4% | 39.4% | 6.8% | 15.3% | 10.6% | 1.7% | 3.5% | 22.6% |
| 60-2 | serum | 3,186,281 | 68.9% | 39.9% | 8.8% | 7.3% | 7.3% | 1.2% | 4.3% | 31.1% |
| 60-3 | serum | 6,538,858 | 76.1% | 43.7% | 10.5% | 9.6% | 7.1% | 1.5% | 3.7% | 23.9% |
| 60-4 | serum | 1,805,464 | 72.1% | 36.7% | 12.3% | 11.2% | 6.1% | 1.5% | 4.4% | 27.9% |
| 60-5 | serum | 2,431,528 | 68.9% | 35.9% | 0.8% | 11.9% | 6.8% | 1.5% | 3.9% | 31.1% |
| 60-6 | serum | 2,917,129 | 81.0% | 61.1% | 2.9% | 2.3% | 3.7% | 1.1% | 9.8% | 19.0% |
| 60-7 | serum | 2,381,431 | 79.0% | 46.0% | 10.3% | 6.9% | 8.4% | 1.7% | 6.7% | 21.0% |
| 60-8 | serum | 5,382,049 | 77.7% | 44.3% | 10.1% | 12.2% | 6.4% | 1.1% | 3.7% | 22.3% |
| 60-9 | serum | 5,727,843 | 76.1% | 43.5% | 7.2% | 10.9% | 9.0% | 2.2% | 3.3% | 23.9% |
| 60-10 | serum | 2,662,171 | 59.6% | 33.3% | 8.0% | 5.8% | 4.8% | 1.4% | 6.2% | 40.4% |
| 60-11 | serum | 250,614 | 64.2% | 31.7% | 8.9% | 4.7% | 13.2% | 1.4% | 4.2% | 35.8% |
| 60-12 | serum | 2,372,536 | 88.4% | 71.8% | 4.3% | 2.9% | 6.4% | 1.0% | 2.0% | 11.6% |
| 60-13 | serum | 1,000,182 | 78.3% | 53.0% | 8.5% | 3.8% | 8.1% | 1.3% | 3.7% | 21.7% |
| 60-14 | serum | 2,961,028 | 90.6% | 76.1% | 6.5% | 3.0% | 2.6% | 0.9% | 1.6% | 9.4% |
| 60-15 | serum | 4,024,243 | 49.3% | 26.3% | 5.4% | 4.1% | 4.6% | 1.4% | 7.4% | 50.7% |
| 60-16 | serum | 1,571,011 | 75.7% | 47.2% | 6.9% | 5.4% | 11.0% | 2.0% | 3.3% | 24.3% |

TABLE 2C-continued

| | Sample statistics | | | ncRNA annotation | | | | | | |
|---|---|---|---|---|---|---|---|---|---|---|
| Sample ID | Samp. Type | Total reads* | Mapped to hg19 | miRNA | rRNA | tRNA | scRNA | Other ncRNA | mRNA | Unmapped to hq19 |
| 60-17 | serum | 5,743,967 | 77.5% | 49.0% | 3.6% | 6.5% | 12.6% | 1.9% | 3.9% | 22.5% |
| 60-18 | serum | 2,082,216 | 71.6% | 38.5% | 16.3% | 6.5% | 4.5% | 1.1% | 4.7% | 28.4% |
| 60-19 | serum | 635,901 | 72.1% | 41.9% | 11.3% | 7.1% | 6.1% | 1.7% | 3.9% | 27.9% |
| 60-20 | serum | 1,293,622 | 63.2% | 33.8% | 13.0% | 4.1% | 4.3% | 1.8% | 8.3% | 36.8% |
| 60-21 | serum | 5,139,556 | 44.1% | 22.0% | 5.7% | 2.2% | 1.9% | 1.7% | 10.5% | 55.9% |
| 60-22 | serum | 1,279,295 | 70.7% | 41.3% | 13.1% | 6.2% | 3.4% | 1.5% | 5.1% | 29.3% |
| 60-23 | serum | 1,083,824 | 55.9% | 25.0% | 10.1% | 5.3% | 4.3% | 1.9% | 9.3% | 44.1% |
| 60-24 | serum | 882,209 | 52.4% | 30.2% | 8.2% | 2.4% | 1.9% | 1.6% | 8.0% | 47.6% |
| 61-1 | serum | 11,192,055 | 90.5% | 70.6% | 4.4% | 7.3% | 5.7% | 0.9% | 1.6% | 9.5% |
| 61-2 | serum | 6,276,539 | 81.8% | 48.3% | 6.4% | 12.6% | 10.2% | 1.4% | 2.9% | 18.2% |
| 61-3 | serum | 4,505,760 | 68.8% | 34.7% | 10.1% | 11.4% | 6.8% | 1.5% | 4.3% | 31.2% |
| 61-4 | serum | 1,106,572 | 79.7% | 44.2% | 12.4% | 10.9% | 6.8% | 1.4% | 4.0% | 20.3% |
| 61-5 | serum | 1,472,992 | 71.6% | 39.5% | 10.0% | 10.3% | 6.3% | 1.5% | 4.0% | 28.4% |
| 61-6 | serum | 646,807 | 67.6% | 29.7% | 9.3% | 5.0% | 2.9% | 1.2% | 19.5% | 32.4% |
| 61-7 | serum | 539,777 | 59.4% | 34.6% | 6.1% | 2.3% | 7.5% | 1.5% | 7.3% | 40.6% |
| 61-8 | serum | 4,709,015 | 48.6% | 27.1% | 6.3% | 3.3% | 3.6% | 1.3% | 7.1% | 51.4% |
| 61-9 | serum | 12,660,231 | 87.9% | 53.3% | 6.0% | 12.6% | 12.2% | 1.8% | 2.0% | 12.1% |
| 61-10 | serum | 854,738 | 81.0% | 48.9% | 11.6% | 6.5% | 9.8% | 1.4% | 2.8% | 19.0% |
| 61-11 | serum | 872,530 | 50.4% | 22.7% | 3.1% | 2.7% | 13.0% | 1.7% | 7.3% | 49.6% |
| 61-12 | serum | 1,306,755 | 87.1% | 70.0% | 5.0% | 2.0% | 6.6% | 1.1% | 2.3% | 12.9% |
| 61-13 | serum | 431,893 | 79.3% | 48.5% | 9.7% | 4.4% | 12.3% | 1.3% | 3.1% | 20.7% |
| 61-14 | serum | 1,512,841 | 89.9% | 67.8% | 11.5% | 4.0% | 3.6% | 1.1% | 1.8% | 10.1% |
| 61-15 | serum | 1,168,656 | 71.2% | 44.9% | 5.8% | 4.3% | 10.5% | 1.6% | 4.2% | 28.8% |
| 61-16 | serum | 1,172,382 | 71.6% | 33.9% | 11.5% | 9.4% | 10.2% | 1.6% | 5.0% | 28.4% |
| 61-17 | serum | 6,013,320 | 77.6% | 48.5% | 6.6% | 8.7% | 8.7% | 1.4% | 3.8% | 22.4% |
| 61-18 | serum | 3,720,800 | 69.1% | 39.3% | 7.6% | 7.4% | 8.3% | 1.1% | 5.3% | 30.9% |
| 61-19 | serum | 339,032 | 74.9% | 45.4% | 8.9% | 7.4% | 7.5% | 1.7% | 4.0% | 25.1% |
| 61-20 | serum | 2,841,274 | 88.7% | 71.4% | 6.9% | 3.6% | 3.4% | 1.1% | 2.2% | 11.3% |
| 61-21 | serum | 3,581,238 | 88.2% | 38.1% | 13.6% | 5.0% | 5.1% | 1.6% | 4.8% | 31.8% |
| 61-22 | serum | 2,713,102 | 43.1% | 24.4% | 3.2% | 1.9% | 2.1% | 1.7% | 9.7% | 56.9% |
| 61-23 | serum | 3,821,613 | 93.9% | 78.7% | 6.5% | 2.7% | 4.2% | 0.7% | 1.0% | 6.1% |
| 61-24 | serum | 858,674 | 74.1% | 50.2% | 12.6% | 3.4% | 2.2% | 1.3% | 4.5% | 25.9% |
| 62-1 | serum | 2,490,299 | 74.3% | 43.9% | 8.8% | 4.5% | 10.7% | 2.0% | 4.4% | 25.7% |
| 62-2 | serum | 20,369,238 | 76.3% | 38.6% | 8.6% | 15.2% | 8.8% | 1.4% | 3.6% | 23.7% |
| 62-3 | serum | 20,976,589 | 77.7% | 51.0% | 7.0% | 5.0% | 9.3% | 1.8% | 3.6% | 22.3% |
| 62-4 | serum | 503,702 | 88.6% | 72.7% | 4.3% | 1.9% | 6.1% | 1.3% | 2.3% | 11.4% |
| 62-5 | serum | 2,014,203 | 72.8% | 44.7% | 7.9% | 7.5% | 7.2% | 1.8% | 3.7% | 27.2% |
| 62-6 | serum | 69,122 | 58.1% | 26.8% | 6.9% | 4.9% | 2.6% | 1.3% | 15.6% | 41.9% |
| 62-7 | serum | 280,398 | 83.1% | 68.9% | 4.5% | 1.6% | 4.1% | 1.2% | 2.6% | 16.9% |
| 62-8 | serum | 8,657,567 | 79.8% | 44.9% | 16.4% | 7.7% | 5.6% | 1.4% | 3.8% | 20.2% |
| 62-9 | serum | 26,489,291 | 80.7% | 54.5% | 8.1% | 4.7% | 8.4% | 2.0% | 3.0% | 19.3% |
| 62-10 | serum | 176,922 | 61.1% | 41.6% | 8.8% | 1.6% | 3.0% | 1.2% | 5.1% | 38.9% |
| 62-11 | serum | 59,160 | 80.1% | 48.7% | 5.8% | 2.7% | 17.1% | 2.2% | 3.5% | 19.9% |
| 62-12 | serum | 172,671 | 72.5% | 43.5% | 13.7% | 3.7% | 4.5% | 1.5% | 5.5% | 27.5% |
| 62-13 | serum | 96,920 | 74.4% | 52.3% | 8.2% | 1.6% | 6.2% | 1.3% | 4.8% | 25.6% |
| 62-14 | serum | 200,966 | 78.3% | 47.6% | 13.3% | 6.4% | 5.5% | 1.6% | 3.9% | 21.7% |
| 62-15 | serum | 294,156 | 71.2% | 48.6% | 9.8% | 3.3% | 3.4% | 1.3% | 4.8% | 28.8% |
| 62-16 | serum | 1,819,503 | 37.4% | 16.3% | 4.2% | 2.3% | 3.4% | 1.6% | 9.6% | 62.6% |
| 62-17 | serum | 15,620,514 | 85.5% | 58.8% | 5.1% | 4.3% | 13.0% | 1.6% | 2.6% | 14.5% |
| 62-18 | serum | 1,360,949 | 73.6% | 40.7% | 11.6% | 4.5% | 10.6% | 1.3% | 5.0% | 28.4% |
| 62-19 | serum | 86,257 | 81.1% | 63.0% | 6.8% | 2.9% | 3.7% | 1.3% | 3.3% | 18.9% |
| 62-20 | serum | 1,692,839 | 93.5% | 77.9% | 6.8% | 2.1% | 3.8% | 1.3% | 1.6% | 6.5% |
| 62-21 | serum | 3,250,197 | 79.5% | 52.4% | 12.2% | 6.5% | 3.7% | 1.4% | 3.4% | 20.5% |
| 62-22 | serum | 198,079 | 75.2% | 51.3% | 10.7% | 3.7% | 3.5% | 1.7% | 4.3% | 24.8% |
| 62-23 | serum | 190,175 | 78.2% | 51.3% | 13.6% | 3.6% | 4.6% | 1.9% | 3.3% | 21.8% |
| 62-24 | serum | 191,997 | 69.9% | 47.2% | 13.1% | 2.1% | 1.7% | 1.0% | 4.8% | 30.1% |

TABLE 2d

| | Sample statistics | | | ncRNA annotation | | | | | | |
|---|---|---|---|---|---|---|---|---|---|---|
| Sample ID | Sample Type | Total reads* | Mapped to HG19 | miRNA | rRNA | tRNA | scRNA | Other ncRNA | mRNA | Unmapped to HG19 |
| 13-1 | urine | 294,880 | 35.8% | 8.0% | 7.1% | 2.4% | 0.5% | 2.4% | 15.5% | 64.2% |
| 13-2 | urine | 27,749,084 | 93.5% | 71.8% | 10.0% | 1.4% | 7.2% | 1.4% | 1.7% | 6.5% |
| 13-3 | urine | 2,428,427 | 64.2% | 11.5% | 8.9% | 33.0% | 0.7% | 1.9% | 7.0% | 35.8% |
| 13-4 | urine | 340,284 | 79.0% | 16.4% | 32.6% | 9.1% | 0.7% | 7.8% | 12.3% | 21.0% |
| 13-5 | urine | 1,695,480 | 54.0% | 24.5% | 8.6% | 6.0% | 1.2% | 2.1% | 11.7% | 46.0% |
| 13-6 | urine | 12,592,770 | 76.1% | 14.6% | 19.1% | 28.5% | 2.7% | 1.6% | 9.5% | 23.9% |
| 13-7 | urine | 2,281,635 | 38.6% | 11.0% | 7.2% | 3.4% | 3.2% | 1.8% | 12.0% | 61.4% |
| 13-8 | urine | 2,267,428 | 65.1% | 28.0% | 8.1% | 15.9% | 3.3% | 2.0% | 7.8% | 34.9% |

TABLE 2d-continued

| | | Sample statistics | | ncRNA annotation | | | | | | |
|---|---|---|---|---|---|---|---|---|---|---|
| Sample ID | Sample Type | Total reads* | Mapped to HG19 | miRNA | rRNA | tRNA | scRNA | Other ncRNA | mRNA | Unmapped to HG19 |
| 13-9 | urine | 5,148,327 | 58.7% | 30.4% | 8.0% | 7.6% | 2.3% | 2.6% | 8.0% | 41.3% |
| 13-10 | urine | 3,864,504 | 80.5% | 41.6% | 10.4% | 11.1% | 6.7% | 5.1% | 5.6% | 19.5% |
| 13-11 | urine | 713,532 | 49.0% | 16.7% | 7.7% | 6.4% | 2.3% | 2.8% | 13.1% | 51.0% |
| 13-12 | urine | 4,430,005 | 76.7% | 7.3% | 9.7% | 51.9% | 0.6% | 1.8% | 6.4% | 23.3% |
| 13-13 | urine | 2,567,540 | 74.4% | 37.3% | 8.7% | 16.8% | 1.1% | 1.5% | 9.0% | 25.6% |
| 13-14 | urine | 1,489,414 | 51.0% | 14.8% | 8.5% | 13.7% | 0.7% | 2.9% | 10.3% | 49.0% |
| 13-15 | urine | 1,945,399 | 61.2% | 25.2% | 10.0% | 11.0% | 3.9% | 1.8% | 9.4% | 38.8% |
| 13-16 | urine | 1,888,077 | 64.4% | 36.8% | 7.6% | 9.7% | 1.5% | 1.4% | 7.3% | 35.6% |
| 13-17 | urine | 4,946,111 | 53.9% | 21.6% | 8.7% | 4.9% | 7.7% | 1.8% | 9.2% | 46.1% |
| 13-18 | urine | 16,059,866 | 57.9% | 27.2% | 6.5% | 13.2% | 1.5% | 2.6% | 6.9% | 42.1% |
| 13-19 | urine | 2,538,223 | 50.5% | 27.8% | 4.1% | 5.9% | 2.5% | 1.6% | 8.7% | 49.5% |
| 13-20 | urine | 1,376,766 | 53.9% | 17.2% | 6.8% | 16.4% | 1.4% | 2.1% | 10.0% | 46.1% |
| 13-21 | urine | 2,759,818 | 36.1% | 10.8% | 7.6% | 2.7% | 0.9% | 1.8% | 12.4% | 63.9% |
| 13-22 | urine | 31,436,066 | 92.7% | 54.3% | 12.5% | 8.0% | 8.0% | 4.9% | 5.1% | 7.3% |
| 13-23 | urine | 2,913,878 | 65.5% | 24.0% | 10.8% | 16.5% | 1.7% | 2.0% | 10.5% | 34.5% |
| 13-24 | urine | 6,480,913 | 82.0% | 23.5% | 16.8% | 35.0% | 1.3% | 1.4% | 4.1% | 18.0% |
| 14-1 | urine | 4,504,174 | 43.2% | 10.1% | 6.2% | 12.2% | 1.2% | 2.4% | 11.1% | 56.8% |
| 14-2 | urine | 1,332,544 | 53.0% | 18.6% | 6.6% | 16.6% | 1.3% | 1.6% | 8.3% | 47.0% |
| 14-3 | urine | 2,182,049 | 49.1% | 31.4% | 3.5% | 4.9% | 0.9% | 1.5% | 6.8% | 50.9% |
| 14-4 | urine | 1,307,198 | 61.5% | 10.9% | 15.1% | 14.2% | 9.0% | 4.6% | 7.7% | 38.5% |
| 14-5 | urine | 2,533,983 | 56.4% | 28.6% | 3.9% | 12.0% | 2.1% | 1.7% | 8.1% | 43.6% |
| 14-6 | urine | 26,215,402 | 93.6% | 38.8% | 10.5% | 20.0% | 14.4% | 7.9% | 2.1% | 6.4% |
| 14-7 | urine | 1,890,566 | 68.1% | 49.0% | 5.0% | 4.7% | 1.3% | 1.2% | 6.9% | 31.9% |
| 14-8 | urine | 1,977,880 | 67.9% | 37.7% | 9.3% | 7.2% | 6.3% | 1.5% | 5.9% | 32.1% |
| 14-9 | urine | 2,577,011 | 56.7% | 22.6% | 7.1% | 10.9% | 3.5% | 4.7% | 7.8% | 43.3% |
| 14-10 | urine | 1,729,192 | 63.5% | 12.4% | 10.6% | 26.4% | 5.3% | 2.0% | 6.8% | 36.5% |
| 14-11 | urine | 1,806,327 | 88.2% | 3.8% | 5.9% | 72.5% | 1.3% | 1.6% | 3.1% | 11.8% |
| 14-12 | urine | 4,963,232 | 69.5% | 10.8% | 4.6% | 44.7% | 3.1% | 1.3% | 6.0% | 30.5% |
| 14-13 | urine | 5,949,060 | 75.5% | 11.1% | 6.9% | 48.6% | 1.4% | 1.4% | 4.2% | 24.5% |
| 14-14 | urine | 1,368,874 | 53.4% | 29.4% | 5.5% | 8.8% | 0.9% | 1.5% | 7.3% | 46.6% |
| 14-15 | urine | 2,424,033 | 68.0% | 10.4% | 8.6% | 38.7% | 3.1% | 1.6% | 5.7% | 32.0% |
| 14-16 | urine | 7,382,381 | 18.9% | 2.7% | 2.1% | 1.5% | 1.0% | 1.6% | 10.0% | 81.1% |
| 14-17 | urine | 26,523,637 | 94.8% | 2.3% | 4.3% | 84.4% | 0.7% | 1.3% | 1.8% | 5.2% |
| 14-18 | urine | 2,823,080 | 77.6% | 49.7% | 7.9% | 10.9% | 2.9% | 1.4% | 4.8% | 22.4% |
| 14-19 | urine | 3,060,905 | 19.6% | 2.8% | 2.1% | 1.7% | 0.3% | 1.2% | 11.8% | 80.4% |
| 14-20 | urine | 2,596,609 | 58.4% | 37.0% | 5.7% | 3.3% | 3.7% | 1.8% | 6.9% | 41.6% |
| 14-21 | urine | 6,541,100 | 62.6% | 29.1% | 9.9% | 9.1% | 4.6% | 1.3% | 8.5% | 37.4% |
| 14-22 | urine | 18,100,365 | 95.8% | 71.9% | 6.1% | 9.2% | 6.0% | 0.9% | 1.8% | 4.2% |
| 14-23 | urine | 1,569,440 | 47.2% | 16.7% | 12.4% | 2.7% | 4.1% | 1.9% | 9.4% | 52.8% |
| 14-24 | urine | 1,581,514 | 49.4% | 27.9% | 5.7% | 5.8% | 1.3% | 1.4% | 7.2% | 50.6% |
| 15-1 | urine | 422,806 | 26.9% | 7.4% | 5.4% | 3.8% | 1.6% | 2.0% | 6.6% | 73.1% |
| 15-2 | urine | 675,779 | 75.9% | 45.1% | 6.8% | 15.4% | 4.1% | 1.5% | 3.0% | 24.1% |
| 15-3 | urine | 1,674,630 | 39.3% | 11.3% | 2.7% | 7.4% | 0.5% | 1.3% | 16.1% | 60.7% |
| 15-4 | urine | 2,026,929 | 26.6% | 2.7% | 3.0% | 14.5% | 0.6% | 0.9% | 4.9% | 73.4% |
| 15-5 | urine | 194,537 | 41.2% | 21.4% | 4.0% | 6.7% | 1.4% | 1.3% | 6.6% | 58.8% |
| 15-6 | urine | 528,446 | 50.4% | 21.7% | 5.1% | 11.2% | 3.3% | 2.0% | 7.1% | 49.6% |
| 15-7 | urine | 1,529,820 | 12.5% | 1.7% | 1.4% | 4.1% | 0.3% | 0.6% | 4.3% | 87.5% |
| 15-8 | urine | 59,214,072 | 98.3% | 1.3% | 1.5% | 94.0% | 0.2% | 1.0% | 0.4% | 1.7% |
| 15-9 | urine | 716,565 | 63.7% | 27.6% | 5.1% | 21.7% | 3.3% | 2.2% | 3.8% | 36.3% |
| 15-10 | urine | 5,299,991 | 95.2% | 1.2% | 3.5% | 88.3% | 0.3% | 1.1% | 0.8% | 4.8% |
| 15-11 | urine | 18,196,375 | 97.9% | 0.7% | 3.0% | 92.0% | 0.5% | 1.1% | 0.6% | 2.1% |
| 15-12 | urine | 541,196 | 52.5% | 10.4% | 5.8% | 27.7% | 2.1% | 2.1% | 4.4% | 47.5% |
| 15-13 | urine | 174,401 | 41.3% | 10.7% | 4.9% | 13.5% | 3.5% | 1.6% | 7.0% | 58.7% |
| 15-14 | urine | 443,969 | 23.9% | 8.2% | 2.5% | 6.0% | 0.4% | 1.0% | 6.0% | 76.1% |
| 15-15 | urine | 4,581,214 | 94.8% | 3.1% | 4.2% | 84.6% | 0.8% | 1.1% | 1.1% | 5.2% |
| 15-16 | urine | 1,940,573 | 16.8% | 7.5% | 0.9% | 1.0% | 0.9% | 0.7% | 5.7% | 83.2% |
| 15-17 | urine | 382,792 | 56.4% | 22.5% | 8.7% | 9.5% | 6.8% | 3.0% | 5.9% | 43.6% |
| 15-18 | urine | 471,469 | 61.8% | 34.5% | 6.2% | 9.2% | 5.6% | 1.7% | 4.5% | 38.2% |
| 15-19 | urine | 302,254 | 32.2% | 13.0% | 3.3% | 7.0% | 1.3% | 1.2% | 6.4% | 67.8% |
| 15-20 | urine | 723,405 | 64.5% | 45.8% | 4.2% | 6.6% | 2.9% | 1.4% | 3.6% | 35.5% |
| 15-21 | urine | 590,741 | 59.5% | 36.4% | 4.2% | 8.4% | 4.6% | 1.4% | 4.4% | 40.5% |
| 15-22 | urine | 709,675 | 77.7% | 34.7% | 13.4% | 22.0% | 3.8% | 1.2% | 2.6% | 22.3% |
| 15-23 | urine | 614,128 | 37.4% | 16.8% | 3.0% | 7.1% | 3.8% | 1.1% | 5.6% | 62.6% |
| 15-24 | urine | 2,286,062 | 89.8% | 69.9% | 5.6% | 8.2% | 3.0% | 1.0% | 1.9% | 10.2% |
| 16-1 | urine | 368,976 | 30.7% | 5.9% | 5.6% | 13.1% | 1.4% | 1.5% | 3.2% | 69.3% |
| 16-2 | urine | 938,633 | 73.7% | 4.4% | 2.7% | 59.4% | 4.9% | 0.8% | 1.4% | 26.3% |
| 16-3 | urine | 569,758 | 41.7% | 25.0% | 5.9% | 4.8% | 1.6% | 1.1% | 3.3% | 58.3% |
| 16-4 | urine | 58,443,672 | 3.5% | 0.0% | 0.1% | 0.2% | 0.0% | 0.2% | 2.9% | 96.5% |
| 16-5 | urine | 462,087 | 22.9% | 5.2% | 4.9% | 8.2% | 0.4% | 0.6% | 3.5% | 77.1% |
| 16-6 | urine | 625,487 | 55.2% | 13.3% | 12.0% | 15.8% | 8.3% | 0.9% | 4.9% | 44.8% |
| 16-7 | urine | 510,207 | 40.5% | 24.2% | 5.0% | 5.6% | 1.4% | 0.8% | 3.5% | 59.5% |
| 16-8 | urine | 609,187 | 42.4% | 4.6% | 11.0% | 20.7% | 2.5% | 0.8% | 2.8% | 57.6% |
| 16-9 | urine | 2,855,499 | 90.4% | 1.2% | 2.6% | 84.0% | 0.6% | 1.2% | 0.7% | 9.6% |
| 16-10 | urine | 1,183,799 | 69.1% | 16.5% | 9.1% | 37.5% | 3.5% | 0.8% | 1.7% | 30.9% |
| 16-11 | urine | 38,976 | 54.1% | 6.5% | 5.5% | 37.0% | 0.7% | 0.8% | 3.7% | 45.9% |

TABLE 2d-continued

| | | Sample statistics | | ncRNA annotation | | | | | | |
|---|---|---|---|---|---|---|---|---|---|---|
| Sample ID | Sample Type | Total reads* | Mapped to HG19 | miRNA | rRNA | tRNA | scRNA | Other ncRNA | mRNA | Unmapped to HG19 |
| 16-12 | urine | 569,205 | 50.9% | 17.3% | 7.2% | 19.2% | 4.3% | 0.6% | 2.2% | 49.1% |
| 16-13 | urine | 769,819 | 63.2% | 14.4% | 8.4% | 32.5% | 4.7% | 0.9% | 2.3% | 36.8% |
| 16-14 | urine | 839,139 | 32.2% | 10.0% | 7.6% | 9.9% | 1.1% | 0.7% | 2.9% | 67.8% |
| 16-15 | urine | 699,868 | 49.8% | 20.6% | 5.5% | 16.7% | 2.8% | 1.1% | 3.2% | 50.2% |
| 16-16 | urine | 4,739,635 | 16.2% | 5.6% | 6.3% | 1.8% | 0.5% | 0.3% | 1.8% | 83.8% |
| 16-17 | urine | 1,034,037 | 34.7% | 20.0% | 4.1% | 5.5% | 1.4% | 0.6% | 3.0% | 65.3% |
| 16-18 | urine | 3,996,226 | 67.9% | 41.1% | 7.1% | 16.3% | 1.4% | 0.8% | 1.2% | 32.1% |
| 16-19 | urine | 50,923,562 | 1.9% | 0.2% | 0.1% | 0.6% | 0.1% | 0.1% | 0.9% | 98.1% |
| 16-20 | urine | 838,535 | 20.5% | 7.5% | 2.9% | 6.2% | 0.7% | 0.6% | 2.6% | 79.5% |
| 16-21 | urine | 789,443 | 36.6% | 21.3% | 4.1% | 4.9% | 2.4% | 0.6% | 3.2% | 63.4% |
| 18-22 | urine | 1,126,386 | 40.1% | 15.8% | 9.1% | 9.7% | 2.1% | 0.7% | 2.7% | 59.9% |
| 16-23 | urine | 549,482 | 35.4% | 12.7% | 4.2% | 12.6% | 1.8% | 0.6% | 2.4% | 64.6% |
| 16-24 | urine | 1,508,648 | 36.8% | 16.0% | 5.4% | 8.7% | 3.0% | 1.0% | 2.7% | 63.2% |
| 17-1 | urine | 1,544,339 | 44.3% | 16.0% | 6.7% | 6.9% | 1.2% | 2.2% | 11.2% | 55.7% |
| 17-2 | urine | 1,000,656 | 76.2% | 40.8% | 12.7% | 11.0% | 2.4% | 2.1% | 7.2% | 23.8% |
| 17-3 | urine | 4,180,666 | 91.6% | 20.7% | 5.5% | 61.1% | 0.7% | 1.3% | 2.4% | 8.4% |
| 17-4 | urine | 1,461,931 | 42.2% | 15.5% | 5.7% | 5.2% | 0.9% | 2.2% | 12.8% | 57.8% |
| 17-5 | urine | 1,715,921 | 63.1% | 13.8% | 16.2% | 22.9% | 1.1% | 1.9% | 7.2% | 36.9% |
| 17-6 | urine | 352,625 | 37.4% | 5.8% | 5.2% | 6.6% | 0.5% | 2.6% | 16.8% | 62.6% |
| 17-7 | urine | 665,204 | 30.4% | 7.8% | 3.9% | 2.8% | 0.2% | 2.2% | 13.5% | 69.6% |
| 17-8 | urine | 2,497,473 | 70.3% | 3.4% | 6.7% | 52.0% | 0.3% | 1.5% | 6.4% | 29.7% |
| 17-9 | urine | 574,670 | 46.8% | 12.9% | 7.3% | 6.6% | 1.0% | 4.1% | 14.9% | 53.2% |
| 17-10 | urine | 529,721 | 52.6% | 24.0% | 6.4% | 9.2% | 0.5% | 2.1% | 10.5% | 47.4% |
| 17-11 | urine | 359,151 | 69.2% | 37.1% | 9.2% | 11.4% | 1.5% | 2.5% | 7.6% | 30.8% |
| 17-12 | urine | 801,246 | 76.6% | 18.1% | 9.6% | 35.9% | 1.9% | 3.0% | 8.1% | 23.4% |
| 17-13 | urine | 396,673 | 69.2% | 42.2% | 6.8% | 9.5% | 1.4% | 1.6% | 7.7% | 30.8% |
| 17-14 | urine | 1,707,505 | 87.3% | 2.2% | 2.4% | 78.2% | 0.1% | 1.3% | 3.1% | 12.7% |
| 17-15 | urine | 317,210 | 38.9% | 14.7% | 5.2% | 3.0% | 0.2% | 2.2% | 13.5% | 61.1% |
| 17-16 | urine | 1,058,167 | 52.9% | 28.1% | 5.9% | 8.4% | 0.7% | 1.7% | 8.1% | 47.1% |
| 17-17 | urine | 977,506 | 64.3% | 42.8% | 3.4% | 4.6% | 1.7% | 2.0% | 9.8% | 35.7% |
| 17-18 | urine | 675,518 | 61.4% | 31.3% | 7.6% | 10.0% | 0.8% | 2.3% | 9.4% | 38.6% |
| 17-19 | urine | 817,965 | 77.6% | 44.4% | 8.3% | 14.2% | 3.6% | 1.9% | 5.3% | 22.4% |
| 17-20 | urine | 742,293 | 53.9% | 28.7% | 6.8% | 5.5% | 1.1% | 1.8% | 10.0% | 46.1% |
| 17-21 | urine | 758,571 | 30.1% | 2.7% | 2.9% | 8.4% | 0.3% | 1.9% | 13.9% | 69.9% |
| 17-22 | urine | 900,205 | 68.0% | 35.5% | 13.7% | 7.9% | 1.0% | 1.9% | 8.1% | 32.0% |
| 17-23 | urine | 644,822 | 46.5% | 21.4% | 3.4% | 5.8% | 0.9% | 2.4% | 12.6% | 53.5% |
| 17-24 | urine | 489,312 | 53.4% | 31.4% | 4.3% | 7.7% | 0.2% | 1.5% | 8.4% | 46.6% |
| 19-1 | urine | 2,004,802 | 22.0% | 7.3% | 4.5% | 3.8% | 0.5% | 0.8% | 5.0% | 78.0% |
| 19-2 | urine | 4,798,154 | 25.9% | 13.6% | 3.8% | 3.4% | 0.4% | 0.8% | 3.9% | 74.1% |
| 19-3 | urine | 3,407,761 | 40.3% | 20.4% | 5.3% | 6.6% | 3.8% | 0.9% | 3.4% | 59.7% |
| 19-4 | urine | 3,690,012 | 69.1% | 47.1% | 4.7% | 6.1% | 6.8% | 1.6% | 2.9% | 30.9% |
| 19-5 | urine | 10,718,682 | 32.2% | 3.3% | 13.2% | 9.0% | 0.8% | 1.0% | 4.9% | 67.8% |
| 19-6 | urine | 2,309,688 | 58.5% | 3.6% | 3.8% | 33.5% | 0.7% | 1.4% | 15.4% | 41.5% |
| 19-7 | urine | 1,168,052 | 27.7% | 9.6% | 5.6% | 3.0% | 0.9% | 0.9% | 7.7% | 72.3% |
| 19-8 | urine | 1,764,803 | 13.8% | 2.1% | 2.8% | 1.8% | 0.1% | 0.7% | 6.2% | 86.2% |
| 19-9 | urine | 1,413,314 | 34.8% | 11.4% | 8.3% | 4.5% | 1.0% | 2.0% | 7.6% | 65.2% |
| 19-10 | urine | 1,670,631 | 62.7% | 43.5% | 6.3% | 5.6% | 3.1% | 0.9% | 3.3% | 37.3% |
| 19-11 | urine | 561,533 | 57.6% | 34.0% | 5.4% | 6.2% | 6.6% | 1.2% | 4.2% | 42.4% |
| 19-12 | urine | 775,793 | 45.5% | 23.4% | 5.8% | 5.9% | 3.5% | 1.2% | 5.8% | 54.5% |
| 19-13 | urine | 705,777 | 31.4% | 2.0% | 10.6% | 8.2% | 1.1% | 1.1% | 8.4% | 68.6% |
| 19-14 | urine | 425,100 | 49.9% | 9.8% | 13.8% | 16.9% | 0.7% | 1.3% | 7.4% | 50.1% |
| 19-15 | urine | 2,891,087 | 37.9% | 2.0% | 3.7% | 25.8% | 0.4% | 0.9% | 5.1% | 62.1% |
| 19-16 | urine | 850,293 | 25.7% | 7.4% | 4.0% | 6.3% | 0.7% | 0.8% | 6.5% | 74.3% |
| 19-17 | urine | 15,203,470 | 79.1% | 5.7% | 4.7% | 62.3% | 3.0% | 1.2% | 2.0% | 20.9% |
| 19-18 | urine | 11,199,089 | 36.5% | 1.2% | 4.5% | 25.8% | 0.5% | 0.7% | 3.7% | 63.5% |
| 19-19 | urine | 803,815 | 41.7% | 16.3% | 4.1% | 13.2% | 1.3% | 1.1% | 5.6% | 58.3% |
| 19-20 | urine | 2,144,806 | 31.1% | 8.0% | 4.2% | 10.3% | 1.7% | 1.1% | 5.7% | 68.9% |
| 19-21 | urine | 1,493,421 | 50.3% | 13.1% | 19.7% | 6.3% | 1.6% | 1.2% | 8.3% | 49.7% |
| 19-22 | urine | 1,304,975 | 67.5% | 38.5% | 11.9% | 5.9% | 3.5% | 1.5% | 6.2% | 32.5% |
| 19-23 | urine | 614,092 | 31.7% | 14.1% | 3.6% | 4.8% | 0.9% | 1.0% | 7.4% | 68.3% |
| 19-24 | urine | 1,266,213 | 51.4% | 29.8% | 6.0% | 5.4% | 2.7% | 1.6% | 5.9% | 48.6% |
| 20-1 | urine | 1,370,385 | 71.7% | 11.9% | 13.1% | 40.0% | 1.4% | 1.8% | 3.6% | 28.3% |
| 20-2 | urine | 1,274,059 | 59.4% | 45.1% | 5.3% | 3.7% | 2.3% | 0.7% | 2.2% | 40.6% |
| 20-3 | urine | 2,890,866 | 37.7% | 20.8% | 3.7% | 2.0% | 8.1% | 0.9% | 2.3% | 62.3% |
| 20-4 | urine | 549,765 | 38.8% | 13.6% | 10.3% | 7.2% | 0.9% | 1.4% | 5.5% | 61.2% |
| 20-5 | urine | 2,196,869 | 70.5% | 4.4% | 5.4% | 57.5% | 0.4% | 1.0% | 1.8% | 29.5% |
| 20-6 | urine | 1,990,102 | 42.6% | 6.3% | 3.4% | 9.1% | 0.5% | 1.4% | 21.9% | 57.4% |
| 20-7 | urine | 16,407,347 | 94.9% | 3.1% | 2.6% | 86.8% | 0.5% | 1.0% | 0.9% | 5.1% |
| 20-8 | urine | 1,790,609 | 72.9% | 10.1% | 8.9% | 48.8% | 0.9% | 1.3% | 2.9% | 27.1% |
| 20-9 | urine | 2,371,005 | 41.2% | 27.3% | 6.5% | 2.7% | 0.8% | 1.5% | 2.5% | 58.8% |
| 20-10 | urine | 1,650,676 | 55.8% | 36.7% | 7.0% | 7.0% | 2.1% | 0.6% | 2.5% | 44.2% |
| 20-11 | urine | 2,688,244 | 94.9% | 67.9% | 14.5% | 5.3% | 5.6% | 0.6% | 1.1% | 5.1% |
| 20-12 | urine | 841,199 | 72.0% | 35.4% | 17.1% | 9.2% | 5.5% | 1.5% | 3.4% | 28.0% |
| 20-13 | urine | 403,094 | 46.6% | 21.1% | 10.5% | 8.0% | 1.4% | 1.0% | 4.5% | 53.4% |
| 20-14 | urine | 540,174 | 38.6% | 12.7% | 10.9% | 8.8% | 0.6% | 0.8% | 4.7% | 61.4% |

TABLE 2d-continued

| | | Sample statistics | | ncRNA annotation | | | | | | |
|---|---|---|---|---|---|---|---|---|---|---|
| Sample ID | Sample Type | Total reads* | Mapped to HG19 | miRNA | rRNA | tRNA | scRNA | Other ncRNA | mRNA | Unmapped to HG19 |
| 20-15 | urine | 1,351,856 | 65.9% | 35.1% | 6.4% | 14.9% | 5.1% | 1.4% | 3.1% | 34.1% |
| 20-16 | urine | 1,468,525 | 16.9% | 6.1% | 3.9% | 1.2% | 0.2% | 0.6% | 4.9% | 83.1% |
| 20-17 | urine | 946,222 | 34.8% | 17.3% | 4.2% | 7.7% | 1.5% | 0.7% | 3.5% | 65.2% |
| 20-18 | urine | 1,377,981 | 54.4% | 35.1% | 5.1% | 5.1% | 1.6% | 1.3% | 6.1% | 45.6% |
| 20-19 | urine | 820,369 | 43.0% | 31.8% | 3.3% | 2.9% | 1.6% | 0.5% | 2.9% | 57.0% |
| 20-20 | urine | 510,255 | 38.5% | 23.6% | 3.4% | 3.3% | 1.3% | 1.0% | 5.9% | 61.5% |
| 20-21 | urine | 1,494,630 | 75.5% | 47.8% | 6.6% | 7.4% | 10.3% | 0.9% | 2.6% | 24.5% |
| 20-22 | urine | 603,895 | 40.1% | 20.7% | 4.0% | 4.0% | 5.6% | 1.1% | 4.8% | 59.9% |
| 20-23 | urine | 888,294 | 16.8% | 5.9% | 2.0% | 2.6% | 1.6% | 0.7% | 4.1% | 83.2% |
| 20-24 | urine | 1,005,209 | 47.6% | 24.9% | 7.0% | 6.2% | 1.4% | 1.1% | 6.9% | 52.4% |
| 21-1 | urine | 532,038 | 29.6% | 5.0% | 6.5% | 1.7% | 0.1% | 2.1% | 14.3% | 70.4% |
| 21-2 | urine | 855,203 | 39.4% | 11.0% | 7.4% | 5.7% | 0.3% | 1.9% | 13.1% | 60.6% |
| 21-3 | urine | 5,018,621 | 53.2% | 22.9% | 11.0% | 8.6% | 1.3% | 2.0% | 7.5% | 46.8% |
| 21-4 | urine | 1,486,817 | 72.7% | 4.0% | 6.2% | 54.3% | 0.3% | 1.7% | 6.1% | 27.3% |
| 21-5 | urine | 520,869 | 40.8% | 19.8% | 4.6% | 3.9% | 0.4% | 1.6% | 10.6% | 59.2% |
| 21-6 | urine | 748,744 | 49.0% | 10.6% | 4.1% | 3.1% | 0.8% | 2.5% | 27.9% | 51.0% |
| 21-7 | urine | 570,018 | 45.9% | 21.8% | 6.8% | 3.8% | 0.9% | 1.6% | 11.2% | 54.1% |
| 21-8 | urine | 967,792 | 35.6% | 5.2% | 8.8% | 7.9% | 0.4% | 1.6% | 11.7% | 64.4% |
| 21-9 | urine | 2,075,831 | 68.3% | 25.8% | 15.1% | 13.4% | 2.8% | 3.1% | 8.0% | 31.7% |
| 21-10 | urine | 859,050 | 74.2% | 17.3% | 31.6% | 14.0% | 1.0% | 2.1% | 8.1% | 25.8% |
| 21-11 | urine | 504,820 | 81.1% | 5.1% | 14.3% | 51.4% | 1.1% | 2.2% | 6.9% | 18.9% |
| 21-12 | urine | 3,555,588 | 89.6% | 5.2% | 12.1% | 65.7% | 0.6% | 1.9% | 4.0% | 10.4% |
| 21-13 | urine | 2,047,651 | 83.7% | 5.0% | 24.6% | 44.7% | 0.7% | 1.8% | 6.9% | 16.3% |
| 21-14, | urine | 943,468 | 76.4% | 7.2% | 7.5% | 53.2% | 0.1% | 1.9% | 6.4% | 23.6% |
| 21-15 | urine | 1,749,130 | 60.2% | 8.9% | 5.6% | 36.2% | 0.2% | 1.5% | 7.8% | 39.8% |
| 21-16 | urine | 838,625 | 32.6% | 7.6% | 6.8% | 2.3% | 0.2% | 1.8% | 13.8% | 67.4% |
| 21-17 | urine | 20,777,900 | 93.0% | 1.0% | 2.9% | 85.6% | 0.0% | 1.4% | 2.0% | 7.0% |
| 21-18 | urine | 180,959 | 42.8% | 16.3% | 8.0% | 4.7% | 0.3% | 1.8% | 13.7% | 57.2% |
| 21-19 | urine | 446,204 | 31.6% | 10.1% | 4.0% | 2.5% | 0.3% | 1.9% | 12.9% | 68.4% |
| 21-20 | urine | 1,026,119 | 37.8% | 15.3% | 6.8% | 2.0% | 0.3% | 1.8% | 11.6% | 62.2% |
| 21-21 | urine | 2,129,596 | 45.7% | 17.6% | 12.0% | 3.8% | 0.8% | 1.6% | 10.0% | 54.3% |
| 21-22 | urine | 664,227 | 49.8% | 25.9% | 6.3% | 3.7% | 0.7% | 1.8% | 11.5% | 50.2% |
| 21-23 | urine | 1,313,377 | 71.1% | 49.2% | 7.2% | 5.8% | 1.2% | 1.7% | 6.0% | 28.9% |
| 21-24 | urine | 3,191,835 | 22.4% | 1.8% | 2.3% | 5.4% | 0.1% | 1.6% | 11.2% | 77.6% |
| 22-1 | urine | 1,062,431 | 39.8% | 14.7% | 6.3% | 5.4% | 0.9% | 1.5% | 10.9% | 60.2% |
| 22-2 | urine | 924,066 | 24.8% | 5.0% | 5.0% | 1.4% | 0.9% | 1.3% | 11.2% | 75.2% |
| 22-3 | urine | 2,082,377 | 66.2% | 3.4% | 6.6% | 47.0% | 0.3% | 1.5% | 7.4% | 33.8% |
| 22-4 | urine | 339,625 | 38.7% | 7.1% | 4.7% | 11.7% | 0.2% | 1.1% | 11.9% | 63.3% |
| 22-5 | urine | 702,210 | 32.8% | 8.6% | 4.4% | 4.9% | 1.0% | 1.3% | 12.5% | 67.2% |
| 22-6 | urine | 2,922,347 | 66.7% | 1.3% | 3.6% | 50.2% | 0.1% | 1.3% | 10.2% | 33.3% |
| 22-7 | urine | 1,190,700 | 46.9% | 8.8% | 5.3% | 20.6% | 0.7% | 1.5% | 10.0% | 53.1% |
| 22-8 | urine | 1,203,952 | 51.8% | 18.4% | 6.4% | 15.7% | 0.4% | 2.2% | 0.8% | 48.2% |
| 22-9 | urine | 1,024,535 | 41.3% | 20.4% | 5.0% | 1.9% | 0.3% | 2.6% | 11.0% | 58.7% |
| 22-10 | urine | 626,385 | 38.2% | 6.9% | 5.6% | 12.7% | 0.4% | 1.4% | 11.3% | 61.8% |
| 22-11 | urine | 1,111,308 | 74.2% | 9.6% | 5.9% | 49.8% | 1.2% | 1.5% | 6.1% | 25.8% |
| 22-12 | urine | 3,884,458 | 88.3% | 3.6% | 5.2% | 74.6% | 0.5% | 1.2% | 3.2% | 11.7% |
| 22-13 | urine | 897,309 | 36.3% | 8.4% | 5.6% | 6.7% | 1.7% | 1.5% | 12.3% | 63.7% |
| 22-14 | urine | 864,391 | 45.5% | 28.0% | 2.6% | 4.6% | 0.7% | 1.2% | 8.4% | 54.5% |
| 22-15 | urine | 2,690,620 | 61.8% | 17.3% | 7.8% | 26.5% | 0.5% | 1.3% | 8.3% | 38.2% |
| 22-16 | urine | 4,322,762 | 39.8% | 19.0% | 3.6% | 4.2% | 1.7% | 1.7% | 9.5% | 60.2% |
| 22-17 | urine | 16,072,989 | 92.7% | 2.7% | 4.0% | 83.0% | 0.1% | 1.0% | 1.9% | 7.3% |
| 22-18 | urine | 435,685 | 29.3% | 8.1% | 3.0% | 3.0% | 0.8% | 1.2% | 13.2% | 70.7% |
| 22-19 | urine | 784,026 | 61.1% | 24.5% | 5.7% | 14.2% | 7.5% | 1.3% | 8.0% | 38.9% |
| 22-20 | urine | 2,790,934 | 72.1% | 11.3% | 6.7% | 43.5% | 0.6% | 2.1% | 7.9% | 27.9% |
| 22-21 | urine | 1,805,170 | 53.5% | 5.2% | 7.5% | 26.2% | 0.4% | 1.8% | 12.5% | 46.5% |
| 22-22 | urine | 1,307,258 | 50.2% | 23.7% | 6.1% | 4.8% | 4.0% | 1.4% | 10.1% | 49.8% |
| 22-23 | urine | 8,793,399 | 83.6% | 19.4% | 7.8% | 12.7% | 37.3% | 1.8% | 4.7% | 16.4% |
| 22-24 | urine | 2,843,363 | 64.3% | 16.1% | 10.3% | 24.7% | 0.3% | 2.0% | 10.9% | 35.7% |
| 23-1 | urine | 330,307 | 45.5% | 7.2% | 9.5% | 9.0% | 0.3% | 2.6% | 16.8% | 54.5% |
| 23-2 | urine | 978,321 | 71.0% | 5.9% | 10.2% | 42.2% | 0.3% | 2.3% | 10.1% | 29.0% |
| 23-3 | urine | 321,271 | 67.8% | 21.5% | 20.0% | 5.3% | 0.4% | 2.7% | 17.9% | 32.2% |
| 23-4 | urine | 783,261 | 60.2% | 23.7% | 9.4% | 12.0% | 0.7% | 2.4% | 11.9% | 39.8% |
| 23-5 | urine | 1,102,009 | 72.5% | 33.6% | 15.8% | 11.5% | 1.0% | 2.0% | 8.6% | 27.5% |
| 23-6 | urine | 1,109,597 | 53.1% | 20.7% | 5.6% | 6.0% | 1.8% | 3.0% | 16.0% | 46.9% |
| 23-7 | urine | 1,237,206 | 33.7% | 8.1% | 2.8% | 2.2% | 0.3% | 2.3% | 18.0% | 66.3% |
| 23-8 | urine | 1,452,215 | 79.7% | 4.4% | 11.5% | 53.6% | 0.1% | 1.8% | 8.3% | 20.3% |
| 23-9 | urine | 1,501,547 | 80.9% | 30.3% | 6.6% | 32.2% | 0.7% | 2.8% | 8.2% | 19.1% |
| 23-10 | urine | 1,195,422 | 73.2% | 22.8% | 10.3% | 28.0% | 0.5% | 2.2% | 9.5% | 26.8% |
| 23-11 | urine | 745,210 | 85.9% | 4.7% | 12.3% | 60.2% | 0.5% | 2.0% | 6.3% | 14.1% |
| 23-12 | urine | 673,342 | 64.7% | 33.7% | 7.7% | 10.1% | 0.9% | 2.0% | 10.4% | 35.3% |
| 23-13 | urine | 1,358,884 | 71.2% | 36.3% | 10.3% | 9.7% | 0.8% | 2.3% | 11.8% | 28.8% |
| 23-14 | urine | 2,207,355 | 65.3% | 21.7% | 7.7% | 23.3% | 0.3% | 2.0% | 10.3% | 34.7% |
| 23-15 | urine | 365,110 | 55.0% | 32.2% | 4.8% | 3.4% | 0.7% | 1.8% | 12.1% | 45.0% |
| 23-16 | urine | 902,322 | 56.0% | 31.5% | 5.6% | 2.7% | 0.6% | 2.1% | 13.4% | 44.0% |
| 23-17 | urine | 566,280 | 59.2% | 24.8% | 5.9% | 8.0% | 0.4% | 2.9% | 17.1% | 40.8% |

TABLE 2d-continued

| | | Sample statistics | | ncRNA annotation | | | | | | |
|---|---|---|---|---|---|---|---|---|---|---|
| Sample ID | Sample Type | Total reads* | Mapped to HG19 | miRNA | rRNA | tRNA | scRNA | Other ncRNA | mRNA | Unmapped to HG19 |
| 23-18 | urine | 27,827,461 | 59.8% | 9.9% | 7.6% | 29.4% | 0.3% | 1.8% | 10.9% | 40.2% |
| 23-19 | urine | 1,679,977 | 43.5% | 14.0% | 8.3% | 6.0% | 0.2% | 1.9% | 13.0% | 56.5% |
| 23-20 | urine | 449,796 | 72.5% | 22.1% | 8.9% | 28.5% | 0.3% | 2.0% | 10.6% | 27.5% |
| 23-21 | urine | 1,824,506 | 55.1% | 21.4% | 6.2% | 7.6% | 0.7% | 2.6% | 16.6% | 44.9% |
| 23-22 | urine | 12,756,803 | 94.4% | 85.4% | 2.8% | 2.3% | 0.8% | 0.6% | 2.5% | 5.6% |
| 23-23 | urine | 426,065 | 62.3% | 25.7% | 13.7% | 6.5% | 0.4% | 2.1% | 13.8% | 37.7% |
| 23-24 | urine | 414,417 | 67.8% | 21.5% | 9.5% | 21.7% | 0.3% | 2.7% | 12.1% | 32.2% |
| 24-1 | urine | 8,078,775 | 83.3% | 0.9% | 2.0% | 78.0% | 0.4% | 0.9% | 1.1% | 16.7% |
| 24-2 | urine | 847,942 | 48.1% | 6.6% | 1.5% | 35.4% | 0.3% | 0.7% | 3.5% | 51.9% |
| 24-3 | urine | 1,893,518 | 36.0% | 10.2% | 5.5% | 9.4% | 6.0% | 1.0% | 3.9% | 64.0% |
| 24-4 | urine | 2,884,336 | 74.5% | 5.8% | 2.9% | 59.4% | 3.2% | 1.1% | 2.1% | 25.5% |
| 24-5 | urine | 4,667,104 | 48.0% | 9.0% | 4.4% | 29.2% | 1.4% | 1.0% | 3.0% | 52.0% |
| 24-6 | urine | 1,435,646 | 47.5% | 6.2% | 5.0% | 30.2% | 1.5% | 0.9% | 3.7% | 52.5% |
| 24-7 | urine | 5,514,056 | 78.3% | 5.9% | 3.4% | 62.5% | 3.1% | 1.1% | 2.5% | 21.7% |
| 24-8 | urine | 27,366,192 | 53.8% | 3.8% | 5.0% | 35.4% | 6.8% | 0.9% | 1.8% | 46.2% |
| 24-9 | urine | 7,152,230 | 81.3% | 43.3% | 9.9% | 19.7% | 5.4% | 1.2% | 1.8% | 18.7% |
| 24-10 | urine | 1,493,045 | 32.4% | 17.2% | 3.7% | 5.0% | 2.9% | 1.0% | 2.6% | 67.6% |
| 24-11 | urine | 4,082,135 | 42.4% | 19.8% | 3.9% | 5.4% | 9.4% | 1.5% | 2.4% | 57.6% |
| 24-12 | urine | 8,707,190 | 86.3% | 4.6% | 5.4% | 71.4% | 2.9% | 1.1% | 1.0% | 13.7% |
| 24-13 | urine | 7,868,487 | 93.3% | 2.2% | 3.5% | 84.6% | 0.6% | 1.1% | 1.3% | 6.7% |
| 24-14 | urine | 12,309,444 | 96.3% | 0.5% | 0.9% | 93.4% | 0.1% | 1.2% | 0.2% | 3.7% |
| 24-15 | urine | 1,523,562 | 68.0% | 18.8% | 4.9% | 38.1% | 2.4% | 1.0% | 2.7% | 32.0% |
| 24-16 | urine | 875,453 | 61.7% | 9.9% | 6.8% | 39.1% | 2.5% | 0.9% | 2.5% | 38.3% |
| 24-17 | urine | 1,629,711 | 40.9% | 20.7% | 2.8% | 9.3% | 3.6% | 1.1% | 3.4% | 59.1% |
| 24-18 | urine | 478,508 | 48.5% | 9.0% | 7.6% | 25.2% | 2.2% | 1.0% | 3.6% | 51.5% |
| 24-19 | urine | 5,106,625 | 94.0% | 1.4% | 1.3% | 89.4% | 0.5% | 1.0% | 0.4% | 6.0% |
| 24-20 | urine | 2,754,660 | 85.2% | 3.5% | 2.6% | 76.3% | 0.7% | 1.0% | 1.1% | 14.8% |
| 24-21 | urine | 10,865,649 | 34.0% | 22.5% | 1.5% | 2.1% | 3.1% | 0.9% | 3.9% | 66.0% |
| 24-22 | urine | 1,283,735 | 62.9% | 12.8% | 14.3% | 28.7% | 3.5% | 1.0% | 2.6% | 37.1% |
| 24-23 | urine | 1,164,553 | 66.3% | 4.6% | 4.0% | 52.1% | 2.1% | 1.1% | 2.4% | 33.7% |
| 24-24 | urine | 393,066 | 27.0% | 4.0% | 4.0% | 13.0% | 0.3% | 0.8% | 4.9% | 73.0% |
| 32-16 | urine | 1,812,064 | 67.8% | 32.7% | 10.3% | 12.5% | 2.0% | 2.5% | 7.8% | 32.2% |
| 32-17 | urine | 3,297,380 | 78.1% | 2.9% | 4.6% | 65.4% | 0.4% | 1.1% | 3.8% | 21.9% |
| 32-18 | urine | 12,414,642 | 96.5% | 3.6% | 2.8% | 86.1% | 2.1% | 1.2% | 0.8% | 3.5% |
| 32-19 | urine | 915,356 | 34.3% | 13.7% | 2.8% | 5.4% | 4.5% | 1.0% | 6.8% | 65.7% |
| 32-20 | urine | 4,339,395 | 92.4% | 2.1% | 3.5% | 84.1% | 0.3% | 1.1% | 1.3% | 7.6% |
| 32-21 | urine | 1,934,573 | 39.8% | 15.0% | 4.2% | 4.5% | 7.6% | 1.7% | 6.8% | 60.2% |
| 32-22 | urine | 3,218,678 | 82.2% | 65.7% | 1.9% | 7.4% | 0.5% | 2.0% | 4.8% | 17.8% |
| 32-23 | urine | 572,348 | 51.5% | 22.0% | 5.3% | 10.0% | 4.0% | 1.7% | 8.5% | 48.5% |
| 32-24 | urine | 1,095,096 | 26.1% | 6.6% | 3.9% | 5.4% | 0.2% | 1.2% | 8.7% | 73.9% |
| 37-13 | urine | 14,058 | 26.2% | 9.0% | 4.3% | 4.7% | 1.2% | 1.1% | 6.0% | 73.8% |
| 37-14 | urine | 78,074 | 57.2% | 27.7% | 4.7% | 19.3% | 1.1% | 0.9% | 3.5% | 42.8% |
| 37-15 | urine | 511,372 | 77.2% | 51.8% | 7.7% | 4.8% | 9.2% | 1.4% | 2.3% | 22.8% |
| 37-16 | urine | 125,534 | 51.9% | 21.9% | 3.4% | 21.2% | 1.2% | 0.7% | 3.4% | 48.1% |
| 37-17 | urine | 600,354 | 38.8% | 14.5% | 6.0% | 11.8% | 0.0% | 0.9% | 4.8% | 61.2% |
| 37-18 | urine | 624,478 | 82.3% | 17.7% | 5.0% | 54.2% | 2.4% | 1.0% | 2.0% | 17.7% |
| 37-19 | urine | 298,959 | 92.0% | 81.3% | 3.4% | 1.9% | 3.8% | 0.5% | 1.0% | 8.0% |
| 37-20 | urine | 219,704 | 34.1% | 17.4% | 4.5% | 5.4% | 0.7% | 0.9% | 5.2% | 65.9% |
| 37-21 | urine | 1,125,579 | 75.7% | 23.8% | 5.1% | 40.0% | 2.0% | 1.3% | 2.6% | 24.3% |

Table 2 Overview of sRNA composition from biofluids. a Summary table listing prevalent HG19-derived sRNA categories and mRNA, as well as remaining HG19-unmapped reads. b, c, d per-sample lists of a for plasma, serum, and urine. Data listed here was generated excluding RNA reads in technical annotation categories (see Table 1).

TABLE 3

| | 13-6/Acute Cell Rej | | | |
|---|---|---|---|---|
| | Total reads 12,712,093 | Un. reads (unassigned) 2,981,620 | | Reads: un. per total 23.5% |
| | | Contig-aligned reads, counts | | min. |
| Subset | Contigs | individual | per all cont. | per un.reads | log(E-value) |
| All generated in sample | 383 | 343,092 | 100.0% | 11.5% | |
| Mapped to unique biological orders | 133 | 202,026 | 56.2% | 6.8% | |
| Mapped contigs, listed by orders | | | | | |
| Eukaryotes | 71 | 149,542 | 41.6% | 5.0% | −26.7 |
| Firmicutes | 17 | 40,641 | 11.3% | 1.4% | −12.2 |
| α-Proteobacteria | 14 | 4,717 | 1.3% | 0.2% | −6.7 |

TABLE 3-continued

| | | | | | |
|---|---|---|---|---|---|
| CFB group bacteria | 16 | 3,742 | 1.0% | 0.1% | −8.3 |
| Σ Additional orders, <5 contigs | 15 | 3,384 | 0.9% | 0.1% | |
| | | | | | |
| Total | 133 | 202,026 | 56.2% | 6.8% | |

Mapped contigs, listed by genera, (species)

| | | | | | |
|---|---|---|---|---|---|
| Amoeba (*Vermamoeba vermiformis*: 48) | 66 | 145,950 | 40.6% | 4.9% | −26.7 |
| *Lactobacillus* sp. | 15 | 39,540 | 11.0% | 1.3% | −12.2 |
| *Prevotella* (*dentalis*: 3) | 8 | 2,173 | 0.6% | 0.1% | −6.7 |
| Σ Additional genera, <2 contigs | 12 | 3,450 | 1.0% | 0.1% | |
| Σ Ambigous genus assignments | 32 | 10,913 | 3.0% | 0.4% | |
| | | | | | |
| Total | 133 | 202,026 | 56.2% | 6.8% | |

14-16, Normal

| Total reads | Un. reads (unassigned) | Reads: un. per total |
|---|---|---|
| 7,415.337 | 5,975,790 | 80.6% |

| Subset | Σ Contigs | Contig-aligned individual read counts | | | min. log(E-value) |
|---|---|---|---|---|---|
| | | absolute | /all cont. | /un.reads | |
| All generated in sample | 465 | 3,123,215 | 100.0% | 52.3% | |
| Mapped to unique biological orders | 207 | 2,374,179 | 76.0% | 39.7% | |

Mapped contigs, by orders

| | | | | | |
|---|---|---|---|---|---|
| Firmicutes | 155 | 2,318,169 | 74.2% | 38.8% | −51.7 |
| Ascomycetes | 20 | 14,845 | 0.5% | 0.2% | −20.0 |
| High GC Gram+ | 9 | 1,817 | 0.1% | 0.0% | −8.0 |
| Bacteria | 8 | 35,513 | 1.1% | 0.6% | −27.2 |
| Mycoplasmas | 5 | 1,463 | 0.0% | 0.0% | −7.4 |
| Σ Additional orders, <5 contigs | 10 | 2,372 | 0.1% | 0.0% | |
| | | | | | |
| Total | 207 | 2,374,179 | 76.0% | 39.7% | |

Mapped contigs, by genera, (species)

| | | | | | |
|---|---|---|---|---|---|
| *Candida* (*albicans*: 6) | 12 | 5,775 | 0.2% | 0.1% | −20.0 |
| *Lactobacillus* (*Delbrueckii*: 6) | 140 | 2,145,551 | 68.7% | 35.9% | −51.7 |
| *Micrococcus luteus* | 5 | 1,391 | 0.0% | 0.0% | −8.0 |
| *Ureaplasma* sp. | 5 | 1,463 | 0.0% | 0.0% | −7.4 |
| Σ Additional genera, <2 contigs | 13 | 61830 | 20.0% | 12.9% | |
| Σ Ambigous genus assignments | 32 | 158,169 | 5.1% | 2.6% | |
| | | | | | |
| Total | 207 | 2,374,179 | 76.0% | 39.7% | |

16-16, Normal

| Total reads | Un. reads (unassigned) | Reads: un. per total |
|---|---|---|
| 4,756,128 | 3,960,757 | 83.3% |

| Subset | Σ Contigs | Contig-aligned individual read counts | | | min. log(E-value) |
|---|---|---|---|---|---|
| | | absolute | /all cont. | /un.reads | |
| All generated in sample | 668 | 2,090,441 | 100.0% | 52.8% | |
| Mapped to unique biological orders | 301 | 1,089,357 | 52.1% | 27.5% | |

Mapped contigs, by orders

| | | | | | |
|---|---|---|---|---|---|
| High GC Gram+ | 104 | 577,883 | 27.6% | 14.6% | −9.4 |
| B-proteobacteria | 41 | 147,278 | 7.0% | 3.7% | −14.0 |
| Eudicots | 33 | 129,981 | 6.2% | 3.3% | −79.0 |
| Firmicutes | 26 | 29,073 | 1.4% | 0.7% | −8.0 |
| Fusobacteria | 24 | 77,873 | 3.7% | 2.0% | −9.0 |
| α-Proteobacteria | 19 | 14,731 | 0.7% | 0.4% | −10.5 |
| CFB group bacteria | 17 | 11,720 | 0.6% | 0.3% | −8.0 |
| Bacteria | 11 | 4,930 | 0.2% | 0.1% | −8.0 |
| γ-Proteobacteria | 10 | 11,291 | 0.5% | 0.3% | −8.0 |
| Σ Additional orders, <5 contigs | 16 | 84,597 | 4.0% | 2.1% | |
| | | | | | |
| Total | 301 | 1,089,357 | 52.1% | 27.5% | |

Mapped contigs, by genera, (species)

| | | | | | |
|---|---|---|---|---|---|
| *Propionibacterium propionicum* | 17 | 233,577 | 11.2% | 5.9% | −9.4 |
| *Corynebacterium* | 16 | 12,975 | 0.6% | 0.3% | −8.5 |
| *Streptococcus* | 16 | 20,600 | 1.0% | 0.5% | −8.0 |
| *Leptotrichia* (*buccalis*: 3) | 13 | 37,220 | 1.8% | 0.9% | −8.5 |
| *Actinomyces* (*meyeri*: 2) | 12 | 25,208 | 1.2% | 0.6% | −24.6 |
| *Neisseria* (*elongata*: 2) | 10 | 24,419 | 1.2% | 0.6% | −12.2 |
| *Candidatus Saccharibacteria* | 7 | 2,512 | 0.1% | 0.1% | −8.0 |

TABLE 3-continued

| | | | | | |
|---|---|---|---|---|---|
| *Actinobaculum schaalii* | 4 | 2,175 | 0.1% | 0.1% | −6.7 |
| *Anacardium occidentale* | 4 | 43,174 | 2.1% | 1.1% | −79.0 |
| *Capnocytophaga* | 2 | 1,578 | 0.1% | 0.0% | −7.7 |
| *Dechloromonas aromatica* | 2 | 510 | 0.0% | 0.0% | −8.5 |
| *Devriecea agamarum* | 2 | 851 | 0.0% | 0.0% | −8.0 |
| Σ Additional genera, <2 contigs | 63 | 230404 | 11.0% | 5.8% | |
| Σ Ambigous genus assignments | 133 | 454,154 | 21.7% | 11.5% | |
| Total | 301 | 1,089,357 | 52.1% | 27.5% | |

14-17/Normal, N/A

| Total reads | Un. reads (unassigned) | Reads: un. per total |
|---|---|---|
| 26,558,639 | 1,358,873 | 5.1% |

| | | Contig-aligned reads, counts | | | min. |
|---|---|---|---|---|---|
| Subset | Contigs | individual | per all cont. | per un.reads | log(E-value) |
| All generated in sample | 249 | 192,514 | 100.0% | 14.2% | |
| Mapped to unique biological orders | 83 | 88,050 | 45.7% | 6.5% | |

Mapped contigs, listed by orders

| | | | | | |
|---|---|---|---|---|---|
| Firmicutes | 40 | 64,853 | 33.7% | 4.8% | −17.2 |
| High GC Gram+ | 14 | 8,212 | 4.3% | 0.6% | −6.5 |
| A-proteobacteria | 8 | 2,633 | 1.4% | 0.2% | −6.0 |
| Enterobacteria | 6 | 2,145 | 1.1% | 0.2% | −8.3 |
| Σ Additional orders, <5 contigs | 15 | 10,207 | 5.3% | 0.8% | |
| Total | 83 | 88,050 | 45.7% | 6.5% | |

Mapped contigs, listed by genera, (species)

| | | | | | |
|---|---|---|---|---|---|
| *Lactobacillus* sp. | 30 | 39,384 | 20.5% | 2.9% | −14.4 |
| *Micrococcus luteus* | 4 | 1,426 | 0.7% | 0.1% | −6.5 |
| Σ Additional genera, <2 contigs | 16 | 15058 | 7.8% | 1.1% | |
| Σ Ambigous genus assignments | 33 | 32,172 | 16.7% | 2.4% | |
| Total | 83 | 88,040 | 45.7% | 6.5% | |

16-4, normal

| Total reads | Un. reads (unassigned) | Reads: un. per total |
|---|---|---|
| 58,464,218 | 56,389,746 | 96.5% |

| | | Contig-aligned individual read counts | | | min. |
|---|---|---|---|---|---|
| Subset | Σ Contigs | absolute | /all cont. | /un.reads | log(E-value) |
| All generated in sample | 1019 | 37,635,015 | 100.0% | 66.7% | |
| Mapped to unique biological orders | 402 | 28,716,054 | 76.3% | 49.1% | |

Mapped contigs, by orders

| | | | | | |
|---|---|---|---|---|---|
| Enterobacteria | 365 | 28,602,751 | 76.0% | 48.9% | −125.7 |
| Ascomycetes | 17 | 7,189 | 0.0% | 0.0% | −9.7 |
| Σ Additional orders, <5 contigs | 20 | 106,114 | 0.3% | 0.2% | |
| Total | 402 | 28,716,054 | 76.3% | 49.1% | |

Mapped contigs, by genera, (species)

| | | | | | |
|---|---|---|---|---|---|
| *Klebsiallae* (*pneumonieae*: 53) | 165 | 1,494,642 | 4.0% | 2.6% | −114.0 |
| *Escherichia coli* | 3 | 1,343,196 | 3.6% | 2.3% | −10.7 |
| *Salmonella enterica* | 3 | 299,819 | 0.8% | 0.5% | −28.5 |
| *Arsenophonus endosymbiont* | 3 | 775 | 0.0% | 0.0% | −7.4 |
| *Fusaria* (*graminearum*: 2) | 3 | 706 | 0.0% | 0.0% | −8.2 |
| Σ Additional genera, <2 contigs | 28 | 7,539,933 | 20.0% | 12.9% | |
| 12/27/201512/27/2015 | 197 | 18,036,983 | 47.9% | 30.9% | |
| Total | 402 | 28,716,054 | 76.3% | 49.1% | |

16-19, Acute cell rejection

| Total reads | Un. reads (unassigned) | Reads: un. per total |
|---|---|---|
| 50,942,549 | 49,939,886 | 98.0% |

| | | Contig-aligned individual read counts | | | min. |
|---|---|---|---|---|---|
| Subset | Σ Contigs | absolute | /all cont. | /un.reads | log(E-value) |
| All generated in sample | 2477 | 41,897,796 | 100.0% | 66.7% | |
| Mapped to unique biological orders | 833 | 26,784,825 | 63.9% | 53.6% | |

TABLE 3-continued

| Mapped contigs, by orders | | | | | |
|---|---|---|---|---|---|
| High GC Gram+ | 251 | 12,703,700 | 30.3% | 24.9% | −26.0 |
| β-Proteobacteria | 171 | 7,740,803 | 18.5% | 15.2% | −41.0 |
| Fusobacteria | 98 | 1,672,841 | 4.0% | 3.3% | −15.3 |
| Firmicutes | 88 | 612,197 | 1.5% | 1.2% | −10.2 |
| Bacteria | 70 | 210,344 | 0.5% | 0.4% | −22.0 |
| CFB group bacteria | 68 | 174,318 | 0.4% | 0.3% | −10.7 |
| γ-Proteobacteria | 32 | 756,939 | 1.8% | 1.5% | −13.7 |
| Eudicots | 17 | 22,303 | 0.1% | 0.0% | −81.3 |
| α-Proteobacteria | 13 | 38,074 | 0.1% | 0.1% | −8.5 |
| ε-Proteobacteria | 6 | 3,629 | 0.0% | 0.0% | −8.5 |
| Σ Additional orders, <5 contigs | 19 | 2,849,677 | 6.8% | 5.6% | |
| Total | 833 | 26,784,825 | 63.9% | 53.6% | |
| Mapped contigs, by genera, (species) | | | | | |
| *Neisseria* sp. (*lactamica*: 6) (*sicca*: 6) | 95 | 1,720,335 | 4.1% | 3.4% | −41.0 |
| *Leptotrichia* sp. (*Buccalis*: 15) | 74 | 1,447,087 | 3.5% | 2.8% | −15.3 |
| *Propionibacterium propionicum* | 51 | 6,533,131 | 15.6% | 12.8% | −26.0 |
| *Streptococcus* sp. | 49 | 376,263 | 0.9% | 0.7% | −10.2 |
| *Actinomyces* sp. | 35 | 802,110 | 1.9% | 1.6% | −10.2 |
| *Candidatus Saccharibacteria* sp. | 27 | 55,254 | 0.1% | 0.1% | −10.2 |
| *Corynebacterium* sp. | 26 | 296,066 | 0.7% | 0.6% | −12.0 |
| *Capnocytophaga* sp. | 13 | 43,209 | 0.1% | 0.1% | −9.5 |
| *Actinobaculum schaalii* | 10 | 1,339,942 | 3.2% | 2.6% | −10.2 |
| *Fusobacterium nucleatum* | 10 | 11,273 | 0.0% | 0.0% | −10.2 |
| *Veillonella parvula* | 9 | 17,279 | 0.0% | 0.0% | −8.5 |
| *Cardiobacterium hominis* | 8 | 5,398 | 0.0% | 0.0% | −13.7 |
| *Prevotella* sp. (*melaninogenica*: 3) | 6 | 4,519 | 0.0% | 0.0% | −8.0 |
| *Dichelobacter nodosus* | 5 | 82,562 | 0.2% | 0.2% | −8.5 |
| *Mesorhizobium* sp. | 4 | 653 | 0.0% | 0.0% | −5.5 |
| *Rothia* sp. | 4 | 16,653 | 0.0% | 0.0% | −8.5 |
| *Anacardium occidentale* | 3 | 4,071 | 0.0% | 0.0% | −81.3 |
| *Campylobacter* sp. | 3 | 651 | 0.0% | 0.0% | −7.5 |
| *Porphyromonas gingivalis* | 3 | 22,698 | 0.1% | 0.0% | −7.0 |
| *Tsukamurella paurometabola* | 3 | 144,033 | 0.3% | 0.3% | −9.2 |
| *Acetohalobium arabaticum* | 2 | 111,686 | 0.3% | 0.2% | −8.0 |
| *Desulfococcus oleovorans* | 2 | 2,706,849 | 6.5% | 5.3% | −8.0 |
| Σ Additional genera, <2 contigs | 117 | 1,799,970 | 8.2% | 12.9% | |
| Σ Ambigous genus assignments | 274 | 9,243,133 | 18.1% | 18.1% | |
| Total | 833 | 26,784,825 | 63.9% | 53.6% | |

Table 3 Identification of Xenobiotic RNA Sources in Selected Urine Samples

Urine samples with at least two million total reads and more than 80% hg19-unmapped reads, 14-16, 16-4, 16-16, 16-19, and two randomly selected samples 14-17 (5.1% unmapped reads) and 13-16 9 were included for this analysis. From each selected samples unmapped sequences larger than 25 nucleotides and represented by at least 30 individual reads were used to generate contigs using the SeqMan (DNASTAR, v 12.3.1.4) Using the parameters: match size: 14, min. match percentage: 97, match spacing: 75, gap penalty: 0, gap length penalty:0.7, max. mismatch end bases: 2. Only contigs with consensus sequences which were at least 30 nt longer and based on at least two unique unmapped sequences. Generated contigs were considered and used as queries for NR database at the National Center of Biotechnology information (NCBI) using the BLASTN program. Numbers of the total contigs generated and those unambiguous assigned to a taxonomic order are listed. For both subsets contributing unmapped total reads used in contig generation are listed and related to all sequences used in contig generation (/all cont.) and to the entire unmapped read counts (/un. reads). For taxonomic evaluation only top score returned target matches were considered irrespective of their number of occurrences within a target sequence or genome, if the E-value for that matched hit was at least $10^{-5}$ Or lower. For assignments of order, genus and species to a contig, taxonomic obtained had to be unambiguous: Only if for any given contig a set of equivalent matches comprised entirely of organisms from the same biological order, that order was assigned. In the same manner, family and species information was assigned, if returned top matches showed no ambiguity.

The resulting taxonomic assignments sorted the number of supporting contigs and the number of participating sequences are listed in the lower two tables, sorted by identified orders and genera, respectively. Species information was included if specific; in cases where several but not all contigs could be unambiguously assigned up to the species level or where evidence for the presence of at least two different species within one genus was found, species information is listed in parenthesis together with the number of supporting contigs.

INCORPORATION OF SEQUENCE LISTING

Incorporated herein by reference in its entirety is the Sequence Listing for the application. The Sequence Listing is disclosed on a computer-readable ASCII text file titled "sequence_listing.txt", created on Jun. 12, 2017. The sequence_listing.txt file is 1,897 bytes in size.

The invention claimed is:

1. A method for isolating RNA from a biological fluid, said method comprising:
   (a) contacting the biological fluid with a denaturing solution comprising at least one of reducing agent and detergent, wherein said denaturing solution is heated to about 50° C., about 55° C., about 60° C. or about 65° C. prior to contacting the biological fluid, to form a biological fluid mixture;
   (b) contacting the biological fluid mixture with a protease to form a protease treated biological fluid mixture;
   (c) contacting the protease treated biological fluid mixture with an organic extraction solution, forming a solution having an aqueous phase containing the RNA and an organic phase and wherein an interphase is absent or significantly reduced;
   (d) binding the RNA to a silica based solid phase by contacting the aqueous phase with said silica based solid phase;
   (e) contacting the silica based solid phase with a first wash solution comprising alcohol, chaotropic agent, and reducing agent; and
   (f) eluting the RNA from the silica based solid phase comprising contacting the silica based solid phase with an aqueous solution to provide isolated RNA.

2. The method of claim 1, wherein said biological fluid is selected from the group consisting of urine, serum, and plasma.

3. The method of claim 1, wherein said biological fluid is homogenized tissue.

4. The method of claim 1, wherein said protease is proteinase K.

5. The method of claim 1, wherein said detergent is an anionic detergent.

6. The method of claim 5, wherein said anionic detergent is SDS.

7. The method of claim 6, wherein said SDS is present at a concentration of at least 2% (w/v), at least 3% (w/v), at least 4% (w/v), or at least 5% (w/v).

8. The method of claim 1, wherein said chaotropic agent is selected from the group consisting of guanidine and urea.

9. The method of claim 1, wherein said reducing agent is selected from the group consisting of DTT, BME, and TCEP.

10. The method of claim 1, wherein said RNA is between 5-500 nucleotides, 5-250 nucleotides, 5-100 nucleotides, or 5-50 nucleotides.

11. The method of claim 1, wherein said organic extraction solution further comprises at least one of chaotropic agent and phenol.

12. The method of claim 1, wherein said organic extraction solution further comprises chloroform.

13. The method of claim 1, wherein chloroform is contacted with the biological fluid after the biological fluid has contacted the organic extraction solution.

14. The method of claim 1, wherein said reducing agent of step (e) is selected from the group consisting of DTT, BME, and TCEP.

15. The method of claim 14, wherein said reducing agent is TCEP.

16. The method of claim 15, wherein said TCEP has a concentration between 1 mM and 20 mM, between 1 mM and 10 mM, or between 1 and 5 mM.

17. The method of claim 8, wherein said chaotropic agent is guanidine.

18. The method of claim 1, wherein said alcohol of step (e) is selected from the group consisting of methanol, ethanol, butanol, and propanol.

19. The method of claim 1, wherein said method further comprises at least one alcohol wash after step (e).

20. The method of claim 1, wherein said aqueous solution of step (f) comprises at least one of water, buffer, and nucleic acid preservative.

* * * * *